United States Patent
Fukushima et al.

(10) Patent No.: US 10,915,021 B2
(45) Date of Patent: Feb. 9, 2021

(54) MONOMER, POLYMER, RESIST COMPOSITION, AND PATTERNING PROCESS

(71) Applicant: Shin-Etsu Chemical Co., Ltd., Tokyo (JP)

(72) Inventors: Masahiro Fukushima, Joetsu (JP); Koji Hasegawa, Joetsu (JP); Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 203 days.

(21) Appl. No.: 16/121,970

(22) Filed: Sep. 5, 2018

(65) Prior Publication Data
US 2019/0079399 A1  Mar. 14, 2019

(30) Foreign Application Priority Data
Sep. 13, 2017  (JP) .................. 2017-175900

(51) Int. Cl.
| | | |
|---|---|---|
| G03F 7/004 | (2006.01) | |
| C08F 12/16 | (2006.01) | |
| G03F 7/033 | (2006.01) | |
| G03F 7/42 | (2006.01) | |
| C08F 2/38 | (2006.01) | |
| C08F 220/18 | (2006.01) | |
| C08F 228/02 | (2006.01) | |
| C08F 12/24 | (2006.01) | |
| C07C 43/225 | (2006.01) | |
| C08F 12/22 | (2006.01) | |
| C08F 12/32 | (2006.01) | |
| C08F 212/32 | (2006.01) | |
| G03F 7/039 | (2006.01) | |
| C09D 125/18 | (2006.01) | |
| C08F 212/14 | (2006.01) | |
| C07C 43/247 | (2006.01) | |
| C07C 39/373 | (2006.01) | |
| C08F 2/50 | (2006.01) | |

(52) U.S. Cl.
CPC ............ *G03F 7/033* (2013.01); *C07C 39/373* (2013.01); *C07C 43/225* (2013.01); *C07C 43/247* (2013.01); *C08F 2/38* (2013.01); *C08F 12/16* (2013.01); *C08F 12/22* (2013.01); *C08F 12/24* (2013.01); *C08F 12/32* (2013.01); *C08F 212/14* (2013.01); *C08F 212/32* (2013.01); *C08F 220/18* (2013.01); *C08F 228/02* (2013.01); *C09D 125/18* (2013.01); *G03F 7/0045* (2013.01); *G03F 7/0046* (2013.01); *G03F 7/0397* (2013.01); *G03F 7/426* (2013.01); *C07C 2601/08* (2017.05); *C07C 2601/14* (2017.05); *C08F 2/50* (2013.01); *C08F 220/1806* (2020.02)

(58) Field of Classification Search
CPC ...... G03F 7/033; G03F 7/0045; G03F 7/0046; G03F 7/0397; G03F 7/426; G03F 7/2037; C08F 12/16; C08F 12/22; C08F 12/24; C08F 12/32; C08F 212/14; C08F 212/32; C08F 212/18
See application file for complete search history.

(56) References Cited

U.S. PATENT DOCUMENTS

| | | | | |
|---|---|---|---|---|
| 4,178,327 A | * | 12/1979 | Hall ................. | C08F 299/0478 525/169 |
| 5,149,743 A | * | 9/1992 | Kennedy ............ | C08F 12/18 525/331.4 |
| 10,007,178 B2 | * | 6/2018 | Hatakeyama ....... | G03F 7/0045 |
| 10,495,968 B2 | * | 12/2019 | Aqad .................. | C08L 73/00 |

(Continued)

FOREIGN PATENT DOCUMENTS

| | | | |
|---|---|---|---|
| JP | 64-9465 A | | 1/1989 |
| JP | 01096202 A | * | 4/1989 |

(Continued)

OTHER PUBLICATIONS

Machine translation of JP-01096202-A (no date).*

(Continued)

*Primary Examiner* — Amanda C. Walke
(74) *Attorney, Agent, or Firm* — Westerman, Hattori, Daniels & Adrian, LLP

(57) ABSTRACT

A monomer having formula (A) is provided. $R^A$ is H, methyl or trifluoromethyl, $X^1$ is a single bond, ether, ester or amide bond, $R^a$ is a $C_1$-$C_{20}$ monovalent hydrocarbon group, $R^b$ is H or an acid labile group, X is halogen, n is an integer of 1 to 4, m is an integer of 0 to 3, and $1 \leq n+m \leq 4$. A resist composition comprising a polymer derived from the monomer has a high sensitivity to high-energy radiation, especially EUV.

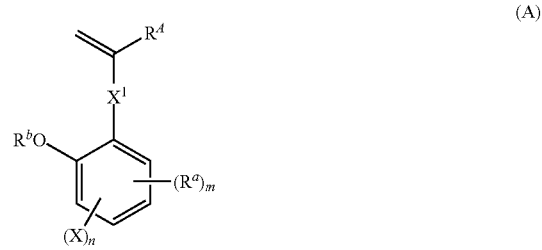

(A)

15 Claims, No Drawings

(56) References Cited

U.S. PATENT DOCUMENTS

2013/0342102 A1    12/2013  Hakoi et al.
2018/0373148 A1*   12/2018  Hatakeyama ......... C08F 220/16

FOREIGN PATENT DOCUMENTS

| JP | 5-204157 A | | 8/1993 | |
|----|----|----|----|----|
| JP | 2007128104 A | * | 5/2007 | |
| JP | 2015-161823 A | | 9/2015 | |
| JP | 2015161823 A | * | 9/2015 | ........... G03F 7/0395 |
| WO | 2013/024777 A1 | | 2/2013 | |
| WO | 2017/037146 A1 | | 3/2017 | |

OTHER PUBLICATIONS

Machine translation of JP-2015161823-A (no date).*
Machine translation of JPS64-9465 (no date).*
Yamamoto et al., "Polymer-Structure Dependence of Acid Generation in Chemically Amplified Extreme Ultraviolet Resists", Japanese Journal of Applied Physics, 2007, vol. 46, No. 7, pp. L142-L144, cited in Specification (3 pages).
Schmidt, Bernd et al., "Synthesis of 8-Aryl-Substituted Coumarins Based on Ring-Closing Metathesis and Suzuki-Miyaura Coupling: Synthesis of a Furyl Coumarin Natural Product from Galipea panamensis", the Journal of Organic Chemistry, vol. 77, 2012, pp. 2360-2361; Cited in CN Office Action dated May 27, 2020.
Office Action dated May 27, 2020, issued in counterpart CN Application No. 201811066172.3, with English translation (14 pages).

* cited by examiner

MONOMER, POLYMER, RESIST COMPOSITION, AND PATTERNING PROCESS

CROSS-REFERENCE TO RELATED APPLICATION

This non-provisional application claims priority under 35 U.S.C. § 119(a) on Patent Application No. 2017-175900 filed in Japan on Sep. 13, 2017, the entire contents of which are hereby incorporated by reference.

TECHNICAL FIELD

This invention relates to a monomer, a polymer, a resist composition comprising the polymer, and a patterning process using the composition.

BACKGROUND ART

To meet the demand for higher integration density and operating speed of LSIs, the effort to reduce the pattern rundle is in rapid progress. The logic devices used in smart phones drive forward the miniaturization technology. Logic devices of 10-nm node are manufactured in a large scale using a multi-patterning lithography process based on ArF lithography.

In the application of lithography to next 7-nm or 5-nm node devices, the increased expense and overlay accuracy of multi-patterning lithography become tangible. The advent of EUV lithography capable of reducing the number of exposures is expected.

Since the wavelength (13.5 nm) of extreme ultraviolet (EUV) is shorter than 1/10 of the wavelength (193 nm) of ArF excimer laser, the EUV lithography achieves a high light contrast, from which a high resolution is expectable. Because of the short wavelength and high energy density of EUV, an acid generator is sensitive to a small dose of photons. It is believed that the number of photons available with EUV exposure is 1/14 of that of ArF exposure. In the EUV lithography, the phenomenon that the edge roughness (LWR) of line patterns or the critical dimension uniformity (CDU) of hole patterns is degraded by a variation of photon number is considered a problem.

Aiming to reduce a photon number variation, an attempt was made to render the resist more absorptive so that the number of photons absorbed in the resist is increased.

Patent Document 1 discloses a halogen-substituted styrene base resin. Among the halogen atoms, iodine is highly absorptive to EUV radiation of wavelength 13.5 nm. Recently Patent Documents 2 and 3 propose to use iodine-substituted resins as EUV resist component. Regrettably, it is not true that a higher sensitivity is obtainable by merely incorporating iodine to increase the number of photons absorbed. With respect to the acid generation in EUV exposure, Non-Patent Document 1 reports that the acid generation efficiency of iodized styrene is only 14% of that of hydroxystyrene.

CITATION LIST

Patent Document 1: JP-A H05-204157
Patent Document 2: JP-A 2015-161823
Patent Document 3: WO 2013/024777
Non-Patent Document 1: Jpn. J. Appl. Physics, Vol. 46, No. 7, pp. L142-L144, 2007

SUMMARY OF INVENTION

For the acid-catalyzed chemically amplified resist, it is desired to develop a resist composition providing a high sensitivity and reducing LWR or improving CDU of hole patterns.

An object of the invention is to provide a resist composition which exhibits a high sensitivity upon exposure to high-energy radiation, especially EUV; and a pattern forming process using the same. Another object is to provide a polymer which serves as a base resin in the resist composition, and a monomer which may be used as a starting material for the polymer.

The inventors have found that better results are obtained from a resist composition comprising, as base resin, a polymer having a phenolic hydroxyl group at ortho-position to the carbon atom on an aromatic ring bonded to the polymer backbone, the phenolic hydroxyl group being optionally protected with an acid labile group, and having a halogen atom on the aromatic ring. When exposed to high-energy radiation, especially EUV, the resist composition exhibits a high sensitivity, improved CDU, and wide process margin.

In one aspect, the invention provides a monomer having the formula (A).

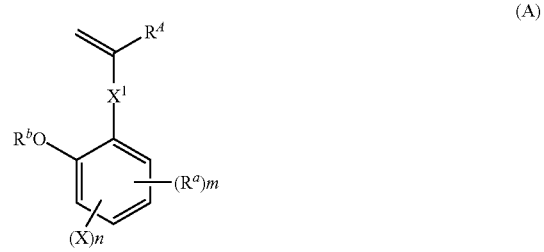

Herein $R^A$ is hydrogen, methyl or trifluoromethyl, $X^1$ is a single bond, ether, ester or amide bond, $R^a$ is a $C_1$-$C_{20}$ monovalent hydrocarbon group in which any constituent methylene moiety may be replaced by an ether bond or carbonyl moiety, where at least two $R^a$ are included, two adjacent $R^a$ may bond together to form an alicyclic structure with the carbon atoms to which they are attached, $R^b$ is hydrogen or an acid labile group, X is halogen, n and m are integers in the range: $1 \leq n \leq 4$, $0 \leq m \leq 3$, and $1 \leq n+m \leq 4$.

Preferably, $X^1$ is a single bond, and X is iodine.

In a second aspect, the invention provides a polymer comprising recurring units to having a partial structure represented by the formula (B) on a side chain.

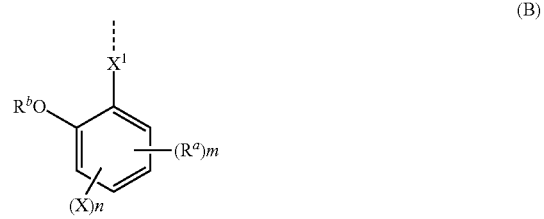

Herein $X^1$, $R^a$, $R^b$, X, n and m are as defined above, the broken line denotes a valance bond to a polymer backbone.

Preferably, the recurring unit has the formula (a).

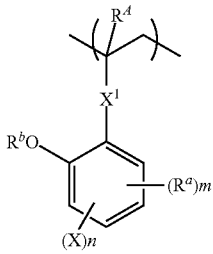

(a)

Herein $R^A$, $R^a$, $R^b$, $X^1$, X, n and m are as defined above.

Preferably, $X^1$ is a single bond, and X is iodine.

The polymer may further comprise recurring units having a group capable of polarity switch under the action of acid. The recurring units having a group capable of polarity switch under the action of acid are preferably represented by the formula (b1) or (b2).

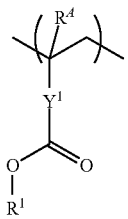

(b1)

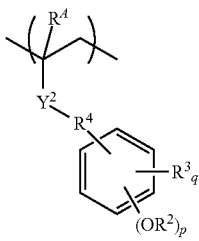

(b2)

Herein $R^A$ is as defined above; $Y^1$ is a single bond, phenylene group, naphthylene group, or a $C_1$-$C_{12}$ linking group containing an ether bond, ester bond or lactone ring $Y^2$ is a single bond, ester bond or amide bond; $R^1$ and $R^2$ are each independently an acid labile group; $R^3$ is fluorine, trifluoromethyl, cyano, $C_1$-$C_6$ alkyl, $C_1$-$C_6$ alkoxy, $C_2$-$C_7$ acyl, $C_2$-$C_7$ acyloxy, or $C_2$-$C_7$ alkoxycarbonyl group: $R^4$ is a single bond or $C_1$-$C_6$ alkylene group in which at least one carbon atom may be replaced by an ether or ester bond, p is 1 or 2, and q is an integer of 0 to 4.

The polymer may further comprise recurring units having an adhesive group which is selected from the group consisting of hydroxyl, carboxyl, lactone ring, carbonate, thiocarbonate, carbonyl, cyclic acetal, ether bond, ester bond, sulfonic acid ester bond, cyano, amide, —O—C(=O)—S—, and —O—C(=O)—NH—.

The polymer may further comprise recurring units of at least one type selected from recurring units having the formulae (d1), (d2) and (d3).

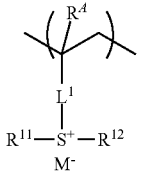

(d1)

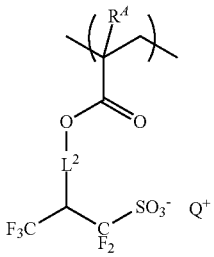

(d2)

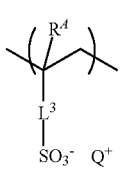

(d3)

Herein $R^A$ is as defined above. $R^1$ and $R^{12}$ are each independently a $C_1$-$C_{20}$ monovalent hydrocarbon group which may contain a heteroatom, $R^{11}$ and $R^{12}$ may bond together to form a ring with the sulfur atom to which they are attached. $L^1$ is a single bond, phenylene group, —C(=O)-$L^{11}$-$L^{12}$-, or —O-$L^{12}$-, $L^{11}$ is —O— or —NH—, $L^{12}$ is a $C_1$-$C_6$ divalent aliphatic hydrocarbon group which may contain a carbonyl, ester bond, ether bond or hydroxyl moiety, or a phenylene group. $L^2$ is a single bond or -$L^{21}$-C(=O)—O—, $L^{21}$ is a $C_1$-$C_{20}$ divalent hydrocarbon group which may contain a heteroatom. L is a single bond, methylene, ethylene, phenylene or fluorinated phenylene group, —C(=O)-$L^{31}$-$L^{32}$-, or —O-$L^{32}$-, $L^{31}$ is —O— or —NH—, $L^{32}$ is a $C_1$-$C_6$ divalent aliphatic hydrocarbon group which may contain a carbonyl, ester bond, ether bond or hydroxyl moiety, or a phenylene group, 1f is a non-nucleophilic counter ion.

$Q^+$ is a sulfonium cation having the formula (d4) or iodonium cation having the formula (d5):

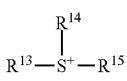

(d4)

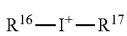

(d5)

wherein $R^{13}$ to $R^{17}$ are each independently a $C_1$-$C_{20}$ monovalent hydrocarbon group which may contain a heteroatom, any two of $R^{13}$, $R^{14}$ and $R^{15}$ may bond together to form a ring with the sulfur atom to which they are bonded.

In a third aspect, the invention provides a resist composition comprising a base resin containing the polymer defined above, an organic solvent, and an acid generator, or a resist composition comprising a base resin containing the polymer defined above, and further comprising units (d1) to (d3), and an organic solvent.

The resist composition may further comprise a quencher and a surfactant.

In a fourth aspect, the invention provides a pattern forming process comprising the steps of coating the resist composition defined above onto a substrate, baking to form a resist film, exposing the resist film to high-energy radiation, and developing the exposed resist film in a developer.

Typically, the high-energy radiation is i-line, KrF excimer laser, ArF excimer laser, EB, or EUV of wavelength 3 to 15 nm.

Advantageous Effects of Invention

A resist composition comprising the inventive polymer as base resin is advantageous when exposed to high-energy radiation, especially EUV of wavelength 13.5 nm. Since halogen, especially iodine is highly absorptive to EUV, it effectively generates secondary electrons during exposure, which are transported to the acid generator to induce efficient acid generation. This contributes to a higher sensitivity. Since the polymer has a phenolic hydroxyl group at the ortho position relative to the backbone, it has an appropriate dissolution rate in alkaline developer. Thus a resist material having a high sensitivity and improved CDU may be designed.

DESCRIPTION OF EMBODIMENTS

As used herein, the singular forms "a," "an" and "the" include plural referents unless the context clearly dictates otherwise. The notation ($C_n$-$C_m$) means a group containing from n to m carbon atoms per group. As used herein, the term "iodized" or "fluorinated" indicates that a compound contains iodine or fluorine. Me stands for methyl, and Ac for acetyl.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
LER: line edge roughness
CDU: critical dimension uniformity Monomer One embodiment of the invention is a polymerizable monomer having the formula (A).

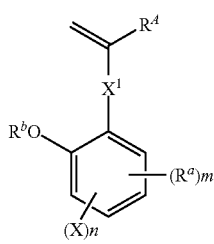

(A)

In formula (A), $R^A$ is hydrogen, methyl or trifluoromethyl. $X^1$ is a single bond, ether bond, ester bond or amide bond. Preferably, $X^1$ is a single bond because a robust polymer backbone is obtained. Where $X^1$ is an ester or amide bond, it is preferred that the oxygen or nitrogen atom in the ester or amide bond unite with the carbon atom on the aromatic ring.

In formula (A), $R^a$ is a $C_1$-$C_2$ monovalent hydrocarbon group in which any constituent methylene moiety may be replaced by an ether bond or carbonyl moiety. Where at least two $R^a$ are included, two adjacent $R^a$ may bond together to form an alicyclic structure with the carbon atoms to which they are attached.

The $C_1$-$C_{20}$ monovalent hydrocarbon group may be straight, branched or cyclic. Suitable examples include straight or branched alkyl groups such as methyl, ethyl, propyl, isopropyl, n-butyl, s-butyl, t-butyl, 2-ethylhexyl, and n-octyl, and monovalent cycloaliphatic saturated hydrocarbon groups such as cyclopentyl, cyclohexyl, norbornyl, tricyclodecanyl, and adamantyl.

Where two adjacent $R^a$ bond together to form an alicyclic structure with the carbon atoms to which they are attached, suitable structures include cyclopropane, cyclobutane, cyclopentane and cyclohexane rings.

In formula (A), $R^b$ is hydrogen or an acid labile group. Where $R^b$ is an acid labile group, it is desirable, though not critical, that the acid labile group form a acetal or tertiary ether structure with the adjacent oxygen atom.

In formula (A), X is halogen. Exemplary of the halogen are fluorine, chlorine, bromine and iodine. Inter alia, bromine and iodine are preferred because of high efficiency of EUV absorption, with iodine being most preferred.

In formula (A), n and m are integers in the range: $1 \le n \le 4$, $0 \le m \le 3$, and $1 \le n+m \le 4$. Preferably, n is an integer of 2 to 4, and m is 0.

Examples of the monomer having formula (A) are shown below, but not limited thereto. Herein $R^A$ and $R^b$ are as defined above.

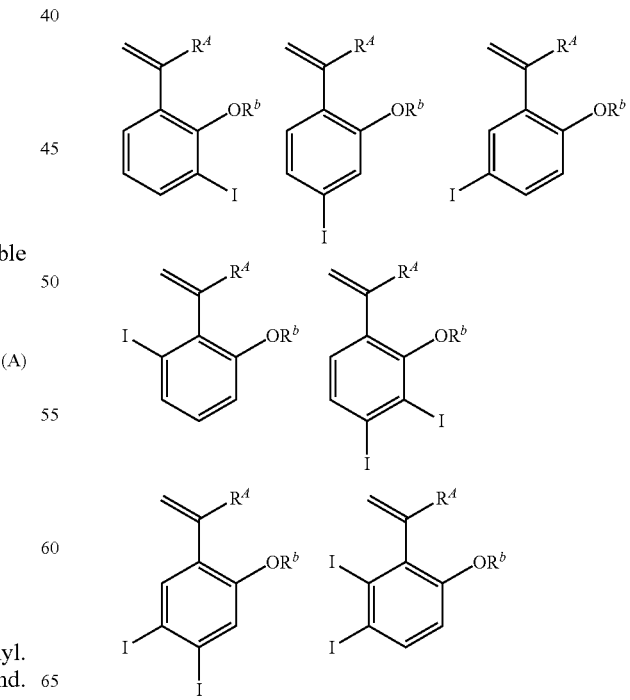

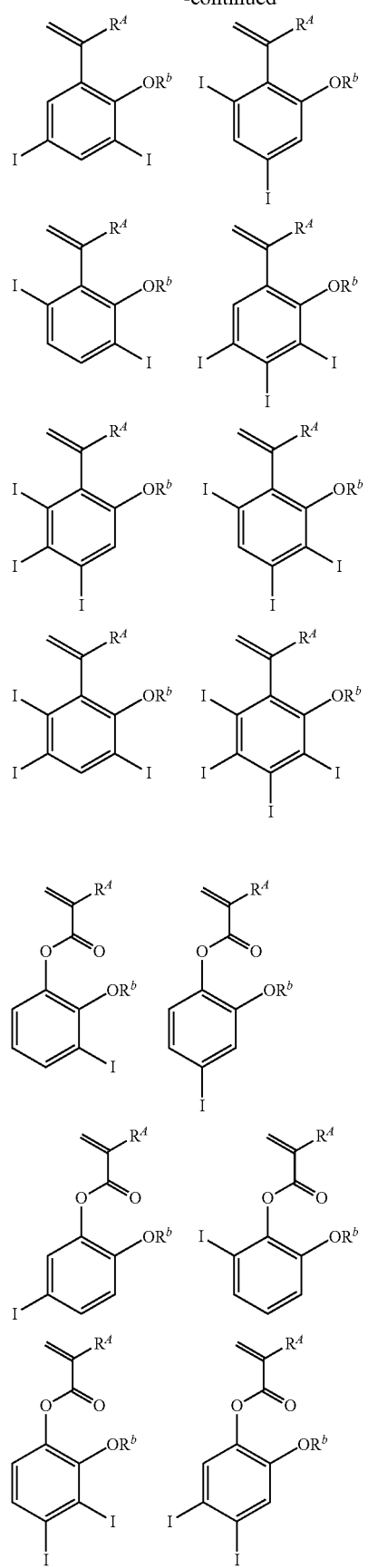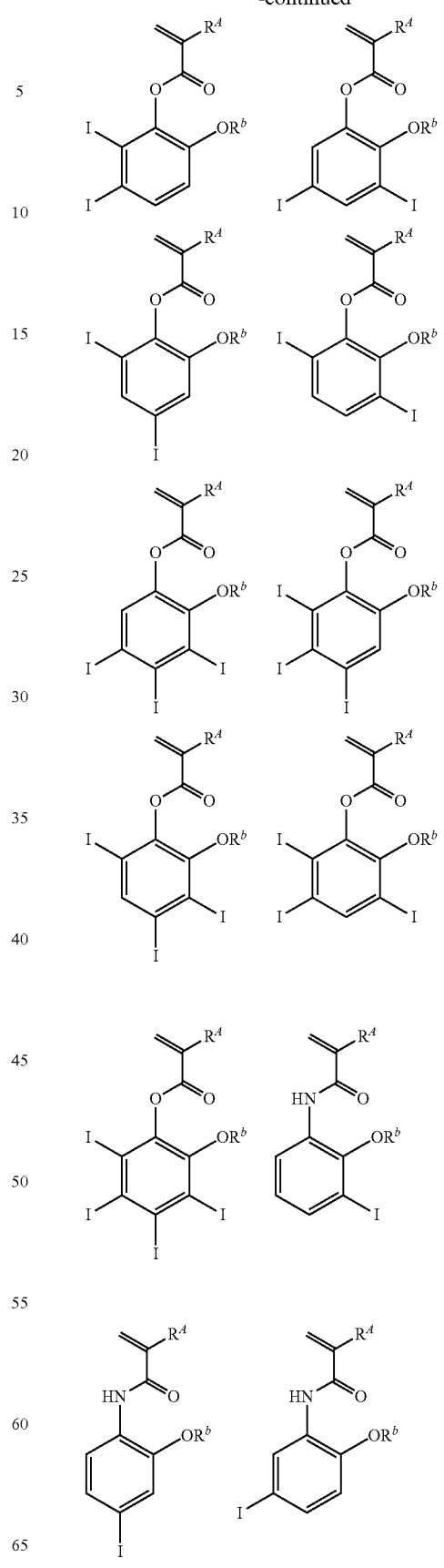

-continued
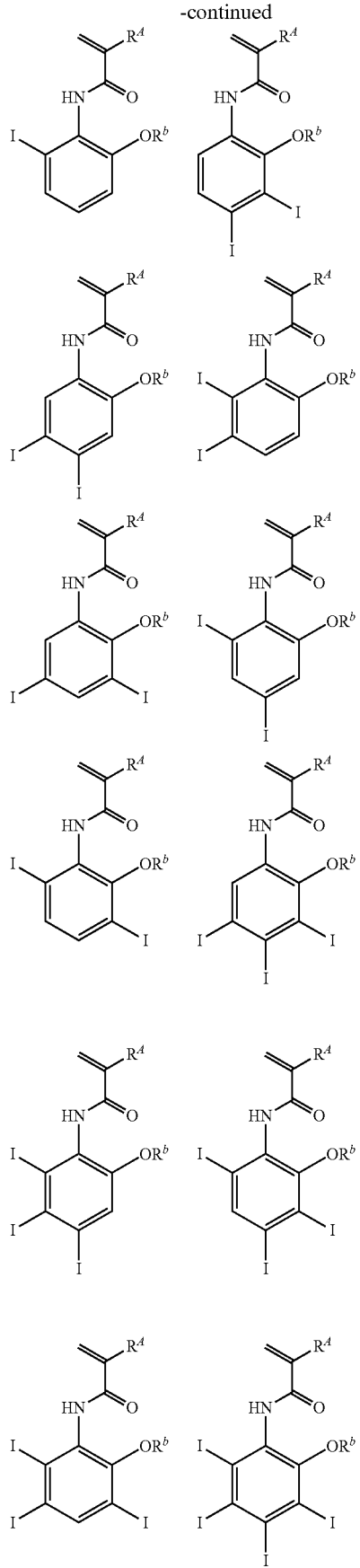
-continued
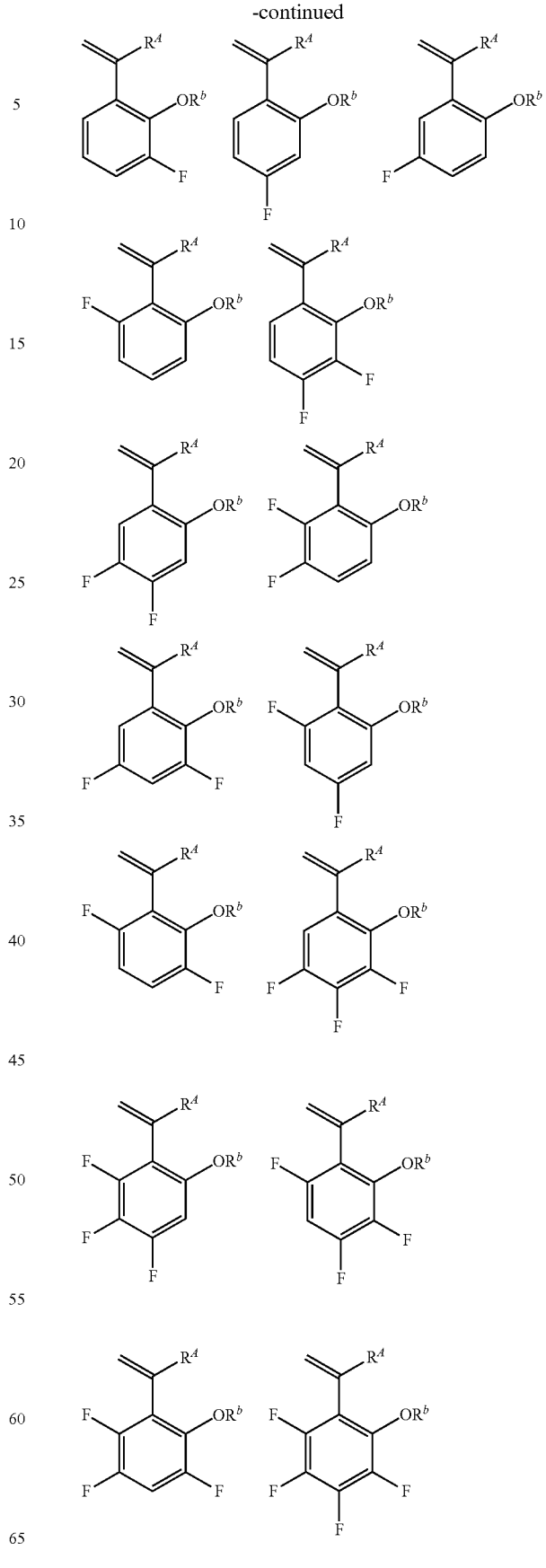

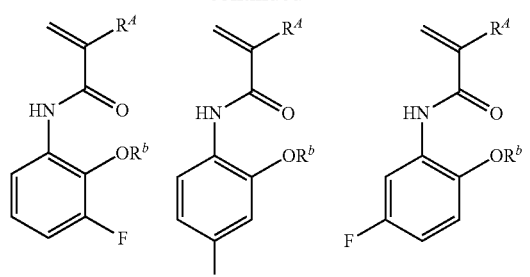
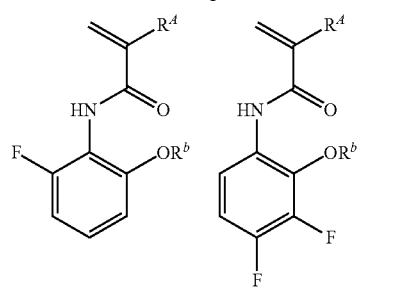
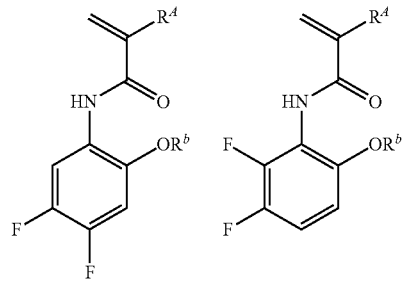
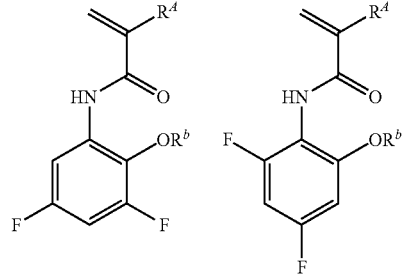
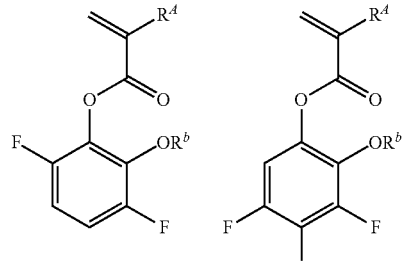
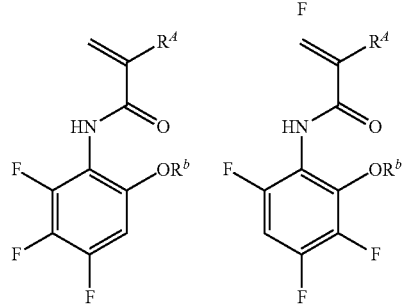
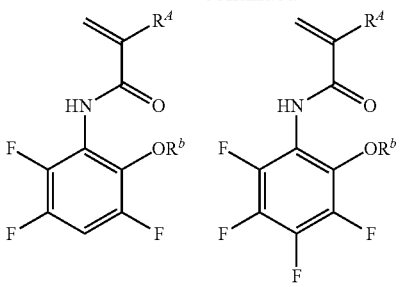
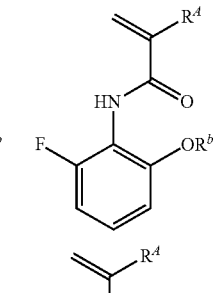
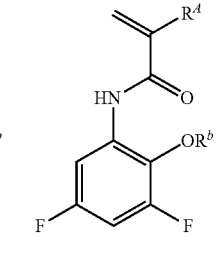
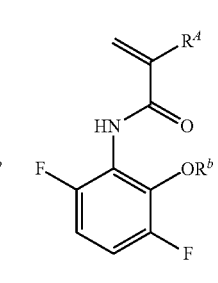

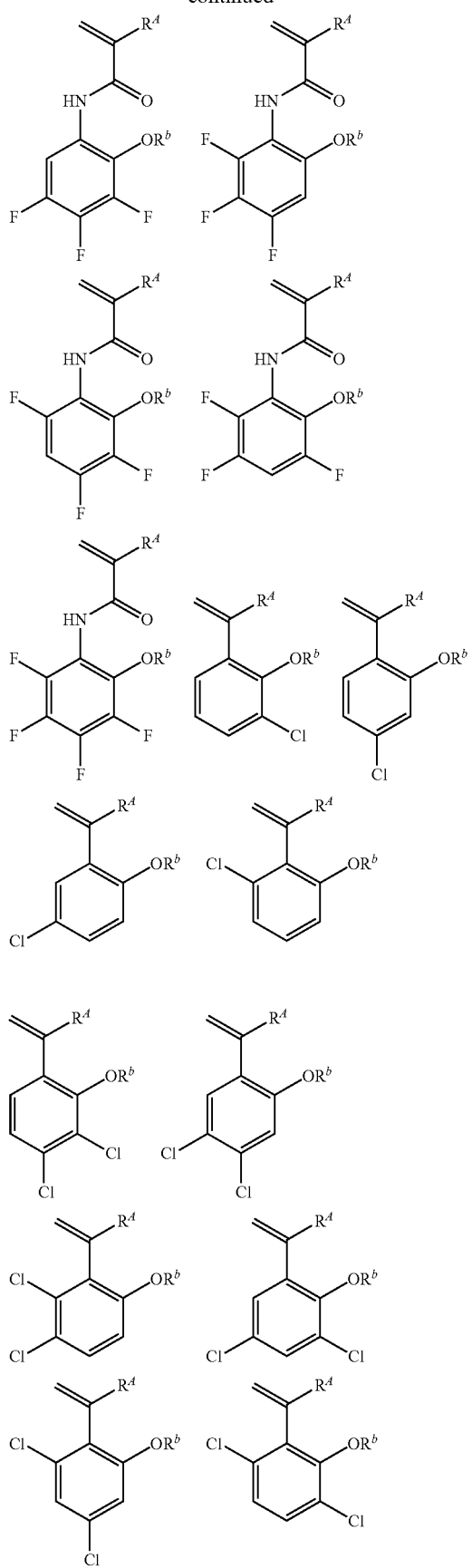
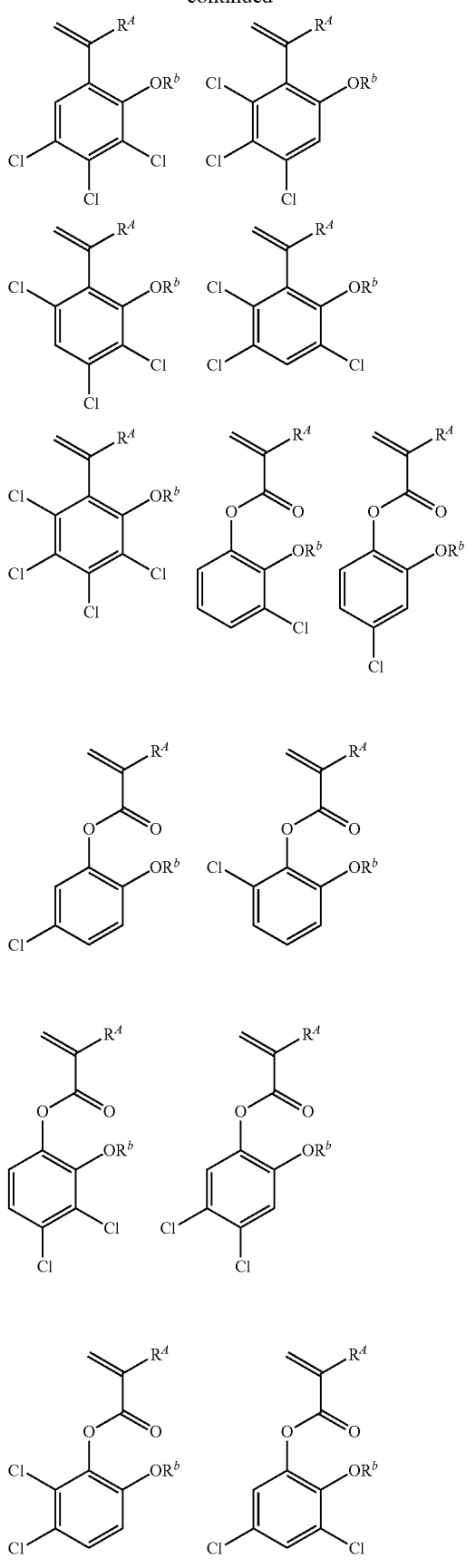

-continued
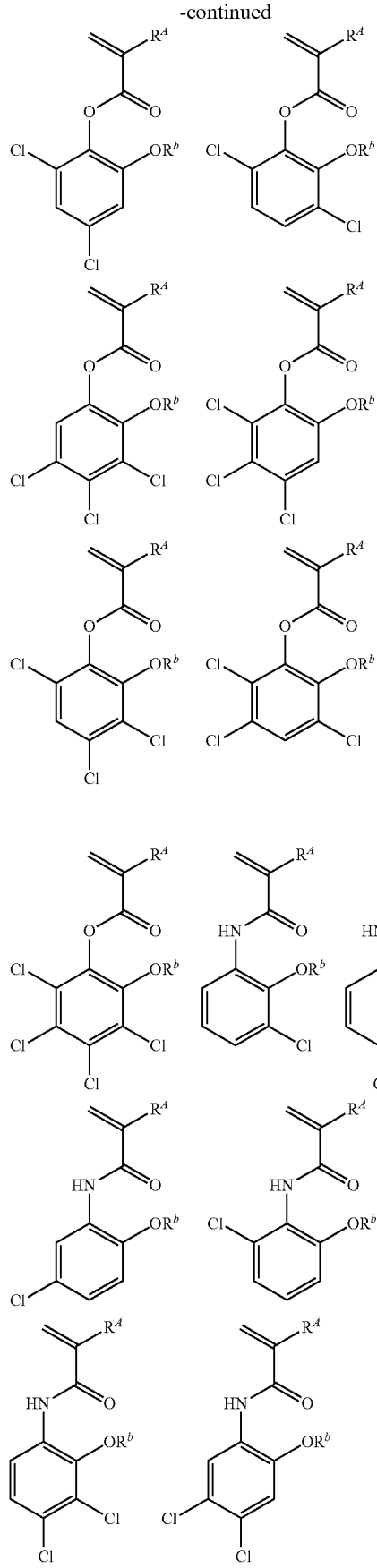
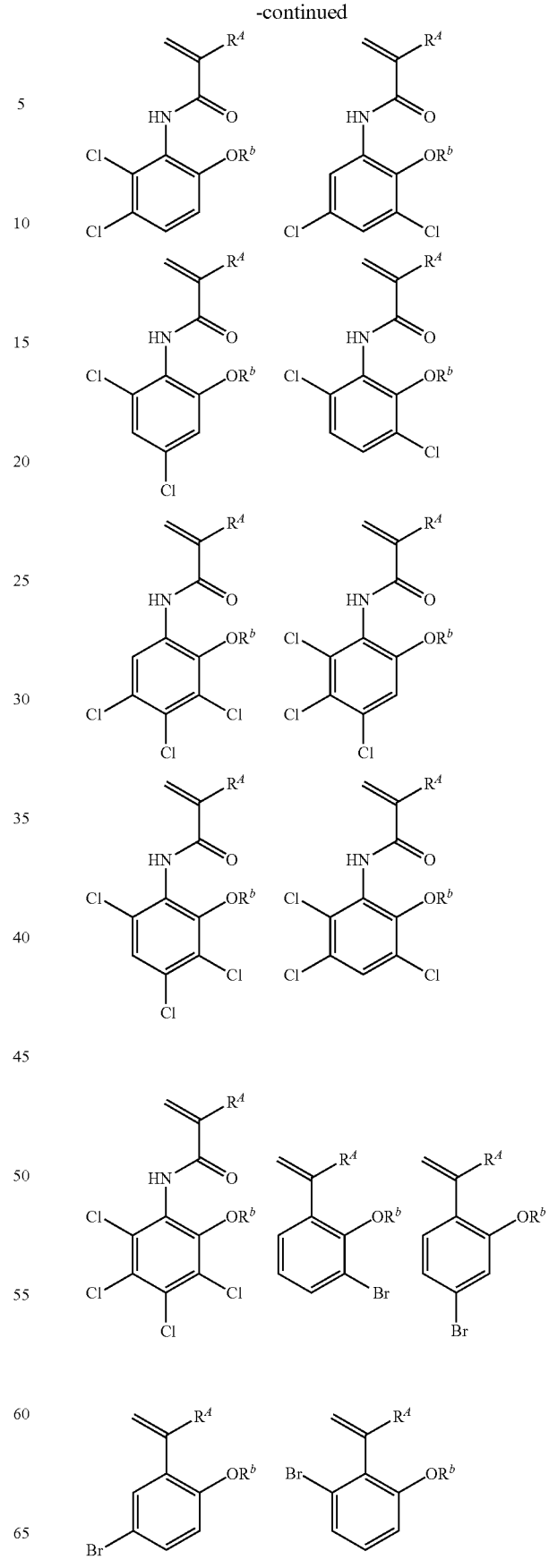

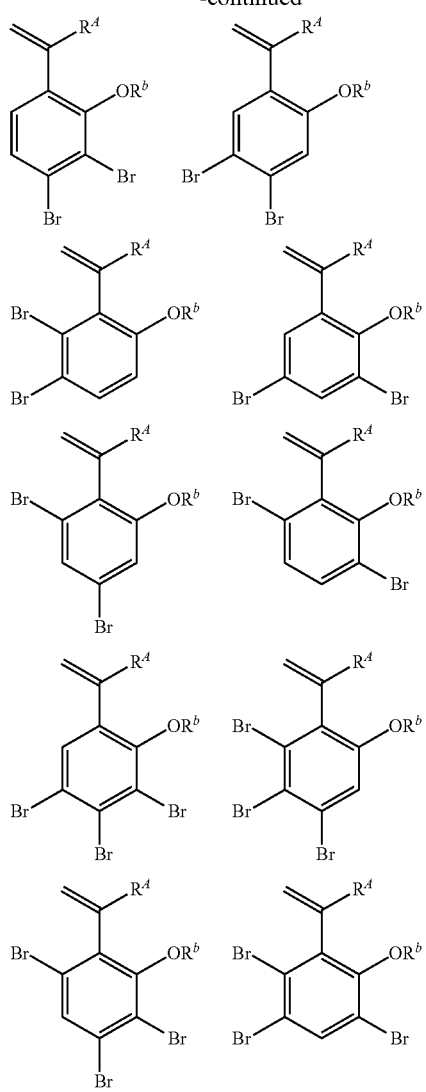
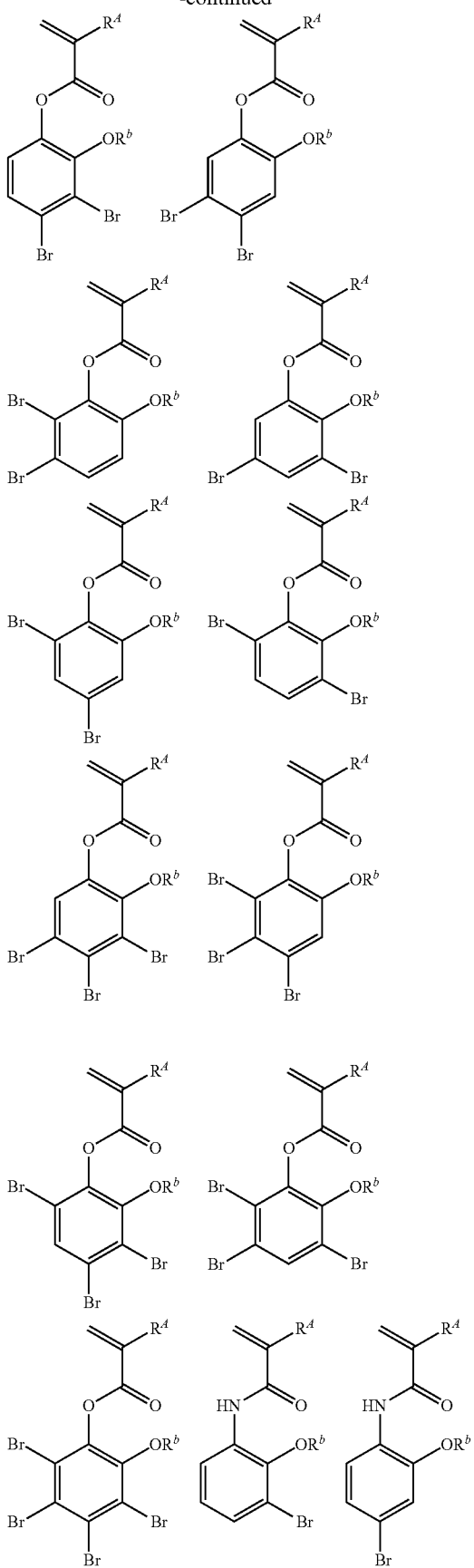

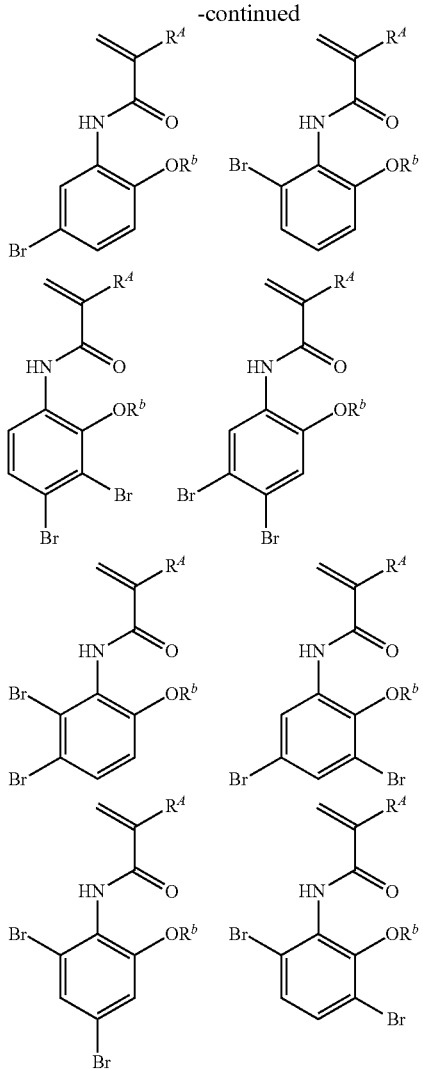
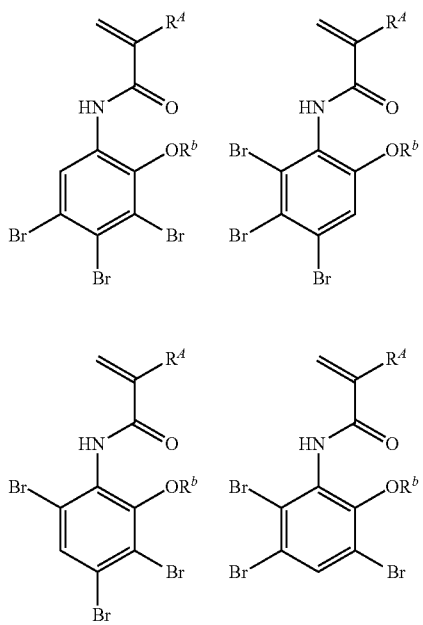

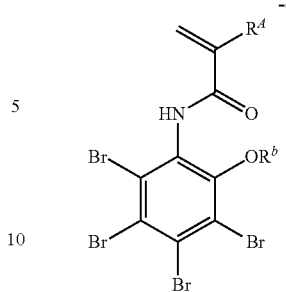

The monomer is characterized by having a phenolic hydroxyl group or a phenolic hydroxyl group protected with an acid labile group, at ortho-position relative to the carbon atom on the aromatic ring bonded to a polymerizable group, and having a halogen atom bonded to a carbon atom on the aromatic ring. When the monomer is incorporated in a polymer, the halogen atom effectively generates secondary electrons during exposure, which are transported to the acid generator to induce efficient acid generation. This contributes to a higher sensitivity. Of the halogen atoms, iodine is most absorptive to high-energy radiation, especially EUV of wavelength 13.5 nm. Thus the sensitivity enhancing effect becomes the most when the halogen is iodine. Also the presence of a phenolic hydroxyl group at ortho-position relative to the polymer backbone ensures an appropriate dissolution rate of the polymer when developed in alkaline developer. When the phenolic hydroxyl group is protected with an acid labile group, deprotection reaction takes place under the action of acid, whereby a phenolic hydroxyl group is recovered, contributing to an improvement in the contrast between exposed and unexposed regions. Due to a synergistic effect of these mechanisms, a resist composition with improved CDU can be designed.

The monomer having formula (A) may be synthesized, for example, by the following reaction although the synthesis route is not limited thereto. The synthesis is described below with reference to a monomer (A) having formula (A) wherein $R^A$ is hydrogen and $X^1$ is a single bond, as a typical example.

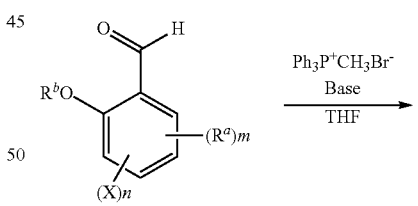

Herein $R^a$, $R^b$, X, n and m are as defined above.

Monomer (A') is obtained by converting a formyl group on an aromatic compound as the starting reactant to a vinyl group through the Wittig reaction.

The reaction may be conducted in the standard procedure. For example, a Wittig reagent is prepared by dissolving a Wittig reagent precursor such as methyltriphenylphosphonium bromide in an ether solvent such as tetrahydrofuran or diethyl ether, and adding a base to the solution while cooling the solution if necessary. The base used herein is desirably a strong base, which is selected from, for example, alkyl lithium reagents such as n-butyllithium and alkali metal salts such as tert-butoxypotassium. Once the Wittig reagent is prepared in the system, the reactant is dissolved in an ether solvent such as tetrahydrofuran or diethyl ether, which is added dropwise to the system and aged, yielding monomer (A').

An amount of the Wittig reagent used is preferably 2.0 to 5.0 moles, more preferably 2.0 to 3.0 moles per mole of the aromatic compound, in consideration of its deactivation by a hydroxyl group on the aromatic compound. An amount in excess of 5.0 moles may be economically disadvantageous due to an increased expense and make the removal of by-product, triphenylphosphine oxide difficult. A reactant having a hydroxyl group protected with an acid labile group may also be used. The reaction may be conducted while cooling or heating if necessary, and typically at a temperature of 0° C. to near the boiling point of the solvent. It is desirable from the standpoint of yield that the reaction time is determined so as to drive the reaction to completion by monitoring the reaction process by gas chromatography (GC) or silica gel thin layer chromatography (TLC). Usually, the reaction time is about 0.5 to 2 hours. From the reaction mixture, the monomer (A') is recovered through an ordinary aqueous workup. If necessary, the monomer may be purified by a standard technique such as distillation, chromatography or recrystallization.

In another route, monomer (A') is obtained, as shown below, by effecting addition reaction to a formyl group on an aromatic compound as the starting reactant with the aid of an organic lithium reagent such as methyllithium or organic magnesium reagent such as methylmagnesium chloride, and dehydrating the resulting compound (A") to convert the relevant group to a vinyl group.

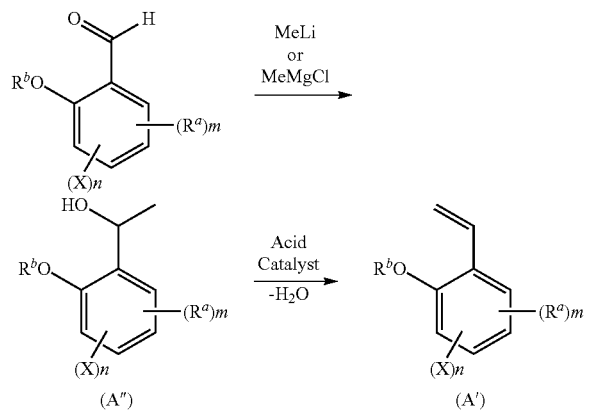

Herein $R^a$, $R^b$, X, n and m are as defined above.

A first stage is to form compound (A") by effecting addition reaction to a formyl group on an aromatic compound as the starting reactant with the aid of an organic lithium reagent such as methyllithium or organic magnesium reagent such as methylmagnesium chloride.

The reaction may be conducted in the standard procedure. The organic lithium reagent such as methyllithium or organic magnesium reagent such as methylmagnesium chloride may be prepared according to the well-known formulation prior to use or commercially available. Where a commercially available reagent is used, it may be diluted with a solvent such as tetrahydrofuran or diethyl ether, depending on the concentration of the reagent as purchased. By adding a solution of the aromatic compound dropwise to the organometallic reagent, compound (A") is obtainable.

An amount of the organometallic reagent used is preferably 2.0 to 4.0 moles, more preferably 2.0 to 3.0 moles per mole of the aromatic compound in consideration of its deactivation by a hydroxyl group on the aromatic compound. An amount in excess of 4.0 moles may be economically disadvantageous due to an increased expense. The reaction may be conducted while cooling or heating if necessary, and typically at a temperature of 0° C. to 50° C. It is desirable from the standpoint of yield that the reaction time is determined so as to drive the reaction to completion by monitoring the reaction process by GC or silica gel TLC. Usually, the reaction time is about 0.5 to 12 hours. From the reaction mixture, the compound (A") is recovered through an ordinary aqueous workup. If necessary, the compound may be purified by a standard technique such as distillation, chromatography or recrystallization.

A second stage is to form monomer (A') by dehydrating a secondary hydroxyl group on compound (A") in the presence of an acid catalyst.

The reaction may be conducted in the standard procedure. The monomer (A') is obtainable by dissolving compound (A") in a hydrocarbon solvent such as n-heptane, toluene or xylene, adding an acid catalyst thereto, and heating the solution to promote dehydration reaction. The acid catalyst used herein is preferably a strong acid, specifically sulfuric acid, nitric acid, p-toluenesulfonic acid or trifluoromethanesulfonic acid. The reaction temperature is typically from 60° C. to the boiling point of the solvent. Preferably, the water formed by reaction is distilled out of the system to accelerate the reaction. It is desirable from the standpoint of yield that the reaction time is determined so as to drive the reaction to completion by monitoring the reaction process by GC or silica gel TLC. Usually, the reaction time is about 1 to 24 hours. From the reaction mixture, the monomer (A') is recovered through an ordinary aqueous workup. If necessary, the monomer may be purified by a standard technique such as distillation, chromatography or recrystallization.

Polymer

The invention also provides a polymer comprising recurring units having a partial structure represented by the formula (B) on a side chain.

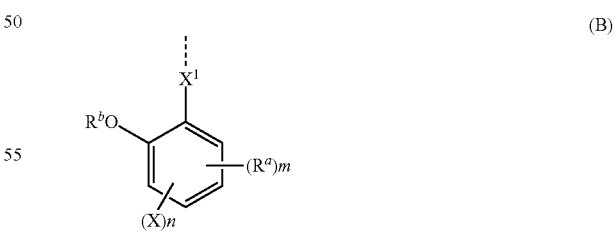

In formula (B), $X^1$, $R^a$, $R^b$, X, n and m are as defined above, and the broken line denotes a valance bond to the polymer backbone. Preferably $X^1$ is a single bond, and X is iodine.

Patent Document 2 describes a polymer comprising recurring units derived from iodized p- or m-hydroxystyrene. Where a styrene structure unit having a phenolic hydroxyl group at p- or m-position to the backbone is used, a structure having a phenolic hydroxyl group projecting outward of the backbone is formed. This structure provides a higher affinity to alkaline developer, from which it is expected that the dissolution rate of the polymer in alkaline developer becomes extremely high. The accelerated dissolution rate allows the positive resist even in the unexposed region to be partially dissolved, leading to degradation of LWR and CDU.

The recurring units having a partial structure of formula (B) are preferably units derived from the monomer having formula (A), that is, recurring units having the formula (a), which are referred to as recurring units (a), hereinafter.

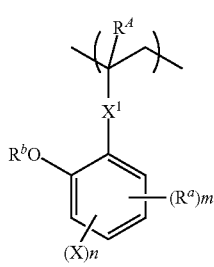
(a)

Herein $R^A$, $X^1$, $R^a$, $R^b$, X, n and m are as defined above.

The inventive polymer may further comprise recurring units having a group capable of polarity switch under the action of acid, which are referred to as recurring units (b), hereinafter. A resist composition comprising a polymer comprising recurring units (b) may be used as a positive tone resist composition adapted to form a positive pattern via alkaline development or a negative tone resist composition adapted to form a negative pattern via organic solvent development.

The recurring units (b) are preferably recurring units having the formula (b1) or recurring units having the formula (b2). These units are referred to as recurring units (b1) and (b2), hereinafter.

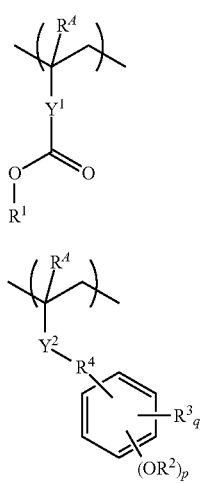

Herein $R^A$ is as defined above. $Y^1$ is a single bond, phenylene group, naphthylene group, or a $C_1$-$C_{12}$ linking group containing an ether bond, ester bond or lactone ring. $Y^2$ is a single bond, ester bond or amide bond. $R^1$ and $R^2$ are each independently an acid labile group. $R^3$ is fluorine, trifluoromethyl, cyano. $C_1$-$C_6$ alkyl. $C_1$-$C_6$ alkoxy, $C_2$-$C_7$ acyl. $C_2$-$C_7$ acyloxy, or $C_2$-$C_7$ alkoxycarbonyl group. R is a single bond or a $C_1$-$C_6$ alkylene group in which at least one carbon atom may be replaced by an ether or ester bond, p is 1 or 2, and q is an integer of 0 to 4.

Illustrative, non-limiting examples of the recurring units (b1) are shown below. Herein $R^A$ and $R^1$ are as defined above.

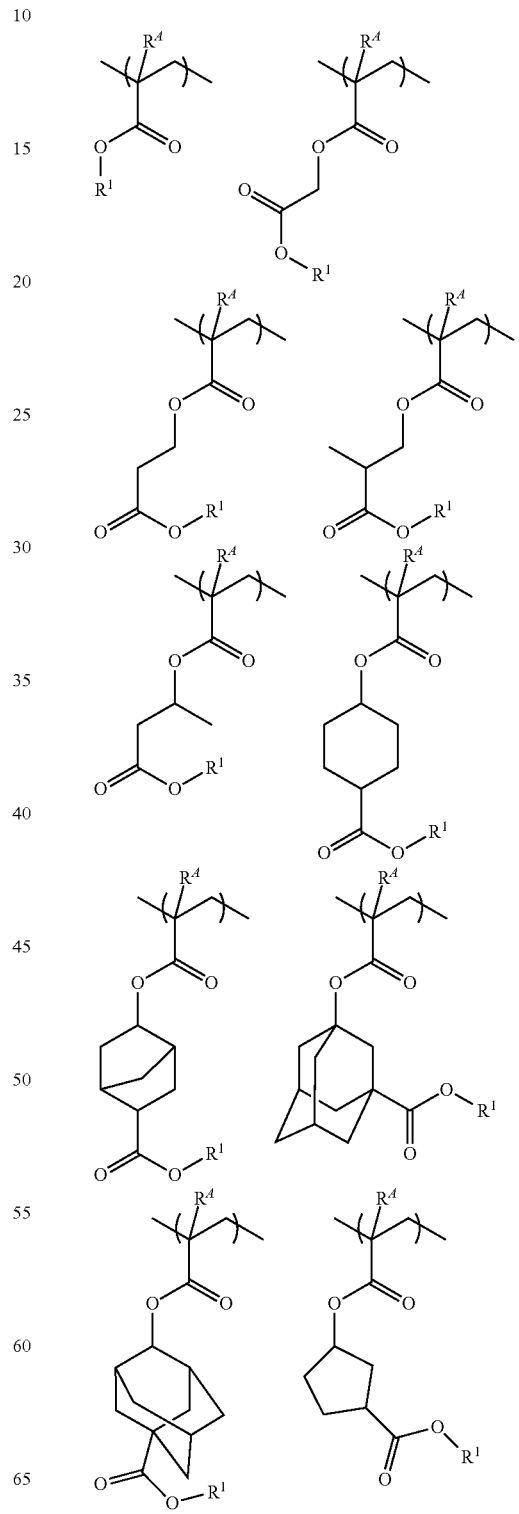

-continued

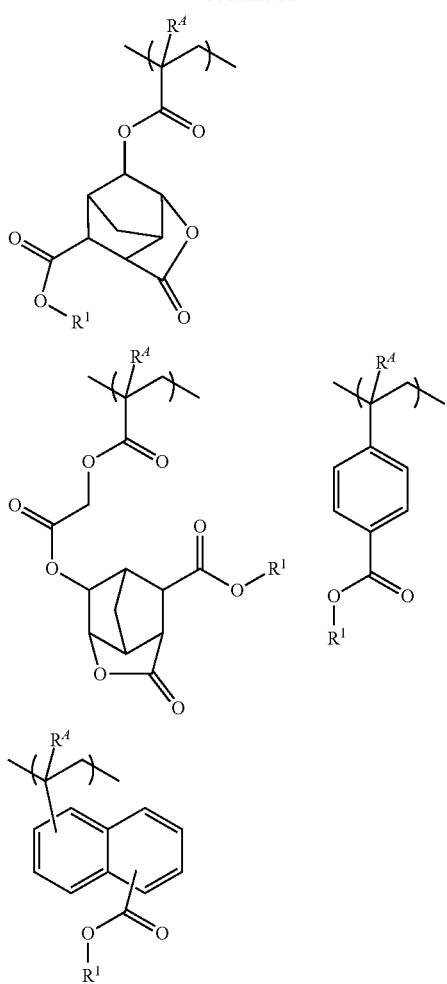

Illustrative, non-limiting examples of the recurring units (b2) are shown below. Herein $R^A$ and $R^2$ are as defined above.

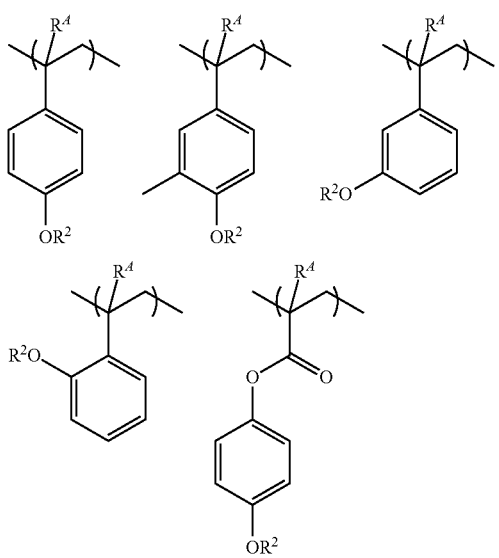

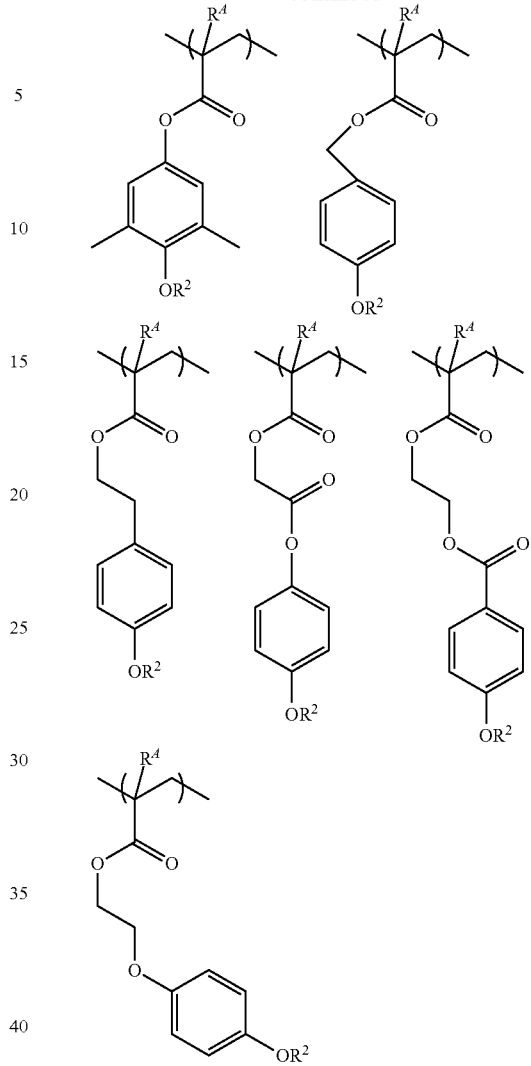

The acid labile groups represented by $R^1$ and $R^2$ in formulae (b1) and (b2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

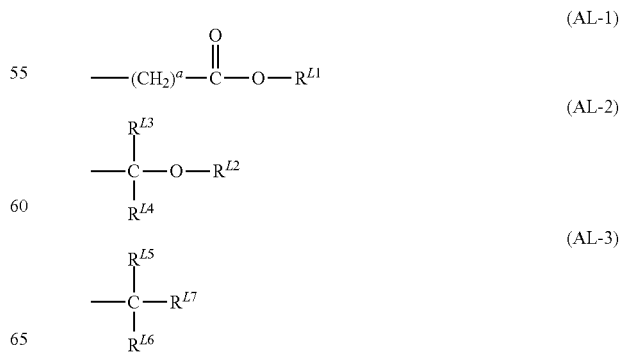

In formulae (AL-1) and (AL-2), $R^{L1}$ and $R^{L2}$ are each independently a monovalent hydrocarbon group which may contain a heteroatom such as oxygen, sulfur, nitrogen or fluorine. The monovalent hydrocarbon groups may be straight, branched or cyclic, and are preferably alkyl groups of 1 to 40 carbon atoms, more preferably 1 to 20 carbon atoms. In formula (AL-1), "a" is an integer of 0 to 10, especially 1 to 5.

In formula (AL-2), $R^{L3}$ and $R^{L4}$ are each independently hydrogen or a monovalent hydrocarbon group which may contain a heteroatom such as oxygen, sulfur, nitrogen or fluorine. The monovalent hydrocarbon groups may be straight, branched or cyclic, and are preferably alkyl groups of 1 to 20 carbon atoms. Any two of $R^{L2}$, $R^{L3}$ and $R^{L4}$ may bond together to form a ring, especially alicyclic, with the carbon atom or carbon and oxygen atoms to which they are attached, the ring containing 3 to 20 carbon atoms, preferably 4 to 16 carbon atoms.

In formula (AL-3), $R^{L5}$, $R^{L6}$ and $R^{L7}$ are each independently a monovalent hydrocarbon group which may contain a heteroatom such as oxygen, sulfur, nitrogen or fluorine. The monovalent hydrocarbon groups may be straight, branched or cyclic, and are preferably alkyl groups of 1 to 20 carbon atoms. Any two of $R^{L5}$, $R^{L6}$ and $R^{L7}$ may bond together to form a ring, especially alicyclic, with the carbon atom to which they are attached, the ring containing 3 to 20 carbon atoms, preferably 4 to 16 carbon atoms.

As the recurring units (b), recurring units which switch from hydrophilic to hydrophobic due to dehydration reaction with the aid of acid, referred to as recurring units (b3), may also be used. When recurring units (b3) are used, the resist composition of the invention may be used as a negative resist composition adapted to form a negative pattern via alkaline development.

Examples of the monomer from which recurring units (b3) are derived are given below, but not limited thereto. Herein $R^A$ is as defined above.

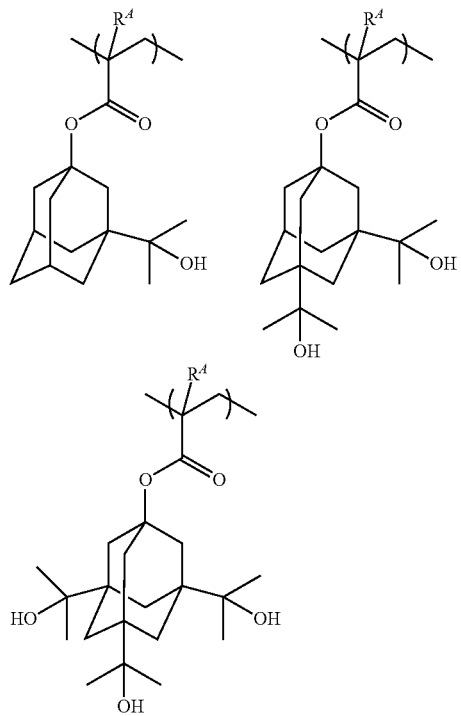

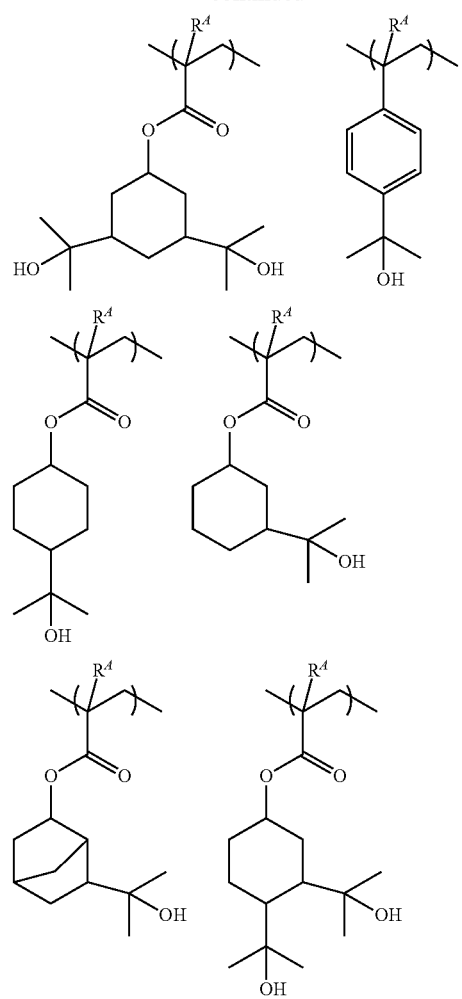

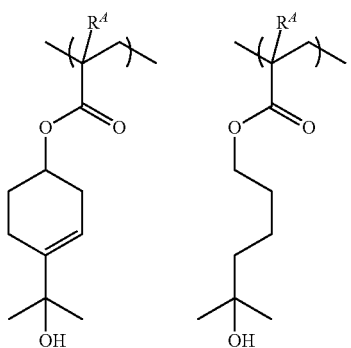

In a preferred embodiment, the polymer may further comprise recurring units (c) having an adhesive group. The adhesive group is selected from among hydroxyl, carboxyl, lactone ring, carbonate, thiocarbonate, carbonyl, cyclic acetal, ether bond, ester bond, sulfonic acid ester bond, cyano, amide, —O—C(=O)—S—, and —O—C(=O)—NH—. Examples of the monomer from which the recurring units (c) are derived are shown below, but not limited thereto. Herein $R^A$ is as defined above.

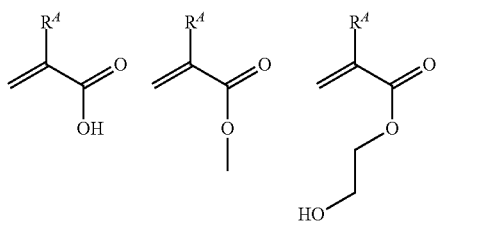

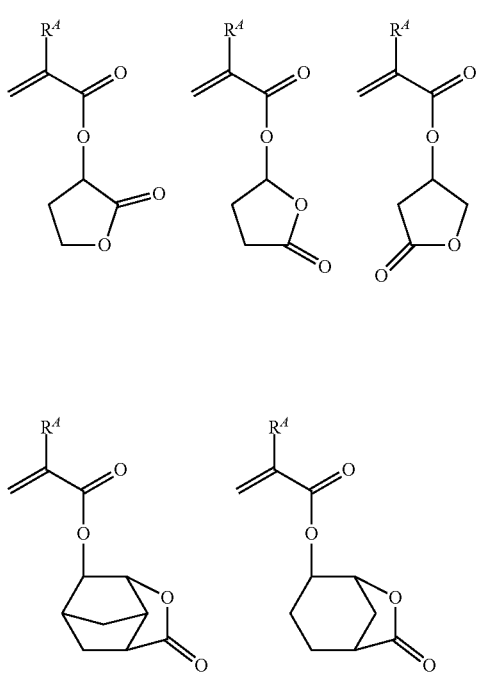

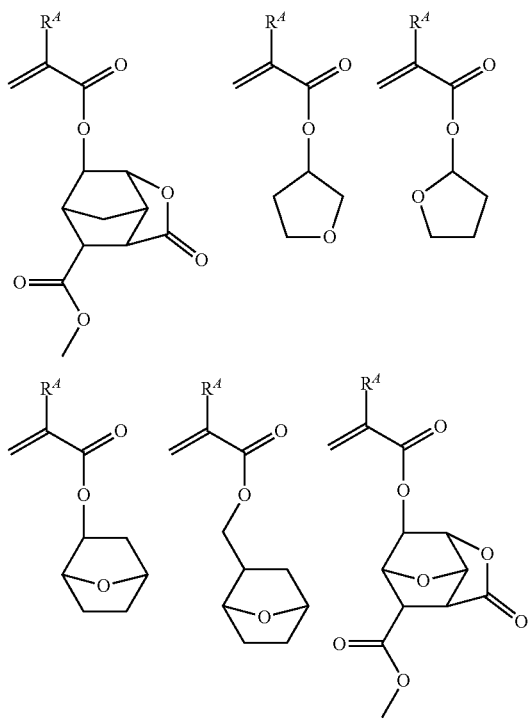

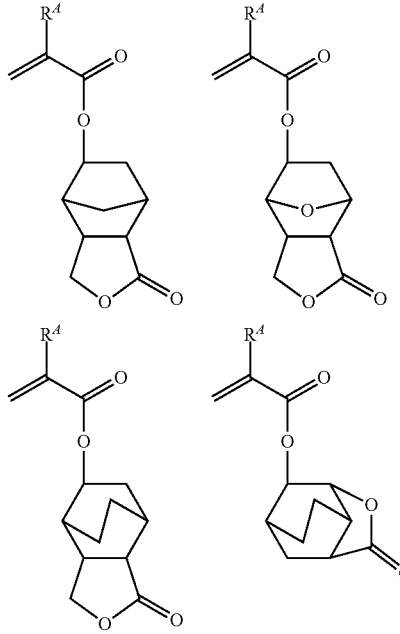

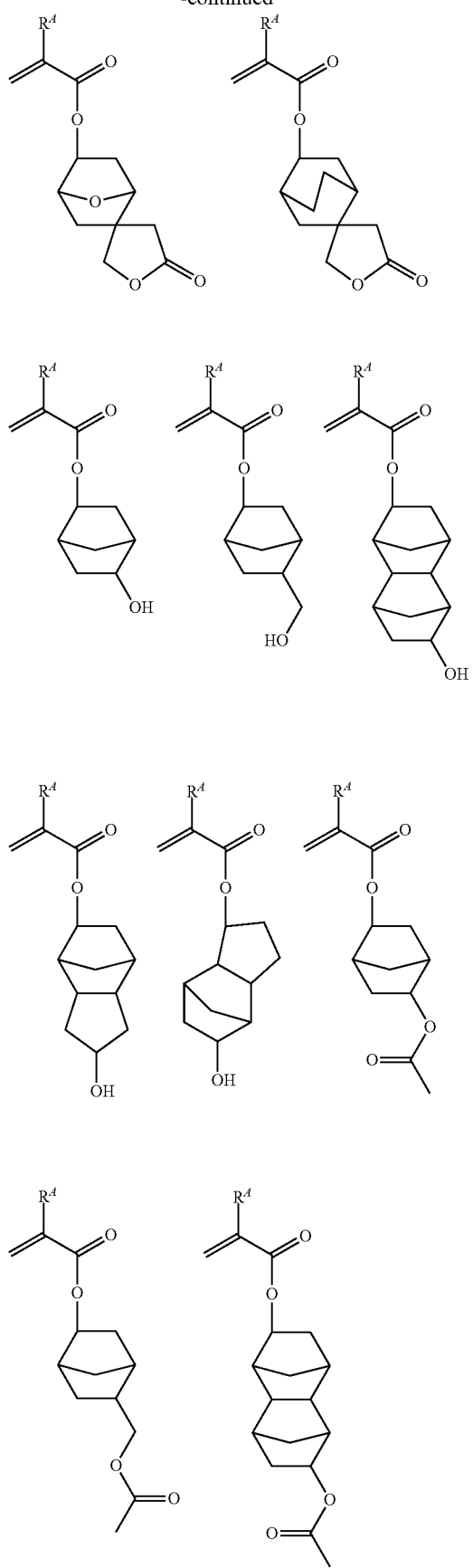
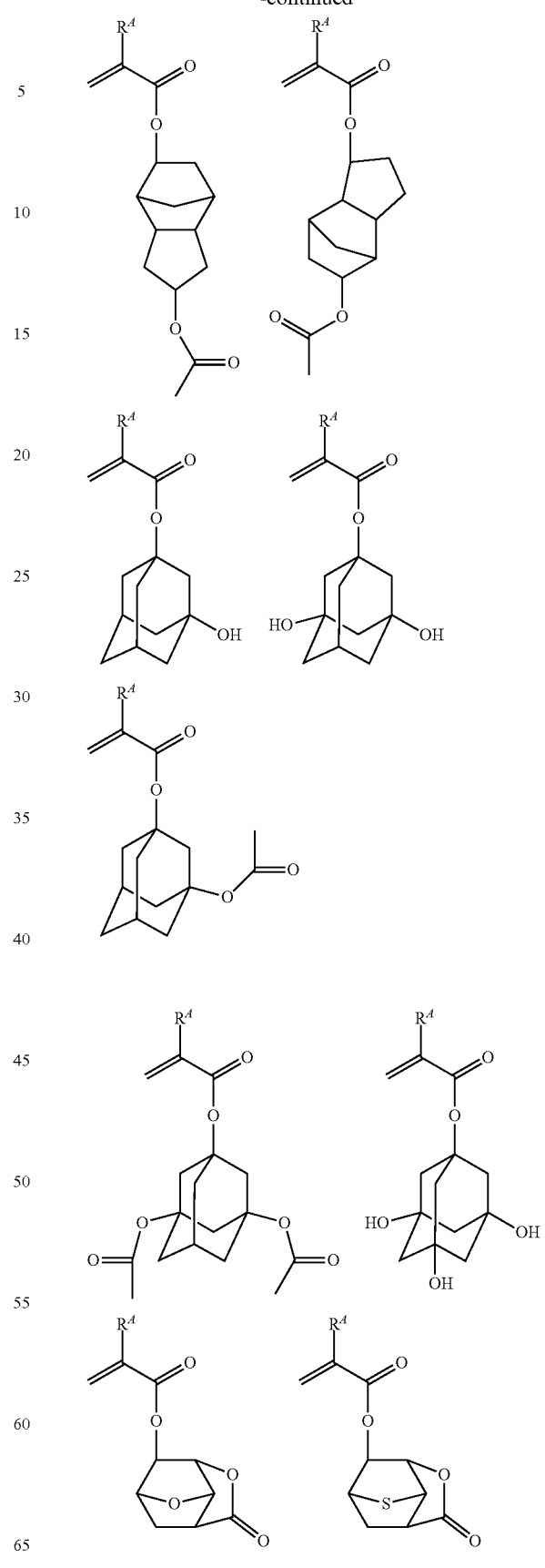

-continued
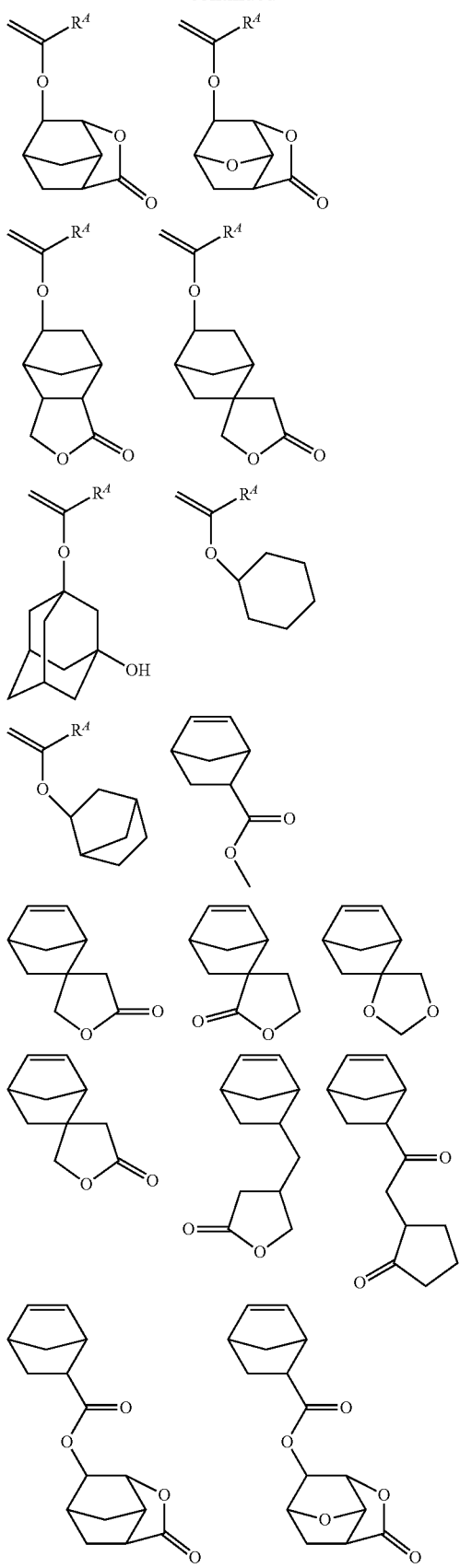
-continued
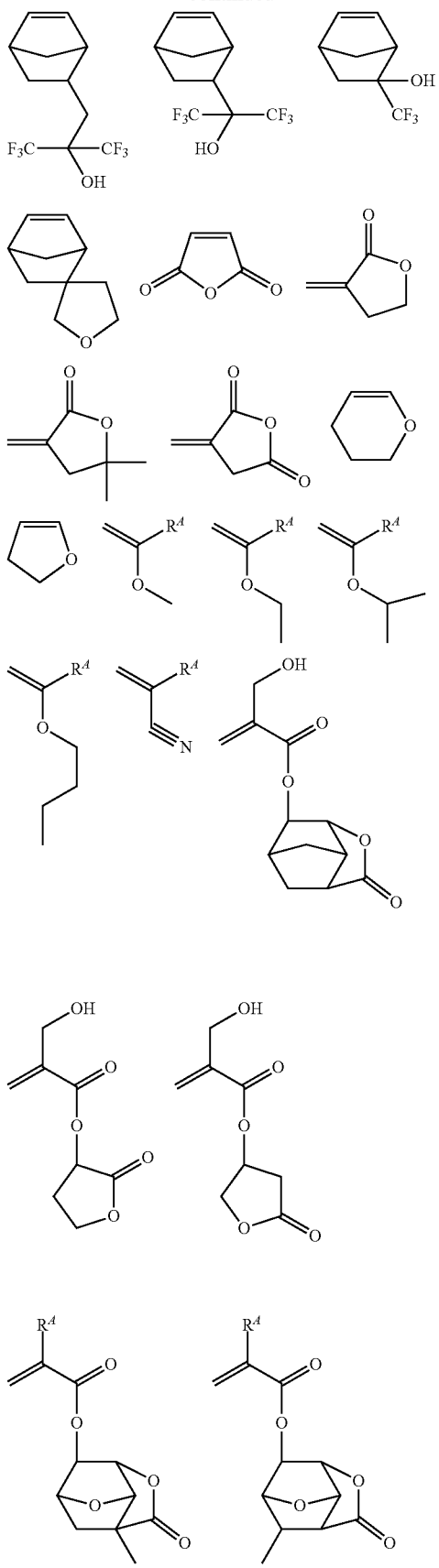

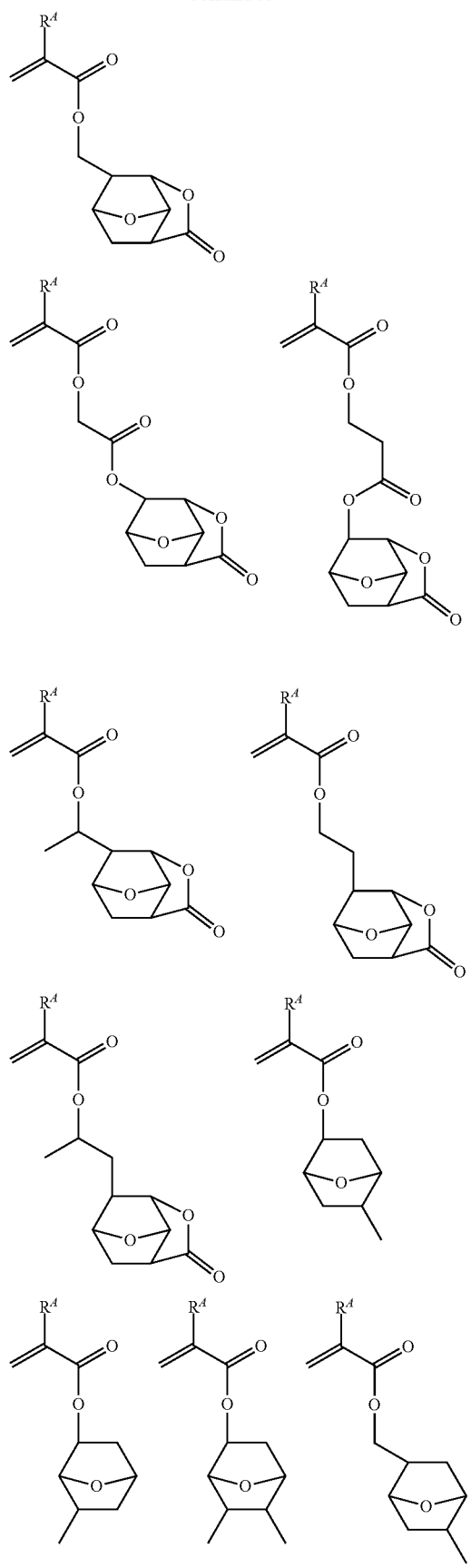
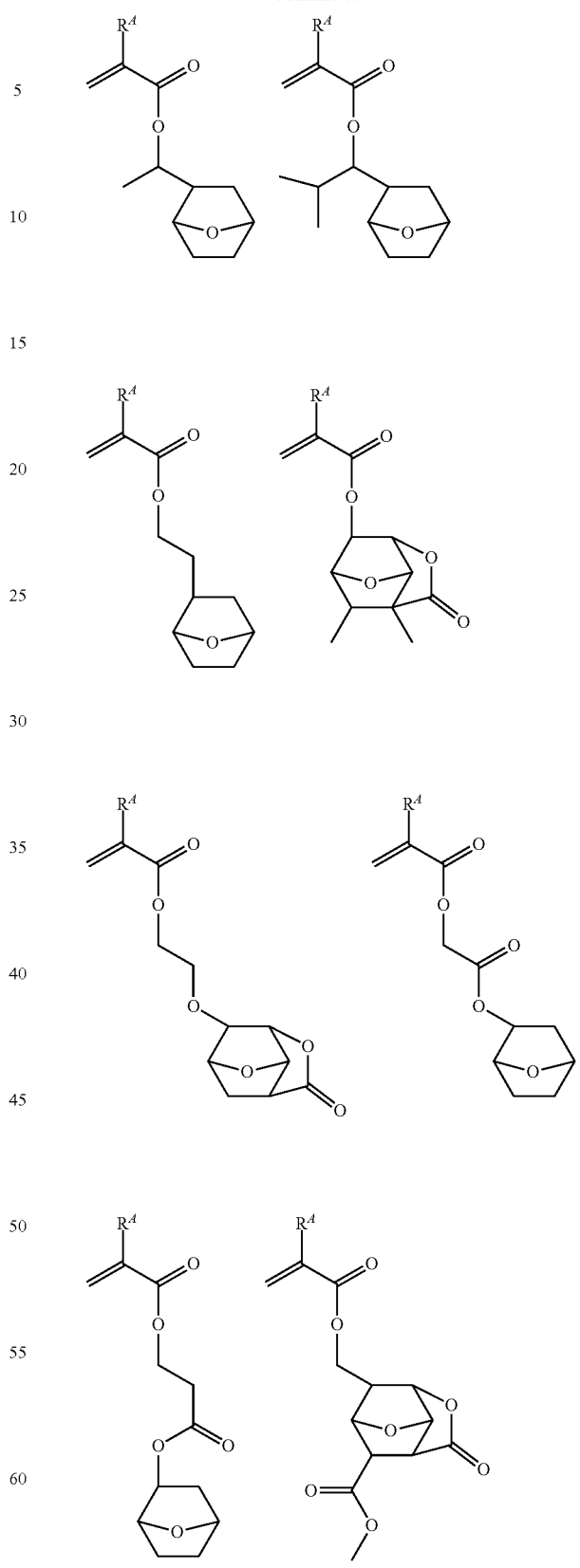

-continued
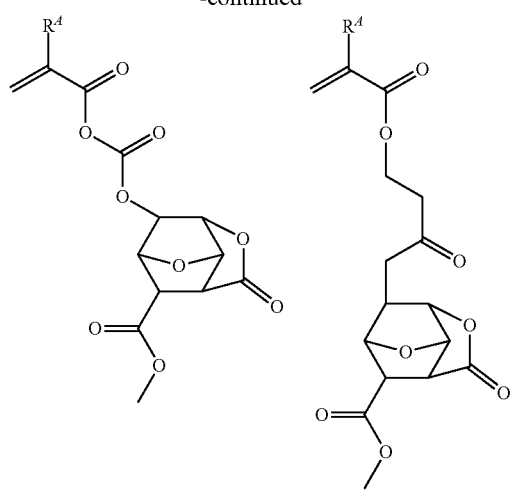
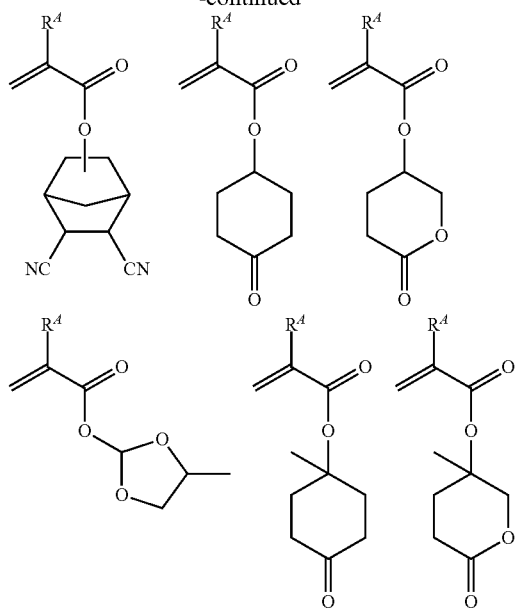
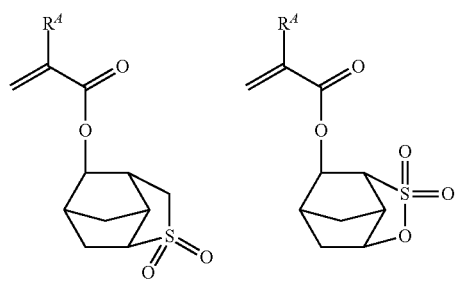
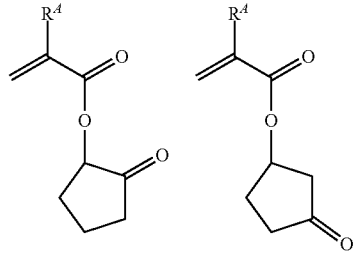
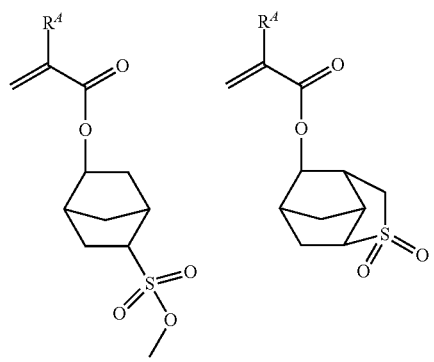
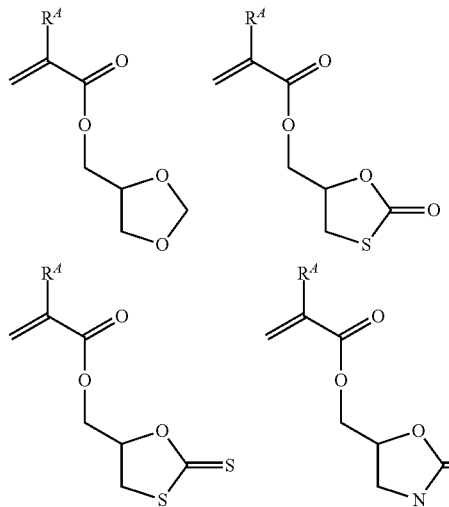
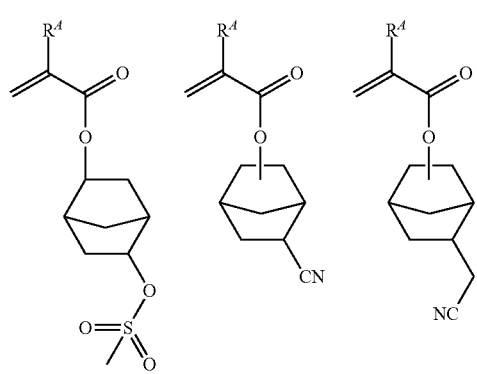
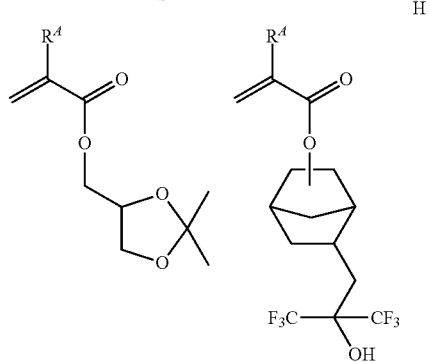

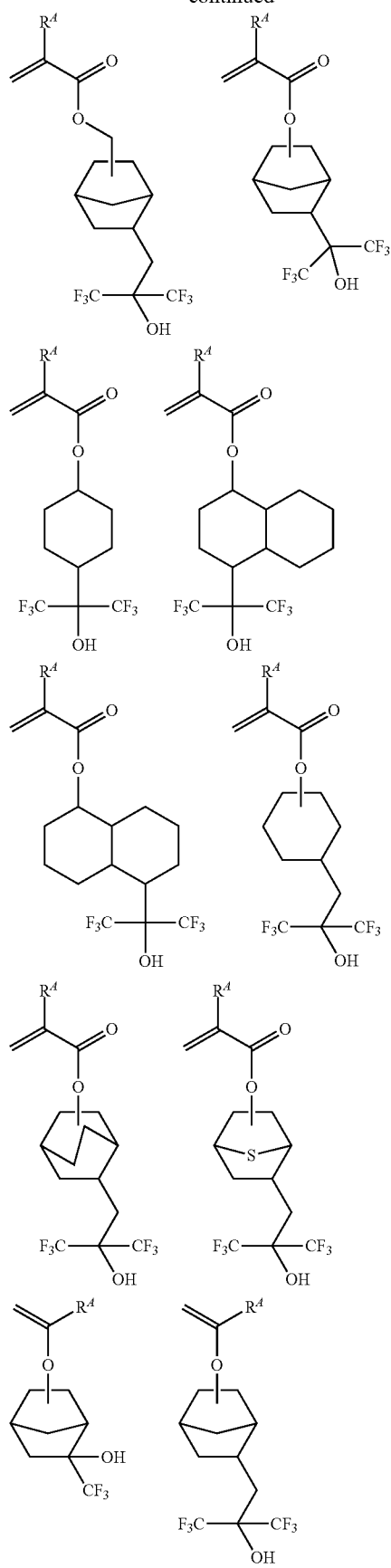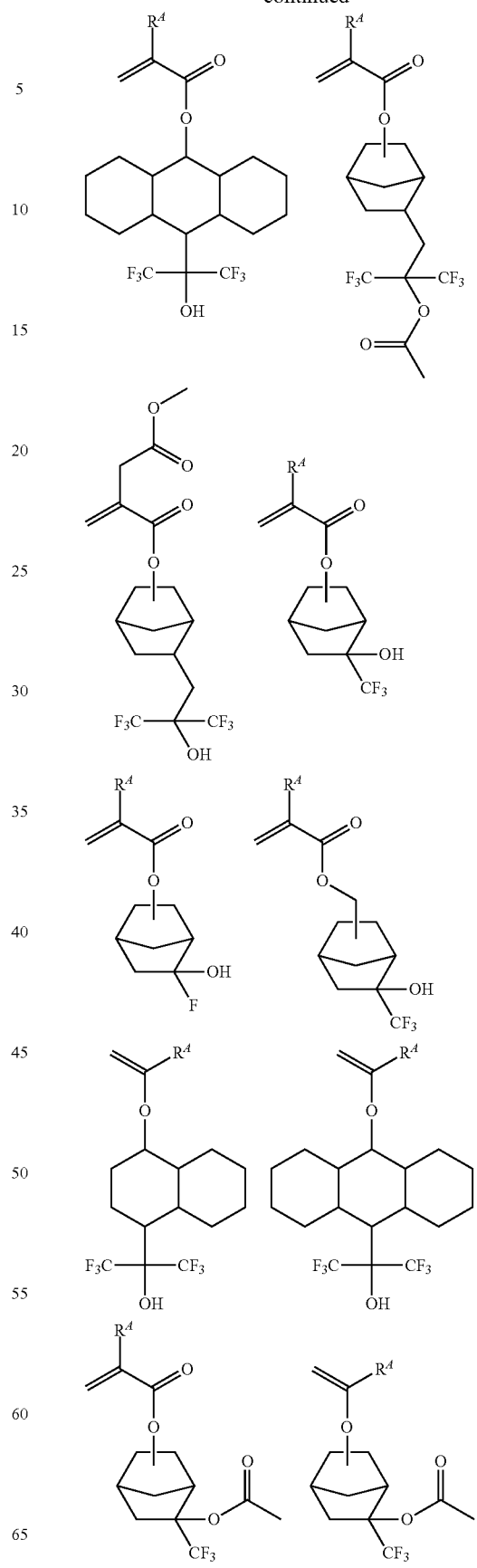

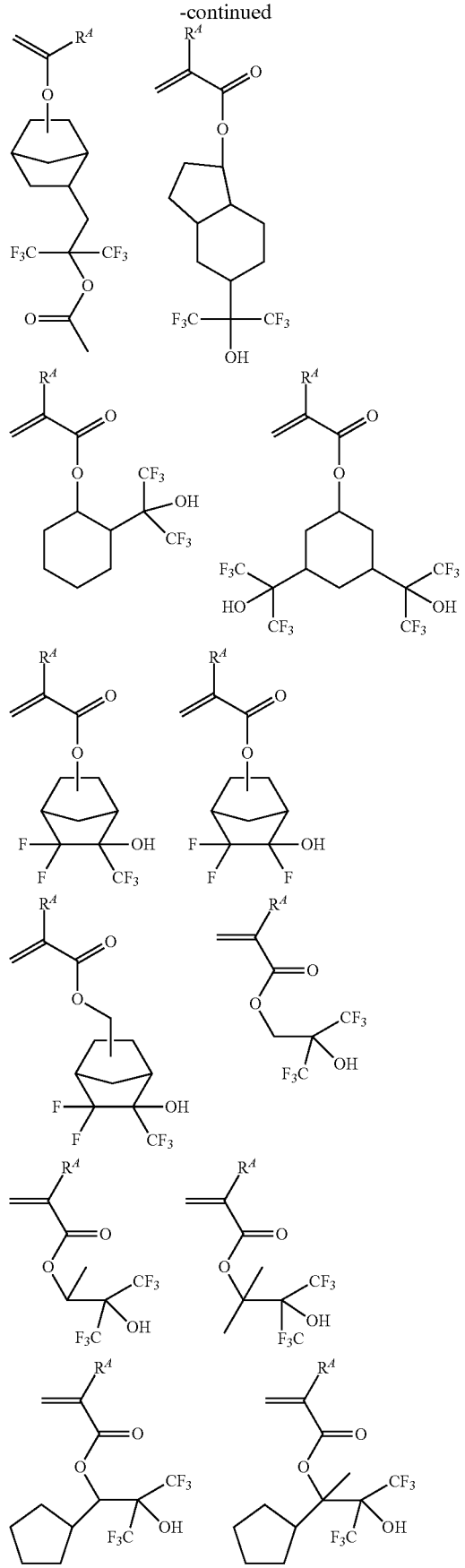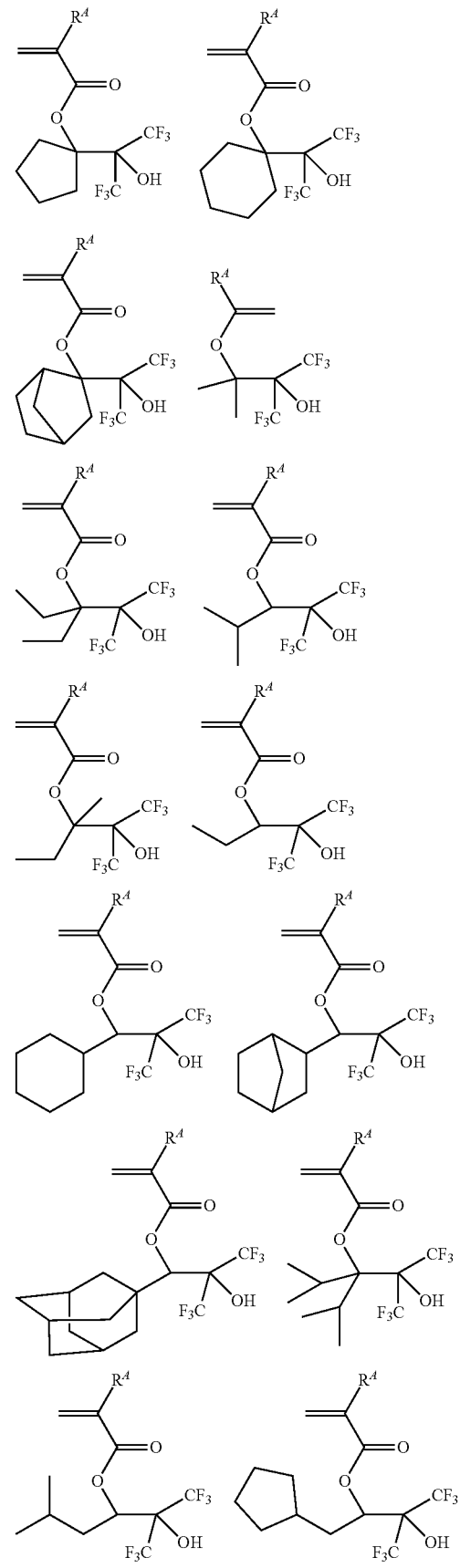

-continued
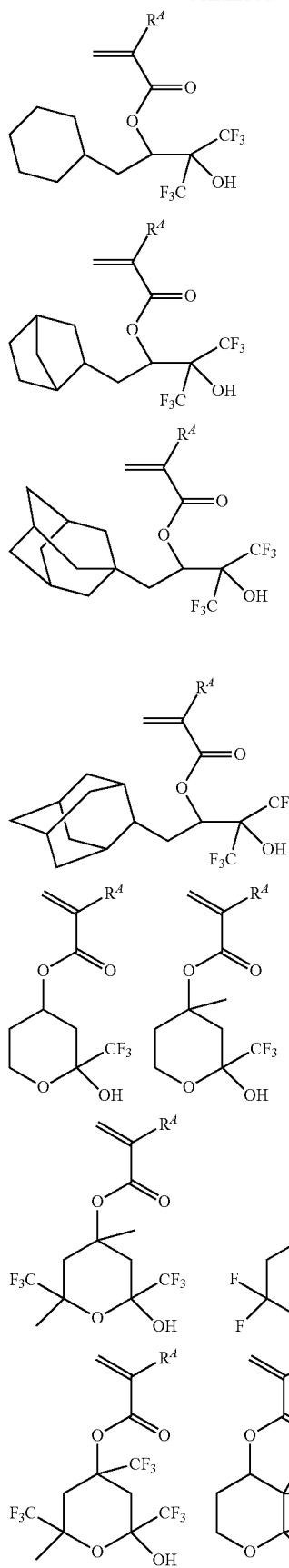
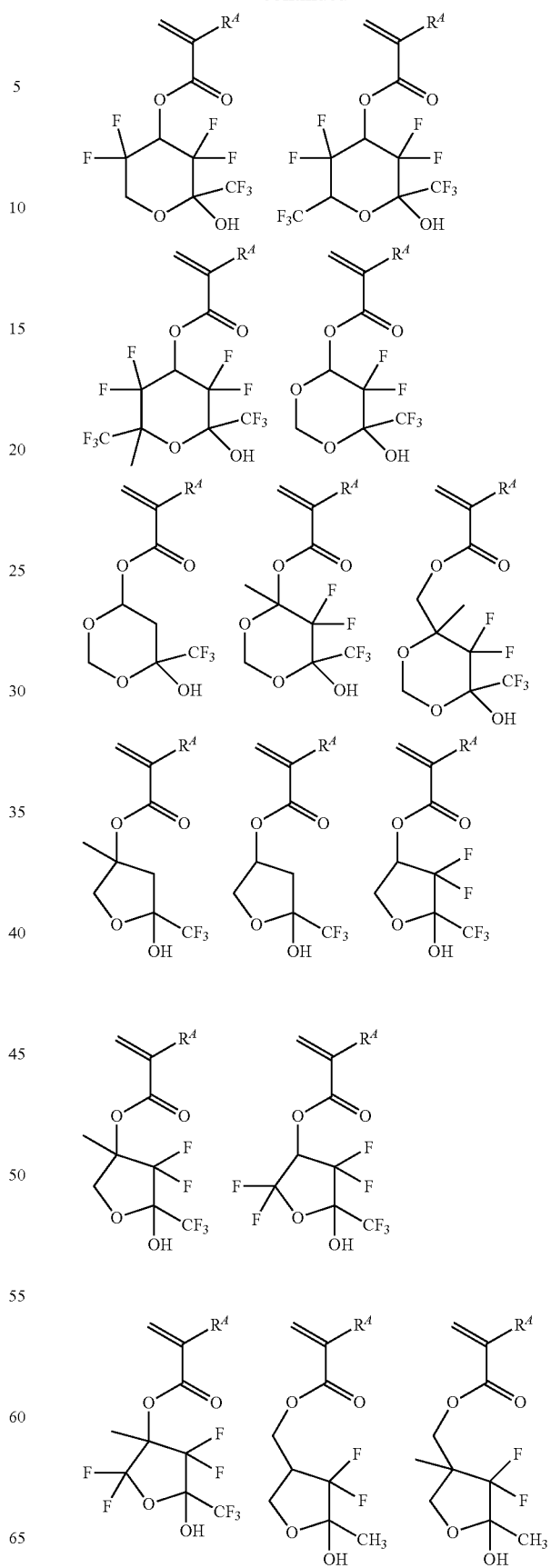

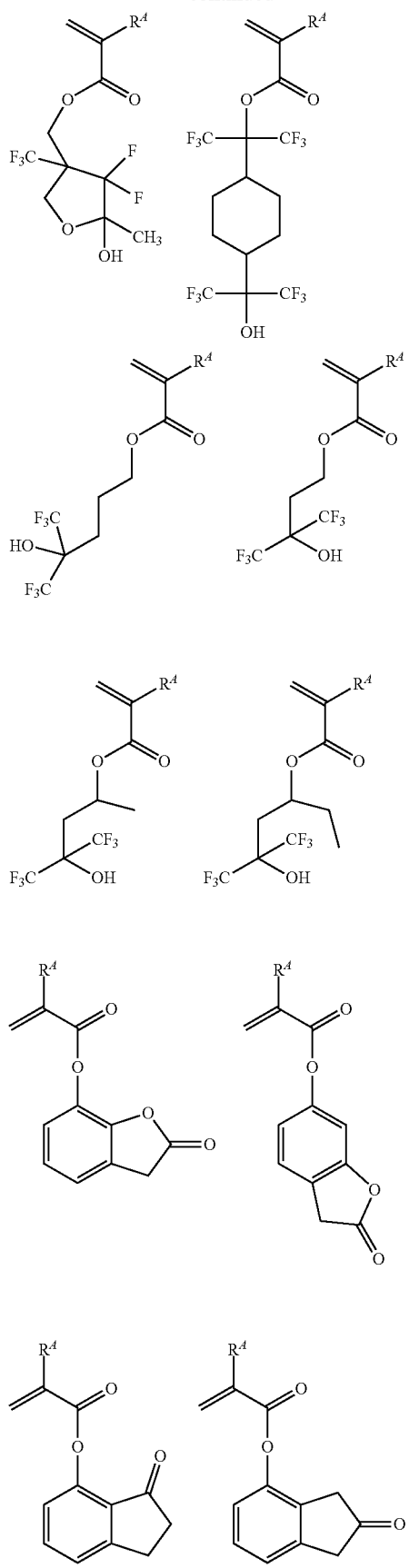
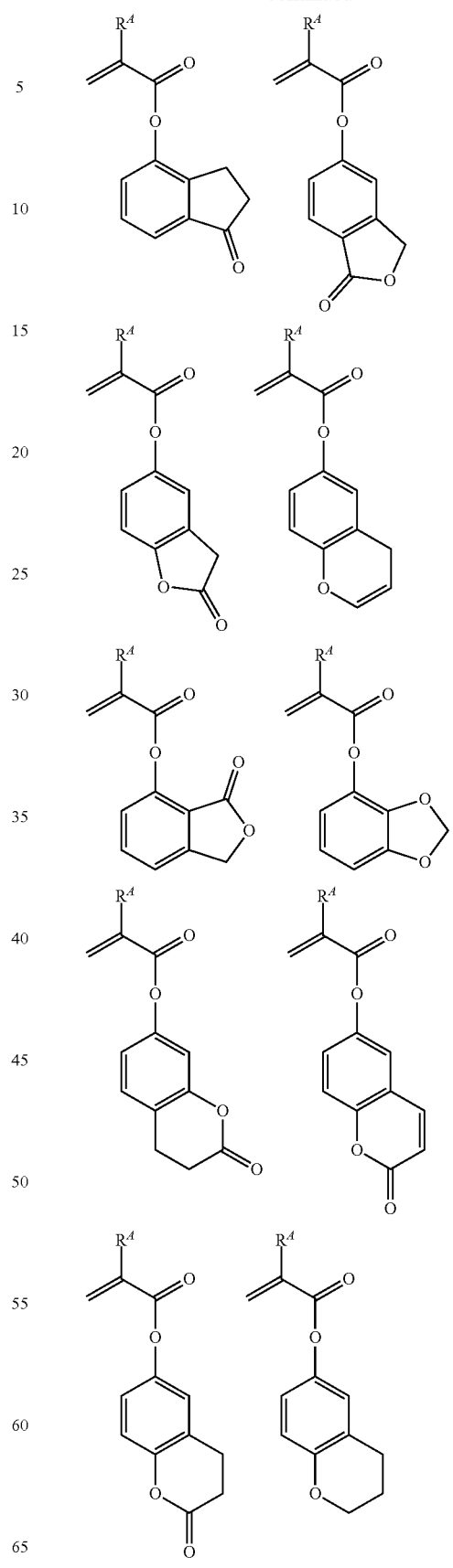

-continued
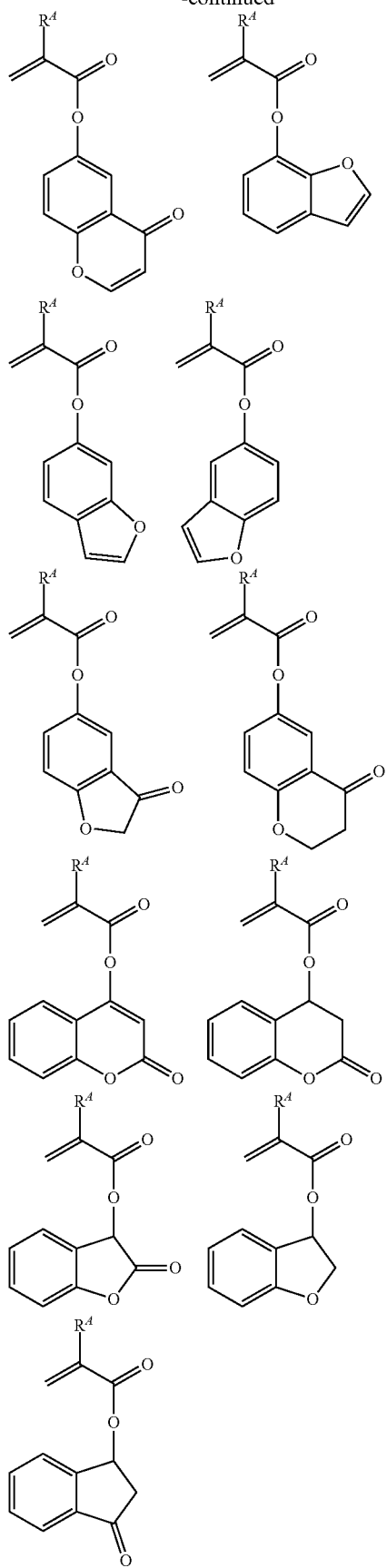
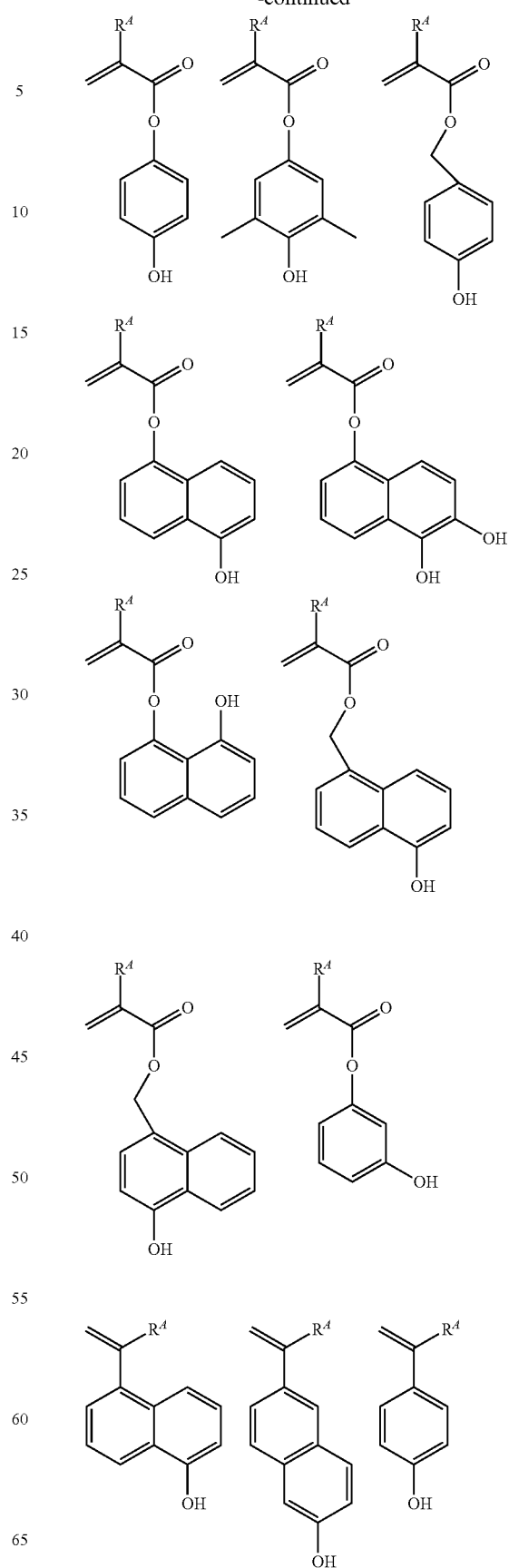

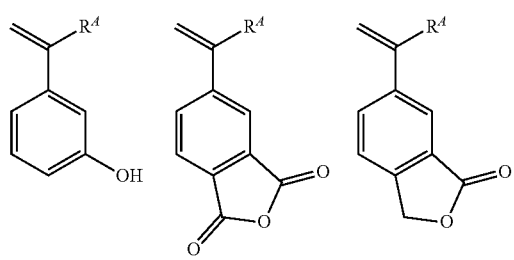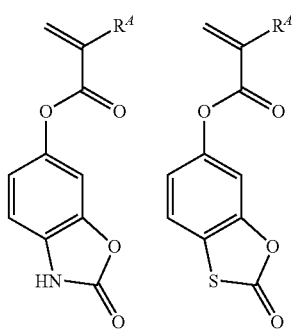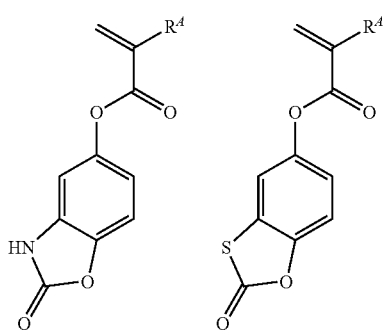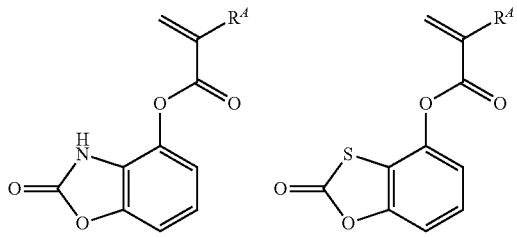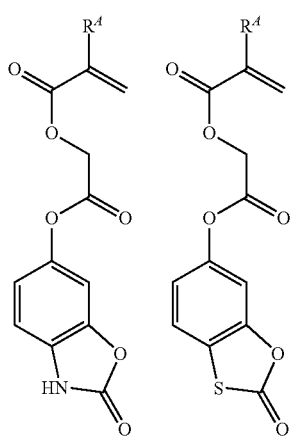

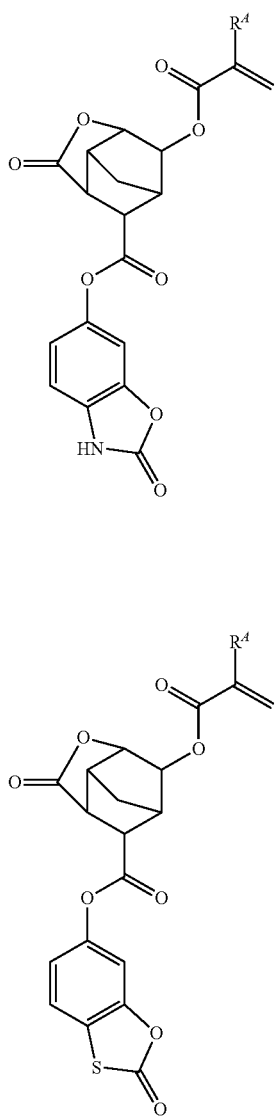

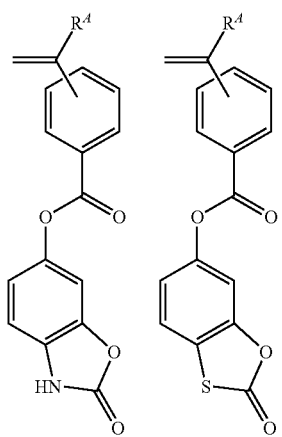

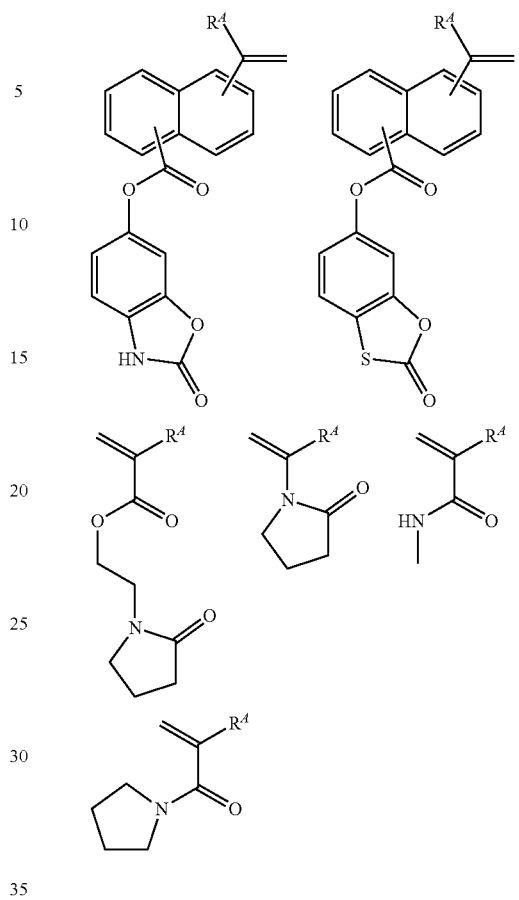

Of the recurring units (c), units having a hydroxyl group or lactone ring are preferred, and units having a phenolic hydroxyl group or lactone ring are more preferred.

In a more preferred embodiment, the polymer may further comprise recurring units of at least one type selected from recurring units represented by the following formulae (d1) to (d3), which are also referred to as recurring units (d1) to (d3).

(d1)

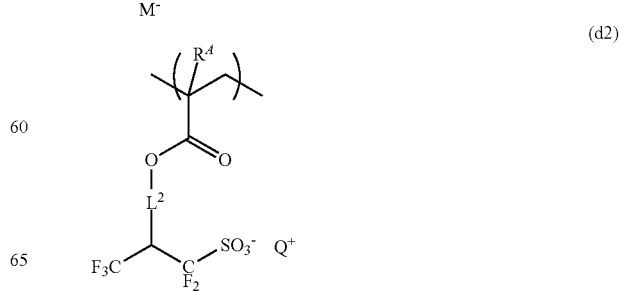

(d2)

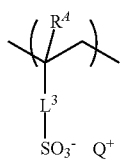

(d3)

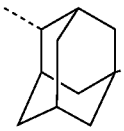 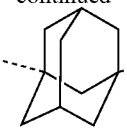

In formulae (d2) and (d3), Q⁺ is a sulfonium cation having the formula (d4) or iodonium cation having the formula (d5).

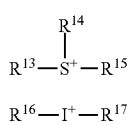

(d4)

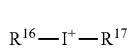

(d5)

In formulae (d1) to (d3), $R^A$ is as defined above. $L^1$ is a single bond, phenylene group, —C(=O)-$L^{11}$-$L^{12}$-, or —O-$L^{12}$-, wherein $L^{11}$ is —O— or —NH—, and $L^{12}$ is a phenylene group, or a $C_3$-$C_6$ divalent aliphatic hydrocarbon group which may contain a carbonyl, ester bond, ether bond or hydroxyl moiety. $L^2$ is a single bond or -$L^{21}$-C(=O)—O—, wherein $L^{21}$ is a $C_1$-$C_{20}$ divalent hydrocarbon group which may contain a heteroatom. $L^3$ is a single bond, methylene, ethylene, phenylene or fluorinated phenylene group, —C(=O)-$L^{31}$-$L^{32}$-, or —O-$L^{32}$-, wherein L is —O— or —NH—, and $L^{32}$ is a phenylene group, or a $C_1$-$C_6$ divalent aliphatic hydrocarbon group which may contain a carbonyl, ester bond, ether bond or hydroxyl moiety. M⁻ is a non-nucleophilic counter ion.

The divalent aliphatic hydrocarbon groups represented by $L^{12}$ and $L^{32}$ may be straight, branched or cyclic. Examples include straight, branched or cyclic divalent saturated aliphatic hydrocarbon groups such as methylene, ethane-1,1-diyl, ethane-1,2-diyl, propane-1,2-diyl, propane-2,2-diyl, propane-1,3-diyl, 2-methylpropane-1,3-diyl, butane-1,3-diyl, butane-2,3-diyl, butane-1,4-diyl, pentane-1,3-diyl, pentane-1,4-diyl, 2,2-dimethylpropane-1,3-diyl, pentane-1,5-diyl, hexane-1,6-diyl, cyclopentane-1,2-diyl, cyclopentane-1,3-diyl, and cyclohexane-1,6-diyl; and straight, branched or cyclic divalent unsaturated aliphatic hydrocarbon groups such as ethene-1,2-diyl, 1-propene-1,3-diyl 2-butene-1,4-diyl, 1-methyl-1-butene-1,4-diyl, and 2-cyclohexene-1,4-diyl.

The optionally heteroatom-containing divalent hydrocarbon group $L^{21}$ may be straight, branched or cyclic. Illustrative, non-limiting examples of the group are shown below.

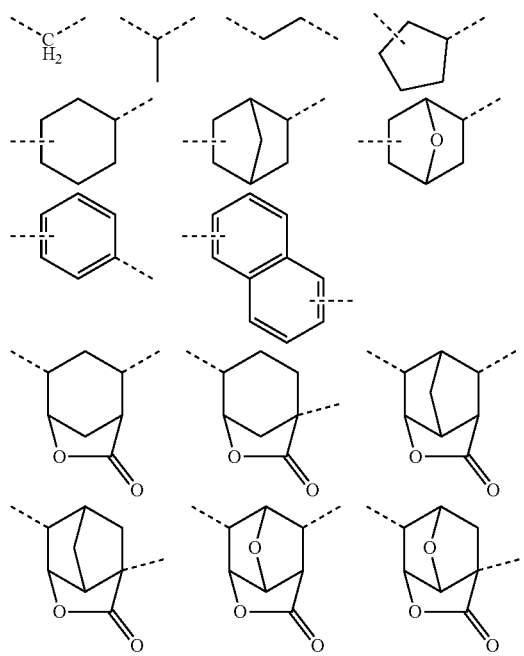

In formulae (d1), (d4) and (d5), $R^{11}$ to $R^{17}$ are each independently a $C_1$-$C_{20}$ monovalent hydrocarbon group which may contain a heteroatom. $R^{11}$ and $R^{12}$ may bond together to form a ring with the sulfur atom to which they are bonded. Any two of $R^{13}$, $R^{14}$ and $R^{15}$ may bond together to form a ring with the sulfur atom to which they are bonded.

The monovalent hydrocarbon groups $R^{11}$ to $R^{17}$ may be straight, branched or cyclic. Suitable examples include straight or branched alkyl groups such as methyl, ethyl, n-propyl, isopropyl, n-butyl, t-butyl; cyclic saturated monovalent hydrocarbon groups such as cyclopropyl, cyclopentyl, cyclohexyl, cyclopropylmethyl, 4-methylcyclohexyl, cyclohexylmethyl, norbornyl, and adamantyl; straight or branched alkenyl groups such as vinyl, 1-propenyl, 2-propenyl, butenyl, and hexenyl; cyclic unsaturated monovalent hydrocarbon groups such as cyclohexenyl; aryl groups such as phenyl, naphthyl and thienyl; and aralkyl groups such as benzyl, 1-phenylethyl and 2-phenylethyl, with the aryl groups being preferred. Also included are the foregoing groups in which at least one hydrogen is substituted by a moiety containing a heteroatom such as oxygen, sulfur, nitrogen or halogen, or in which at least one carbon is substituted by a moiety containing a heteroatom such as oxygen, sulfur or nitrogen, so that the group may contain a hydroxyl, cyano, nitro, carbonyl, sulfonyl, ether bond, ester bond, sulfonic acid ester bond, carbonate, lactone ring, sultone ring, carboxylic anhydride, or haloalkyl moiety.

Binding an acid generator to the polymer backbone is effective for reducing acid diffusion and preventing the resolution from lowering due to blur by acid diffusion. Additionally, edge roughness (LER, LWR) is improved because the acid generator is uniformly dispersed.

Where $R^{11}$ and $R^{12}$, taken together, form a ring with the sulfur atom, or where any two of $R^{13}$, $R^{14}$ and $R^{15}$, taken together, form a ring with the sulfur atom, examples of the ring are shown below, but not limited thereto.

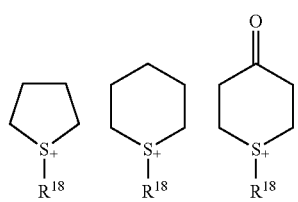

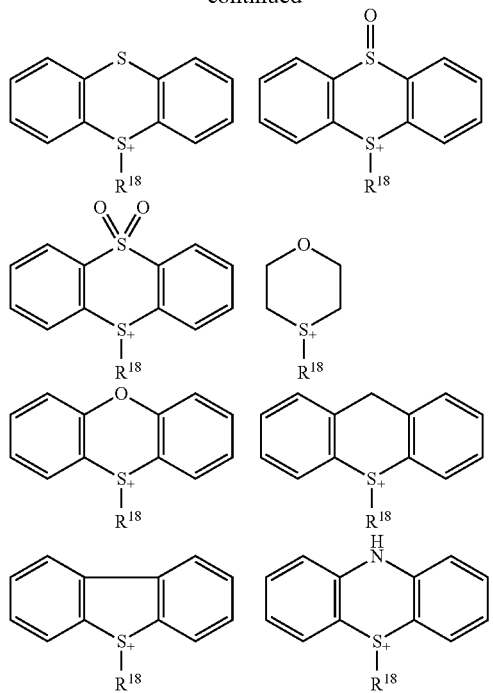
In the formulae, $R^{18}$ is a $C_1$-$C_{20}$ monovalent hydrocarbon group which may contain a heteroatom. Suitable monovalent hydrocarbon groups are as exemplified above for $R^{11}$ to $R^{17}$.
Illustrative, non-limiting examples of the sulfonium cation of formula (d4) are given below.
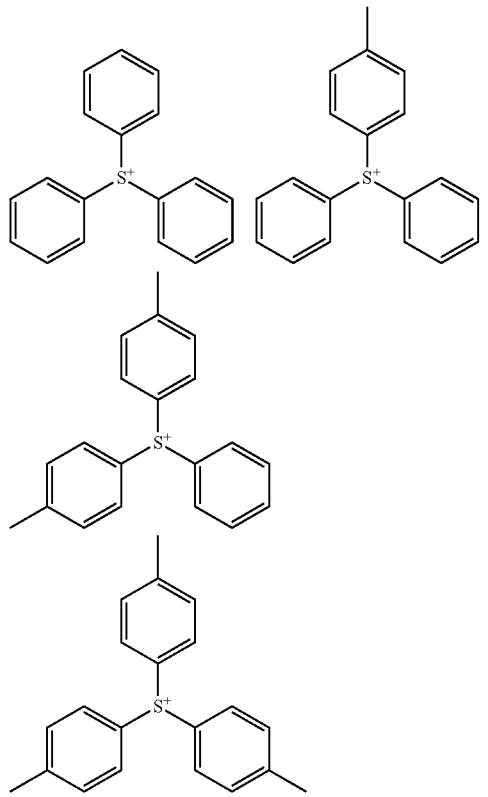
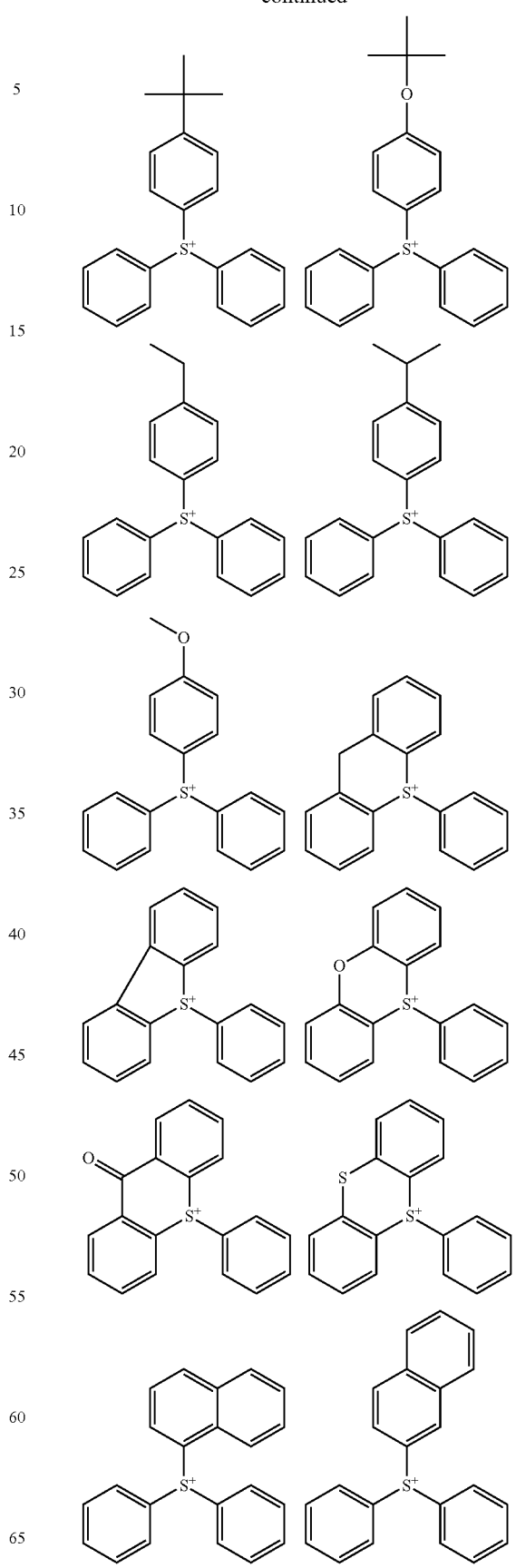

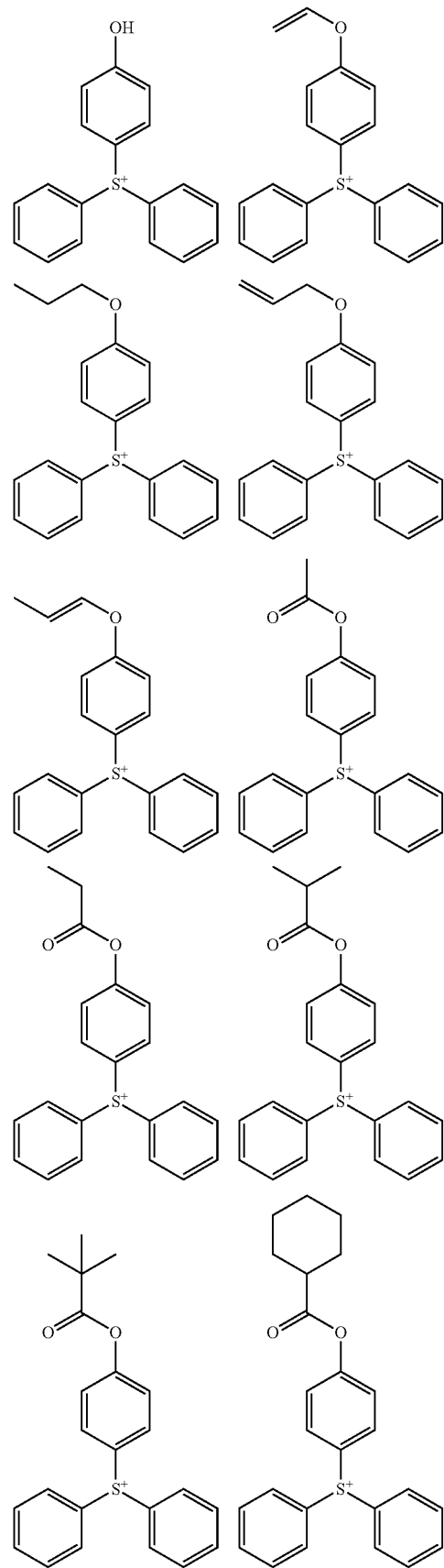
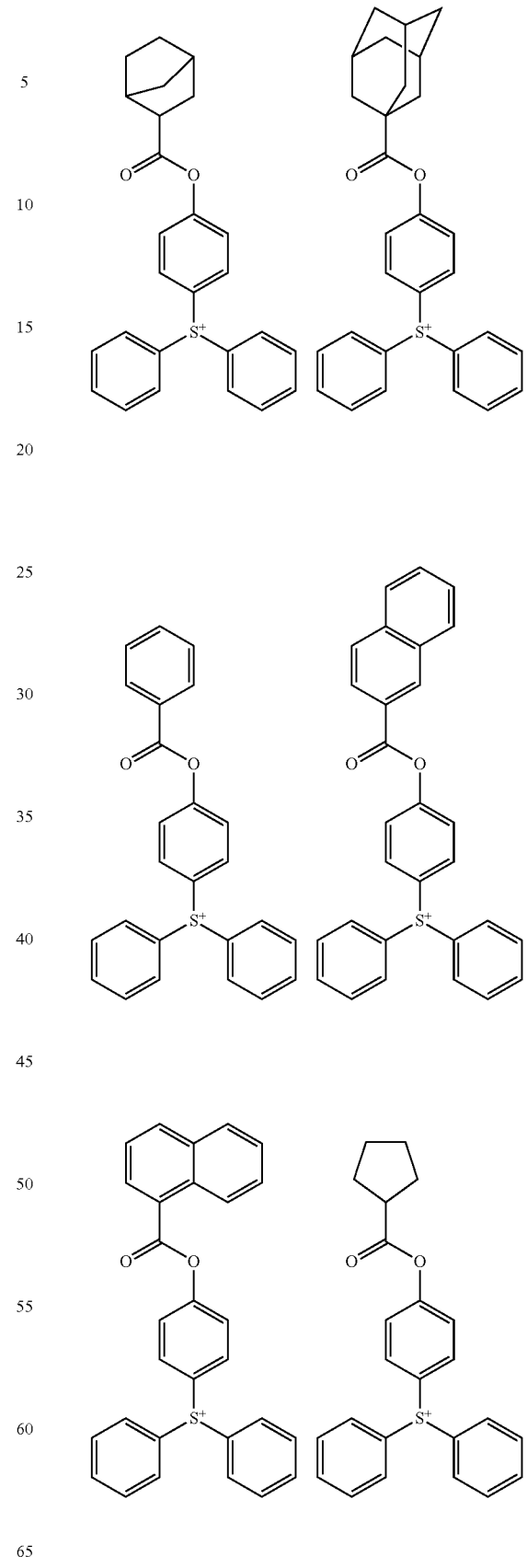

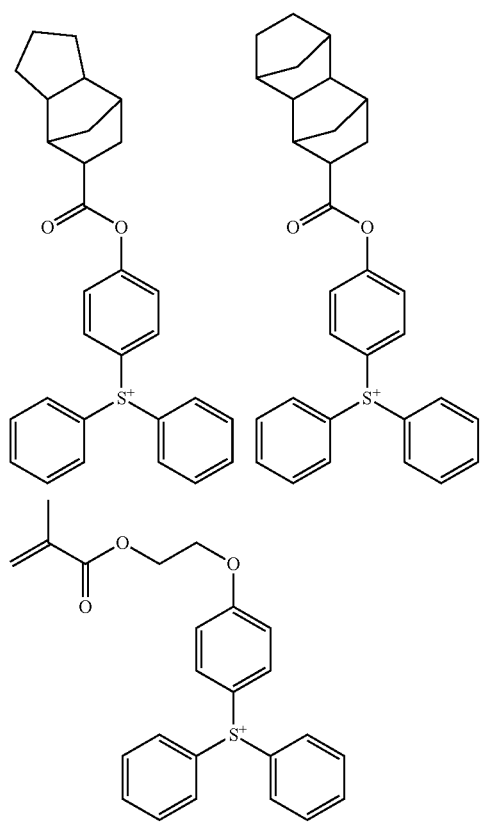
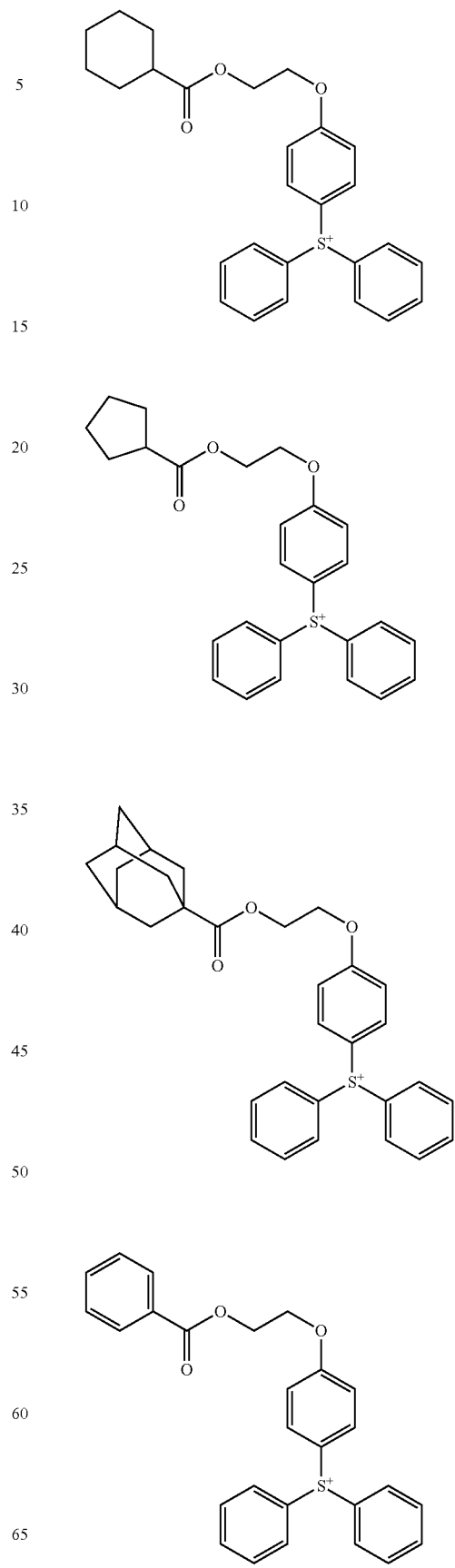

61
-continued
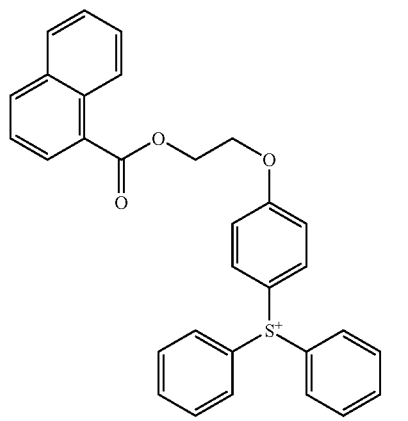
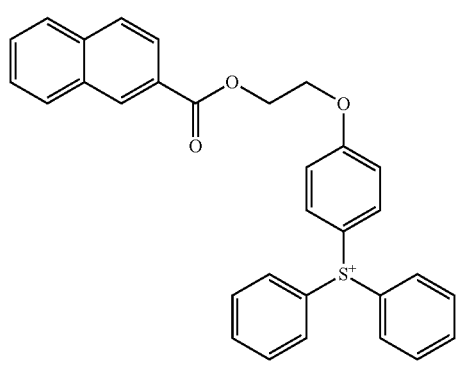
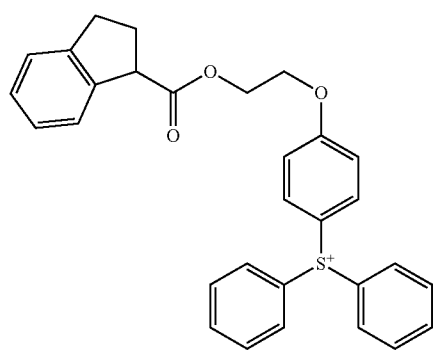
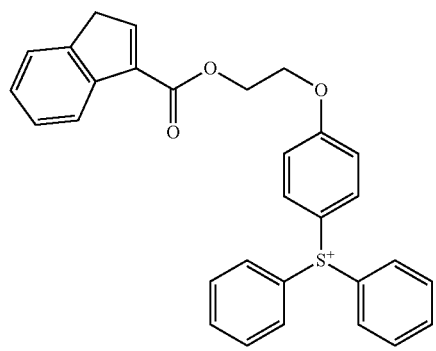
62
-continued
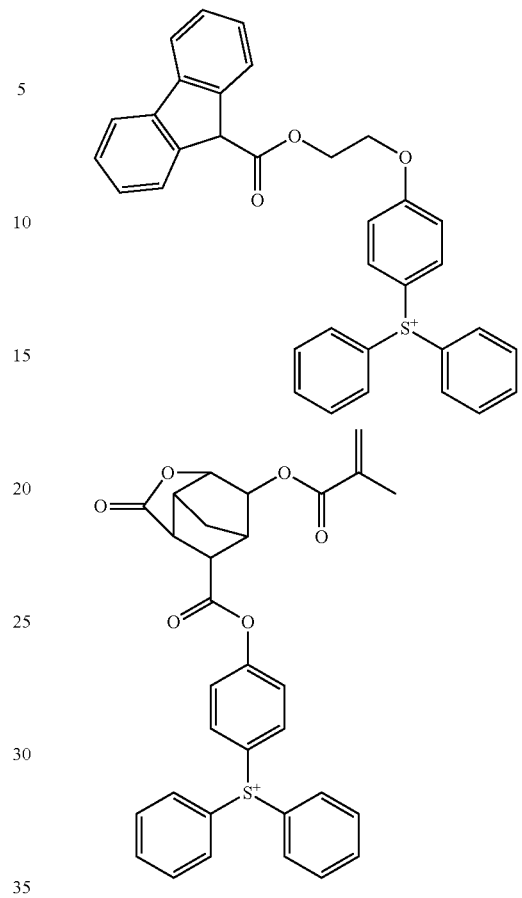
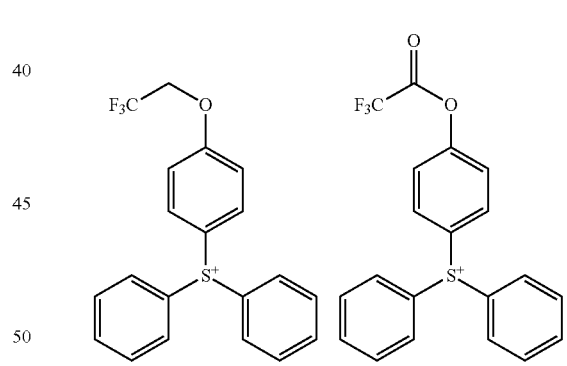
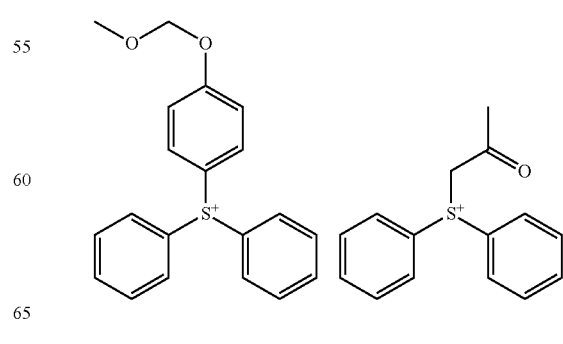

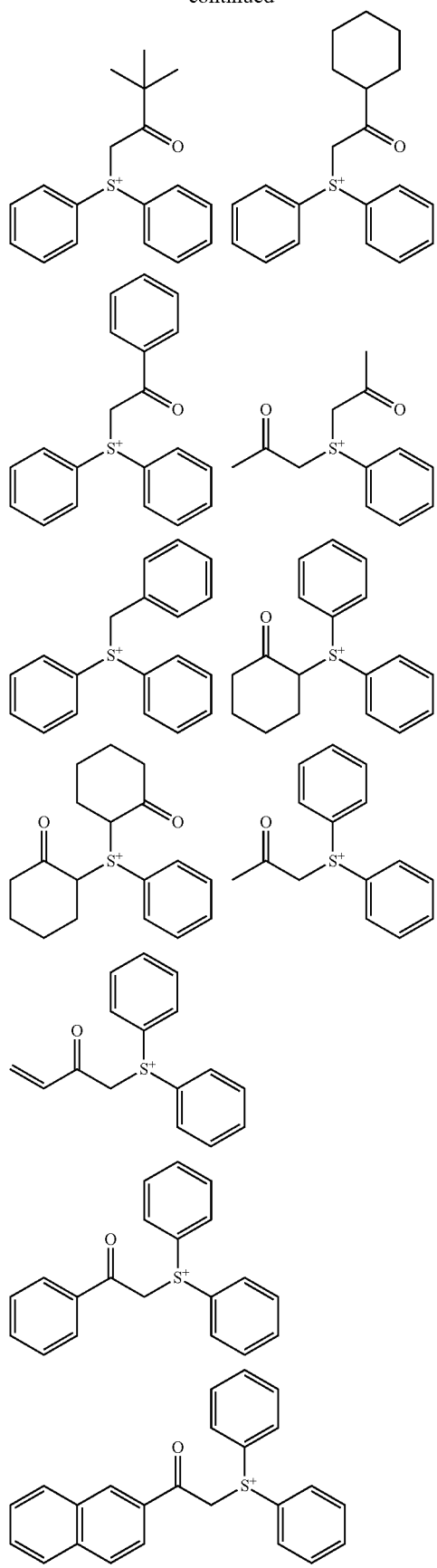
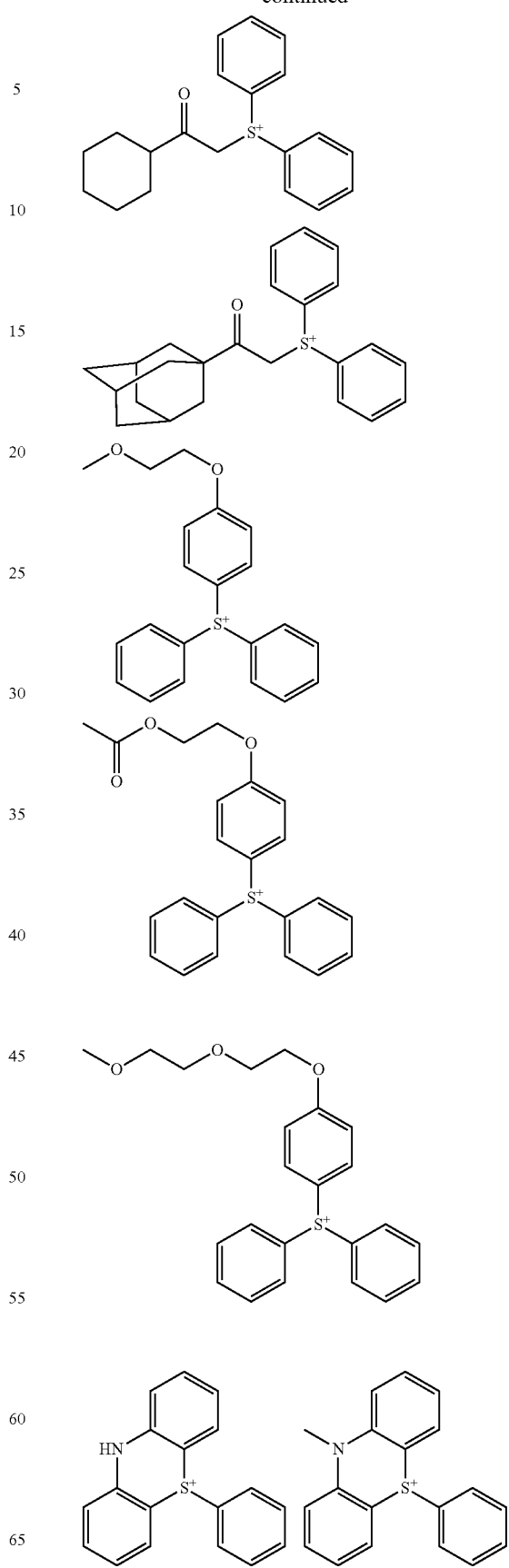

-continued
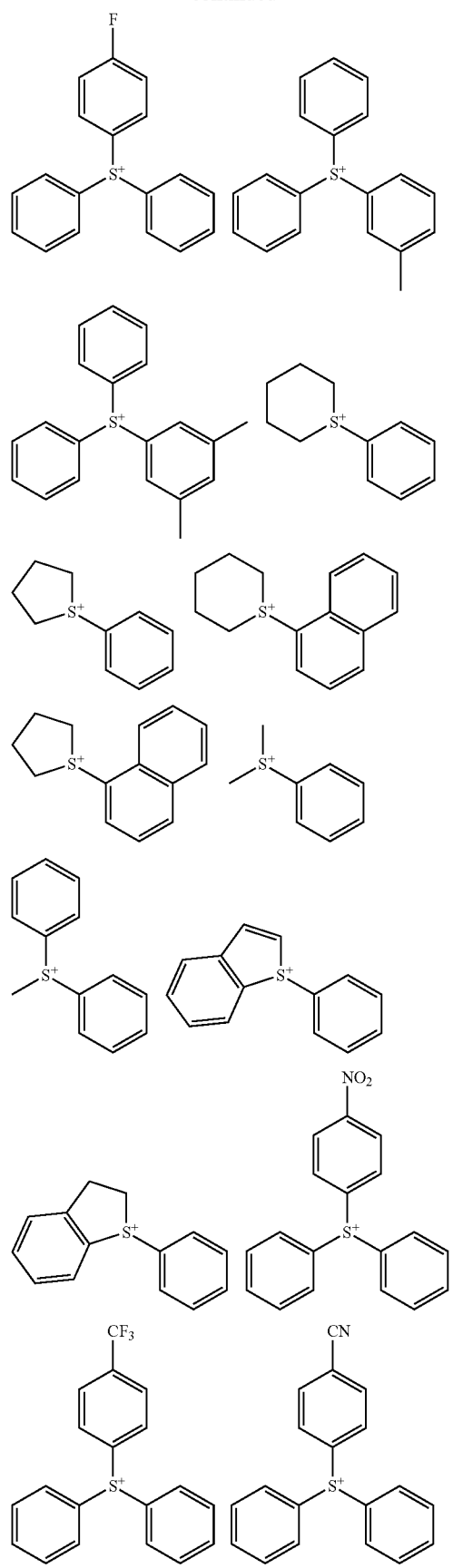
-continued
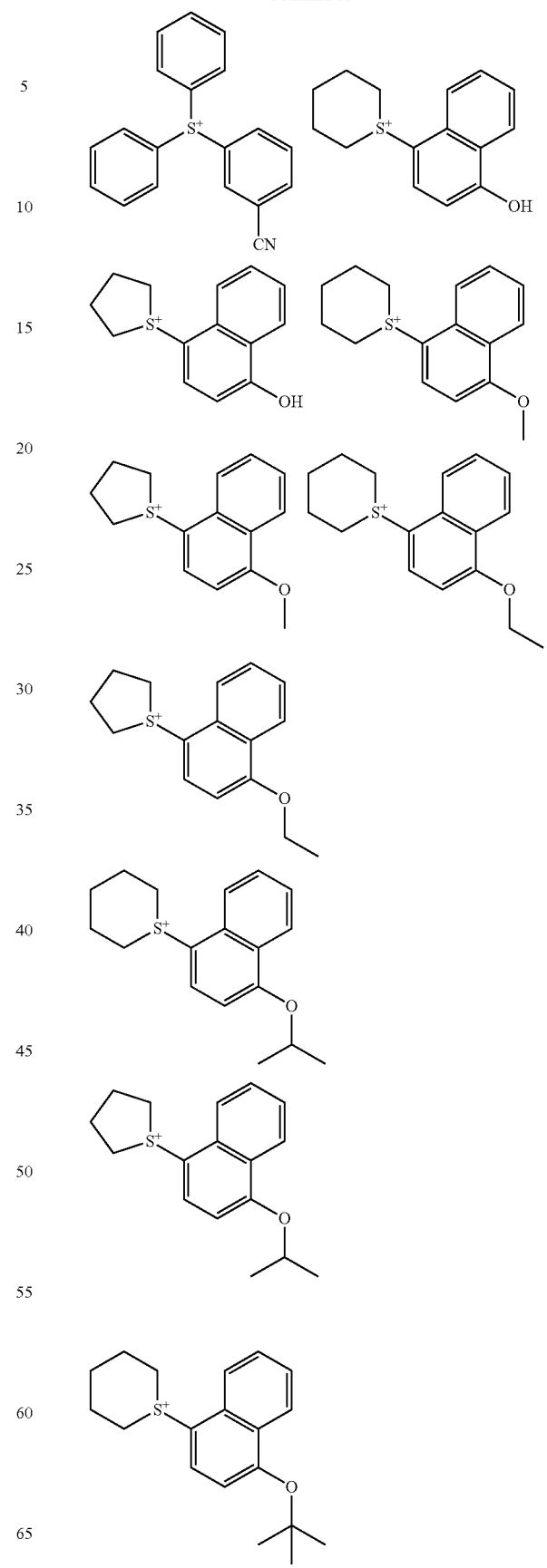

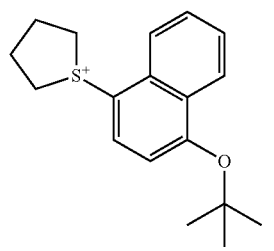
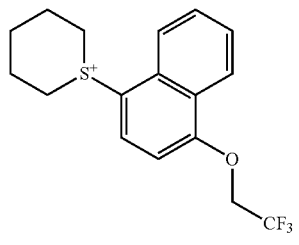
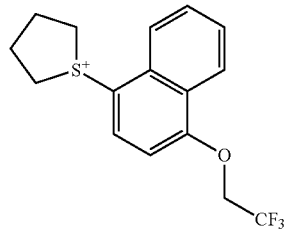
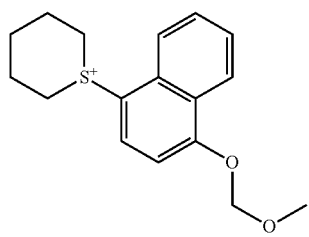
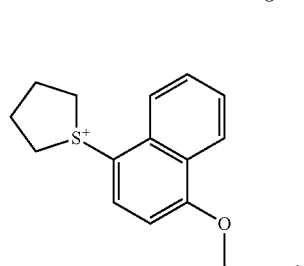
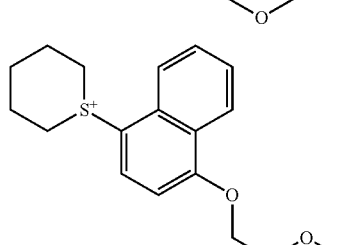
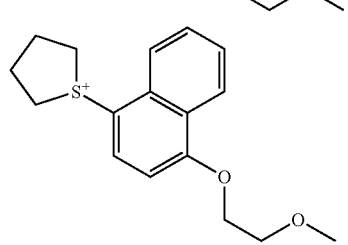
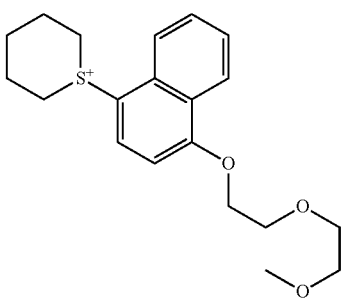
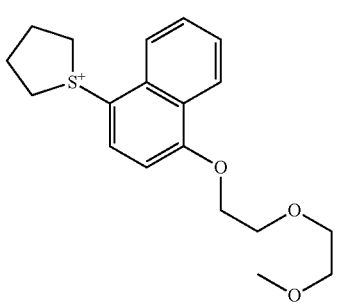
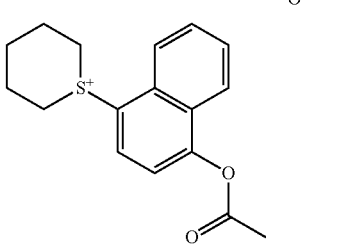
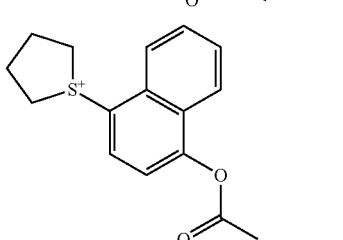
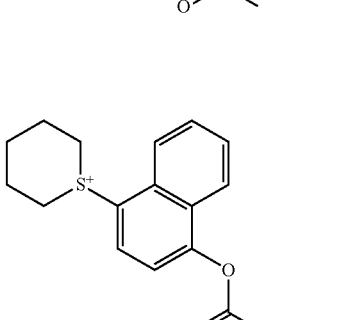
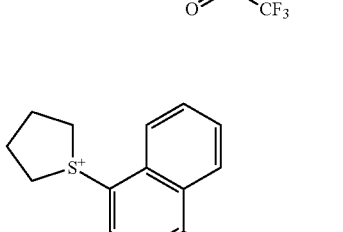
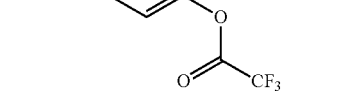

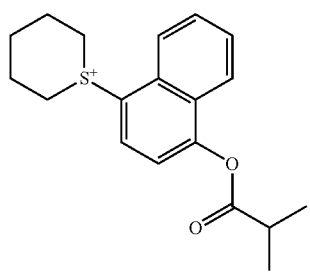
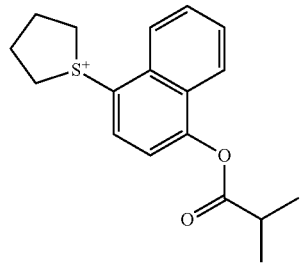
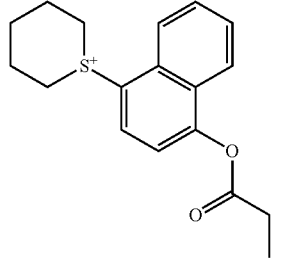
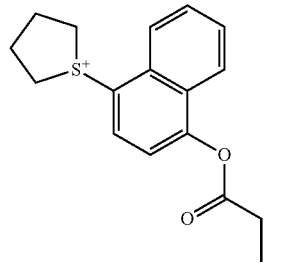
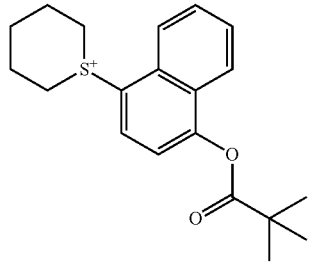
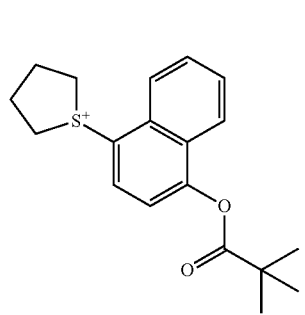
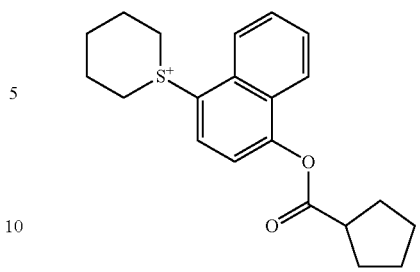
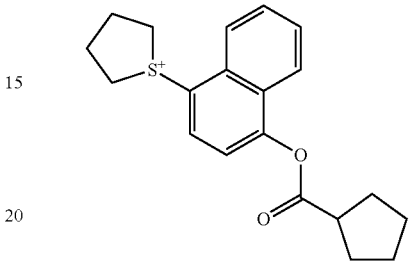
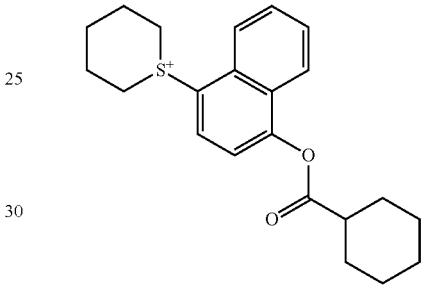
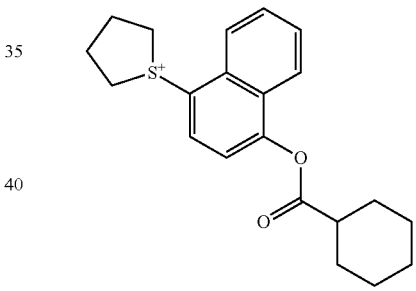
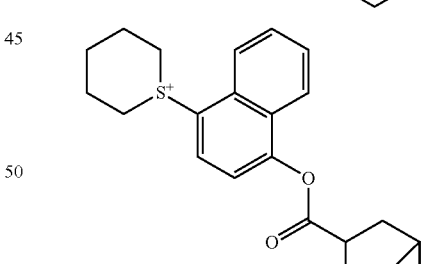
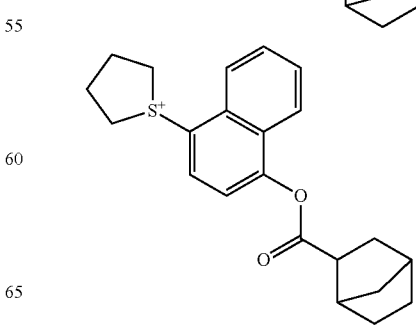

71
-continued
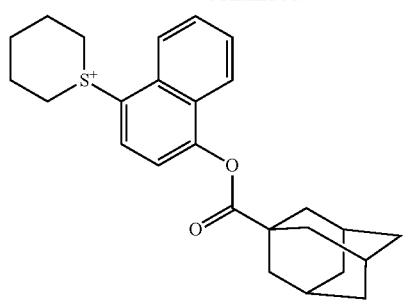
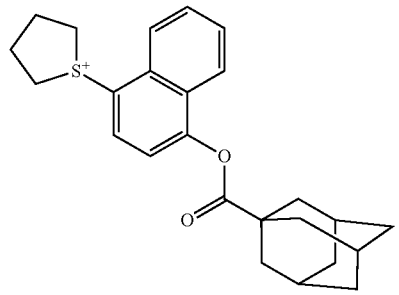
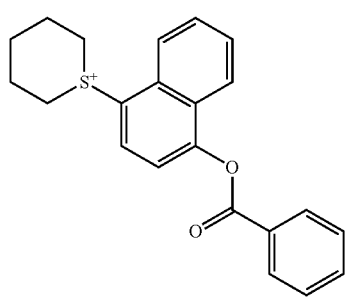
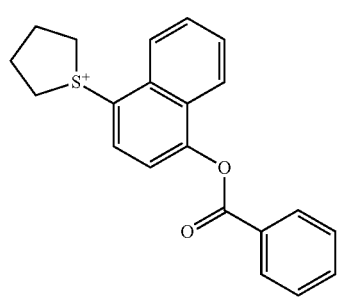
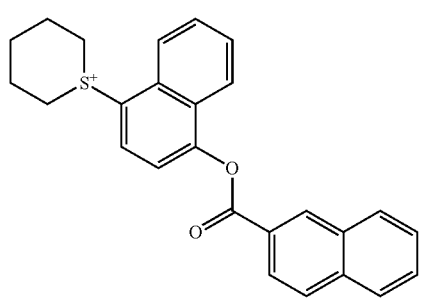
72
-continued
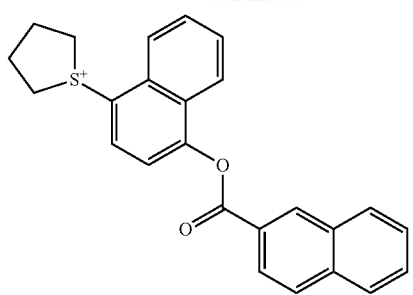
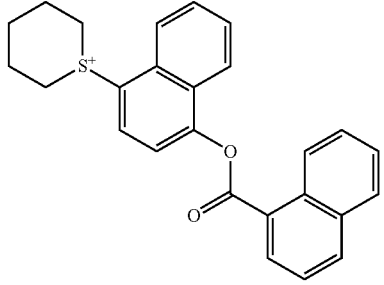
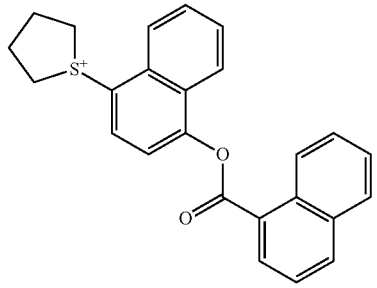
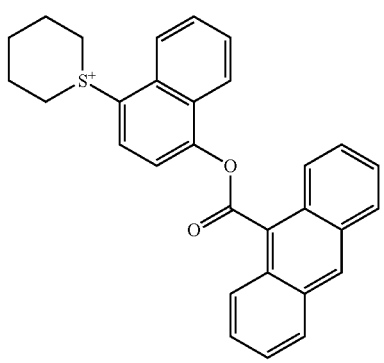
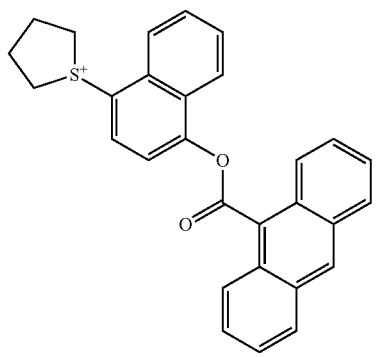

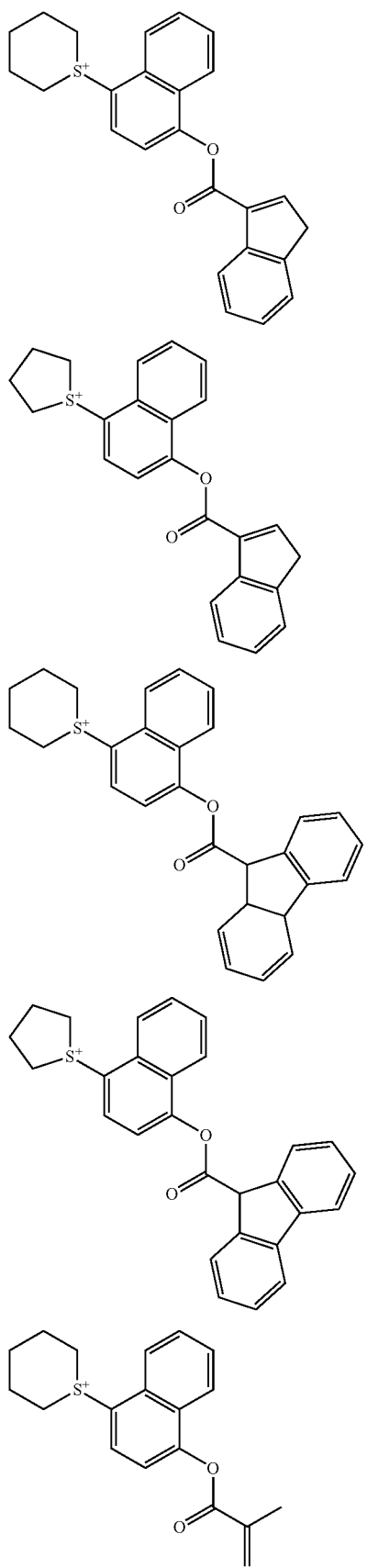
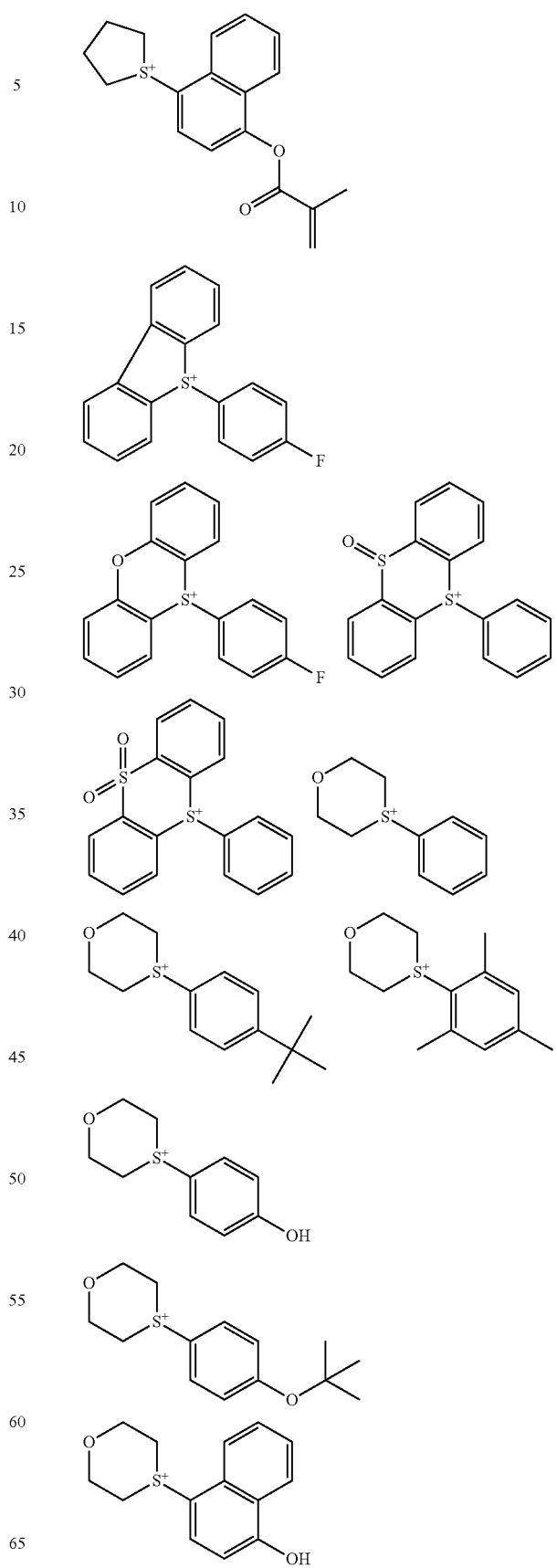

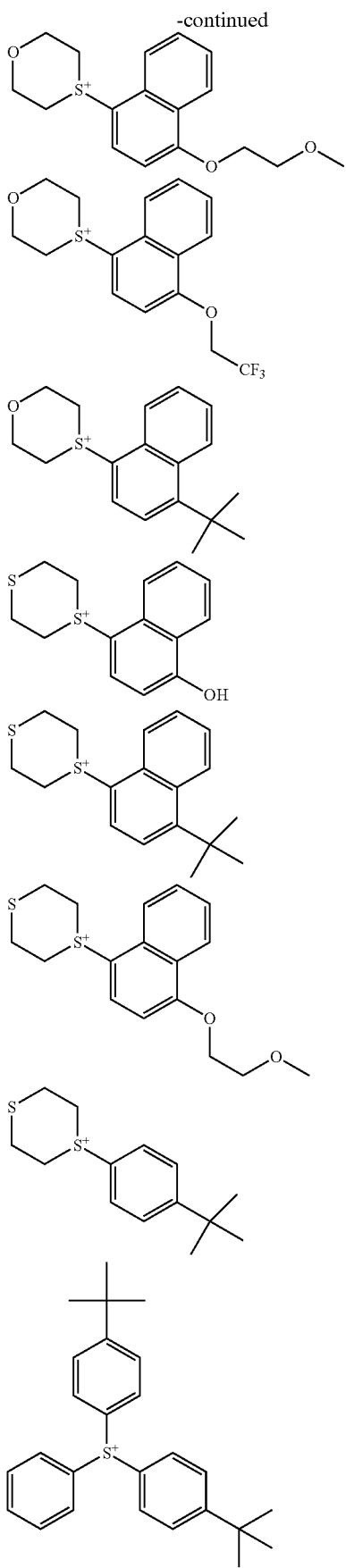
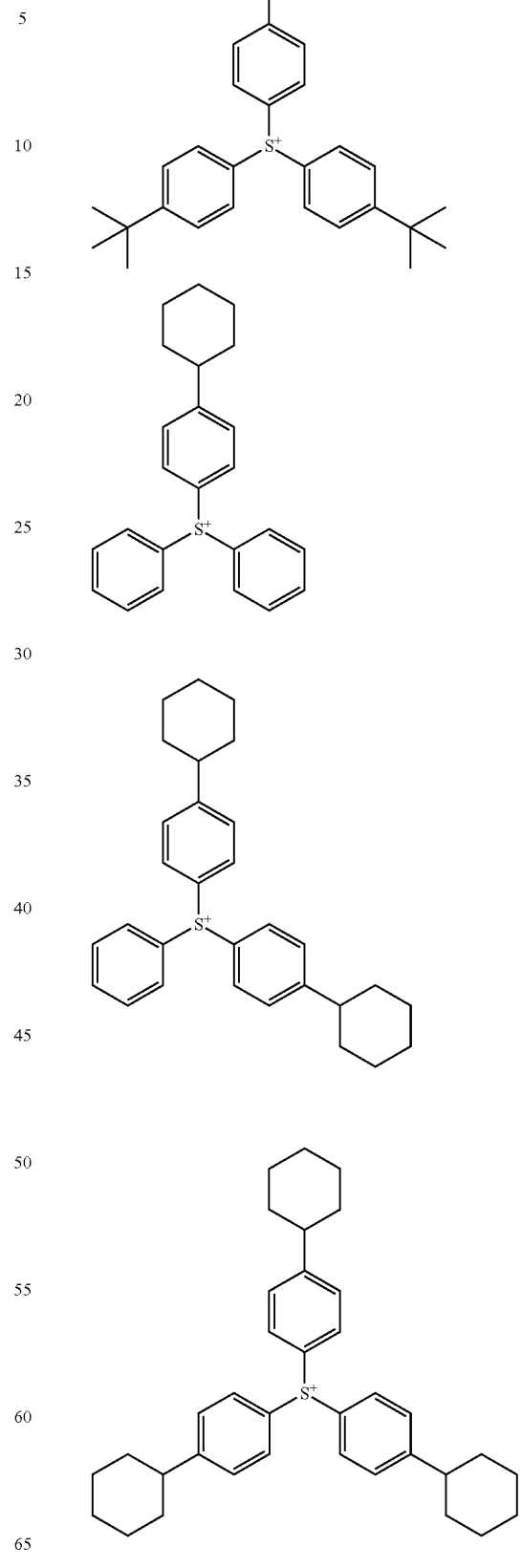

77
-continued
78
-continued
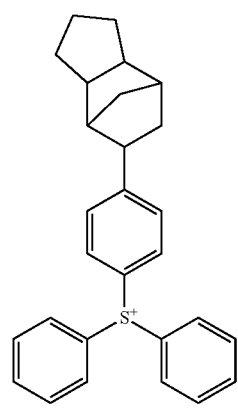
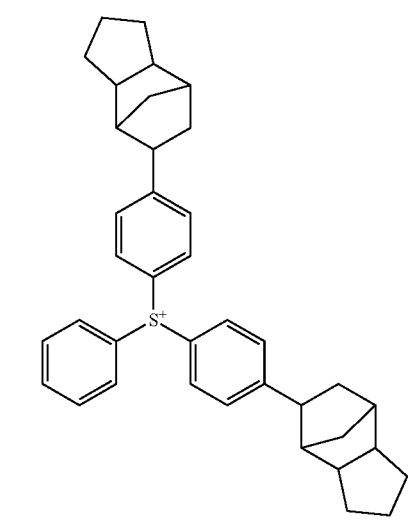
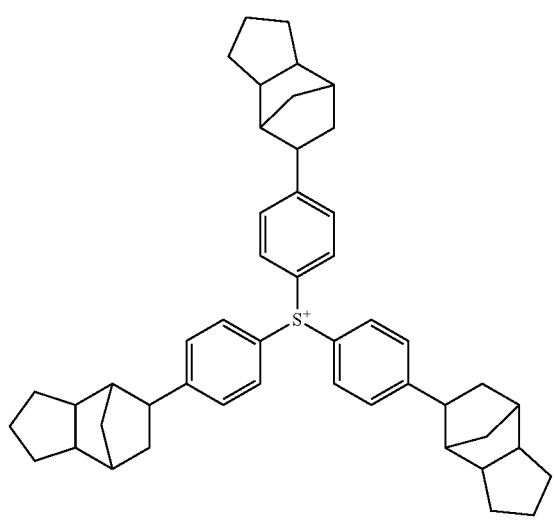
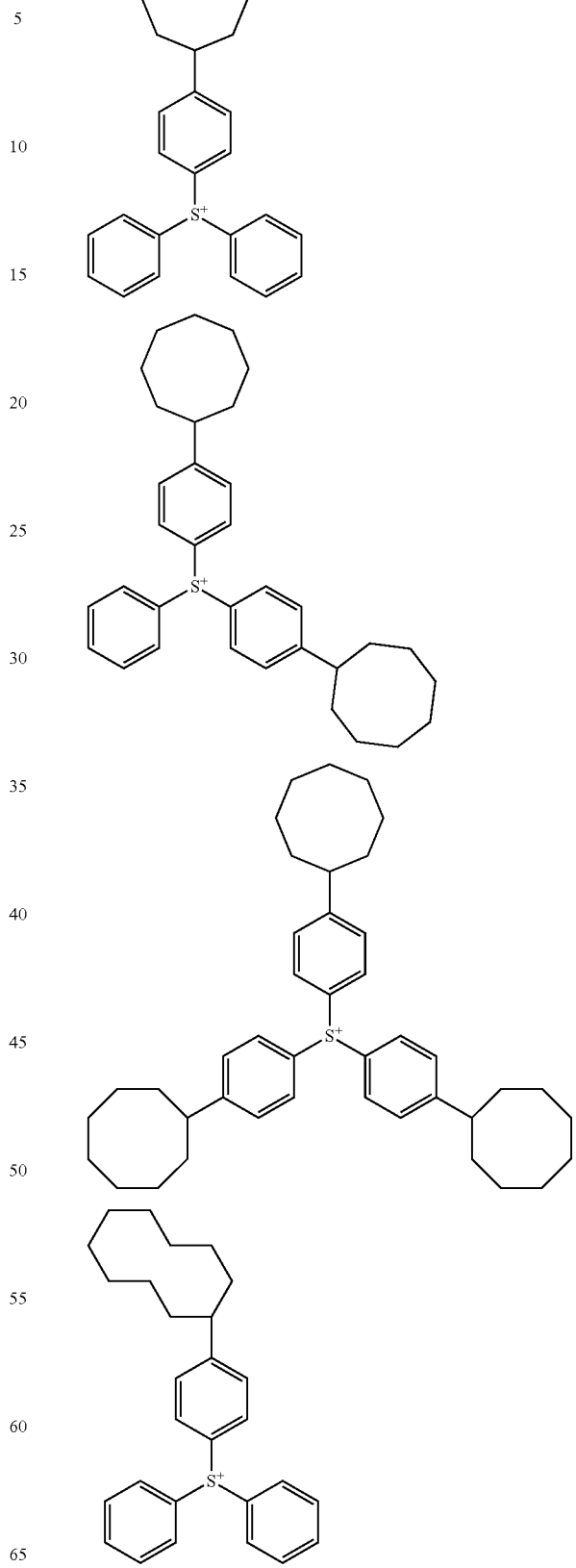

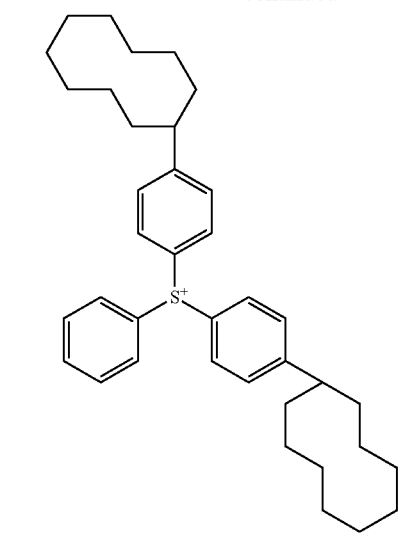
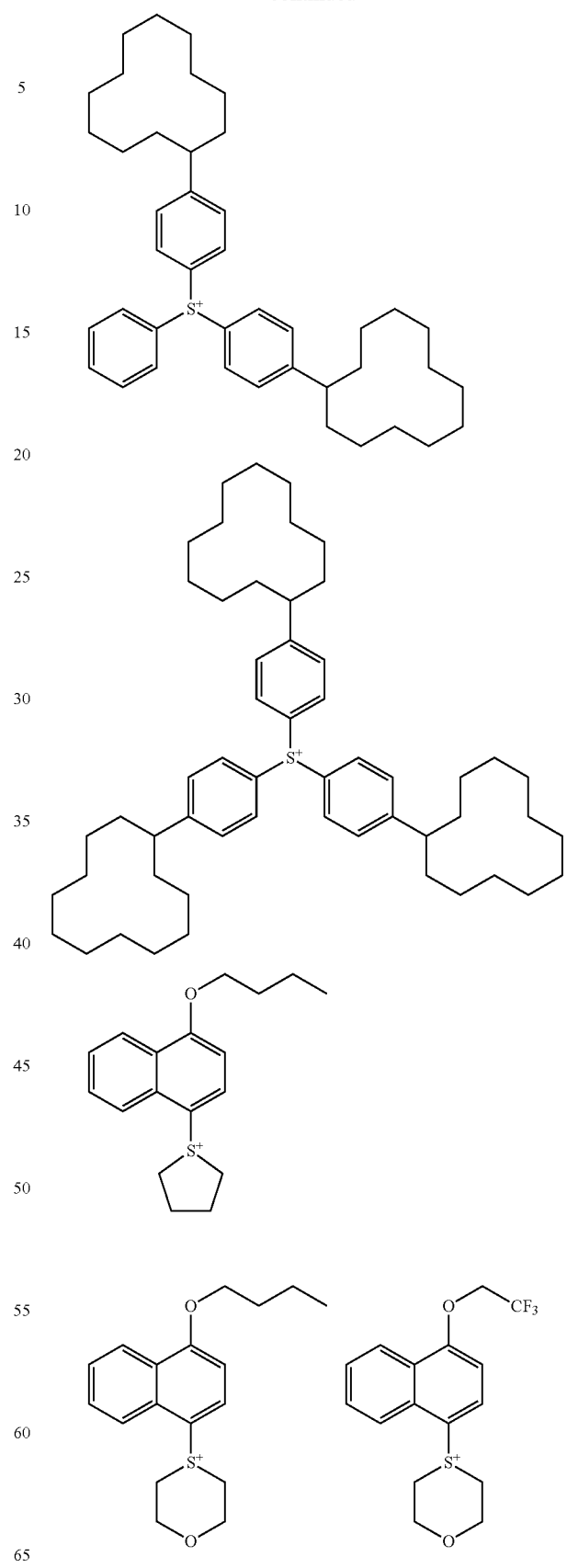

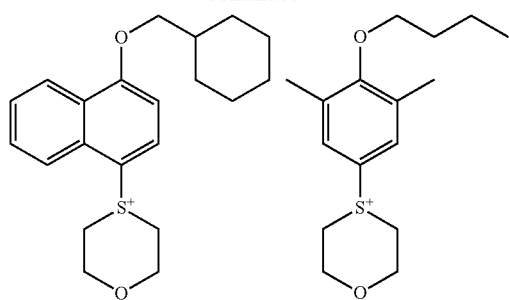
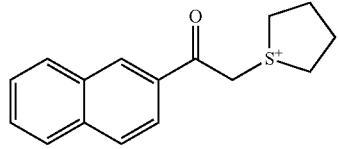
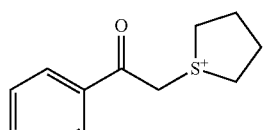
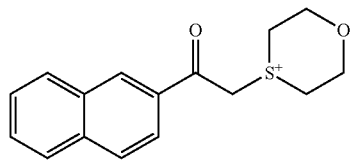
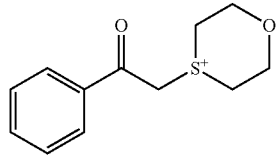
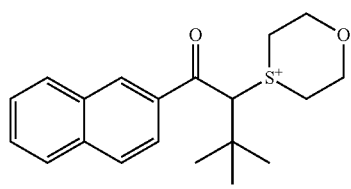
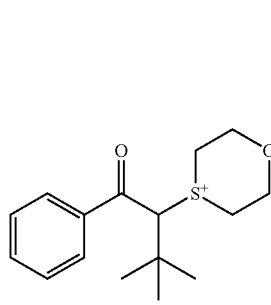
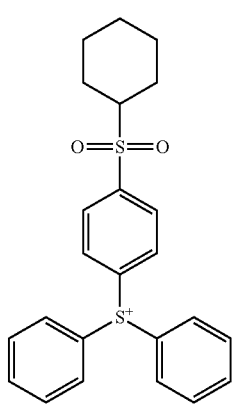
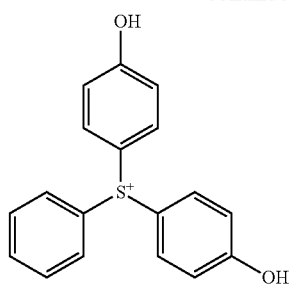
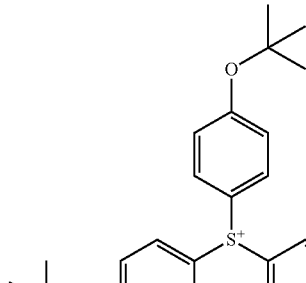
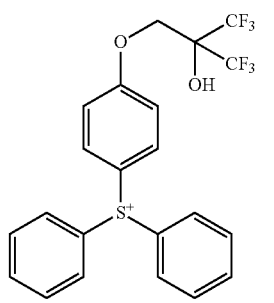
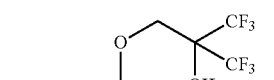
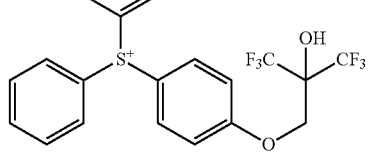
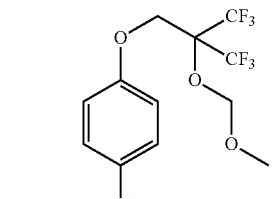

-continued

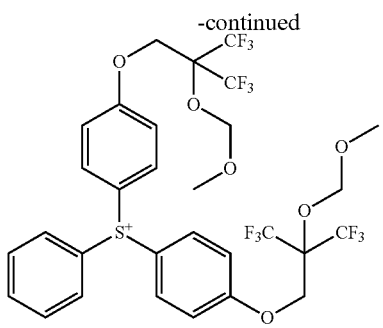

Illustrative, non-limiting examples of the iodonium cation of formula (d5) are given below.

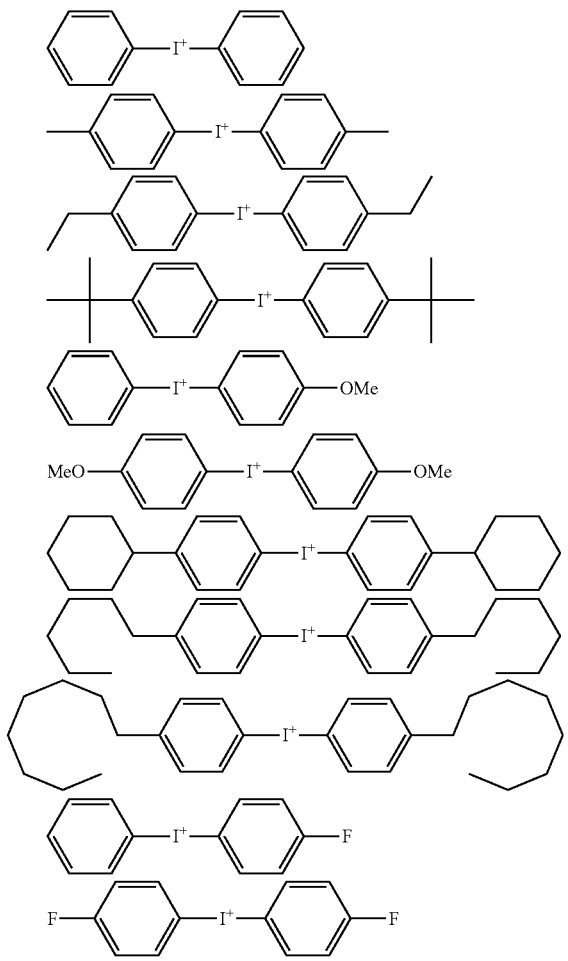

Examples of the non-nucleophilic counter ion represented by M⁻ include halide ions such as chloride and bromide ions; fluoroalkylsulfonate ions such as triflate, 1,1,1-trifluoromethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; and methide ions such as tris(trifluoromethylsulfonyl)methide and tris(perfluoroethylsulfonyl)methide.

Also included are a sulfonate ion which is fluorinated at α-position as represented by the formula (F-1) and a sulfonate ion which is fluorinated at α- and β-positions as represented by the formula (F-2).

(F-1)

(F-2)

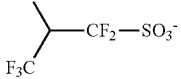

In formula (F-1), $R^{19}$ is hydrogen, or a $C_1$-$C_{20}$ alkyl group, $C_2$-$C_{20}$ alkenyl group or $C_6$-$C_{20}$ aryl group, which may have an ether bond, ester bond, carbonyl moiety, lactone ring or fluorine atom. Herein the alkyl and alkenyl groups may be straight, branched or cyclic.

In formula (F-2), $R^{20}$ is hydrogen, or a $C_1$-$C_{30}$ alkyl group, $C_2$-$C_{30}$ acyl group, $C_2$-$C_{20}$ alkenyl group, $C_6$-$C_{20}$ aryl group or $C_1$-$C_{20}$ aryloxy group, which may have an ether bond, ester bond, carbonyl moiety or lactone ring. Herein the alkyl, acyl and alkenyl groups may be straight, branched or cyclic.

Examples of the recurring units (d1) are given below, but not limited thereto. Notably $R^4$ is as defined above.

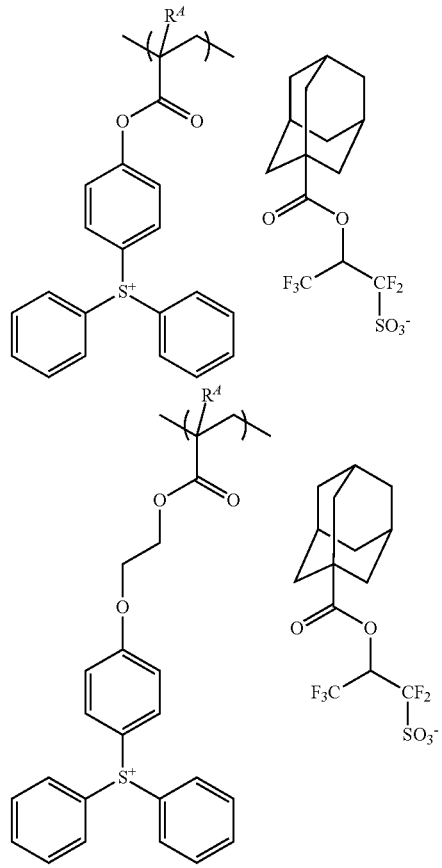

Examples of the recurring units (d2) are given below, but not limited thereto. Notably $R^4$ is as defined above.

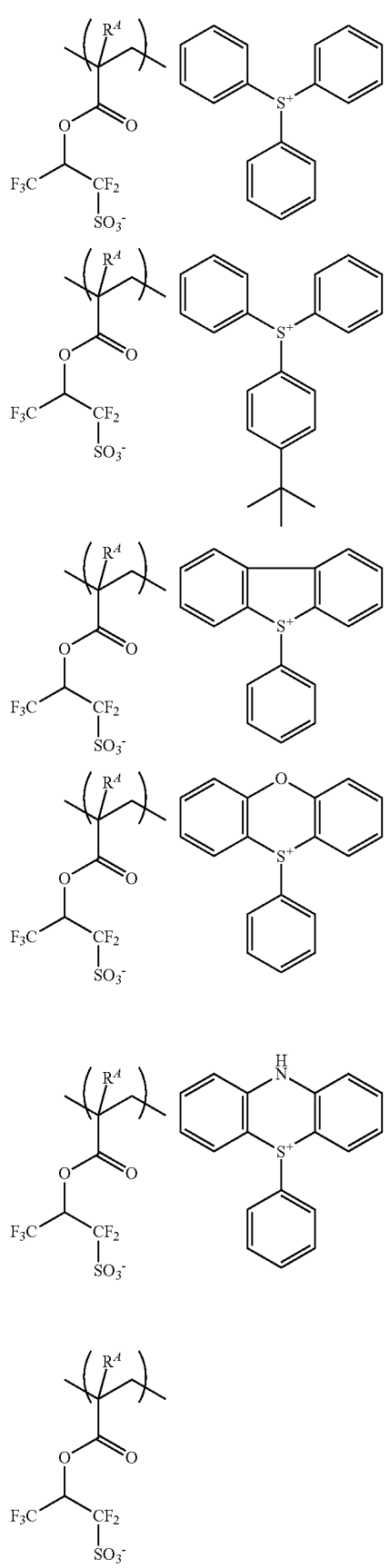

-continued
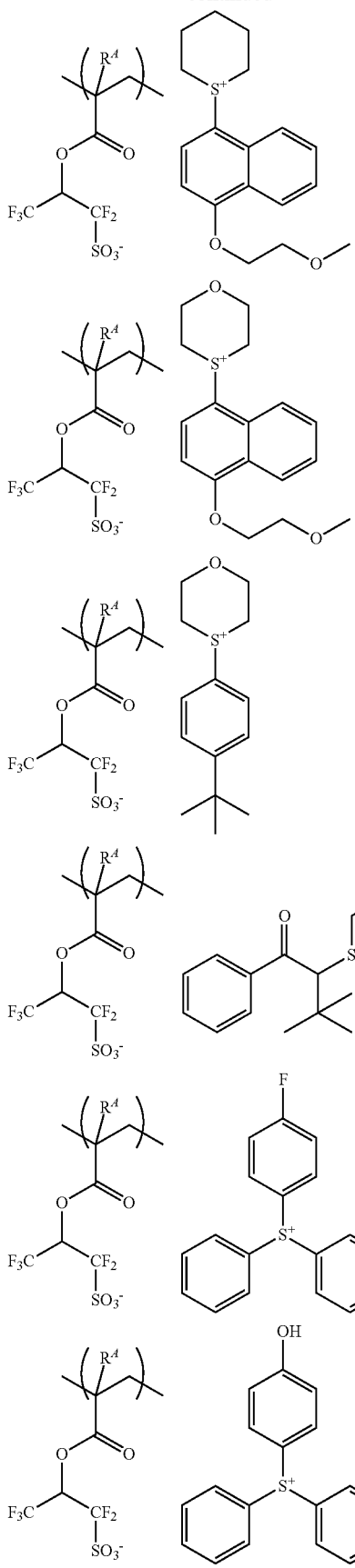
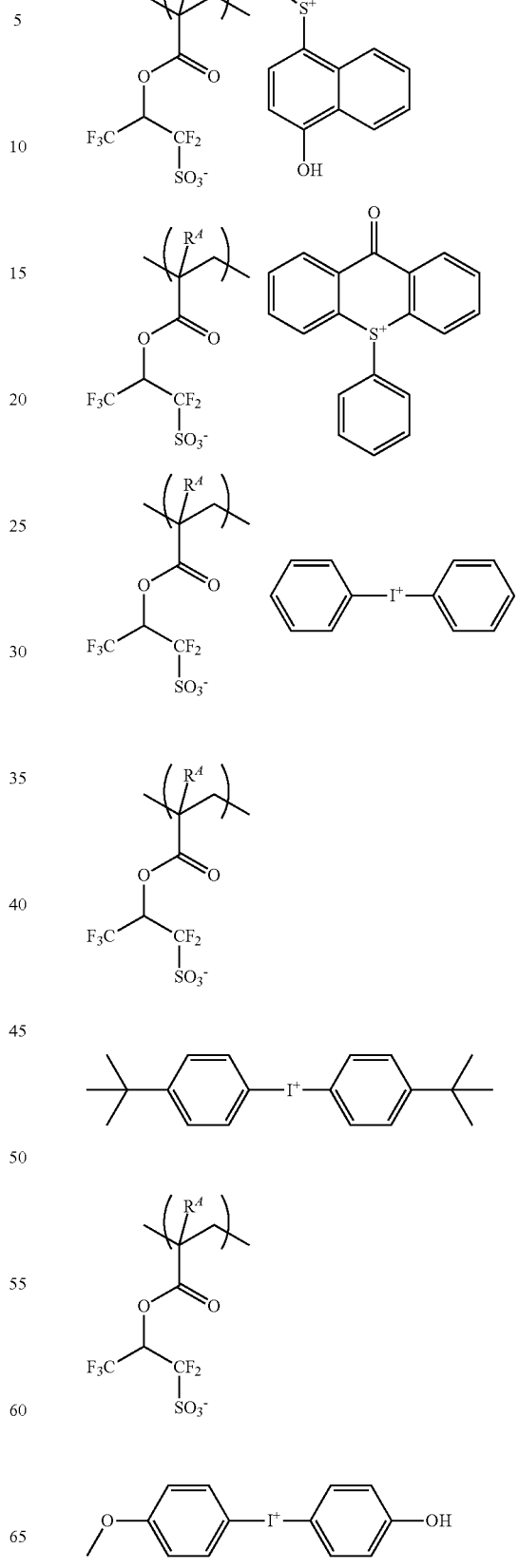

89
-continued
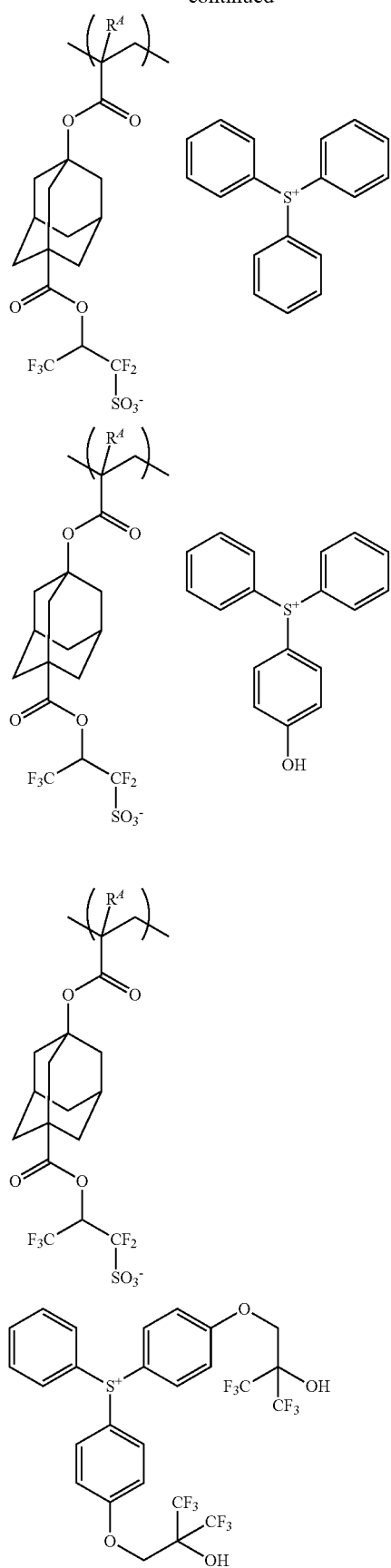
90
-continued
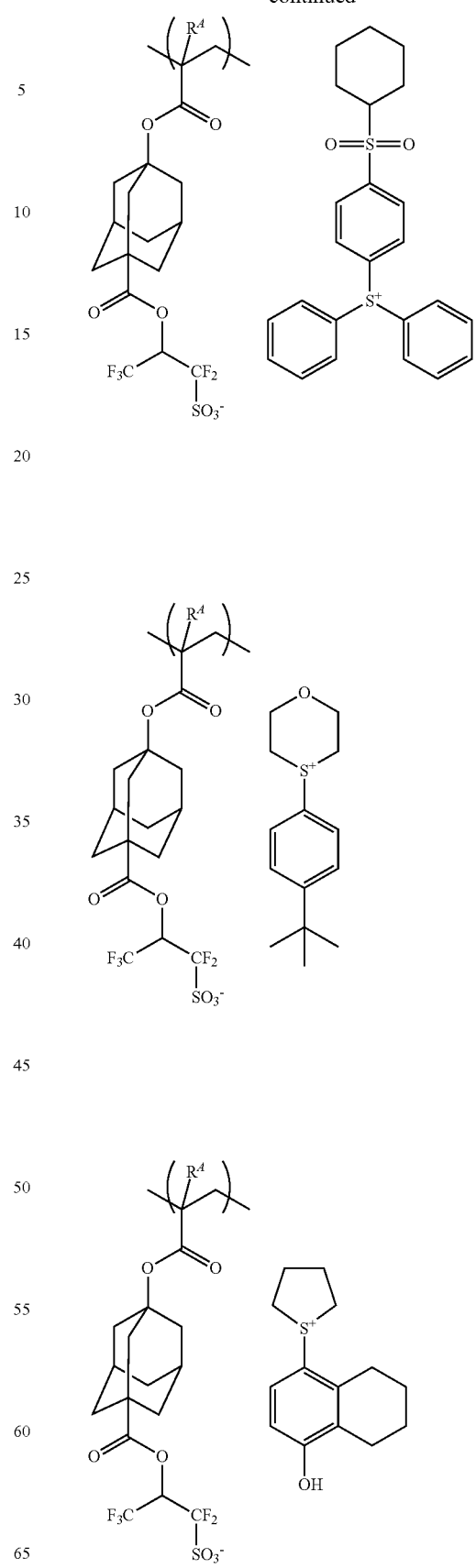

91
-continued
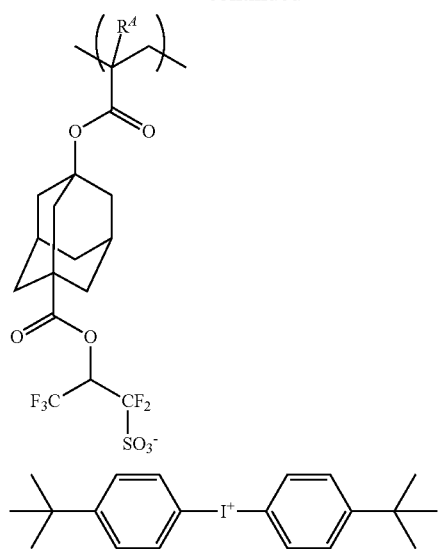
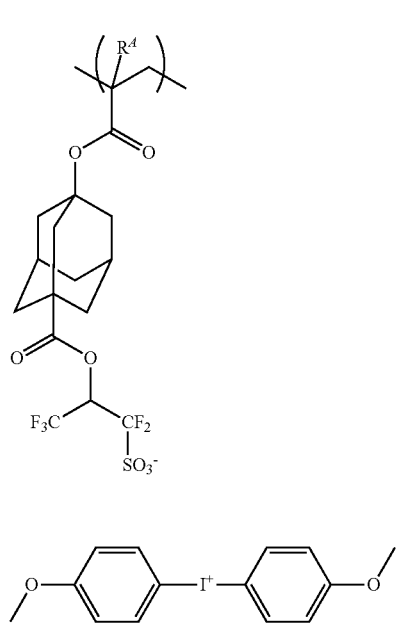
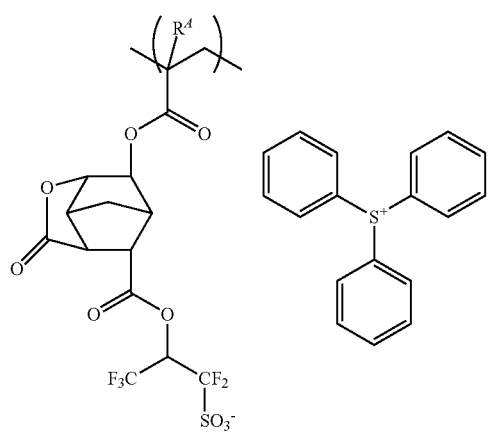
92
-continued
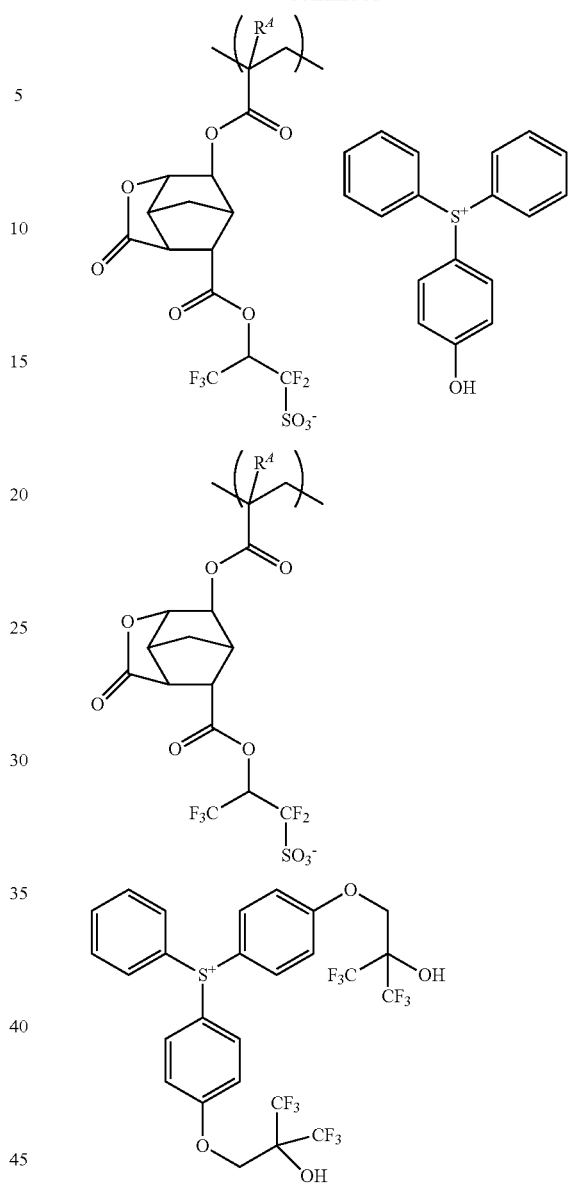
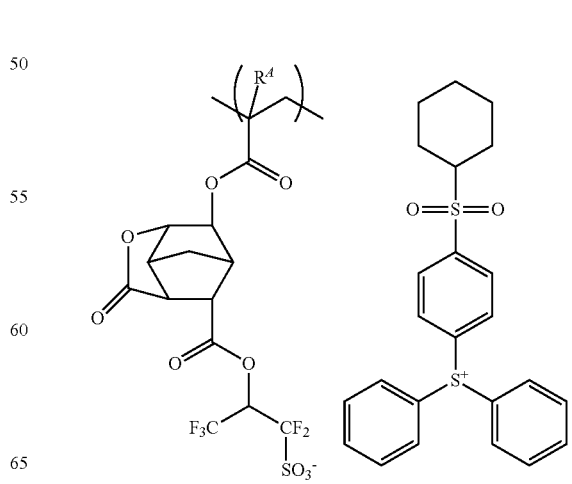

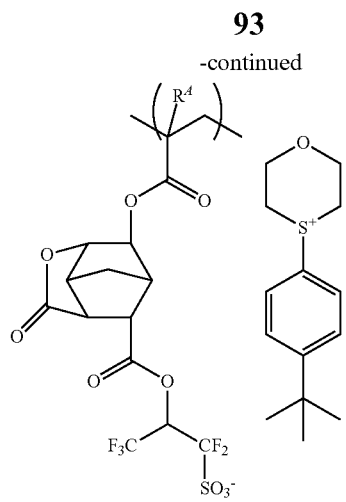
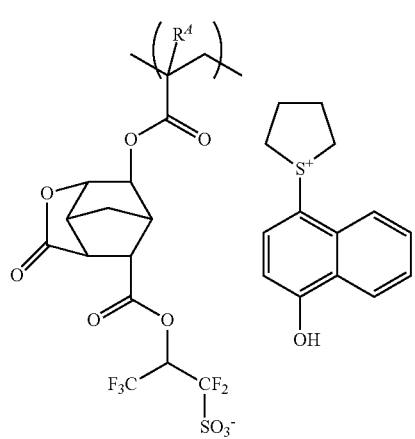
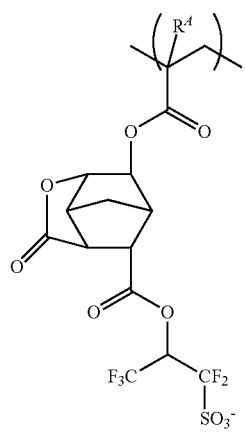
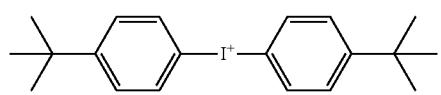
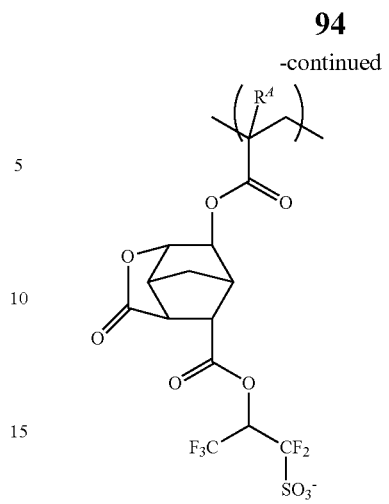
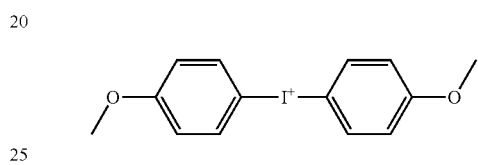
Examples of the recurring units (d3) are given below, but not limited thereto. Notably $R^A$ is as defined above.
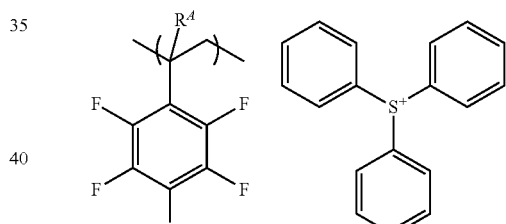
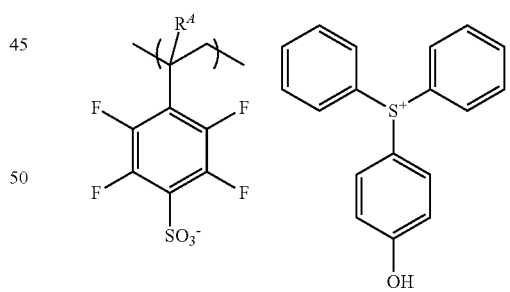
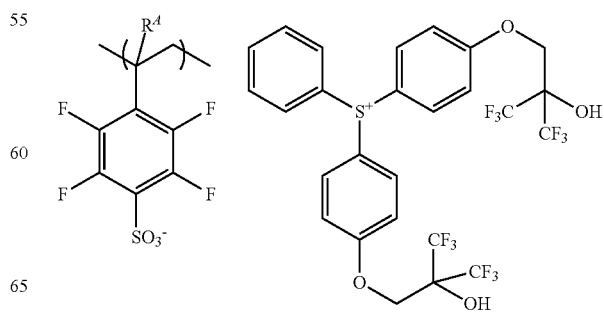

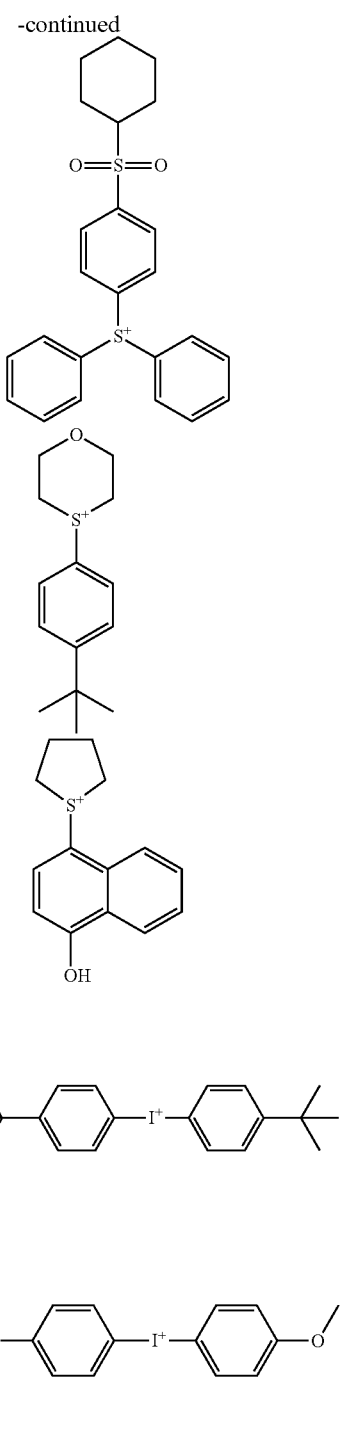

Besides the recurring units (d1) to (d3), the inventive polymer may further comprise recurring units having a sulfonic acid, imidic acid or methide acid anion bonded to the backbone or recurring units having a sulfonium cation bonded to the backbone as described in JP 5548473, paragraphs [0129]-[0151], or recurring units derived from a monomer containing a sulfonic acid anion as described in WO 2011/070947, paragraphs [0034]-[0038].

The recurring units (d1) to (d3) function as an acid generator. Binding an acid generator to the polymer backbone is effective for reducing acid diffusion and preventing the resolution from lowering due to blur by acid diffusion. Additionally, edge roughness (LER, LWR) is improved because the acid generator is uniformly dispersed.

In a preferred embodiment, the polymer may further comprise recurring units (e) derived from indene, acenaphthylene, chromone, coumarin or norbornadiene compounds, as represented by the following formulae (e1) to (e5).

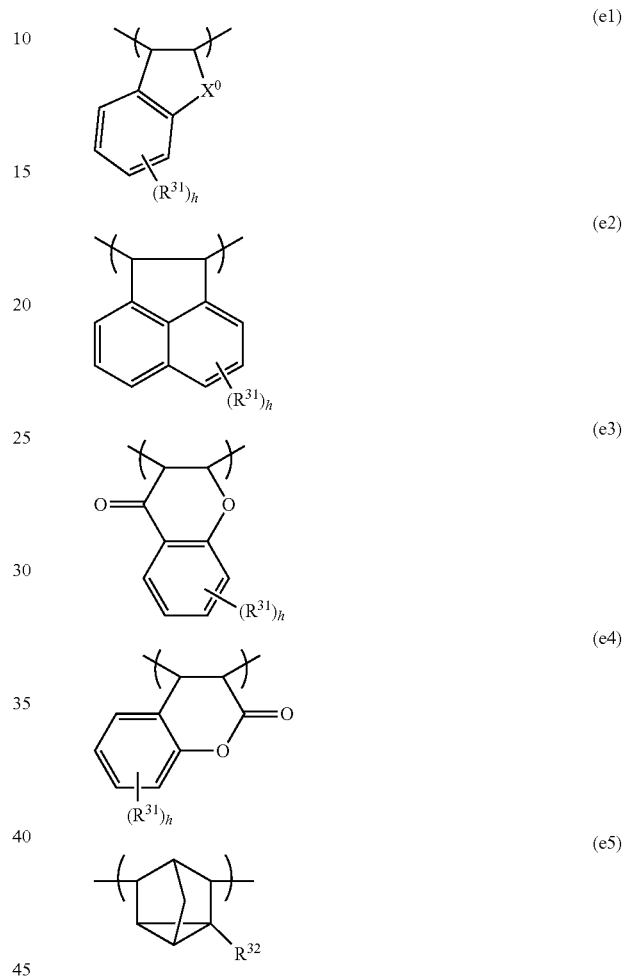

Herein $R^{31}$ is each independently a $C_1$-$C_{30}$ alkyl group, $C_1$-$C_{30}$ haloalkyl group, hydroxy group, $C_1$-$C_{30}$ alkoxy group, $C_1$-$C_{30}$ acyl group, $C_2$-$C_{30}$ alkoxycarbonyl group, $C_6$-$C_{10}$ aryl group, halogen, or 1,1,1,3,3,3-hexafluoro-2-propanol group, and h is 0 or 1. $R^{32}$ is hydrogen, a $C_1$-$C_{30}$ alkyl group, $C_1$-$C_{30}$ haloalkyl group, hydroxy group, $C_1$-$C_{30}$ alkoxy group, $C_1$-$C_{30}$ acyl group, $C_2$-$C_{30}$ alkoxycarbonyl group, $C_6$-$C_{10}$ aryl group, halogen, or 1,1,1,3,3,3-hexafluoro-2-propanol group. $X^0$ is methylene, oxygen or sulfur. The foregoing alkyl, haloalkyl, alkoxy, acyl and alkoxycarbonyl groups may be straight, branched or cyclic.

In a preferred embodiment, the polymer may further comprise recurring units (f) derived from styrene, vinylnaphthalene, vinylanthracene, vinylpyrene or methyleneindane compounds.

In the polymer, a fraction of recurring units (a) to (1) is preferably in the range: $0<a<1.0$, $0\le b1<1.0$, $0\le b2<1.0$, $0<b1+b2<1.0$, $0\le c\le0.9$, $0<d1\le0.5$, $0\le d2\le0.5$, $0\le d3\le0.5$, $0\le d1+d2+d3\le0.5$, $0\le e1\le0.5$, $0\le e2\le0.5$, $0\le e3\le0.5$, $0\le e4\le0.5$, $0\le e5\le0.5$, $0\le e1+e2+e3+e4+e5\le0.5$, and $0\le f\le0.5$; more preferably $0.02\le a\le0.8$, $0\le b1\le0.7$, $0\le b2\le0.7$, $0.1\le b1+$ b2≤0.7, 0<c≤0.8, 0≤d1≤0.4, 0≤d2≤0.4, 0≤d3≤0.4, 0≤d1+ d2+d3≤0.4, 0≤e1≤0.4, 0≤e2≤0.4, 0≤e3≤0.4, 0≤e4≤0.4. 0≤e5≤0.4, 0≤e1+e2+e3+e4+e5≤0.4, and 0≤f≤0.4; even more preferably 0.05≤a≤0.7, 0≤b1≤0.6, 0≤b2≤0.6, 0.1≤b1+ b2≤0.6, 0<c≤0.7, 0≤d1≤0.3, 0≤d2≤0.3, 0≤d3≤0.3, 0≤d1+ d2+d3≤0.3, 0≤e1≤0.3, 0≤e2≤0.3, 0≤e3≤0.3, 0≤e4≤0.3, 0≤e5≤0.3, 0≤e1+e2+e3+e4+e5≤0.3, and 0≤f≤0.3. Notably, a+b1+b2+c+d1+d2+d3+e1+e2+e3+e4+e5+f=1.

The polymer should preferably have a weight average molecular weight (Mw) in the range of 1,000 to 500,000, and more preferably 2,000 to 30,000, as measured by GPC versus polystyrene standards using tetrahydrofuran (THF) solvent. The range of Mw ensures that the resist composition is fully heat resistant and alkaline soluble.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the polymer should preferably have a narrow dispersity (Mw/Mn) of 1.0 to 2.0, especially 1.0 to 1.5, in order to provide a resist composition suitable for micropatterning to a small feature size.

The polymer may be synthesized by any desired methods, for example, by dissolving one or more monomers selected from the monomers corresponding to the recurring units (a) to (f) in an organic solvent, adding a radical polymerization initiator thereto, and heating for polymerization. Examples of the organic solvent which can be used for polymerization include toluene, benzene, THF, diethyl ether, dioxane, cyclohexane, cyclopentane, methyl ethyl ketone, and γ-butyrolactone. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the reaction temperature is 50 to 80° C. and the reaction time is 2 to 100 hours, more preferably 5 to 20 hours.

When a hydroxy-bearing monomer is copolymerized, a corresponding monomer in which the hydroxyl group has been replaced by an acetal group which is susceptible to deprotection with acid, typically ethoxyethoxy, may be used, and polymerization be followed by deprotection with weak acid and water. Alternatively, the hydroxyl group may have been replaced by an acetyl, formyl or pivaloyl group, and polymerization be followed by alkaline hydrolysis.

When hydroxystyrene or hydroxyvinylnaphthalene is copolymerized, an alternative method is possible. Specifically, acetoxystyrene or acetoxyvinyinaphthalene is used instead of hydroxystyrene or hydroxyvinylnaphthalene, and after polymerization, the acetoxy group is deprotected by alkaline hydrolysis, for thereby converting the relevant units to hydroxystyrene or hydroxyvinylnaphthalene units. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

Resist Composition

A further embodiment of the invention is a resist composition comprising a base resin containing the polymer defined above, and an organic solvent. The base resin may be a blend of inventive polymers which are different in compositional ratio, Mw and/or Mw/Mn.

Organic Solvent

Examples of the organic solvent used herein are described in JP-A 2008-111103, paragraphs [0144]-[0145] (U.S. Pat. No. 7,537,880). Suitable organic solvents include ketones such as cyclohexanone and methyl n-pentyl ketone; alcohols such as 3-methoxybutanol, 3-methyl-3-methoxybutanol, 1-methoxy-2-propanol, and 1-ethoxy-2-propanol: ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether, esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, which may be used alone or in admixture.

The organic solvent is preferably used in an amount of 50 to 10,000 parts, more preferably 100 to 5,000 parts by weight per 100 parts by weight of the base resin.

Acid Generator

The resist composition may include an acid generator (also referred to as acid generator of addition type) in order for the composition to function as a chemically amplified resist composition. Typical of the acid generator used herein is a photoacid generator (PAG) capable of generating an acid in response to actinic light or radiation. Where the polymer as the base resin contains recurring units (d1) to (d3), that is, when the acid generator is bound in the polymer, the acid generator of addition type is not essential.

The PAG is any compound capable of generating an acid upon exposure to high-energy radiation. Suitable PAGs include sulfonitan salts, iodonium salts, sulfonyldiazomethane, N-sulfonyloxyimide, and oxime-O-sulfonate acid generators. Exemplary PAGs are described in U.S. Pat. No. 7,537,880 (JP-A 2008-111103, paragraphs [0122]-[0142]).

As the PAG, sulfonium salts having the formula (1-1) and iodonium salts having the formula (1-2) are also preferably used.

In formulae (1-1) and (1-2). $R^{101}$, $R^{102}$, $R^{103}$, $R^{104}$ and $R^{105}$ are each independently a $C_1$-$C_{20}$ monovalent hydrocarbon group which may contain a heteroatom, and any two of $R^{101}$, $R^{102}$ and $R^{103}$ may bond together to form a ring with the sulfur atom to which they are attached. The monovalent hydrocarbon groups may be straight, branched or cyclic, and examples thereof are as exemplified above for $R^{11}$ to $R^{17}$ in formulae (d1), (d4) and (d5).

Examples of the cation moiety in the sulfonium salt having formula (1-1) are as exemplified above for the cation having formula (d4). Examples of the cation moiety in the iodonium salt having formula (1-2) are as exemplified above for the cation having formula (d5).

In formulae (1-1) and (1-2), X⁻ is an anion selected from the formulae (1A) to (1D).

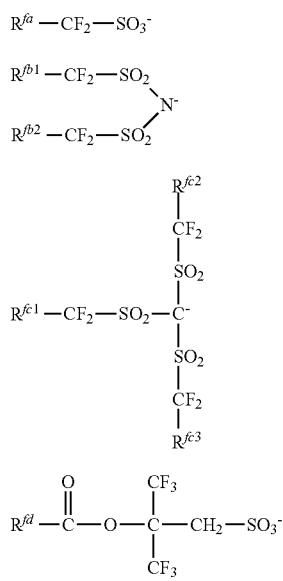

In formula (1A), $R^{fa}$ is fluorine or a $C_1$-$C_{40}$ monovalent hydrocarbon group which may contain a heteroatom. The monovalent hydrocarbon groups may be straight, branched or cyclic, and examples thereof are as will be exemplified for $R^{105}$ later.

Of the anions of formula (1A), a structure having formula (1A') is preferred.

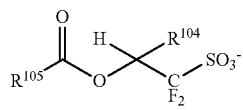

(1A')

In formula (1A'), $R^{104}$ is hydrogen or trifluoromethyl, preferably trifluoromethyl. $R^{105}$ is a $C_1$-$C_{38}$ monovalent hydrocarbon group which may contain a heteroatom. Suitable heteroatoms include oxygen, nitrogen, sulfur and halogen, with oxygen being preferred. Those monovalent hydrocarbon groups of 6 to 30 carbon atoms are preferred because a high resolution is available in fine pattern formation. The monovalent hydrocarbon groups may be straight, branched or cyclic. Suitable monovalent hydrocarbon groups include straight or branched alkyl groups such as methyl, ethyl, propyl, isopropyl, butyl, isobutyl, s-butyl, t-butyl, pentyl, neopentyl, cyclopentyl, hexyl, heptyl, 2-ethylhexyl, nonyl, undecyl, tridecyl, pentadecyl, heptadecyl, and icosanyl; monovalent saturated cycloaliphatic hydrocarbon groups such as cyclohexyl, 1-adamantyl, 2-adamantyl, 1-adamantylmethyl, norbomyl, norbomylmethyl, tricyclodecanyl, tetracyclododecanyl, tetracyclododecanylmethyl, and dicyclohexylmethyl; monovalent unsaturated aliphatic hydrocarbon groups such as allyl and 3-cyclohexenyl; and aralkyl groups such as benzyl and diphenylmethyl. Suitable heteroatom-containing monovalent hydrocarbon groups include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl. Also included are the foregoing groups in which at least one hydrogen is substituted by a moiety containing a heteroatom such as oxygen, sulfur, nitrogen or halogen, or in which at least one carbon is substituted by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic acid anhydride or haloalkyl moiety.

With respect to the synthesis of the sulfonium salt having an anion of formula (1A'), reference is made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the anion having formula (1A) are shown below, but not limited thereto.

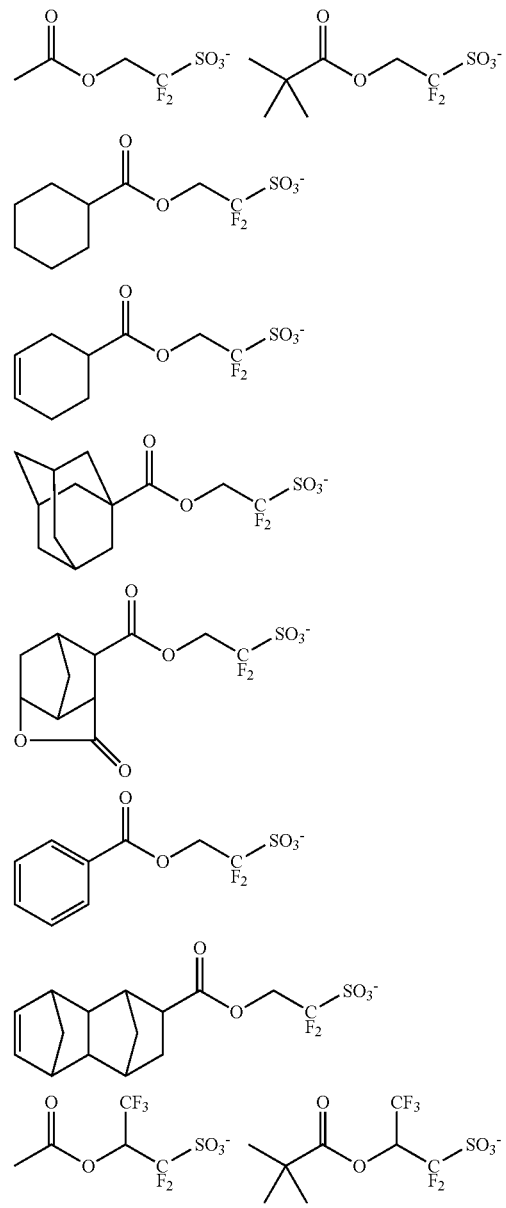

101
-continued
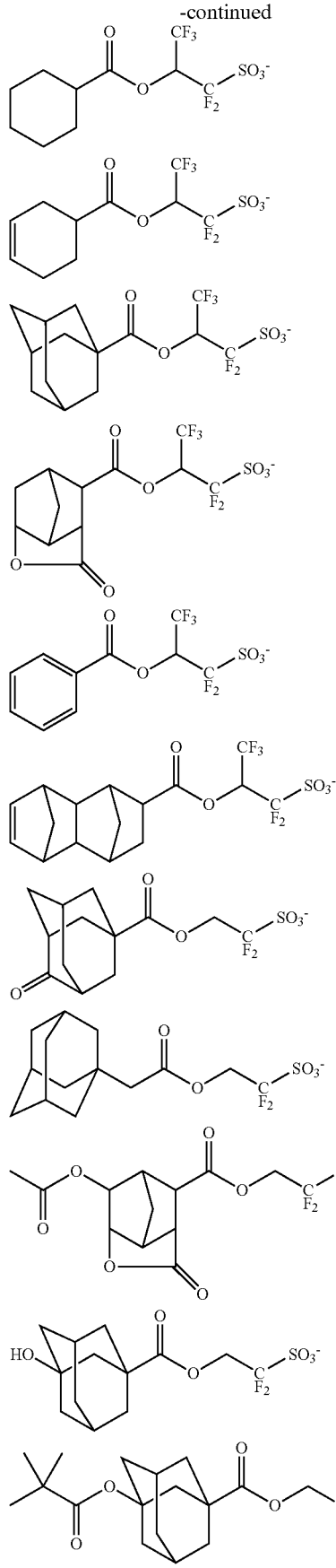
102
-continued
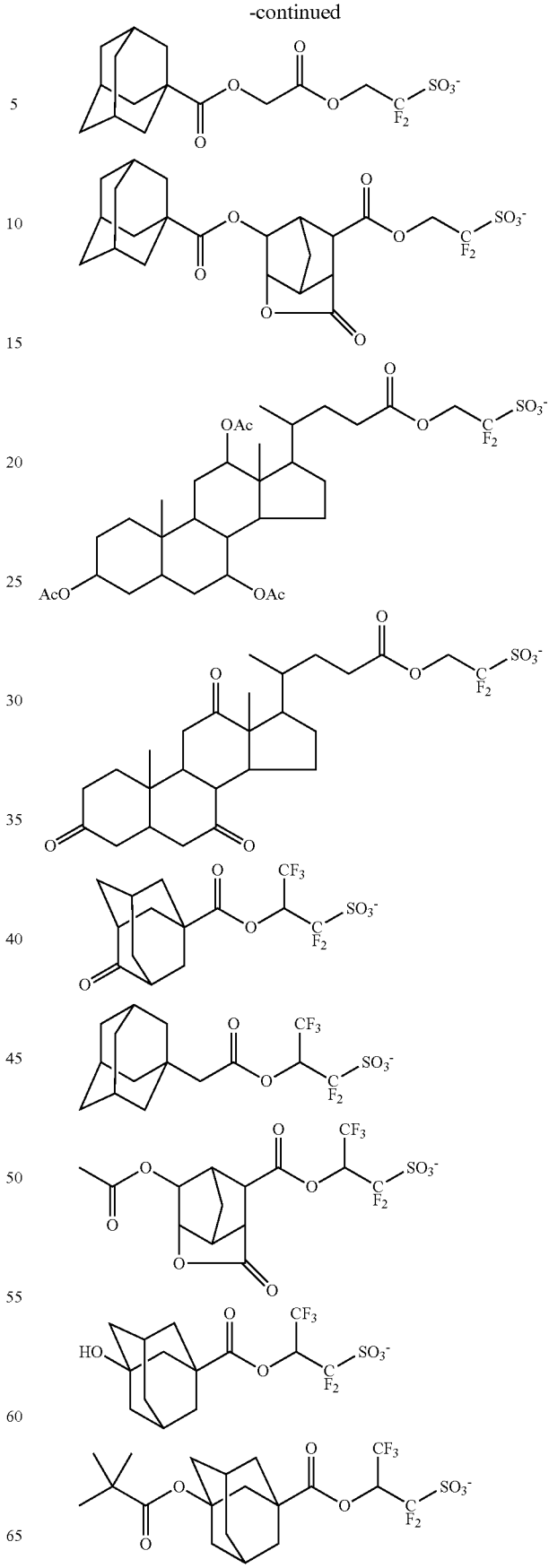

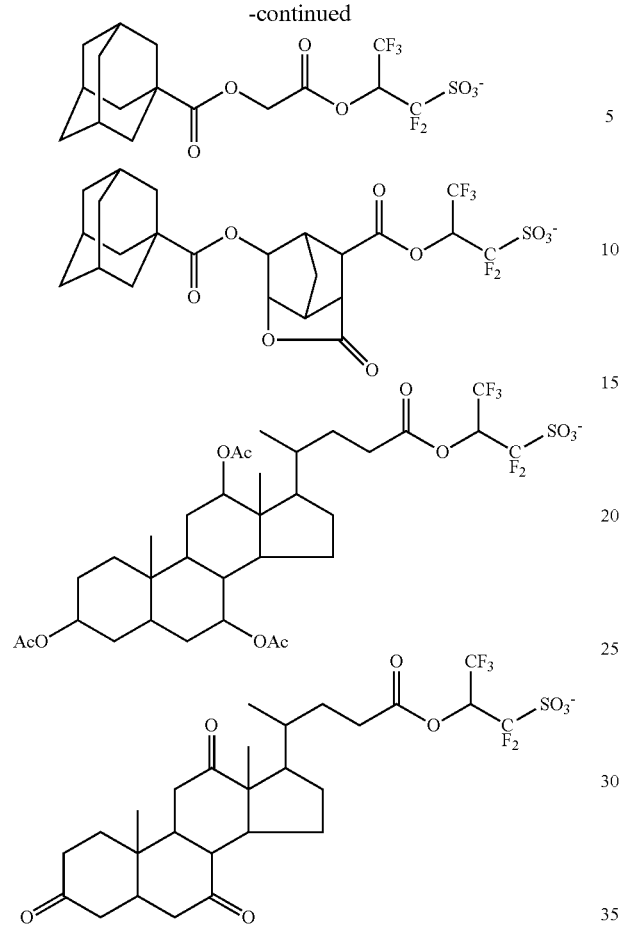

In formula (1B), $R^{fb1}$ and $R^{fb2}$ are each independently fluorine or a $C_1$-$C_{40}$ monovalent hydrocarbon group which may contain a heteroatom. The monovalent hydrocarbon groups may be straight, branched or cyclic, and examples thereof are as exemplified above for $R^{105}$. Preferably $R^{fb1}$ and $R^{fb2}$ each are fluorine or a straight $C_1$-$C_4$ fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and preferably the pair is a fluorinated ethylene or fluorinated propylene group.

In formula (1C), $R^{fc1}$, $R^{fc2}$ and $R^{fc3}$ are each independently fluorine or a $C_1$-$C_{40}$ monovalent hydrocarbon group which may contain a heteroatom. The monovalent hydrocarbon groups may be straight, branched or cyclic, and examples thereof are as exemplified above for $R^{105}$. Preferably $R^{fc1}$, $R^{fc2}$ and $R^{fc3}$ each are fluorine or a straight $C_1$-$C_4$ fluorinated alkyl group. A pair of $R^{fc1}$ and $R^{fc2}$ may bond together to form a ring with the linkage (—$CF_2$—$SO_2$—$C^-$—$SO_2$—$CF_2$—) to which they are attached, and preferably the pair is a fluorinated ethylene or fluorinated propylene group.

In formula (1D), $R^{fd}$ is a $C_1$-$C_{40}$ monovalent hydrocarbon group which may contain a heteroatom. The monovalent hydrocarbon groups may be straight, branched or cyclic, and examples thereof are as exemplified above for $R^{105}$.

With respect to the synthesis of the sulfonium salt having an anion of formula (1D), reference is made to JP-A 2010-215608 and JP-A 2014-133723.

Examples of the anion having formula (1D) are shown below, but not limited thereto.

-continued

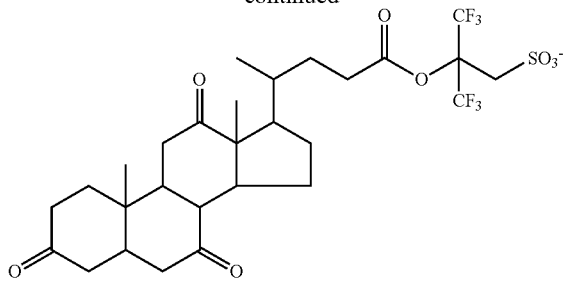

The compound having the anion of formula (1D) has a sufficient acid strength to cleave acid labile groups in the base polymer because it is free of fluorine at α-position of sulfo group, but has two trifluoromethyl groups at β-position. Thus the compound is a useful PAG.

Further, compounds having the formula (2) are also useful as the PAG.

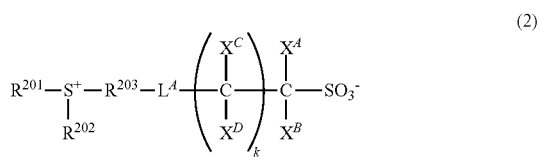

(2)

In formula (2), $R^{201}$ and $R^{202}$ are each independently a $C_1$-$C_{30}$ monovalent hydrocarbon group which may contain a heteroatom. $R^{203}$ is a $C_1$-$C_{30}$ divalent hydrocarbon group which may contain a heteroatom. Any two of $R^{201}$, $R^{202}$ and $R^{203}$ may bond together to form a ring with the sulfur atom to which they are attached. $L^A$ is a single bond or ether bond, or a $C_1$-$C_{20}$ divalent hydrocarbon group which may contain a heteroatom. $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or to trifluoromethyl, and k is an integer of 0 to 3.

The monovalent hydrocarbon groups may be straight, branched or cyclic and include straight or branched alkyl groups such as methyl, ethyl, propyl, isopropyl, n-butyl, s-butyl, t-butyl, n-pentyl, t-pentyl, n-hexyl, n-octyl, n-nonyl, n-decyl, and 2-ethylhexyl; monovalent saturated cyclic hydrocarbon groups such as cyclopentyl, cyclohexyl, cyclopentylmethyl, cyclopentylethyl, cyclopentylbutyl, cyclohexylmethyl, cyclohexylethyl, cyclohexylbutyl, norbornyL oxanorbornyl, tricyclo[5.2.1.0$^{2,6}$]decanyl, and adamantyl; and aryl groups such as phenyl, naphthyl and anthracenyl. Also included are the foregoing groups in which at least one hydrogen is substituted by a heteroatom such as oxygen, sulfur, nitrogen or halogen, or in which at least one carbon is substituted by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic acid anhydride or haloalkyl moiety.

The divalent hydrocarbon groups may be straight, branched or cyclic, and examples thereof include linear or branched alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic divalent hydrocarbon groups such as cyclopentanediyl, cyclohexanediyl, norbornanediyl, and adamantanediyl, and unsaturated cyclic divalent hydrocarbon groups such as phenylene and naphthylene. Also included are the foregoing groups in which at least one hydrogen atom is substituted by an alkyl group such as methyl, ethyl, propyl, n-butyl or t-butyl, or in which at least one hydrogen atom is substituted by a moiety containing a heteroatom such as oxygen, sulfur, nitrogen or halogen, or in which at least one carbon atom is substituted by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic acid anhydride or haloalkyl moiety. Suitable heteroatoms include oxygen, nitrogen, sulfur and halogen, with oxygen being preferred.

Of the PAGs having formula (2), those having formula (2') are preferred.

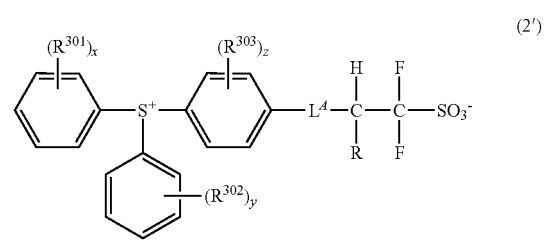

(2')

In formula (2'), $L^A$ is as defined above. R is hydrogen or trifluoromethyl, preferably trifluoromethyl. $R^{301}$, $R^{302}$ and $R^{303}$ are each independently hydrogen or a $C_1$-$C_{20}$ monovalent hydrocarbon group which may contain a heteroatom. The monovalent hydrocarbon groups may be straight, branched or cyclic, and examples thereof are as exemplified above for $R^{105}$. The subscripts x and y each are an integer of 0 to 5, and z is an integer of 0 to 4.

Examples of the PAG having formula (2) are shown below, but not limited thereto. Herein R is as defined above.

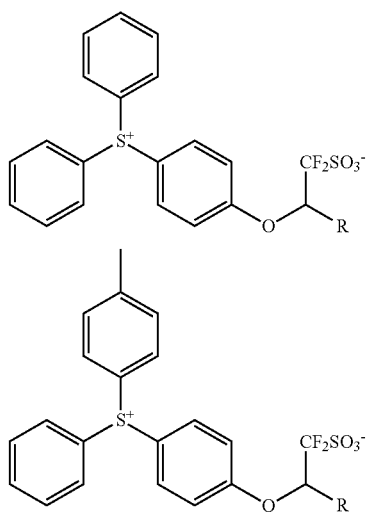

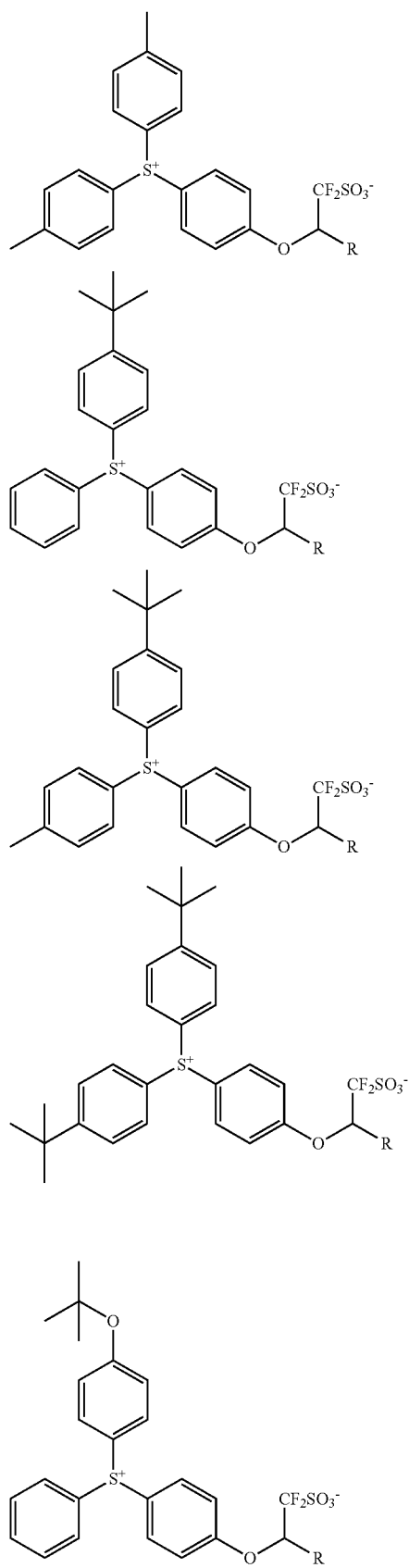
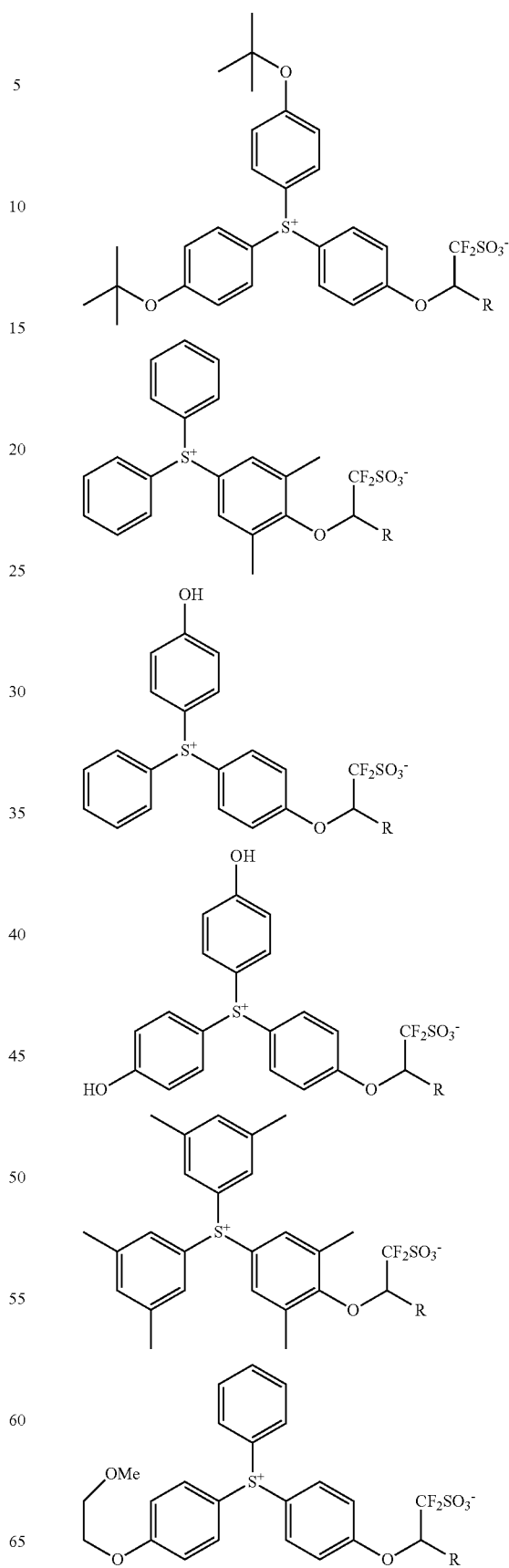

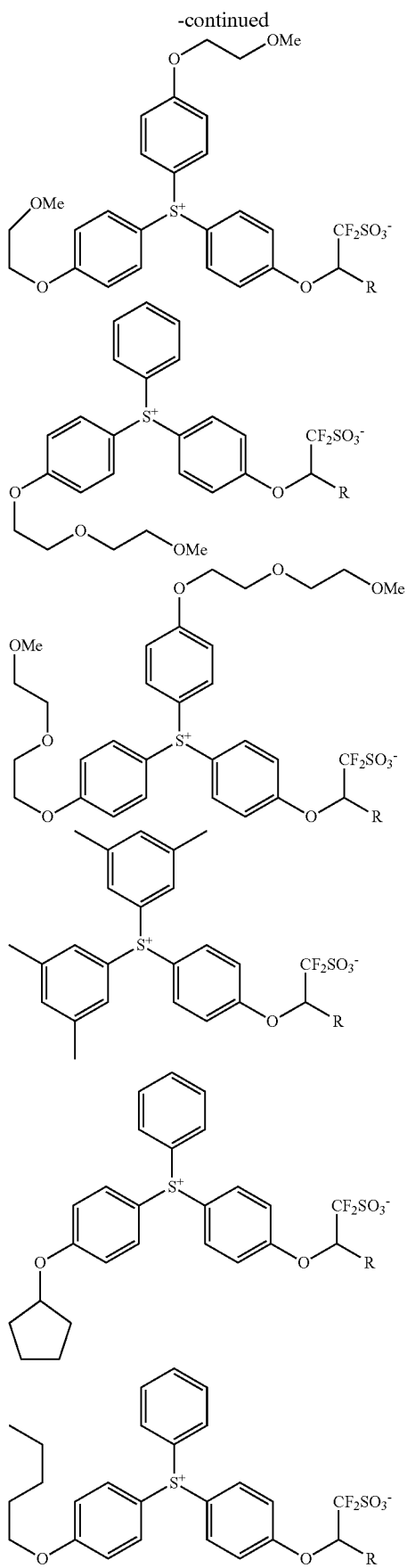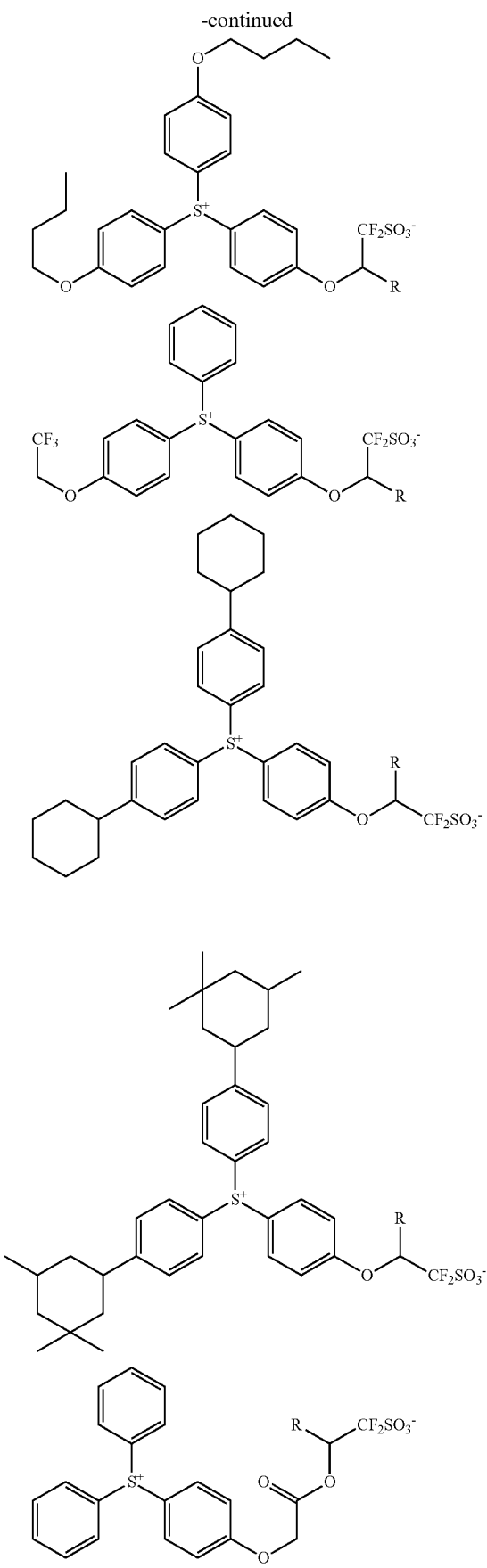

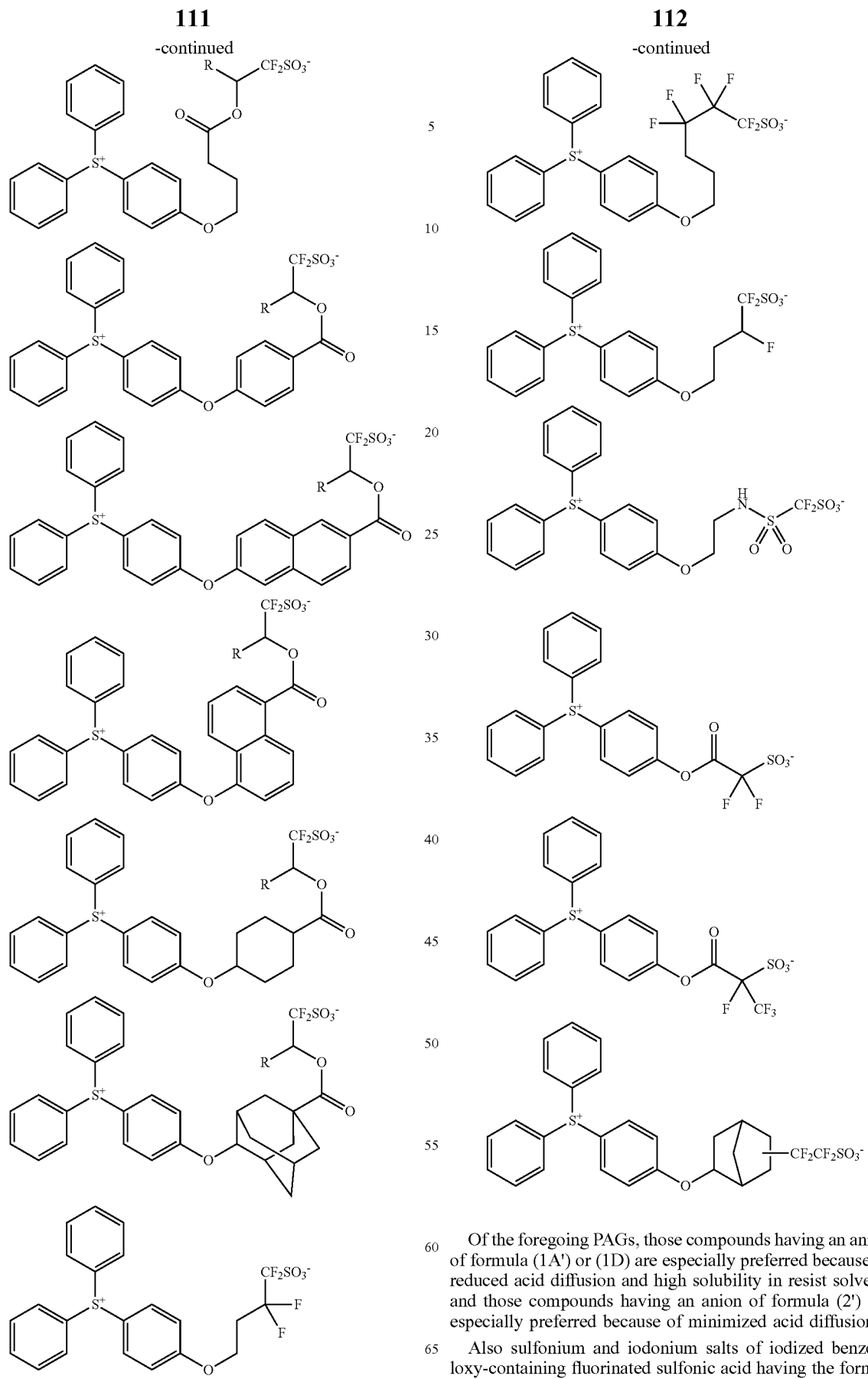

Of the foregoing PAGs, those compounds having an anion of formula (1A') or (1D) are especially preferred because of reduced acid diffusion and high solubility in resist solvent, and those compounds having an anion of formula (2') are especially preferred because of minimized acid diffusion.

Also sulfonium and iodonium salts of iodized benzoyloxy-containing fluorinated sulfonic acid having the formulae (3-1) and (3-2) are useful as the PAG.

(3-1)

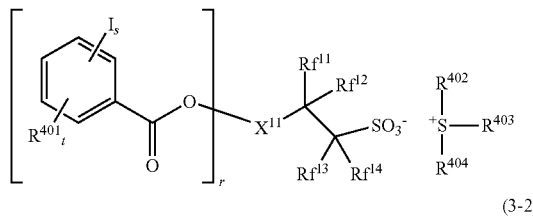

(3-2)

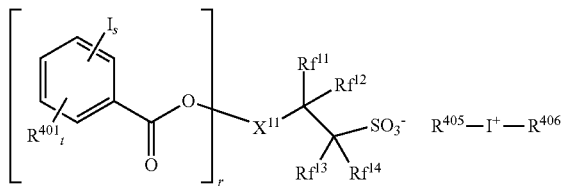

In formulae (3-1) and (3-2), $R^{401}$ is hydrogen, hydroxyl, carboxyl, nitro, cyano, fluorine, chlorine, bromine, amino group, or a $C_1$-$C_{20}$ alkyl, $C_1$-$C_{20}$ alkoxy, $C_2$-$C_{20}$ alkoxycarbonyl, $C_2$-$C_{20}$ acyloxy or $C_1$-$C_4$ alkylsulfonyloxy group, which may contain fluorine, chlorine, bromine, hydroxy, amino or alkoxy moiety, or —$NR^{407}$—$C(=O)$—$R^{408}$ or —$NR^{407}C(=O)$—O—$R^{408}$, wherein $R^{407}$ is hydrogen, or a $C_1$-$C_6$ alkyl group which may contain halogen, hydroxy, alkoxy, acyl or acyloxy moiety, $R^{408}$ is a $C_1$-$C_{16}$ alkyl or $C_2$-$C_{16}$ alkenyl group, or $C_6$-$C_{12}$ aryl group, which may contain halogen, hydroxy, alkoxy, acyl or acyloxy moiety.

$X^{11}$ is a single bond or a $C_1$-$C_{20}$ divalent linking group when r=1, or a $C_1$-$C_{20}$ tri- or tetravalent linking group when r=2 or 3, the linking group optionally containing an oxygen, sulfur or nitrogen atom. $Rf^{11}$ to $Rf^{14}$ are each independently hydrogen, fluorine or trifluoromethyl, at least one of $Rf^{11}$ to $Rf^{14}$ being fluorine or trifluoromethyl, or $Rf^{11}$ and $Rf^{12}$, taken together, may form a carbonyl group.

$R^{402}$, $R^{403}$, $R^{404}$, $R^{405}$ and $R^{406}$ are each independently a $C_1$-$C_{12}$ alkyl group, $C_2$-$C_{12}$ alkenyl group, $C_2$-$C_{12}$ alkynyl group, $C_6$-$C_{20}$ aryl group, $C_7$-$C_{12}$ aralkyl group or $C_7$-$C_{12}$ aryloxyalkyl group, in which at least one hydrogen (one or more or even all hydrogen atoms) may be substituted by a hydroxy, carboxy, halogen, cyano, oxo, amide, nitro, sultone, sulfone or sulfonium salt-containing moiety, or in which at least one carbon may be substituted by an ether, ester, carbonyl, carbonate or sulfonic acid ester moiety. $R^{402}$ and $R^{403}$ may bond together to form a ring with the sulfur atom to which they are attached. The subscript r is an integer of 1 to 3, s is an integer of 1 to 5, and t is an integer of 0 to 3.

The foregoing alkyl, alkoxy, alkoxycarbonyl, acyloxy, alkylsulfonyloxy, alkenyl and alkynyl groups may be straight, branched or cyclic.

Further, sulfonium and iodonium salts of iodized benzene-containing fluorinated sulfonic acid having the formulae (3-3) and (3-4) are useful as the PAG.

(3-3)

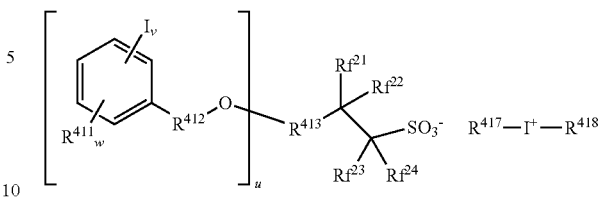

(3-4)

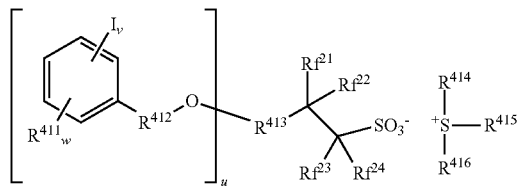

In formulae (3-3) and (3-4). $R^{411}$ is each independently a hydroxyl, $C_1$-$C_{20}$ alkyl or alkoxy group, $C_2$-$C_{20}$ acyl or acyloxy group, fluorine, chlorine, bromine, amino, or alkoxycarbonyl-substituted amino group. $R^{412}$ is each independently a single bond or $C_1$-$C_4$ alkylene group. $R^{413}$ is a single bond or $C_1$-$C_{20}$ divalent linking group when u=1, or a $C_1$-$C_{20}$ tri- or tetravalent linking group when u=2 or 3, the linking group optionally containing an oxygen, sulfur or nitrogen atom.

$Rf^{21}$ to $Rf^{24}$ are each independently hydrogen, fluorine or trifluoromethyl, at least one of $Rf^{21}$ to $Rf^{24}$ being fluorine or trifluoromethyl, or $Rf^{21}$ and $Rf^{22}$, taken together, may form a carbonyl group.

$R^{414}$, $R^{415}$, $R^{416}$, $R^{417}$ and $R^{418}$ are each independently a $C_1$-$C_{12}$ alkyl group, $C_2$-$C_{12}$ alkenyl group, $C_6$-$C_{20}$ aryl group or $C_7$-$C_{12}$ aralkyl or aryloxoalkyl group, in which at least one hydrogen (one or more or even all hydrogen atoms) may be substituted by a hydroxyl, carboxyl, halogen, cyano, oxo, amide, nitro, sultone, sulfone, or sulfonium salt-containing moiety, or in which at least one carbon may be substituted by an ether, ester, carbonyl, carbonate or sulfonic acid ester moiety. $R^{414}$ and $R^{415}$ may bond together to form a ring to with the sulfur atom to which they are attached. The subscript u is an integer of 1 to 3, v is an integer of 1 to 5, and w is an integer of 0 to 3.

The foregoing alkyl, alkoxy, acyl, acyloxy and alkenyl groups may be straight, branched or cyclic.

The cation moiety in the sulfonium salt having formula (3-1) or (3-3) is as exemplified above for the cation moiety in formula (d4). The cation moiety in the iodonium salt having formula (3-2) or (3-4) is as exemplified above for the cation moiety in formula (d5).

Examples of the anion moiety in the onium salts having formulae (3-1) to (3-4) are given below, but not limited thereto.

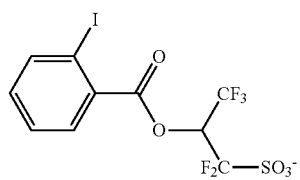

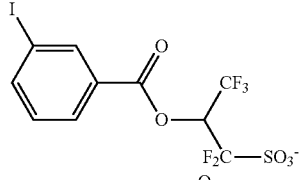

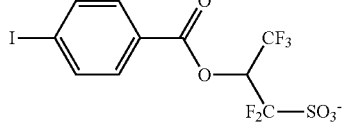

-continued
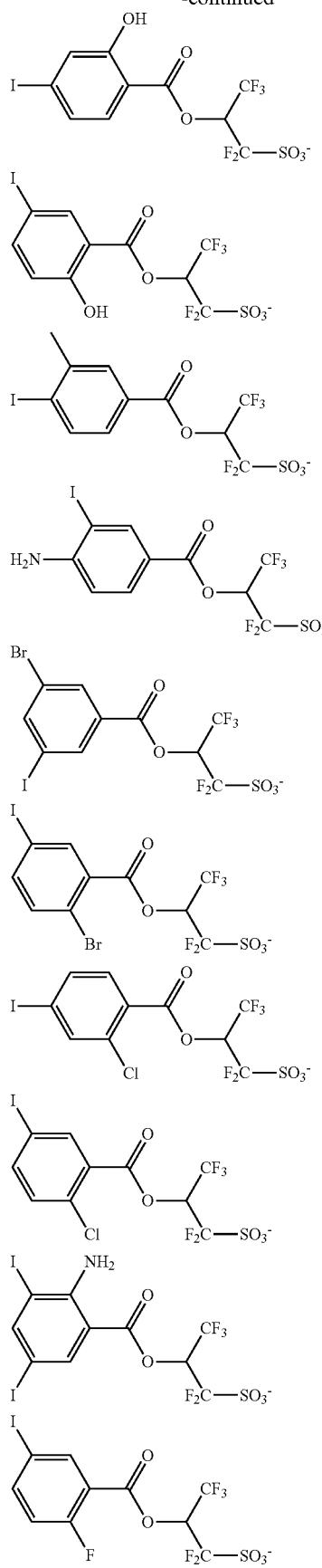
-continued
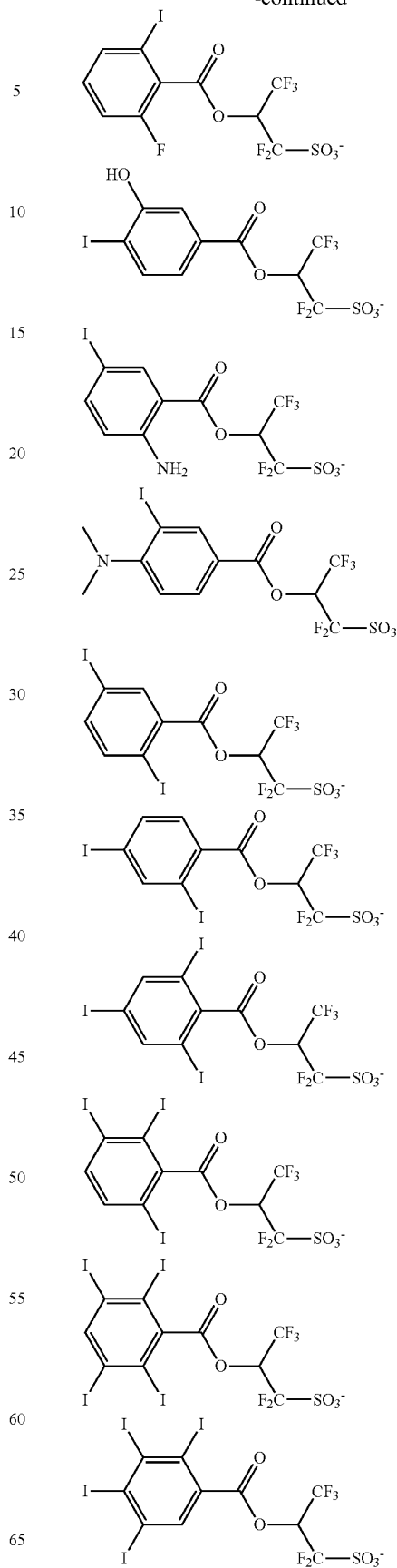

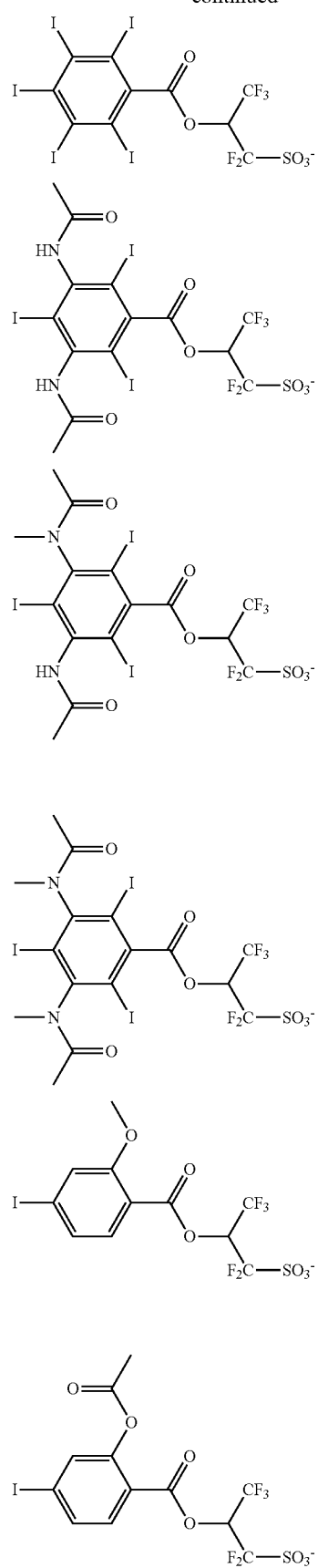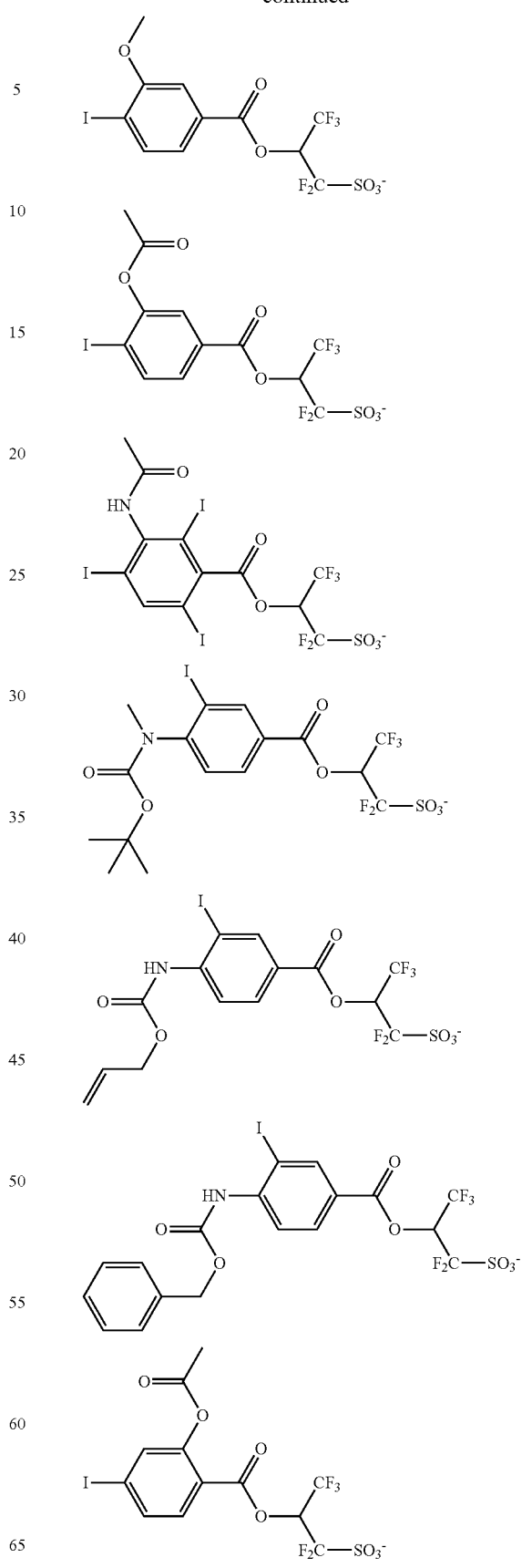

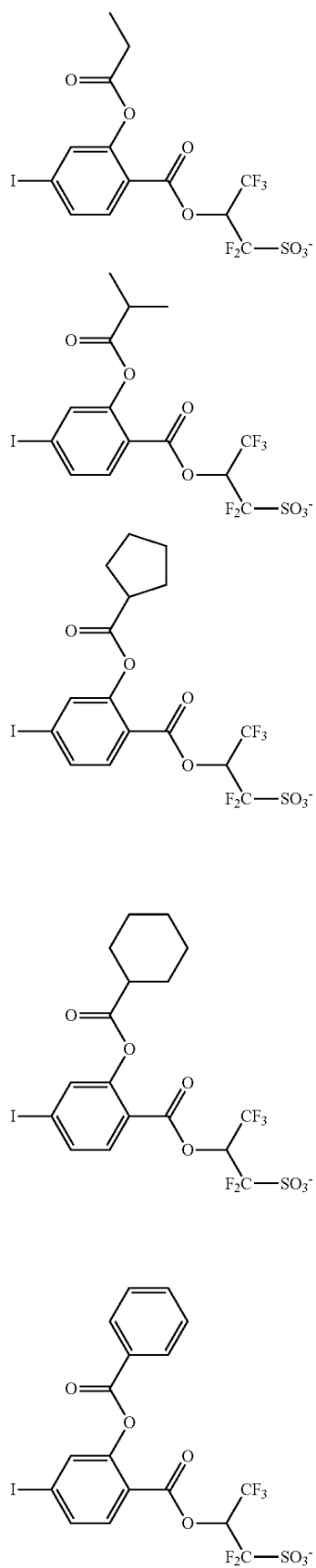
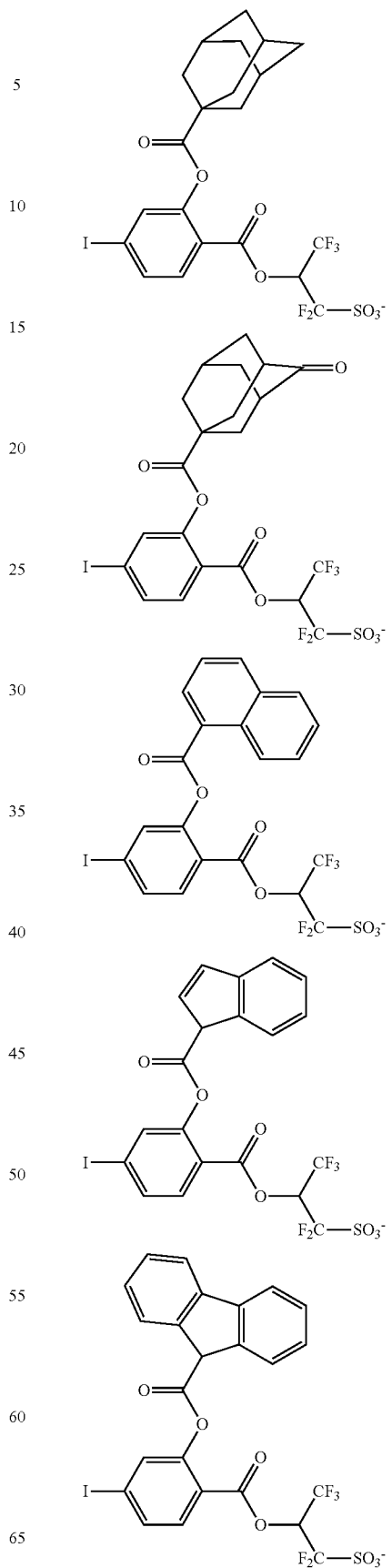

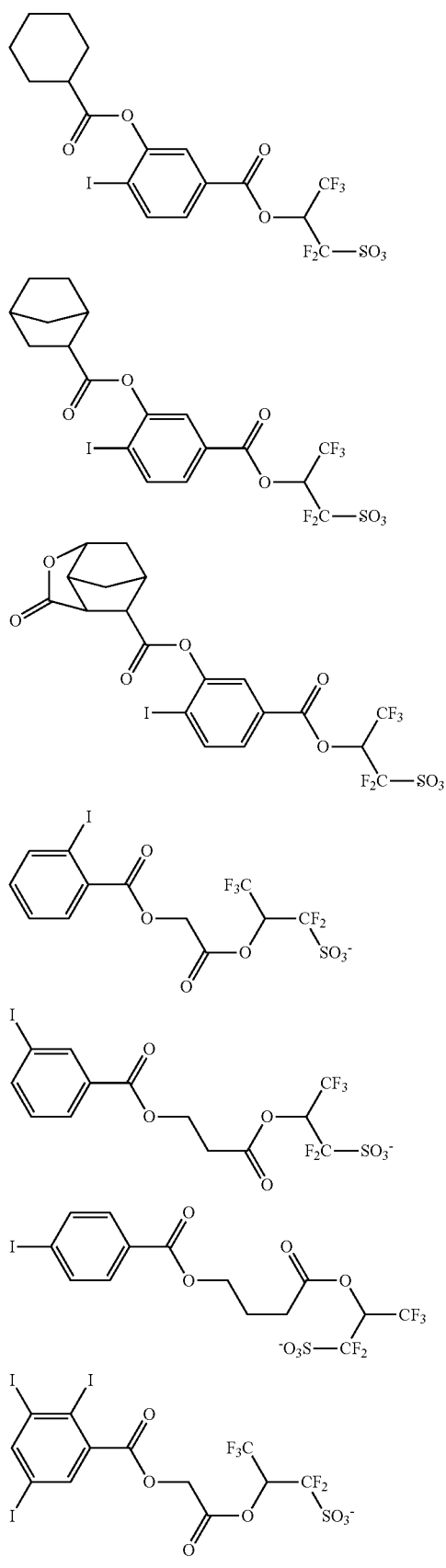
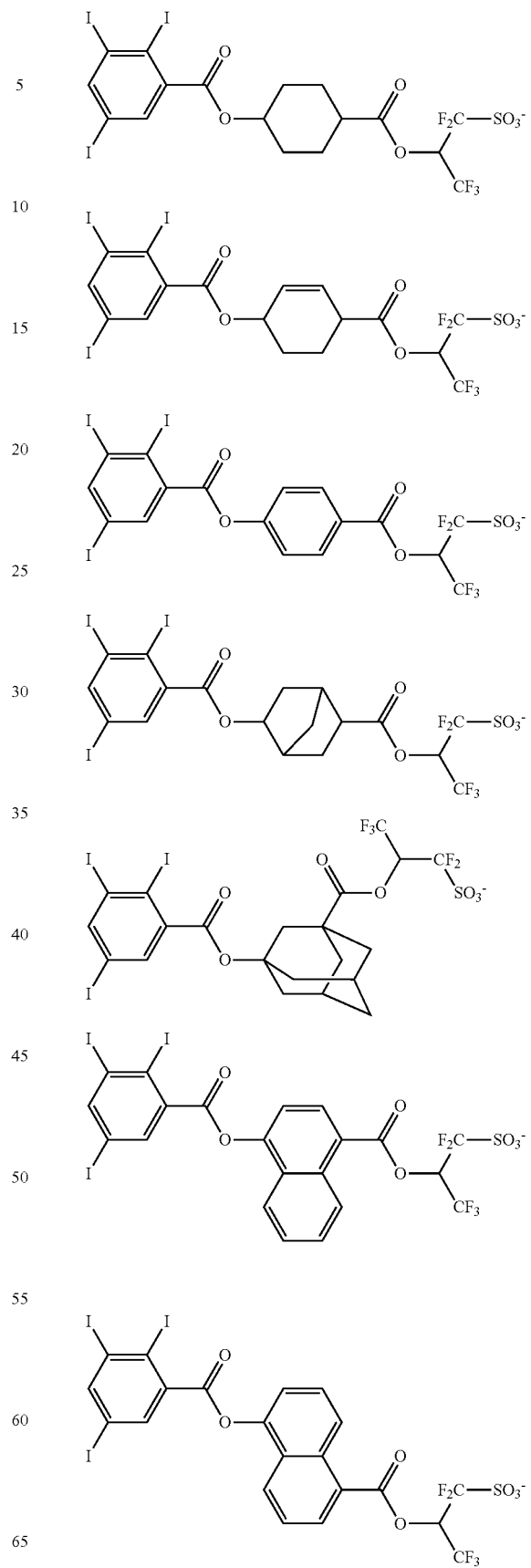

123
-continued
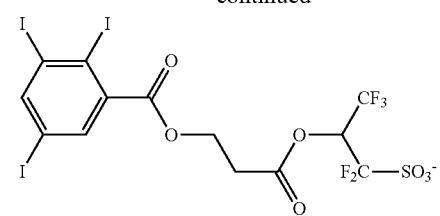
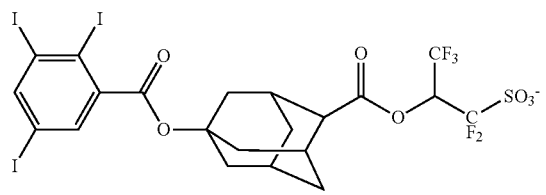
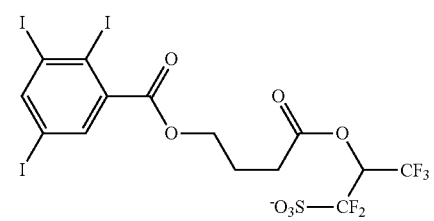
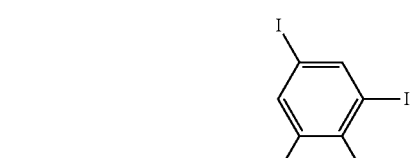
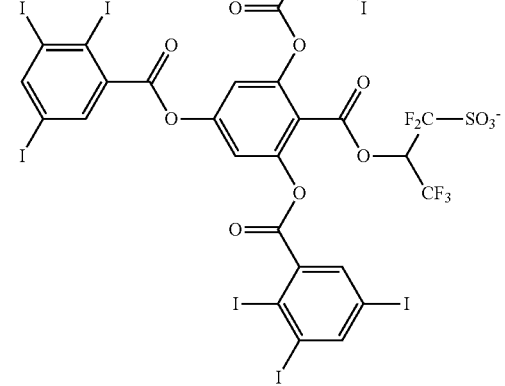
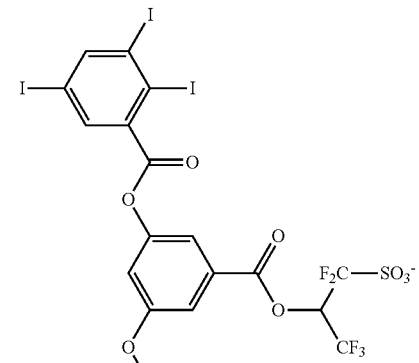
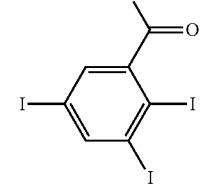
124
-continued
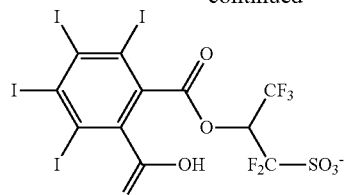
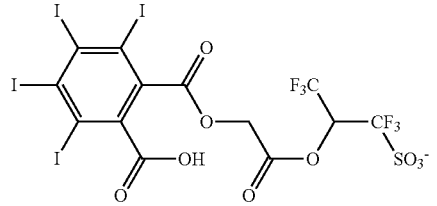
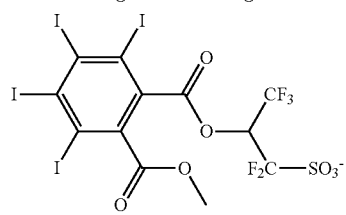
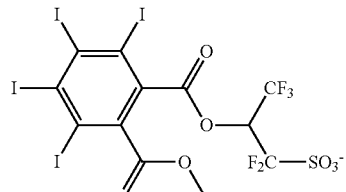
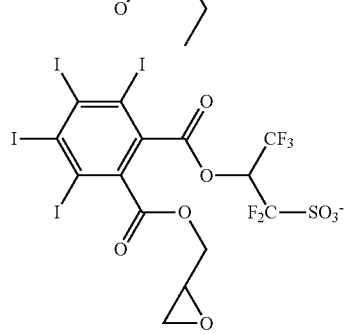
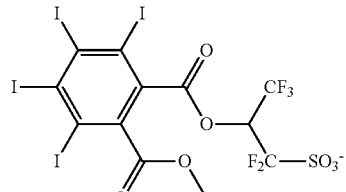
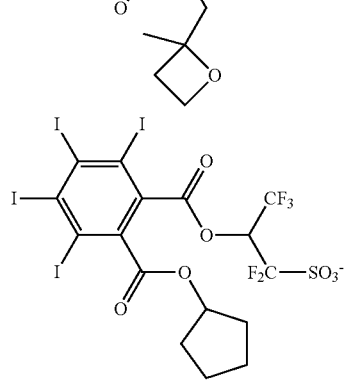

-continued
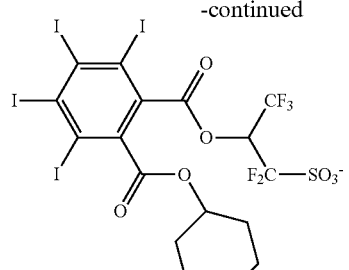
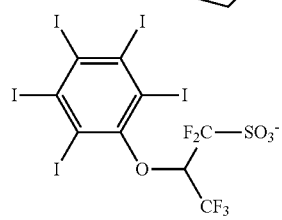
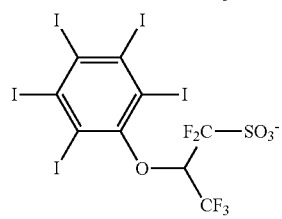
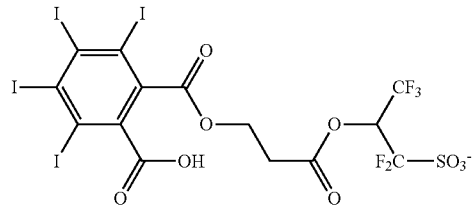
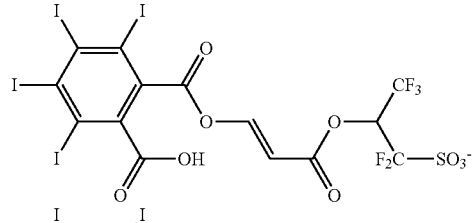
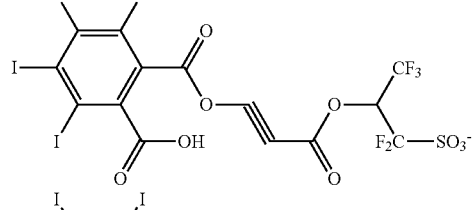
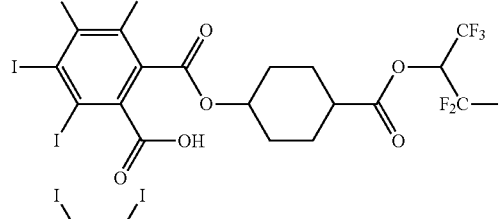
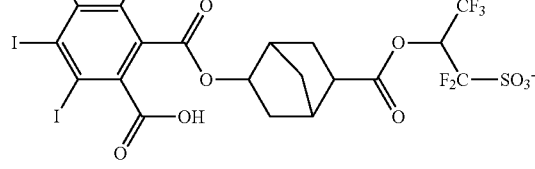
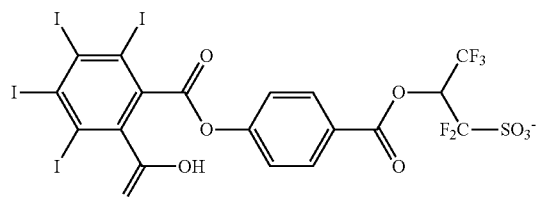
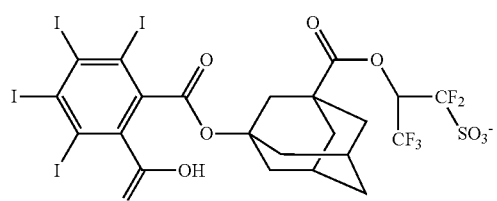
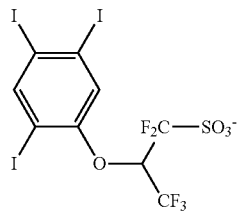
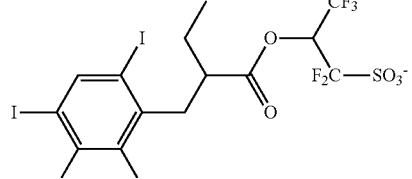
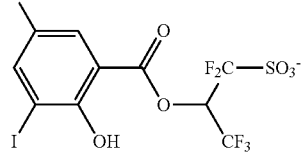
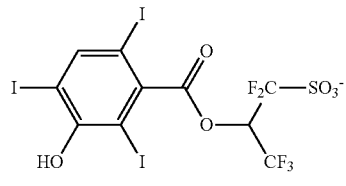
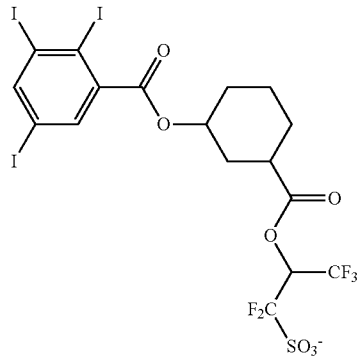

127
-continued
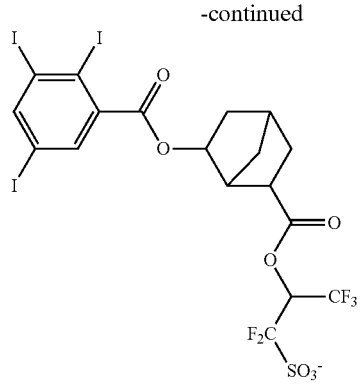
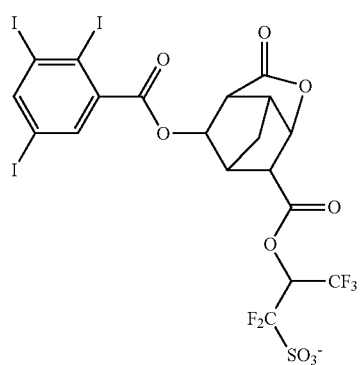
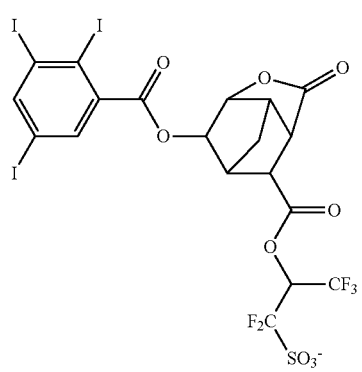
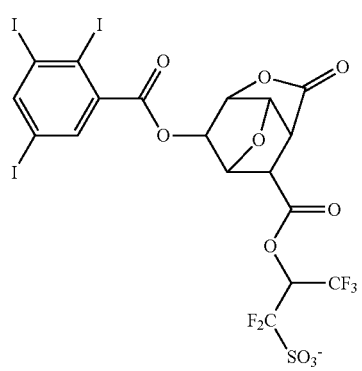
128
-continued
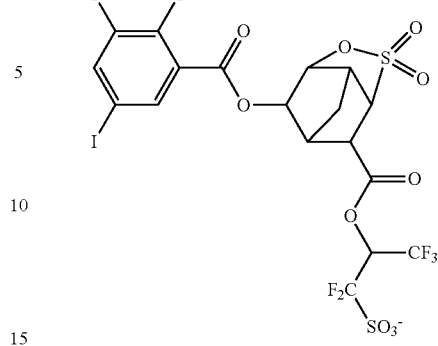
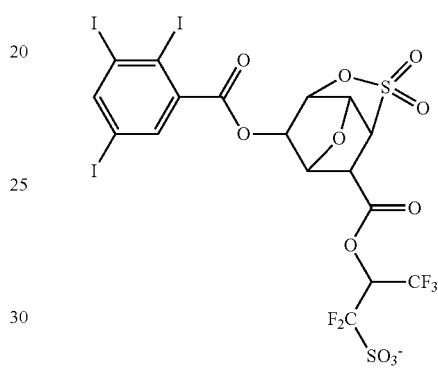
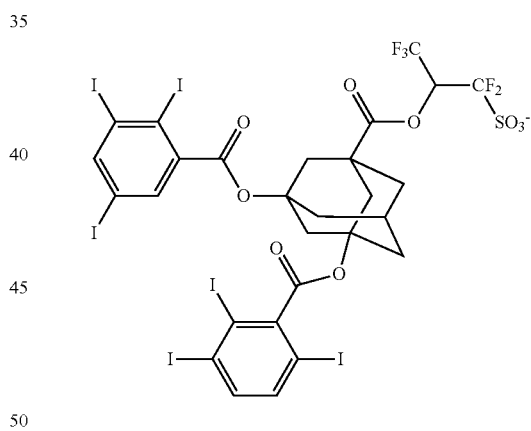
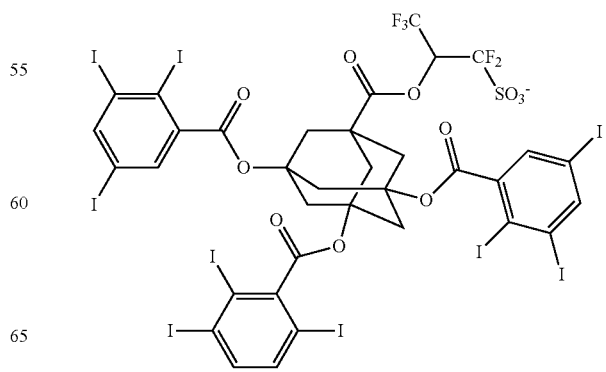

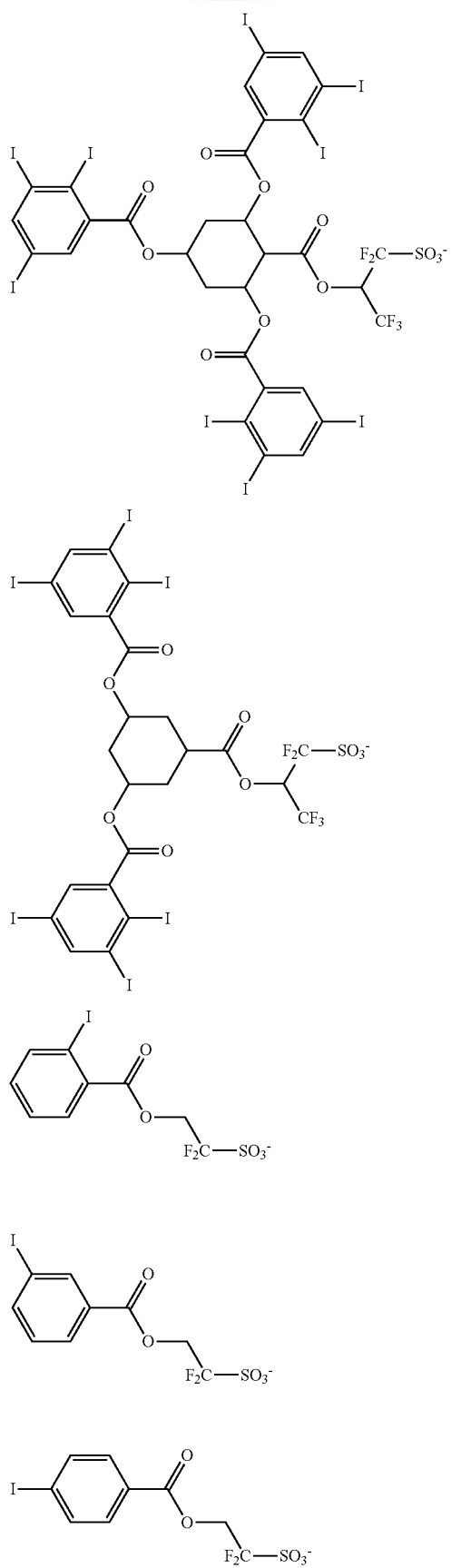
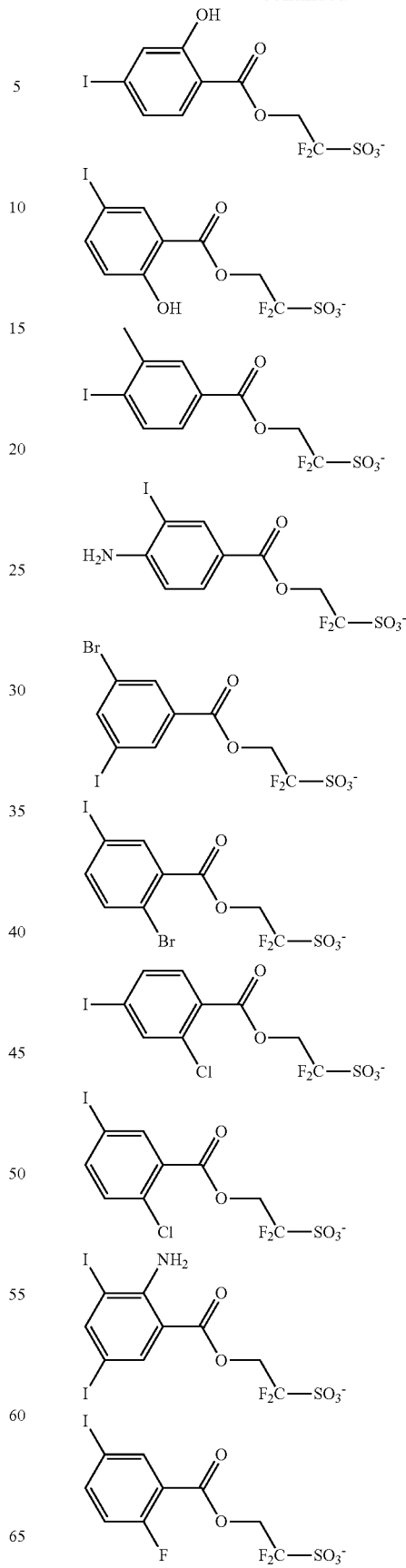

131
-continued
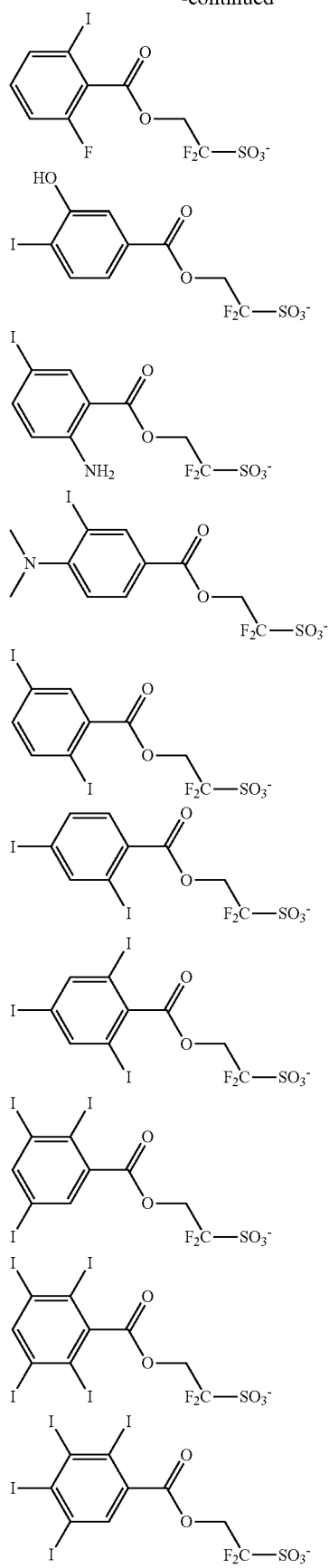
132
-continued
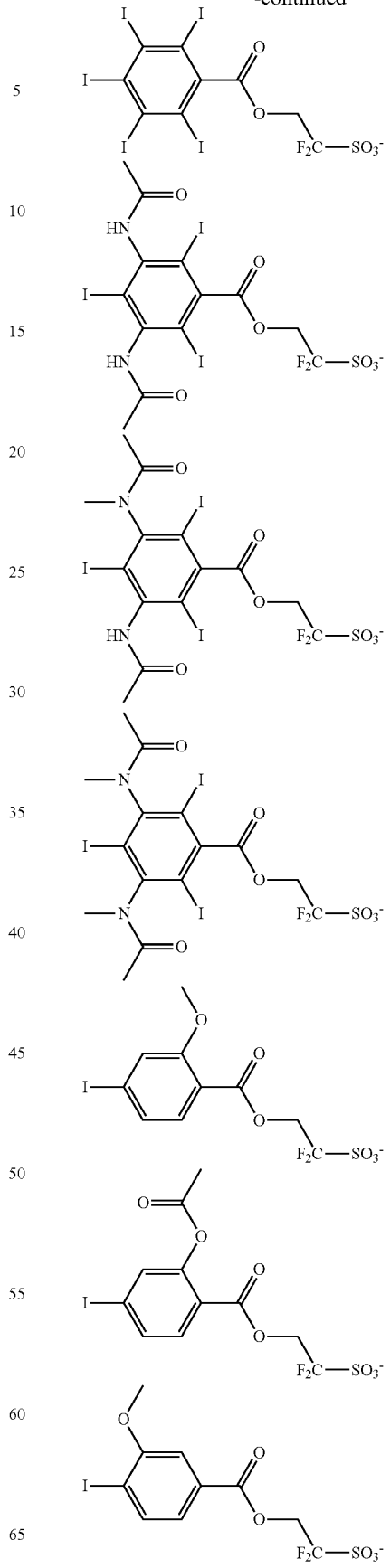

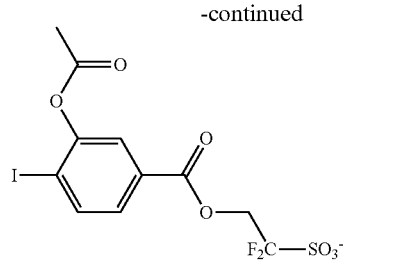
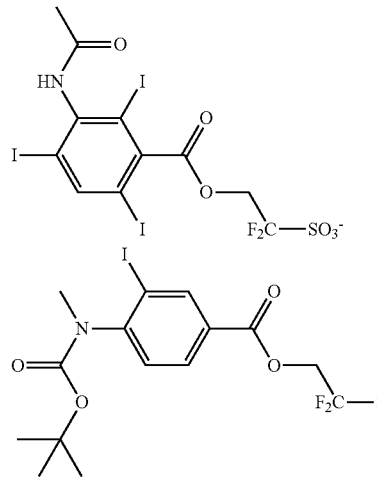
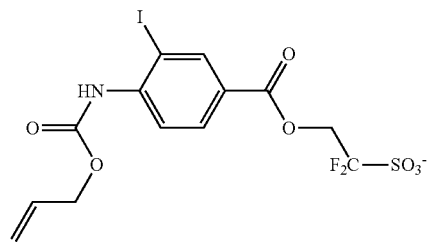
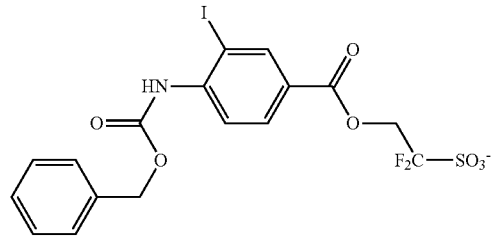
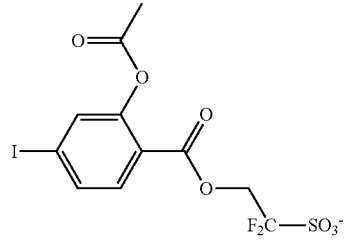
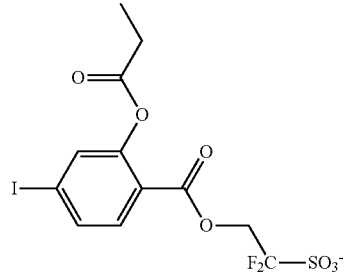
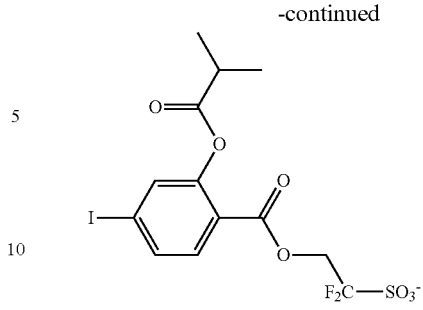
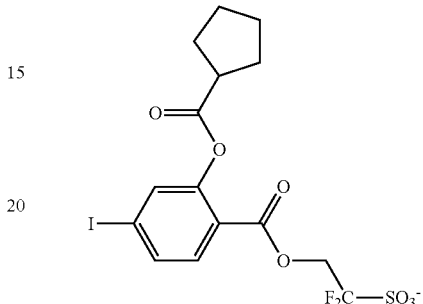
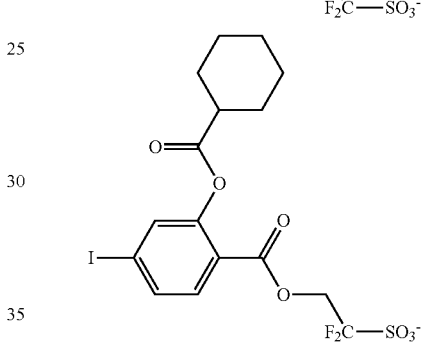
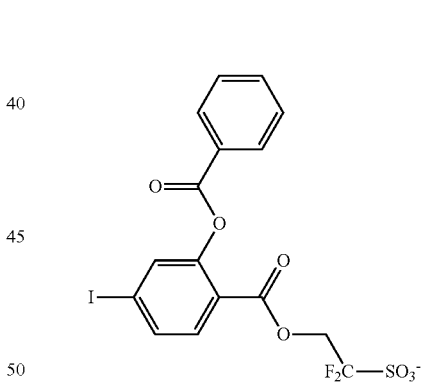
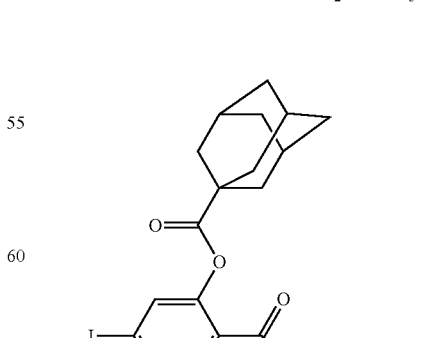
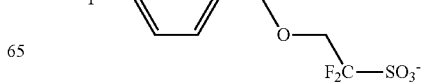

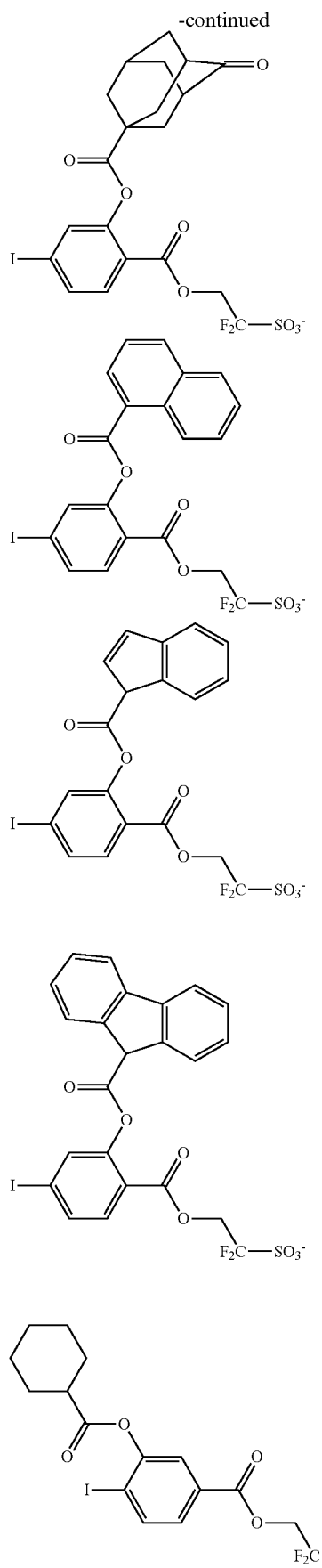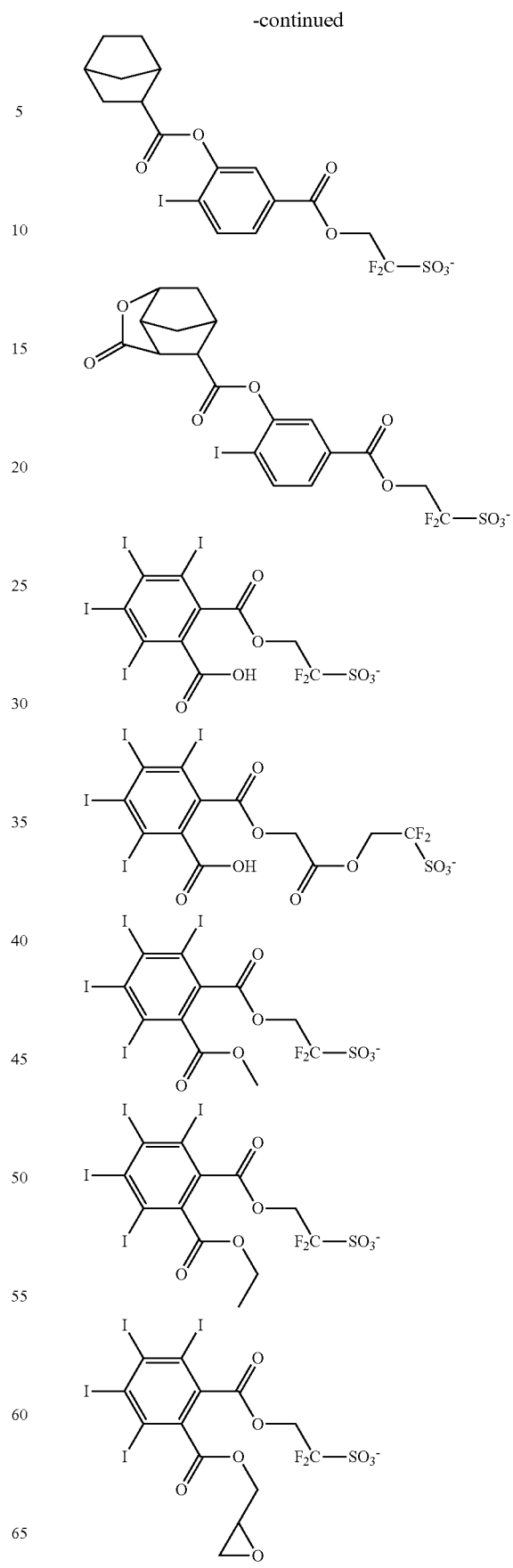

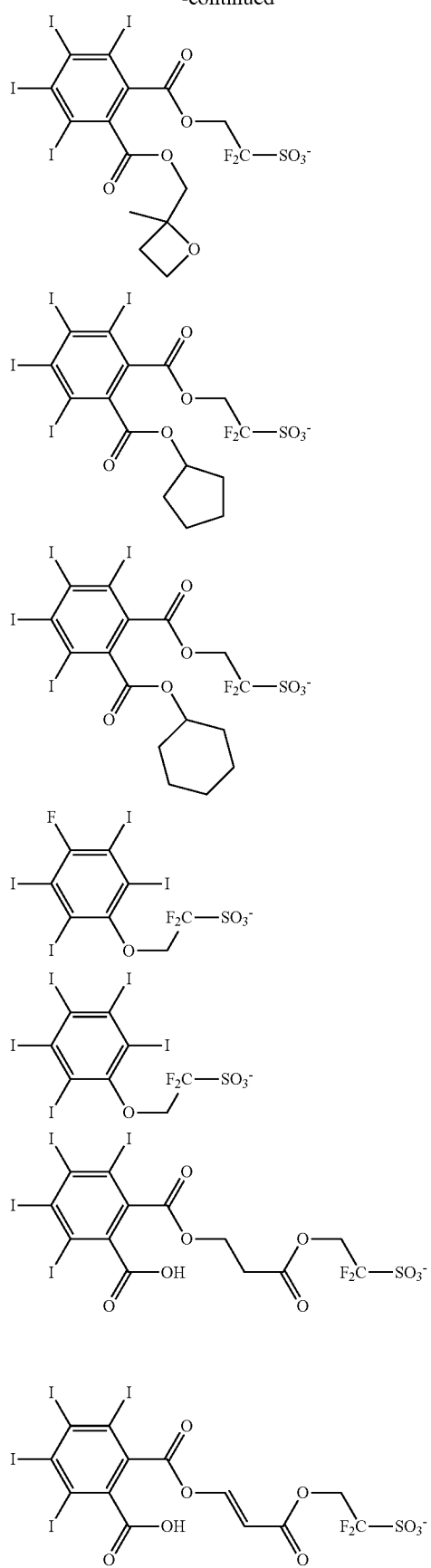
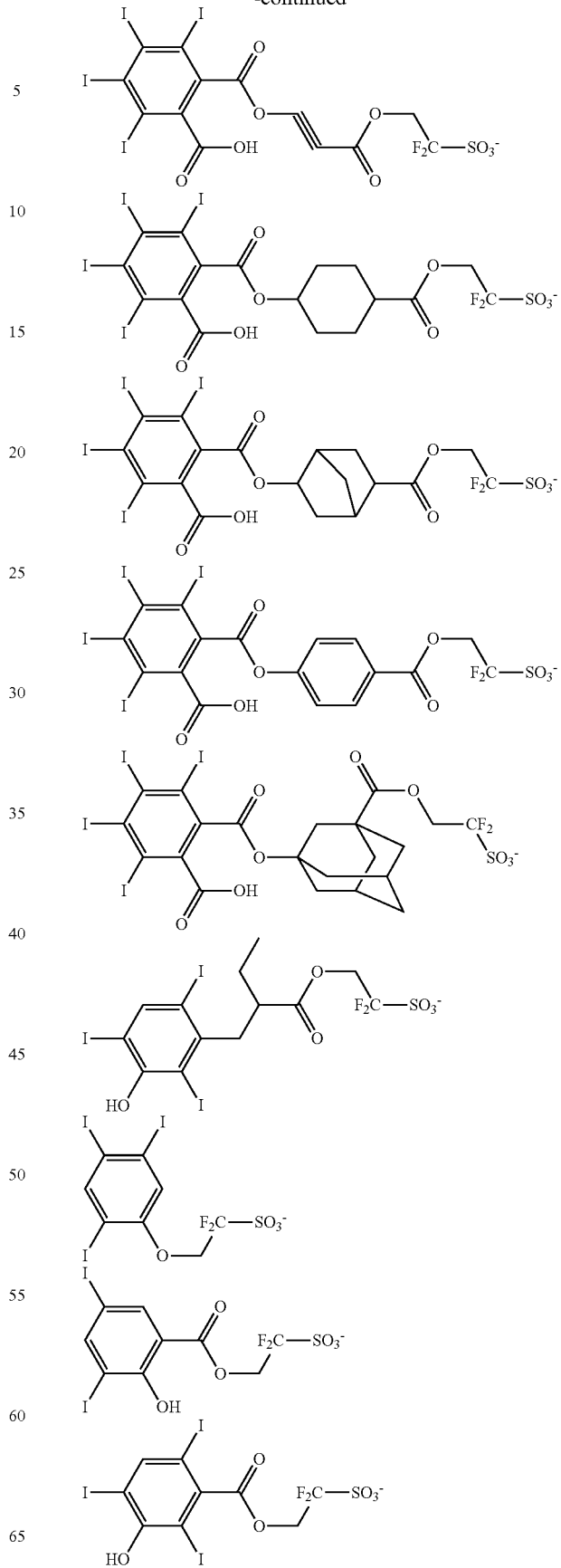

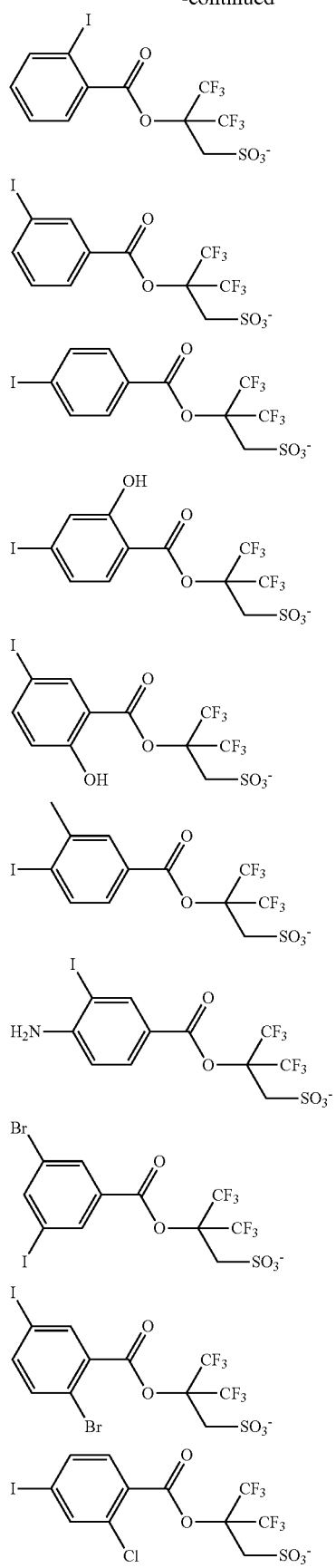
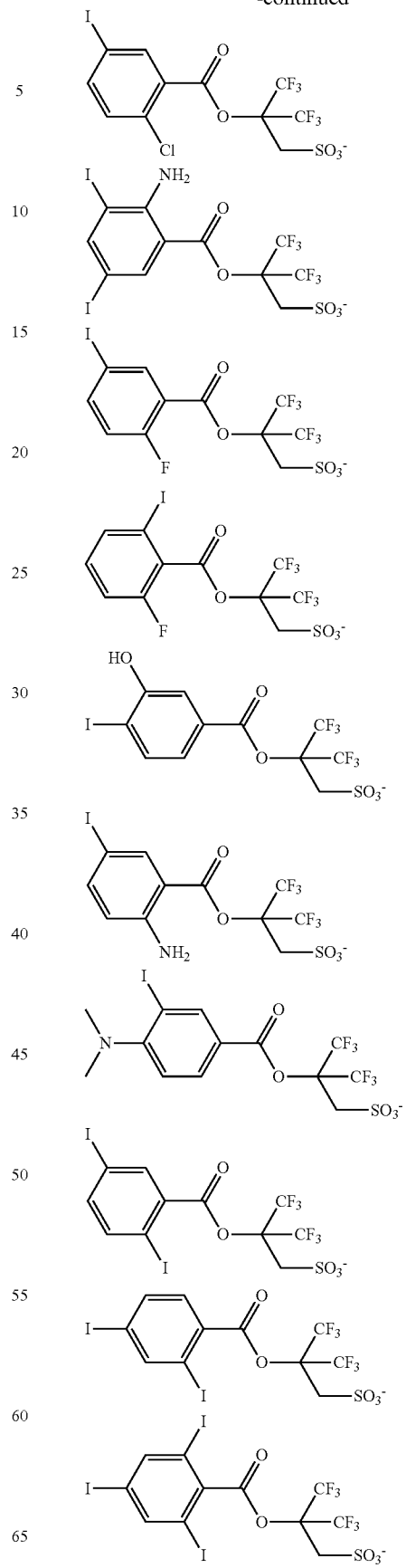

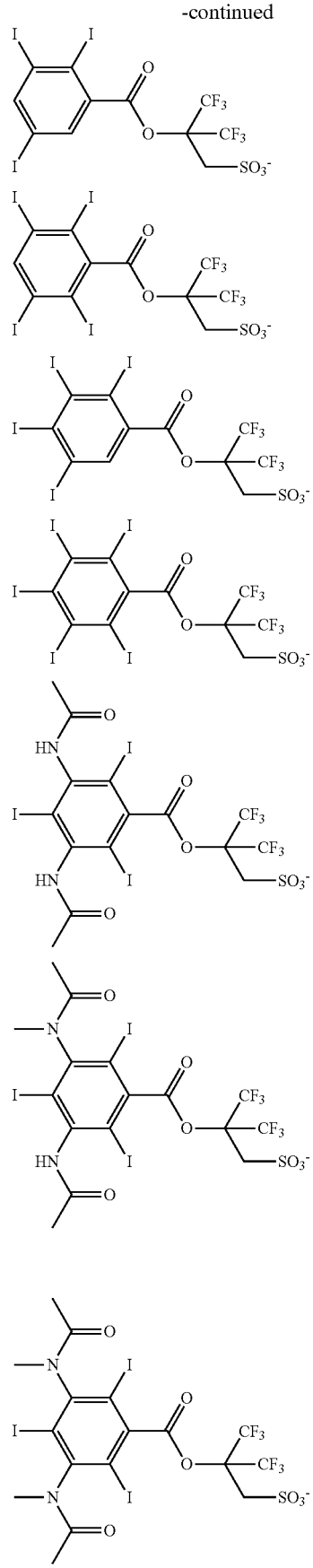
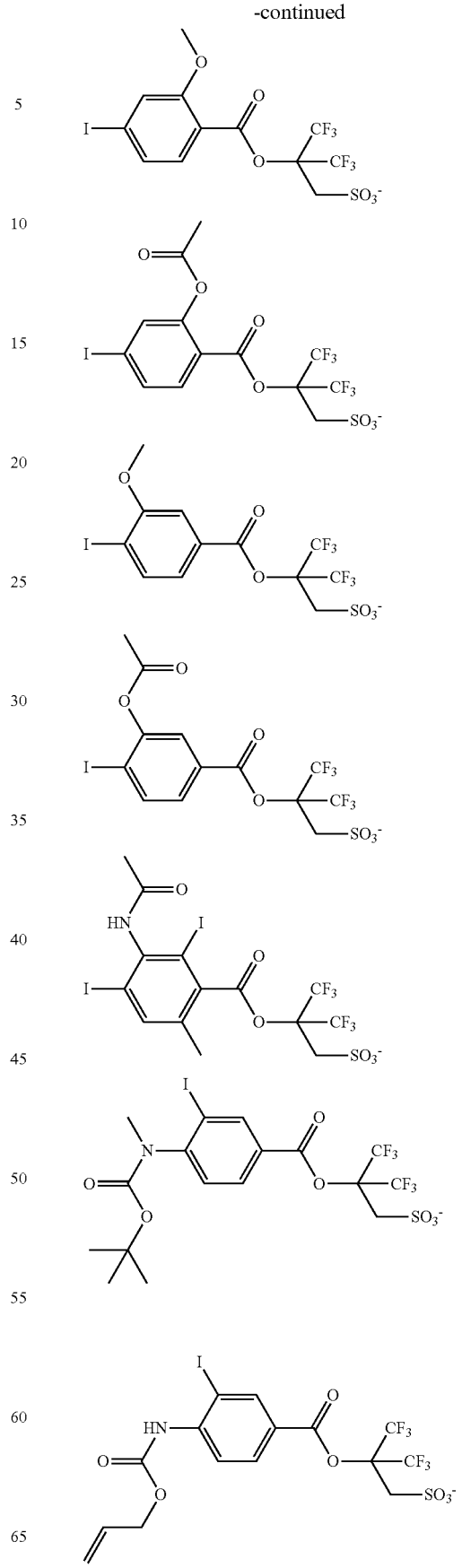

143
-continued
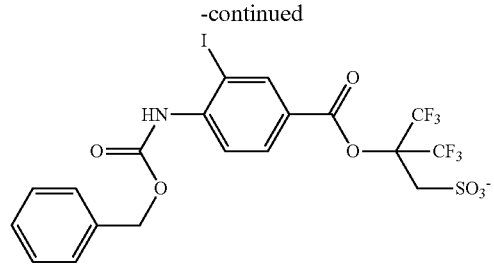
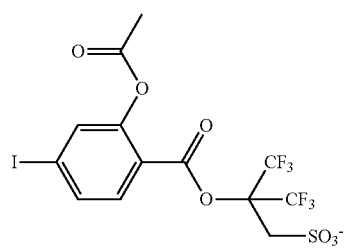
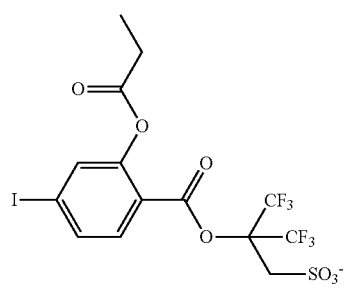
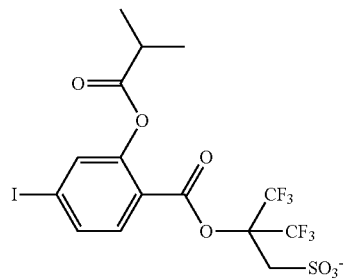
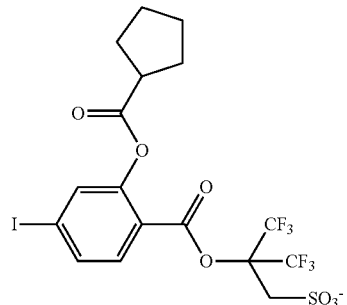
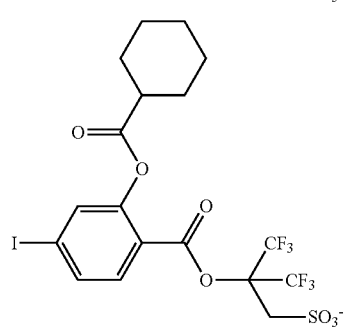
144
-continued
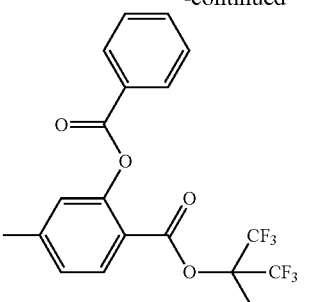
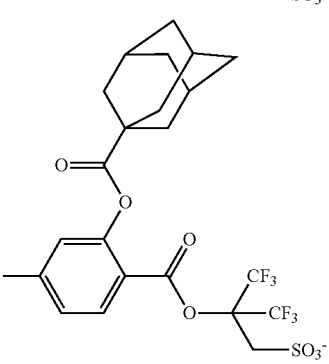
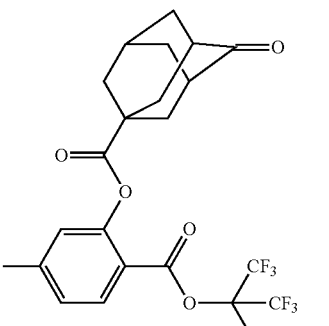
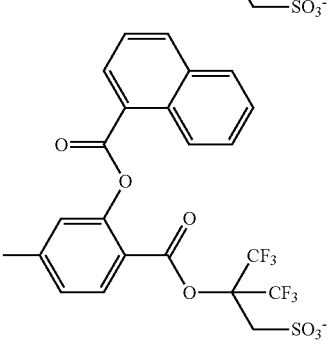
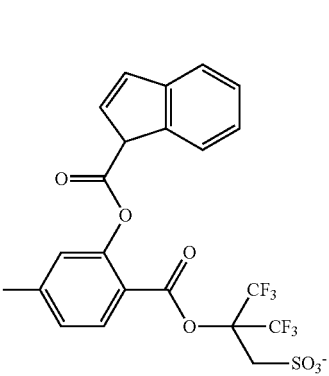

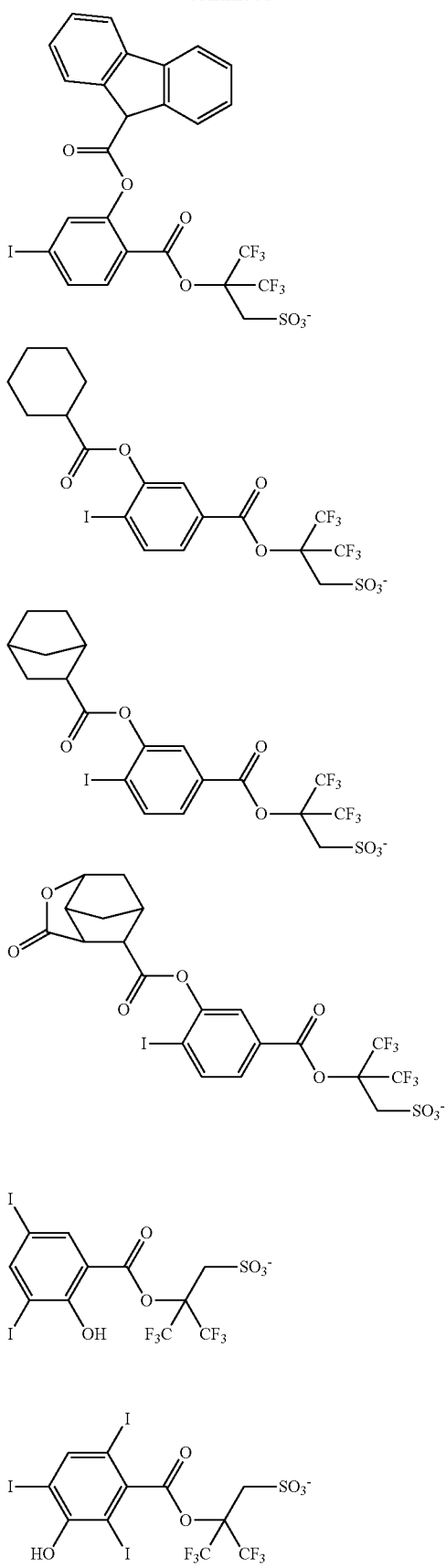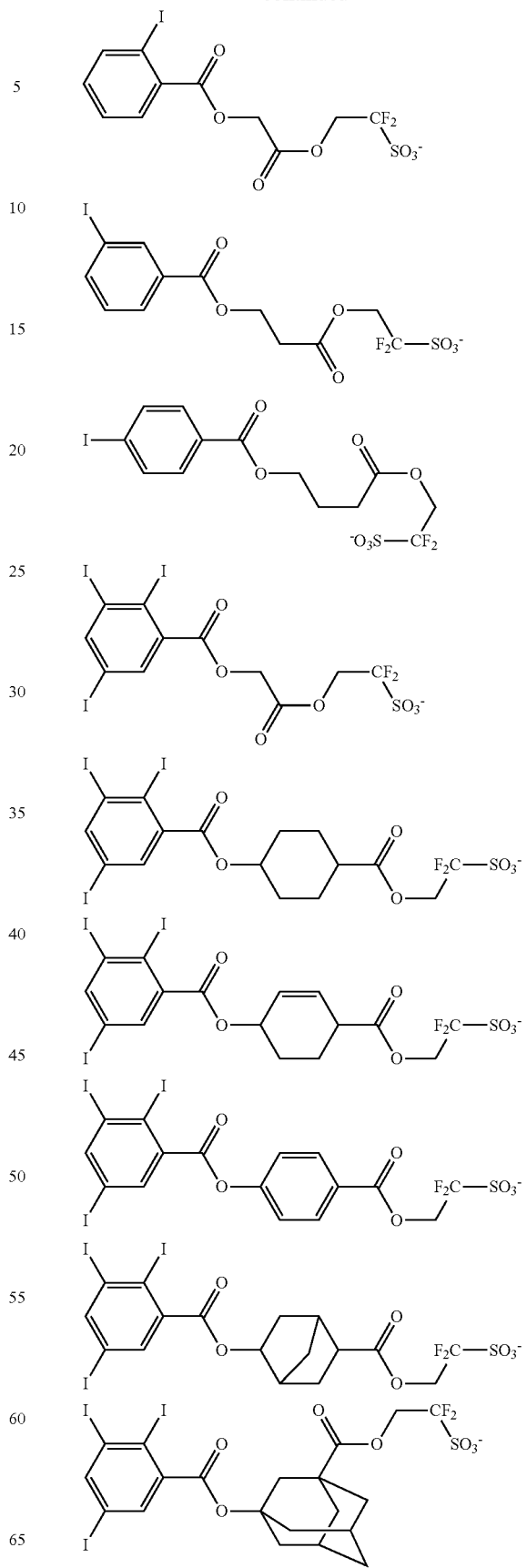

147
-continued
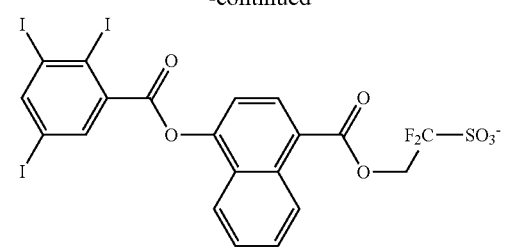
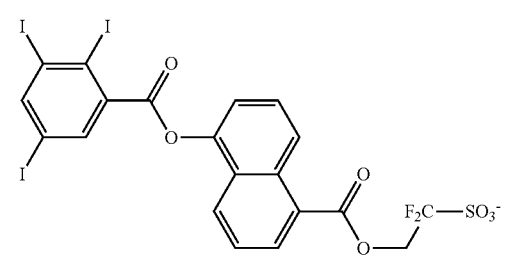
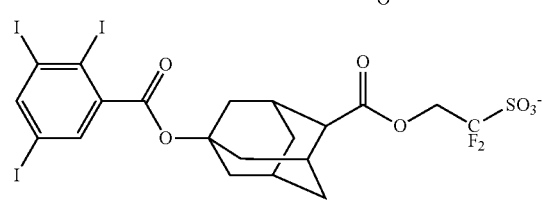
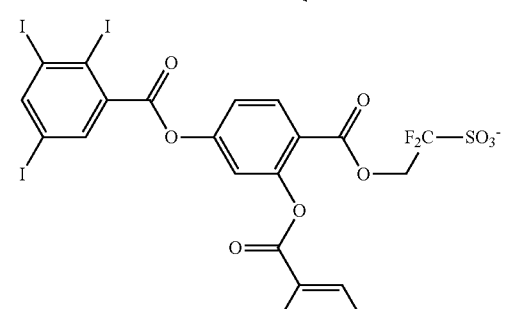
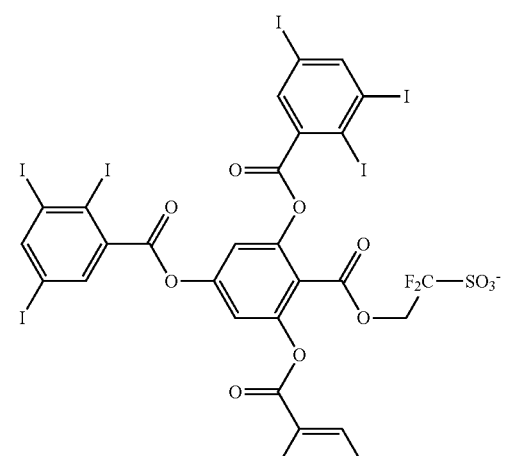
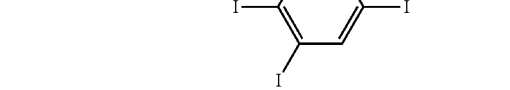
148
-continued
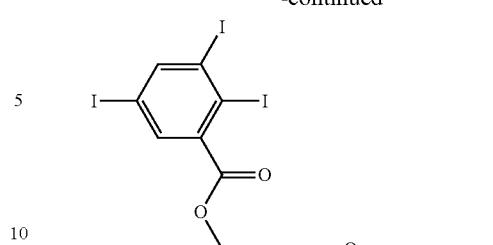
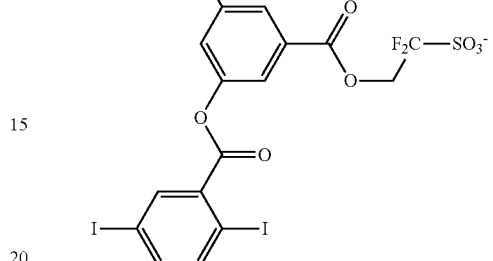
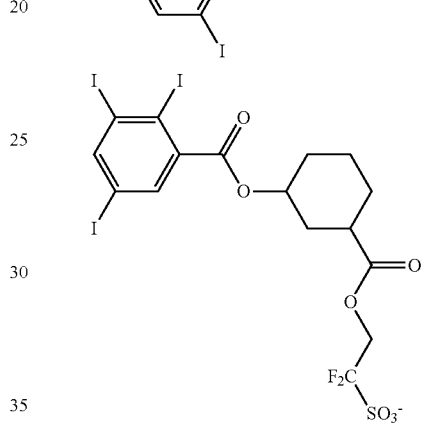
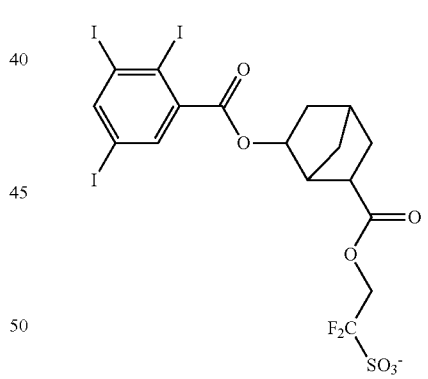
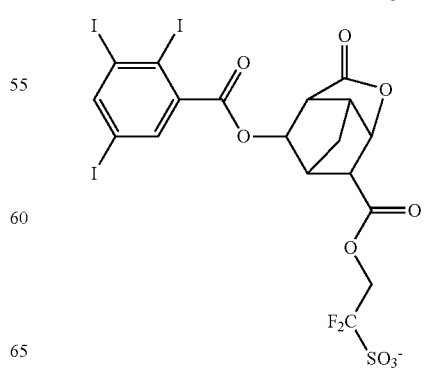

149
-continued
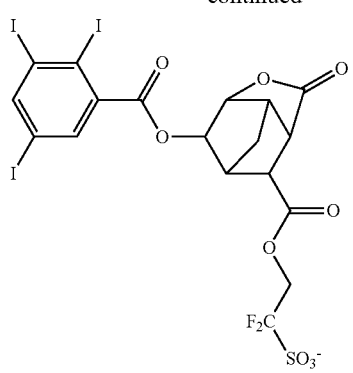
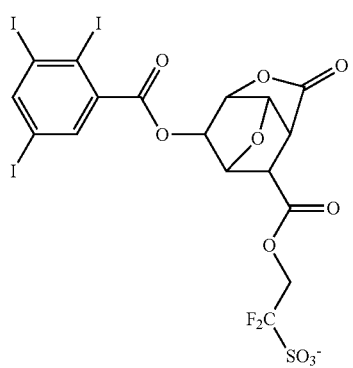
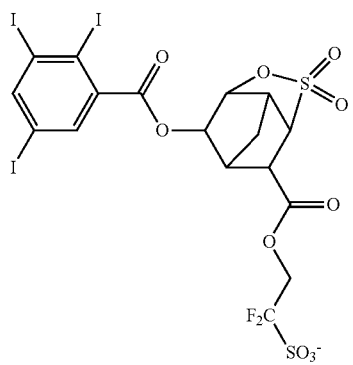
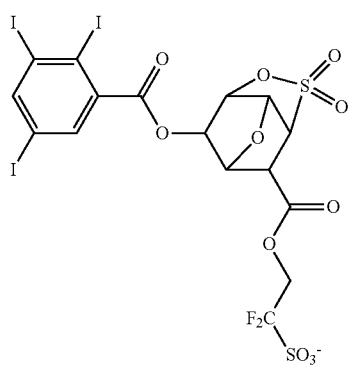
150
-continued
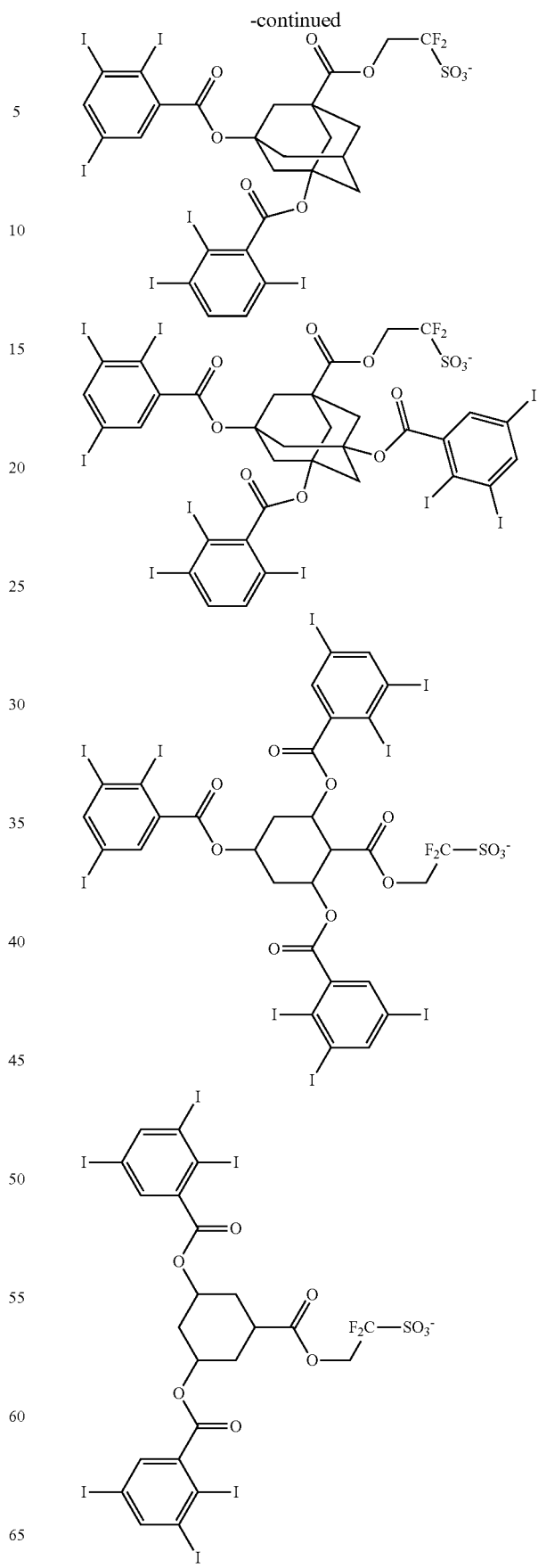

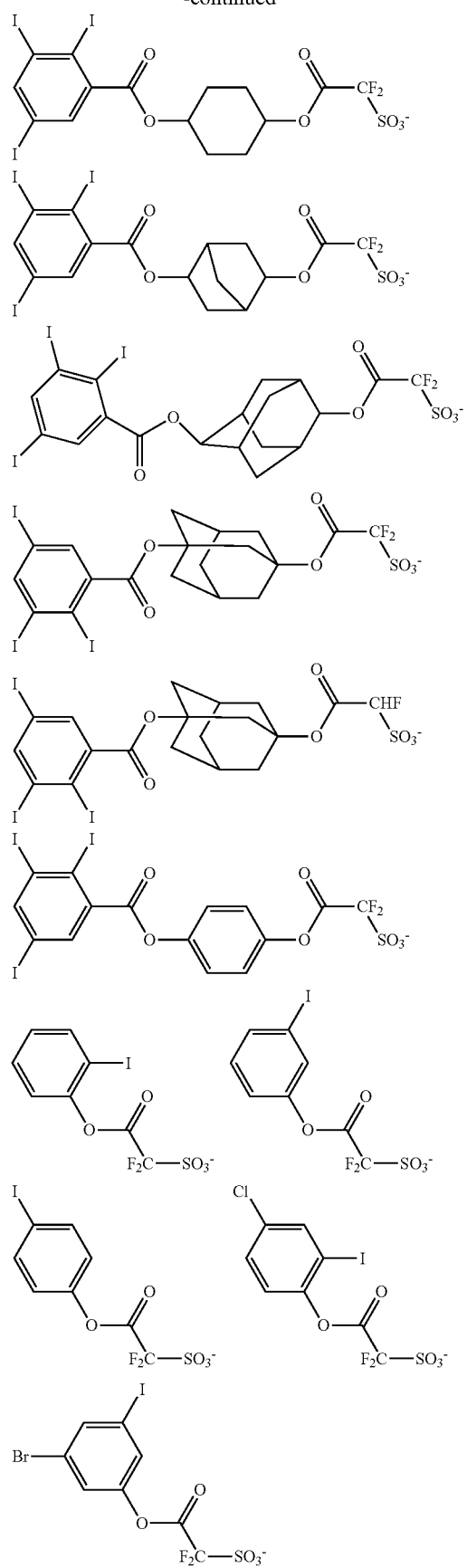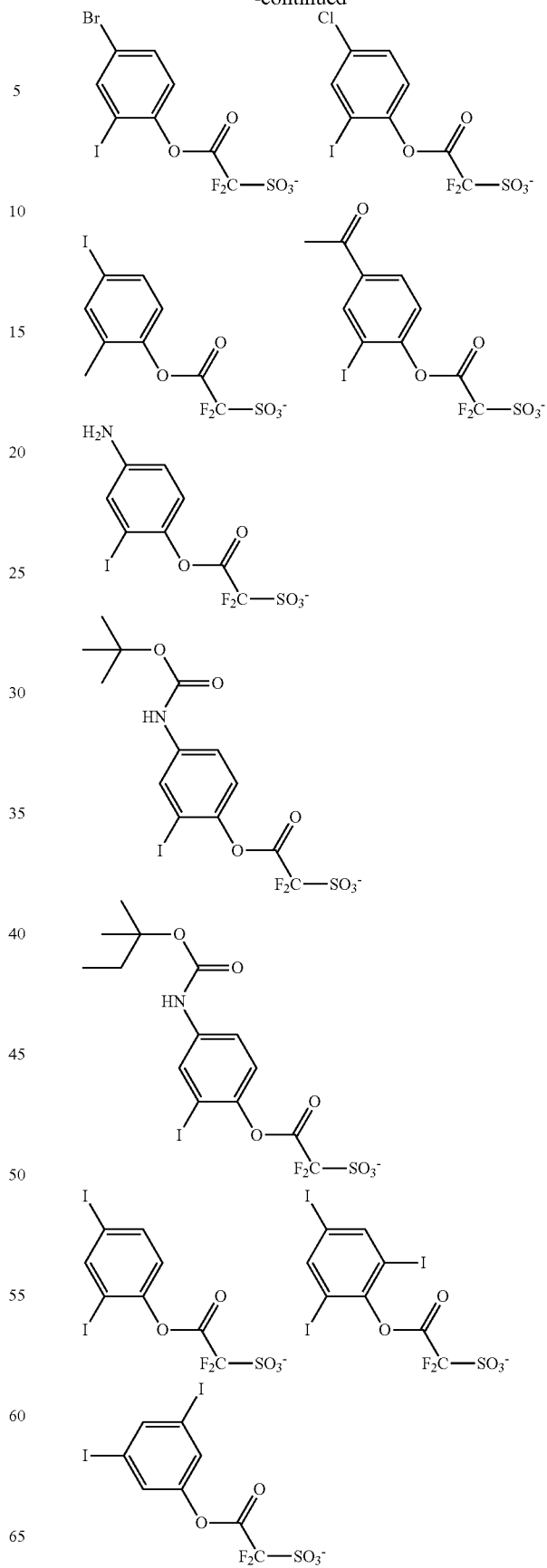

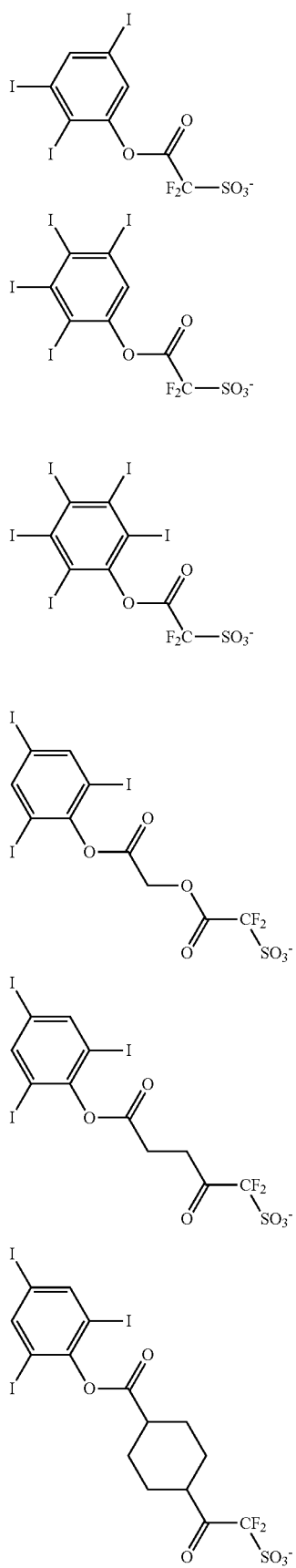
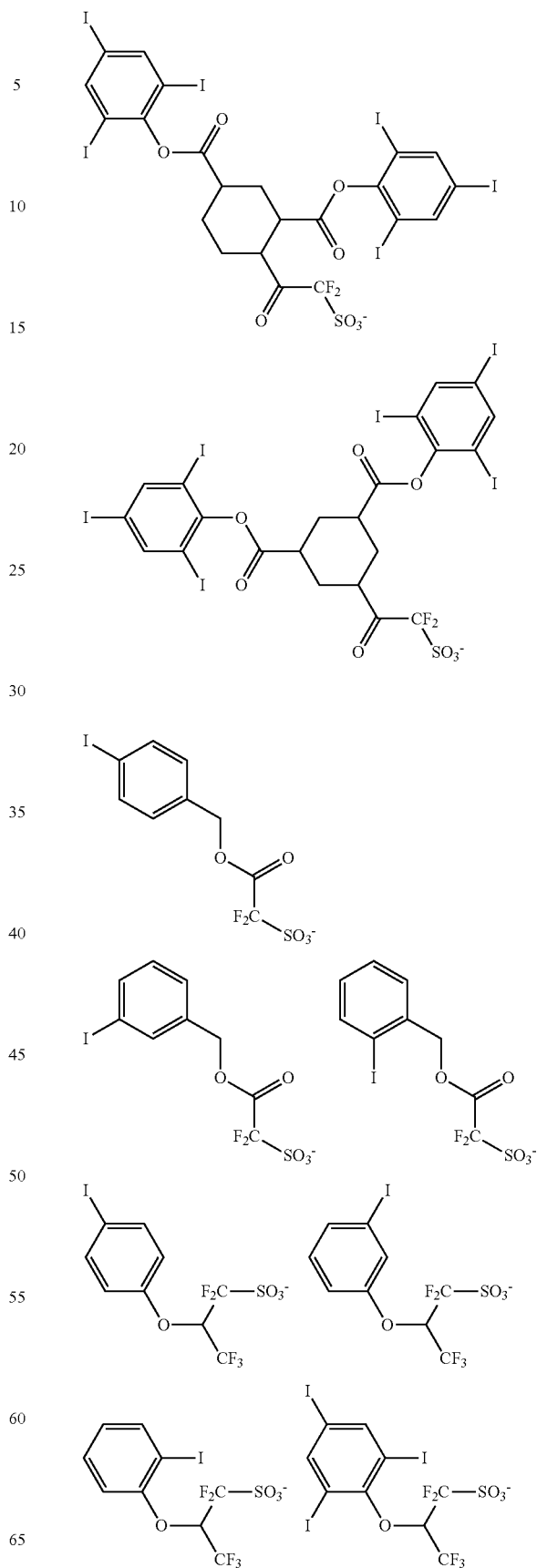

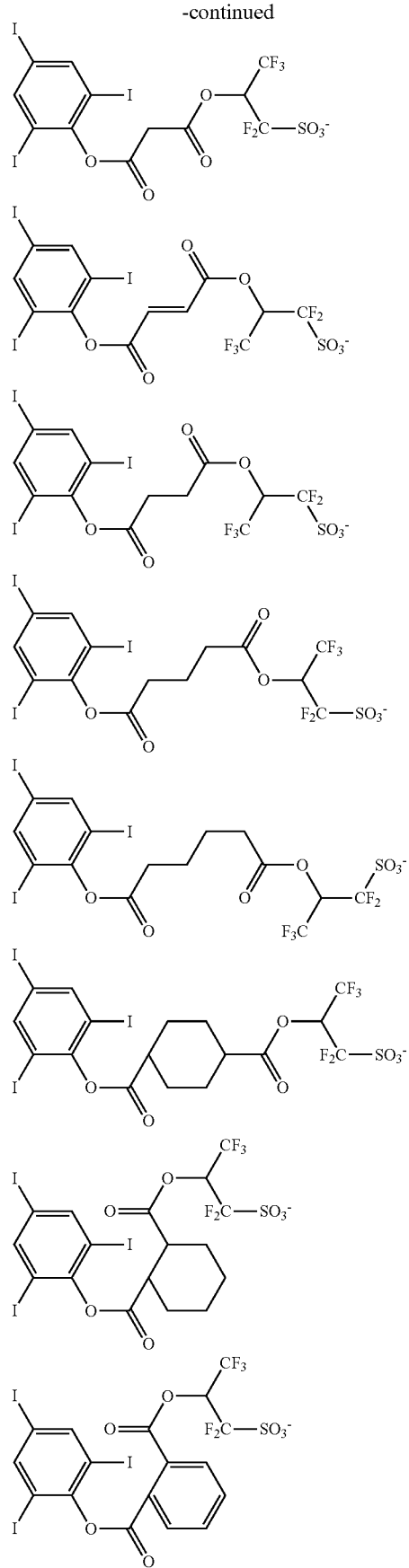
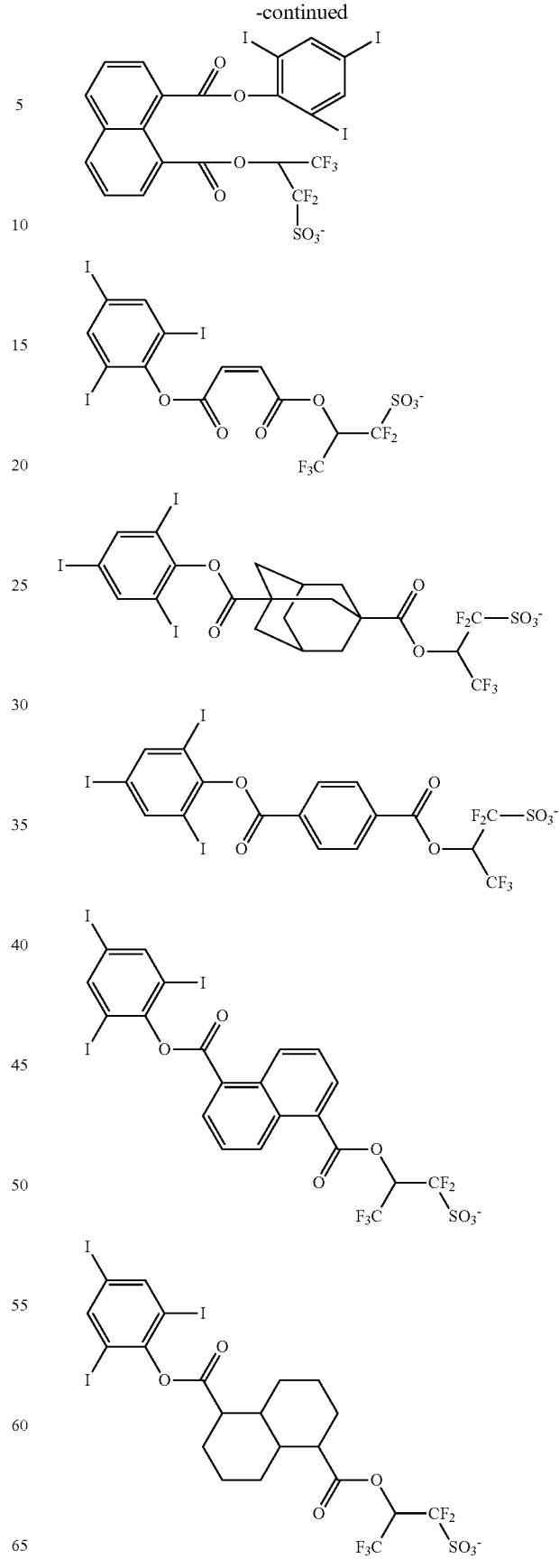

157
-continued
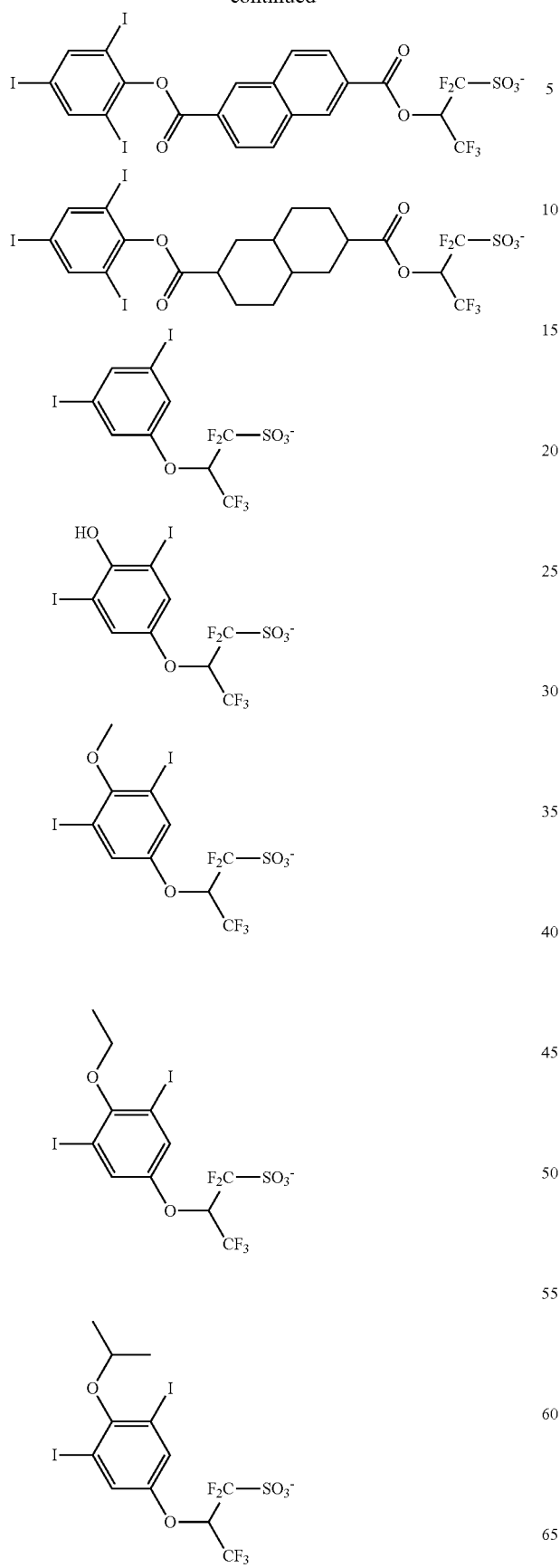
158
-continued
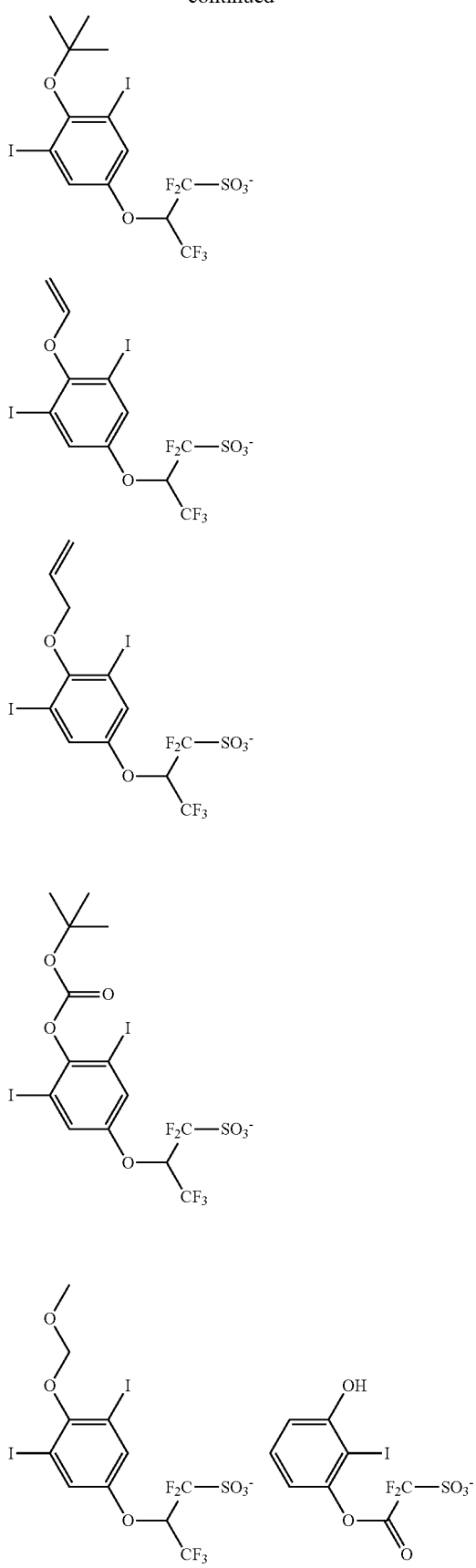

-continued
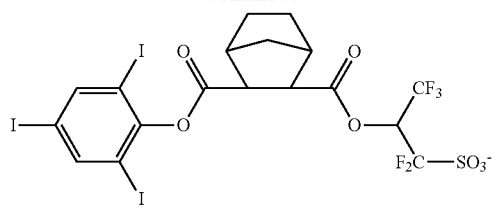
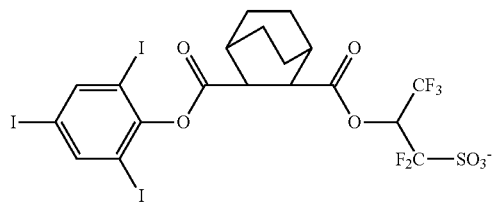
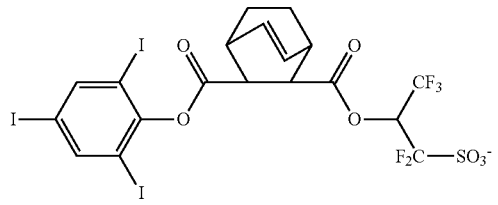
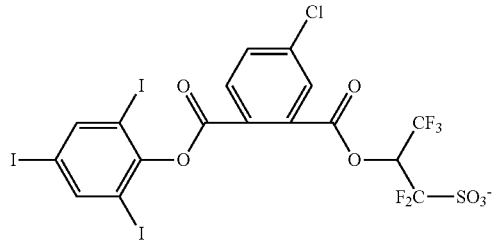
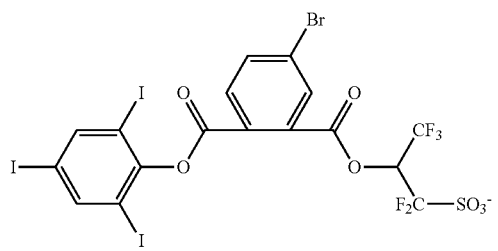
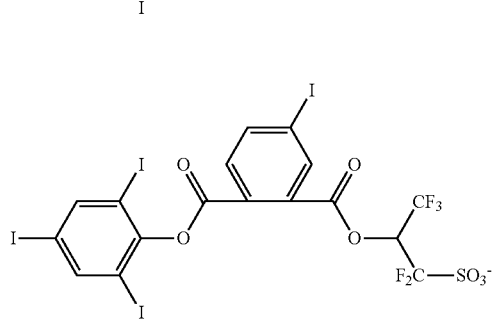
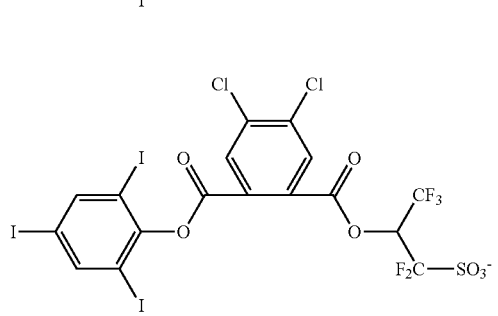
-continued
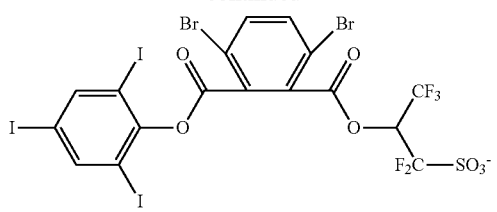
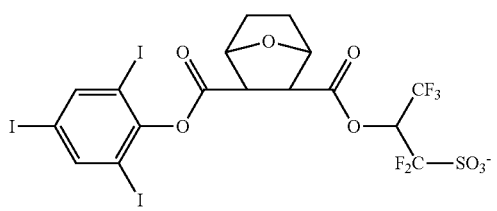
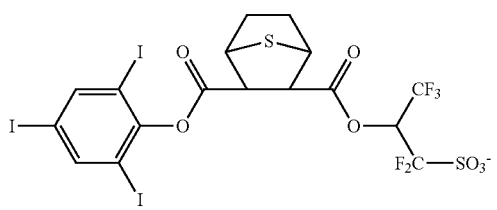
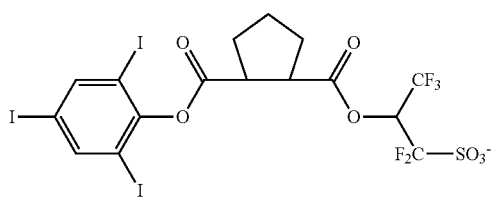
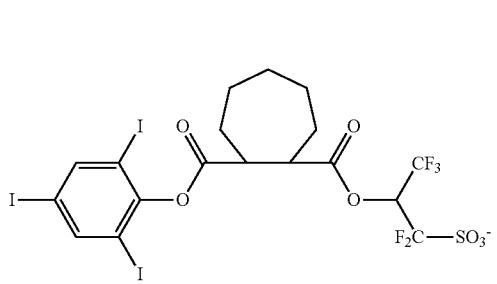
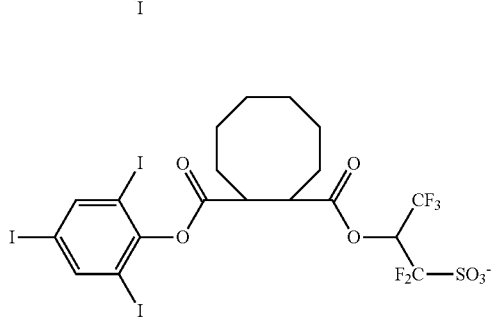
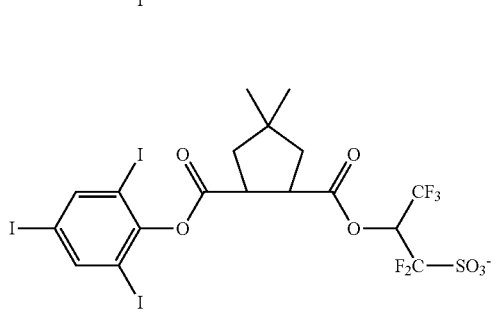

-continued
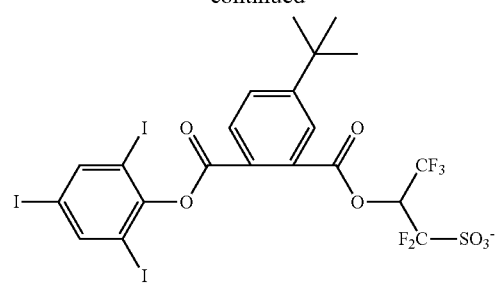
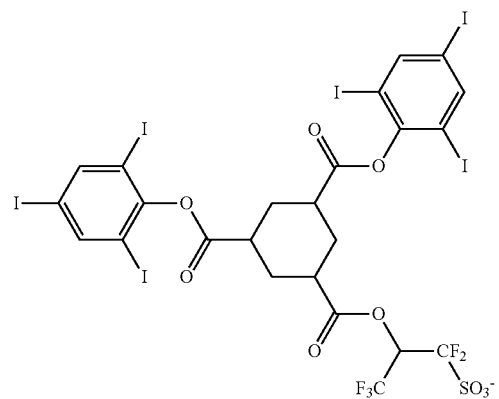
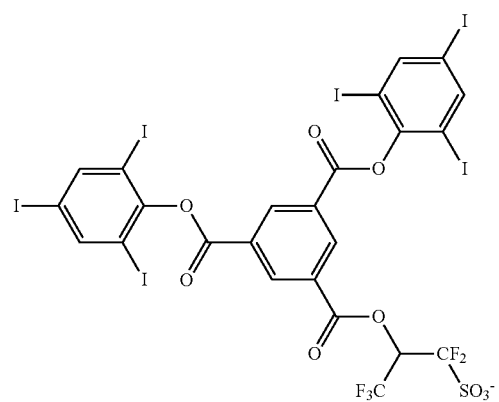
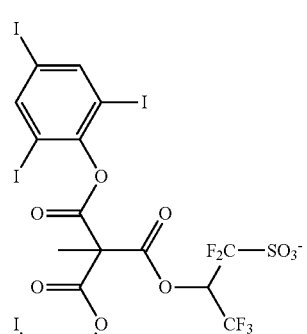
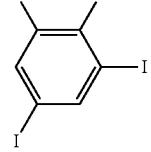
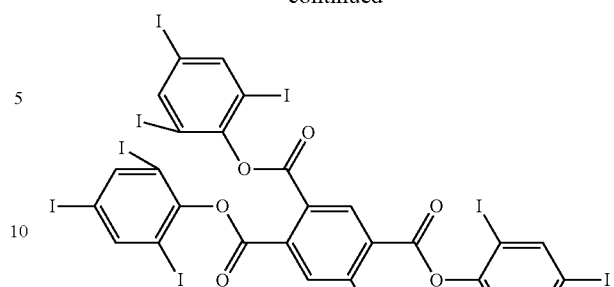
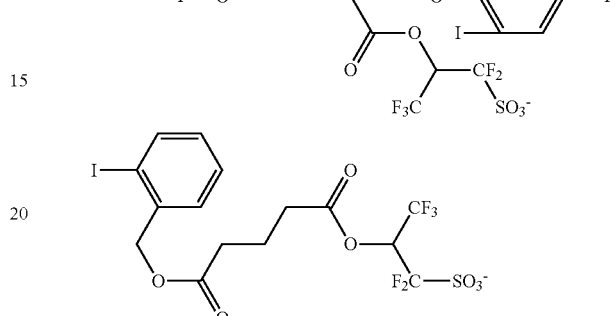
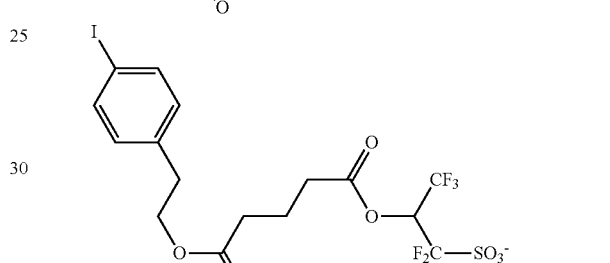
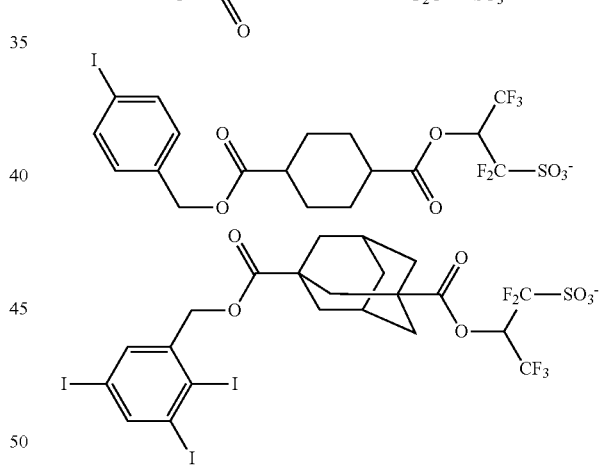
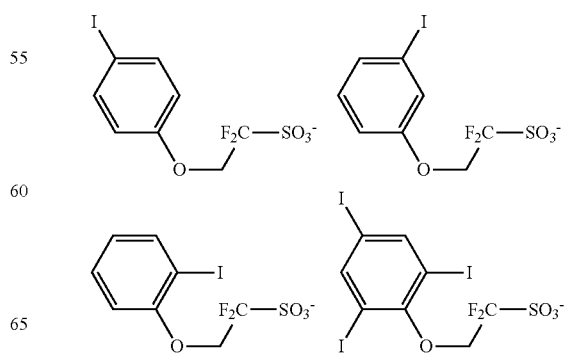

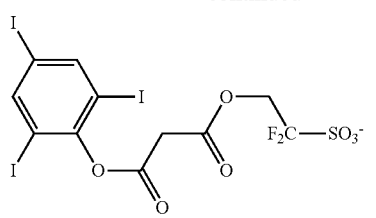
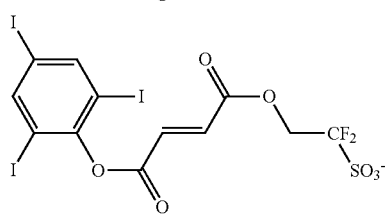
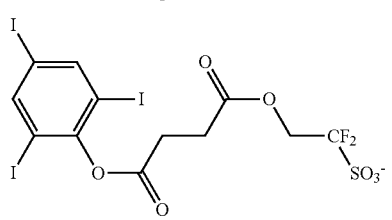
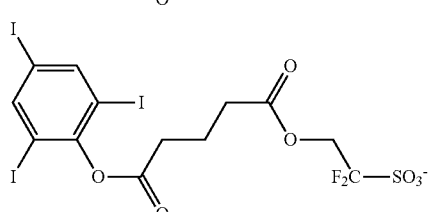
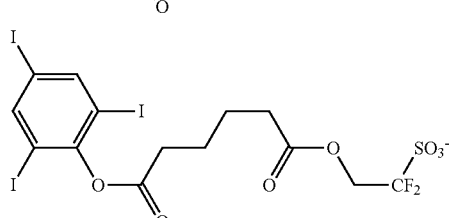
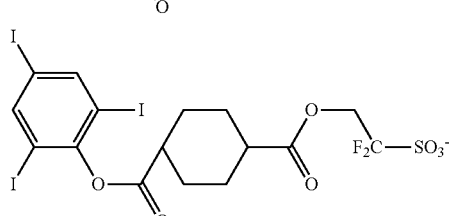
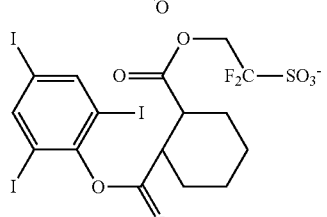
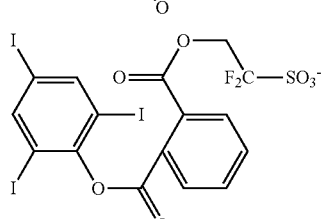
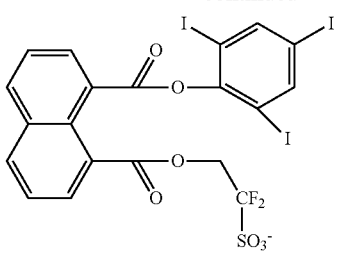
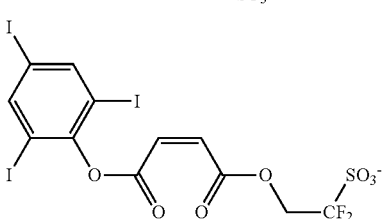
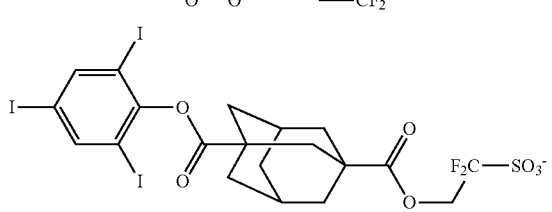
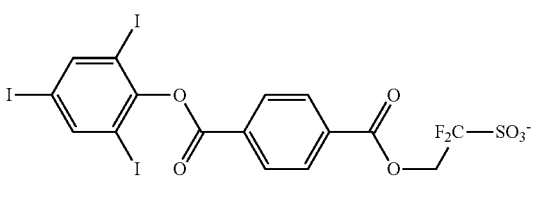
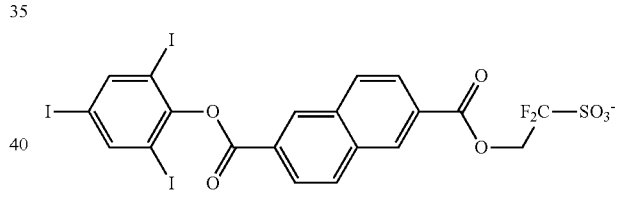
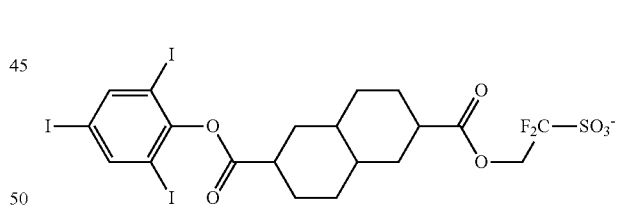
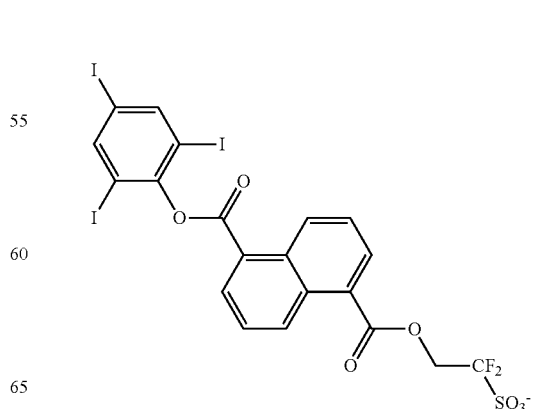

165
-continued
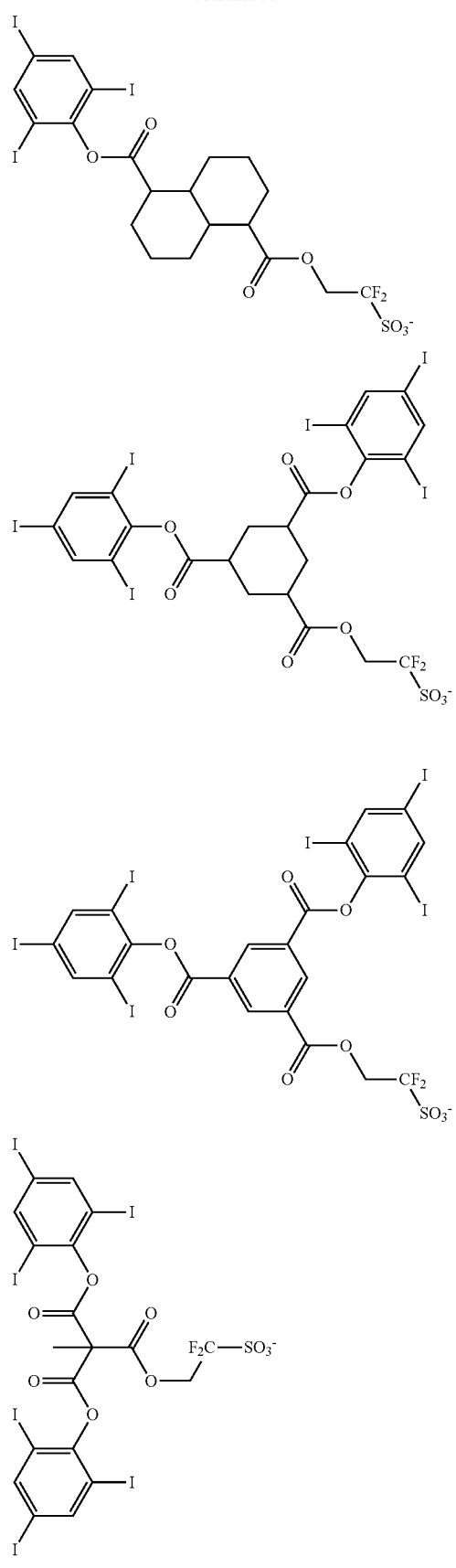
166
-continued
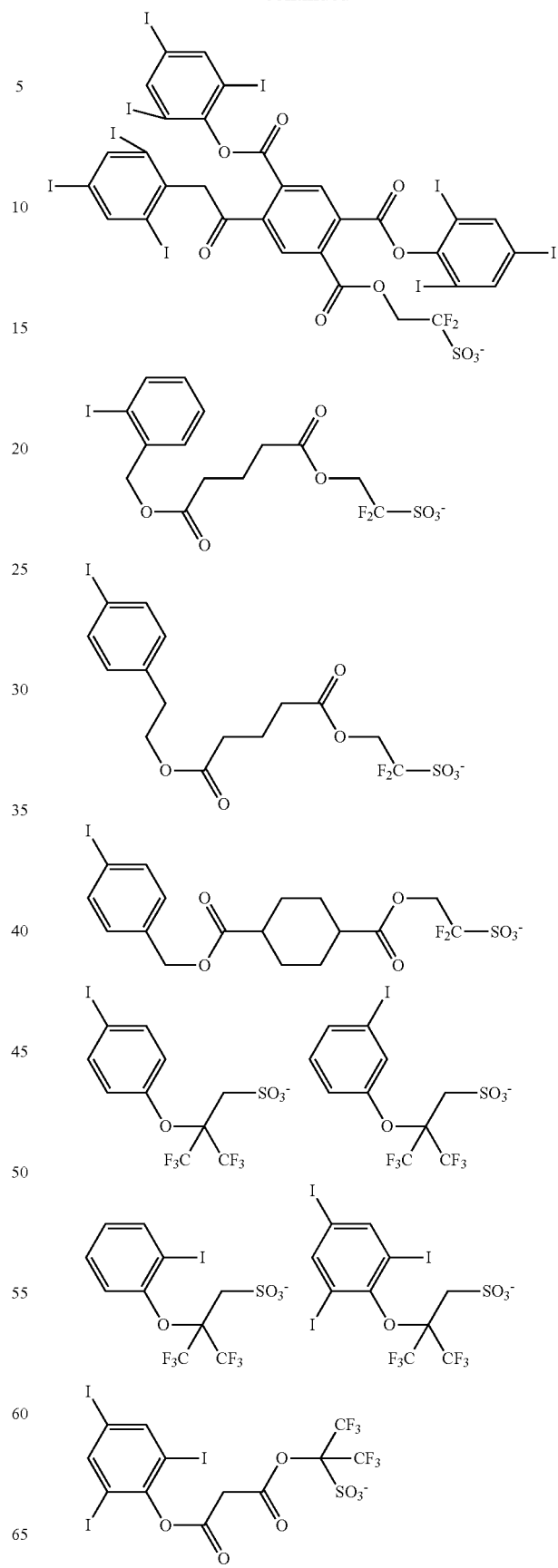

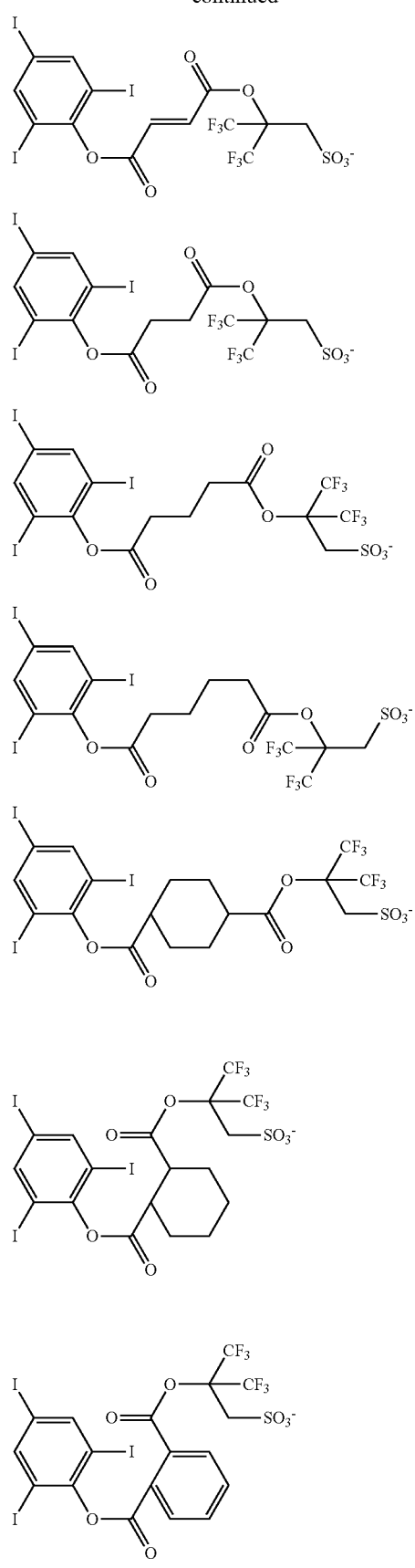
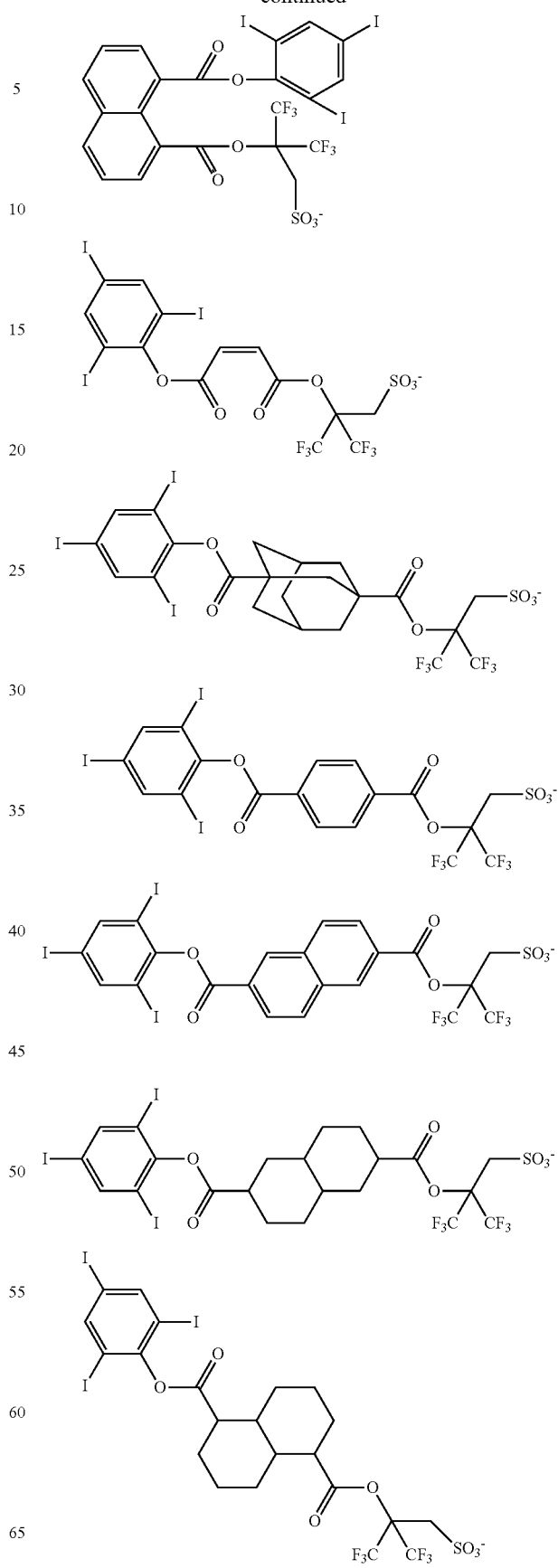

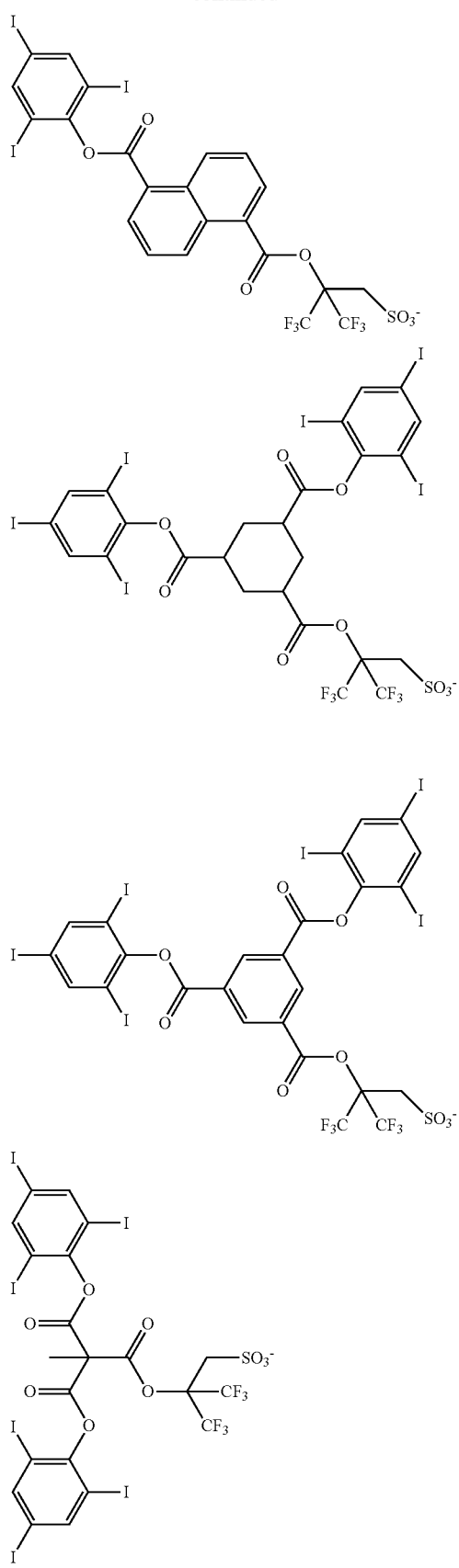
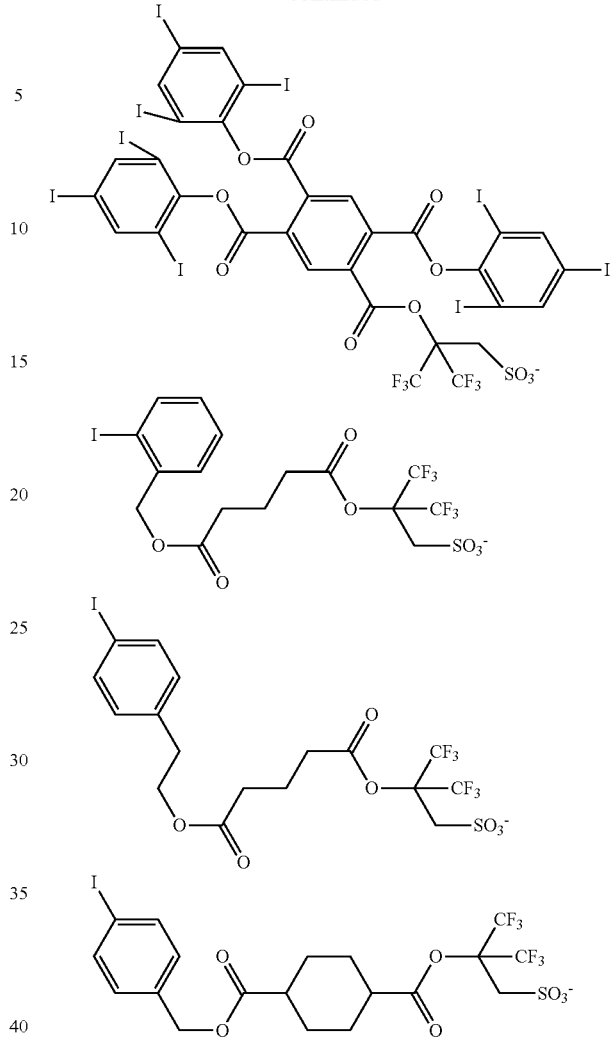

When the resist composition contains the acid generator of addition type, an appropriate amount of the generator added is 0.1 to 50 parts, more preferably 1 to 40 parts by weight per 100 parts by weight of the base resin.

Other Components

The resist composition may further comprise any additives such as a quencher, dissolution regulator, surfactant, and acetylene alcohol.

The addition of the quencher to the resist composition is effective, for example, for reducing the rate of acid diffusion in the resist film, thus contributing to a further improvement in resolution. Suitable quenchers are basic compounds including those described in JP-A 2008-111103, paragraphs [0146]-[0164] (U.S. Pat. No. 7,537,880). Preferred are primary, secondary and tertiary amine compounds, specifically amine compounds having a hydroxyl group, ether bond, ester bond, lactone ring, cyano group or sulfonic ester bond. An appropriate amount of the basic compound added as the quencher is 0 to 100 parts, more preferably 0.001 to 50 parts by weight per 100 parts by weight of the base resin.

Also useful are quenchers of polymer type as described in JP-A 2008-239918 (U.S. Pat. No. 7,598,016). The polymeric quencher segregates at the resist surface after coating and thus enhances the rectangularity of resist pattern. When a protective film is applied on the resist film, the polymeric quencher is also effective for preventing any film thickness loss of resist pattern or rounding of pattern top. When the polymeric quencher is added, its amount is arbitrary as long as the benefits of the invention are not impaired.

Also an onium salt of sulfonic acid which is not fluorinated at α-position as represented by the formula (4) or an onium salt of carboxylic acid as represented by the formula (5) is useful as the quencher.

(4)

(5)

Herein $R^{501}$, $R^{502}$ and $R^{503}$ are each independently hydrogen, halogen exclusive of fluorine, or a $C_1$-$C_{40}$ monovalent hydrocarbon group which may contain a heteroatom. Any two of $R^{501}$, $R^{502}$ and $R^{503}$ may bond together to form a ring with the carbon atom to which they are attached. $R^{504}$ is a $C_1$-$C_{40}$ monovalent hydrocarbon group which may contain a heteroatom. $M^+$ is an onium cation. The monovalent hydrocarbon groups may be straight, branched or cyclic.

The onium salt of sulfonic acid which is not fluorinated at α-position is described in U.S. Pat. No. 8,795,942 (JP-A 2008-158339). The PAGs capable of generating sulfonic acid which is not fluorinated at α-position are exemplified in JP-A 2010-155824, paragraphs [0019]-[0036] and JP-A 2010-215608, paragraphs [0047]-[0082]. The onium salts of carboxylic acid are described in JP 3991462.

The anion in formula (4) or (5) is a conjugated base of weak acid. As used herein, the weak acid indicates an acidity insufficient to deprotect an acid labile group from an acid labile group-containing unit in the base resin. The onium salt having formula (4) or (5) functions as a quencher when used in combination with an onium salt type PAG having a conjugated base of a strong acid, typically a sulfonic acid which is fluorinated at α-position as the counter anion.

In a system using a mixture of an onium salt capable of generating a strong acid (e.g., α-position fluorinated sulfonic acid) and an onium salt capable of generating a weak acid (e.g., α-position non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

In particular, since sulfonium salts and iodonium salts of an α-position non-fluorinated sulfonic acid and a carboxylic acid are photo-decomposable, those portions receiving a high light intensity are reduced in quenching capability and increased in the concentration of an α-position fluorinated sulfonic acid, imide acid, or methide acid. This enables to form a pattern having an improved contrast in exposed area, further improved depth of focus (DOF) and satisfactory dimensional control.

If a PAG capable of generating a strong acid is an onium salt, an exchange from the strong acid generated upon exposure to high-energy radiation to a weak acid as above can take place, but it never happens that the weak acid generated upon exposure to high-energy radiation collides with the unreacted onium salt capable of generating a strong acid to induce a salt exchange. This is because of a likelihood of an onium cation forming an ion pair with a stronger acid anion.

In case the acid labile group is an acetal group which is very sensitive to acid, the acid for eliminating the protective group need not necessarily be an α-fluorinated sulfonic acid, imide acid or methide acid. Sometimes, deprotection reaction may take place even with α-position non-fluorinated sulfonic acid. In this case, since an onium salt of sulfonic acid cannot be used as the quencher, an onium salt of carboxylic acid is preferably used alone as the quencher.

Of the onium salts of α-position non-fluorinated sulfonic acid and carboxylic acid, sulfonium salts of sulfonic acid having the following formula (4') and sulfonium salts of carboxylic acid having the following formula (5') are preferred.

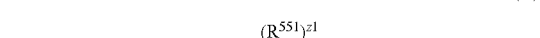

(4')

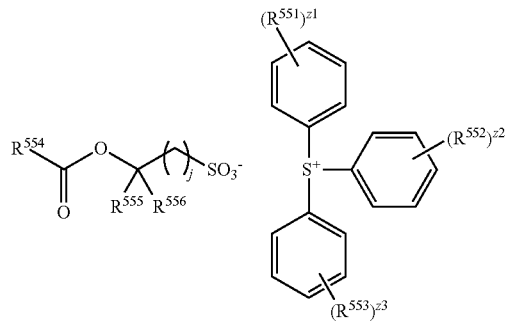

(5')

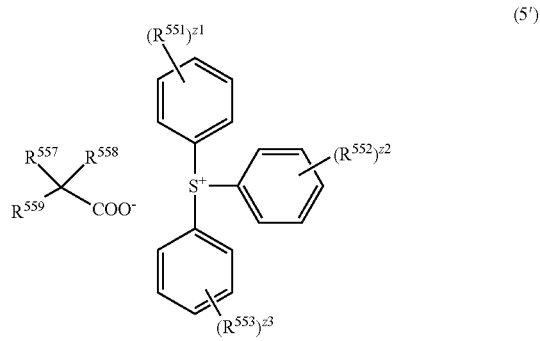

Herein $R^{551}$, $R^{552}$ and $R^{553}$ are each independently a $C_3$-$C_2$ monovalent hydrocarbon group which may contain a heteroatom. Any two of $R^{551}$, $R^{552}$ and $R^{553}$ may bond together to form a ring with the atom to which they are attached and intervening atoms. $R^{554}$ is a $C_1$-$C_{40}$ monovalent hydrocarbon group which may contain a heteroatom. $R^{555}$ and $R^{556}$ are each independently hydrogen or trifluoromethyl. $R^{557}$ and $R^{558}$ are each independently hydrogen, fluorine or trifluoromethyl. $R^{559}$ is hydrogen, hydroxyl, a $C_1$-$C_{35}$ monovalent hydrocarbon group which may contain a heteroatom, or optionally substituted $C_6$-$C_{30}$ aryl group. The subscript j is an integer of 1 to 3, $z^1$, $z^2$ and $z^3$ are each independently an integer of 0 to 5. The monovalent hydrocarbon groups may be straight, branched or cyclic.

The onium salt as quencher may be used alone or in admixture of two or more. An appropriate amount of the quencher is 0 to 50 parts, preferably 0.001 to 50 parts, more preferably 0.01 to 20 parts by weight, per 100 parts by weight of the base resin. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile. The inclusion of quencher is also effective for improving adhesion to the substrate.

The addition of the surfactant to the resist composition is effective for facilitating or controlling coating operation. Exemplary surfactants are described in JP-A 2008-111103, paragraphs [0165]-[0166]. An appropriate amount of the surfactant added is 0 to 10 parts, more preferably 0.0001 to 5 parts by weight per 100 parts by weight of the base resin.

The addition of the dissolution regulator to the resist composition is effective for exaggerating a difference in dissolution rate between exposed and unexposed regions, thus contributing to a further improvement in resolution. Exemplary dissolution regulators are described in U.S. Pat. No. 7,771,914 (JP-A 2008-122932, paragraphs [0155]-[0178]). An appropriate amount of the dissolution regulator added is 0 to 50 parts, more preferably 0 to 40 parts by weight per 100 parts by weight of the base resin.

Exemplary acetylene alcohols are described in JP-A 2008-122932, paragraphs [0179]-[0182]. An appropriate amount of the acetylene alcohol added is 0 to 2%, more preferably 0.02 to 1% by weight of the resist composition.

Also a polymeric additive may be added for improving the water repellency on surface of a resist film as spin coated. The water repellency improver may be used in the topcoatless immersion lithography. The preferred water repellency improvers include fluoroalkyl-containing polymers and polymers having a specific structure with a 1,1,1,3,3,3-hexafluoro-2-propanol residue, with their examples being described in JP-A 2007-297590 and JP-A 2008-111103. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellency improver and is effective for preventing evaporation of acid during PEB and any hole pattern opening failure after development. An appropriate amount of the water repellency improver is 0.1 to 20 parts, preferably 0.5 to 10 parts by weight per 100 parts by weight of the base resin.

As alluded to previously, the polymer is advantageously used as a base resin in a resist composition. Specifically, a base resin containing the polymer is combined with any desired components including an organic solvent, acid generator, dissolution regulator, basic compound, and surfactant to formulate a resist composition. This resist composition has a very high sensitivity in that the dissolution rate in developer of the polymer in exposed areas is accelerated by catalytic reaction. In addition, the resist film has a high dissolution contrast, resolution, exposure latitude, and process adaptability, and provides a good pattern profile after exposure, yet better etch resistance, and minimal proximity bias because of restrained acid diffusion. By virtue of these advantages, the composition is fully useful in commercial application and suited as a pattern-forming material for the fabrication of VLSIs. Particularly when an acid generator is included to formulate a chemically amplified resist composition capable of utilizing acid catalyzed reaction, the composition has a higher sensitivity and is further improved in the properties described above.

Process

The resist composition, typically chemically amplified resist composition comprising a base resin containing the polymer, an acid generator, an organic solvent, and a basic compound is used in the fabrication of various integrated circuits. Pattern formation using the resist composition may be performed by well-known lithography processes. The process generally involves coating, prebake, exposure, and development. If necessary, any additional steps may be added.

The resist composition is first applied onto a substrate on which an integrated circuit is to be formed (e.g, Si, $SiO_2$, SiN, SiON, TiN, WSi, BPSG, SOG, or organic antireflective coating) or a substrate on which a mask circuit is to be formed (e.g., Cr, CrO, CrON, $MoSi_2$ or $SiO_2$) by a suitable coating technique such as spin coating, roll coating, flow coating, dip coating, spray coating or doctor coating. The coating is prebaked on a hot plate at a temperature of 60 to 150° C. for 10 seconds to 30 minutes, preferably 80 to 120° C. for 30 seconds to 20 minutes. The resulting resist film is generally 0.1 to 2.0 µm thick.

If desired, a protective film may be formed on the resist film. The protective film is preferably formed of an alkaline developer-soluble composition so that both formation of a resist pattern and stripping of the protective film may be achieved during development. The protective film has the functions of restraining outgassing from the resist film, filtering or cutting off out-of-band (OOB) light having a wavelength of 140 to 300 am emitted by the EUV laser (other than 13.5 nm), and preventing the resist film from assuming T-top profile or from losing its thickness under environmental impacts.

The resist film is then exposed to a desired pattern of high-energy radiation such as UV, deep-UV, EUV, EB, x-ray, soft x-ray, excimer laser light, γ-ray or synchrotron radiation directly or through a mask. The exposure dose is preferably about 1 to 200 $mJ/cm^2$, more preferably about 10 to 100 $mJ/cm^2$, or 0.1 to 100 $\mu C/cm^2$, more preferably 0.5 to 50 $\mu C/cm^2$. The resist film is further baked (PEB) on a hot plate at 60 to 150° C. for 10 seconds to 30 minutes, preferably at 80 to 120° C. for 30 seconds to 20 minutes.

Thereafter the resist film is developed with a developer in the form of an aqueous base solution for 3 seconds to 3 minutes, preferably 5 seconds to 2 minutes by conventional techniques such as dip, puddle or spray techniques. Suitable developers are 0.1 to 10 wt %, preferably 2 to 5 wt % aqueous solutions of tetramethylammonimn hydroxide (TMAH), tetraethylammonium hydroxide (TEAH), tetrapropylammonium hydroxide (TPAH) and tetrabutylammonium hydroxide (TBAH). In the embodiment wherein the polymer contains recurring units (b1) and/or (b2), the resist film in the exposed region is dissolved in the developer whereas the resist film in the unexposed region is not dissolved, whereby a positive pattern is formed on the substrate. In the embodiment wherein the polymer contains recurring units (b3), a negative resist pattern is formed on the substrate. It is appreciated that the resist composition of the invention is best suited for micro-patterning using such high-energy radiation as EB, EUV, x-ray, soft x-ray, γ-ray and synchrotron radiation among others.

Although TMAH aqueous solution is generally used as the developer, TEAH, TPAH and TBAH having a longer alkyl chain are effective in inhibiting the resist film from being swollen during development and thus preventing pattern collapse. JP 3429592 describes an example using an aqueous TBAH solution for the development of a polymer comprising recurring units having an alicyclic structure such as adamantane methacrylate and recurring units having an acid labile group such as tert-butyl methacrylate, the polymer being water repellent due to the lack of hydrophilic groups.

The TMAH developer is most often used as 2.38 wt % TMAH aqueous solution, which corresponds to 0.26N. The TEAH, TPAH, and TBAH aqueous solutions should preferably have an equivalent normality. The concentration of TEAH, TPAH, and TBAH that corresponds to 0.26N is 3.84 wt %, 5.31 wt %, and 6.78 wt %, respectively.

When a pattern with a line size of 32 am or less is resolved by the EB and EUV lithography, there arises a phenomenon that lines become wavy, lines merge together, and merged lines collapse. It is believed that this phenomenon occurs because lines are swollen in the developer and the thus expanded lines merge together. Since the swollen lines containing liquid developer are as soft as sponge, they readily collapse under the stress of rinsing. For this reason, the developer using a long-chain alkyl developing agent is effective for preventing film swell and hence, pattern collapse.

In the embodiment wherein the polymer contains recurring units (b1) and/or (b2), a negative pattern can be formed from the resist composition by organic solvent development. The developer used to this end is at least one solvent selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-peutyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene, and mesitylene. The solvents may be used alone or in admixture.

EXAMPLE

Examples and Comparative Examples are given below for further illustrating the invention, but they should not be construed as limiting the invention thereto. All parts (pbw) are by weight. Mw is measured versus polystyrene standards by GPC using THF solvent.

[1] Synthesis of Polymerizable Monomers

Example 1-1

Synthesis of Monomer 1

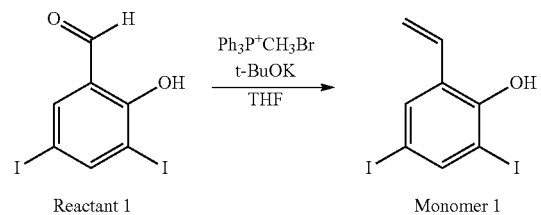

Reactant 1          Monomer 1

In nitrogen atmosphere, 89.3 g of methyltriphenylphosphonium bromide was dissolved in 400 mL of THF. With cooling in an ice bath, 28.1 g of tert-butoxypotassium in powder form was added to the solution. The solution was aged for 30 minutes in the ice bath, after which a solution of 37.4 g of Reactant 1 in 100 mL of THF was added dropwise. The reaction solution was aged for 30 minutes and then cooled, after which 200 mL of water was added dropwise to quench the reaction. This was followed by extraction with 400 mL of ethyl acetate and ordinary aqueous workup. Then the solvent was distilled off. The residue was purified by silica gel column chromatography, yielding Monomer 1 as white crystal (amount 31.4 g. yield 84%).

The product was analyzed by IR and $^1$H-NMR spectroscopy, with the results shown below.

IR (D-ATR):

ν=3403, 3084, 3057, 3023, 1834, 1750, 1717, 1658, 1623, 1569, 1543, 1442, 1414, 1394, 1370, 1323, 1303, 1258, 1235, 1202, 1126, 1100, 1038, 1023, 994, 915, 863, 804, 757, 734, 697, 664, 584, 542, 530 cm$^{-1}$ $^1$H-NMR (600 MHz in DMSO-d6):

δ=9.64 (1H, s), 7.89 (1H, s), 7.73 (1H, s), 6.90 (1H, dd), 5.89 (1H, d), 5.28 (1H, d) ppm Examples 1-2 to 1-7

Synthesis of Monomers 2 to 7

Monomers 2 to 7 shown below were synthesized by the same method as in Example 1-1 aside from using the corresponding reactants instead of Reactant 1.

Monomer 2

Monomer 3

Monomer 4

Monomer 5

Monomer 6

Monomer 7

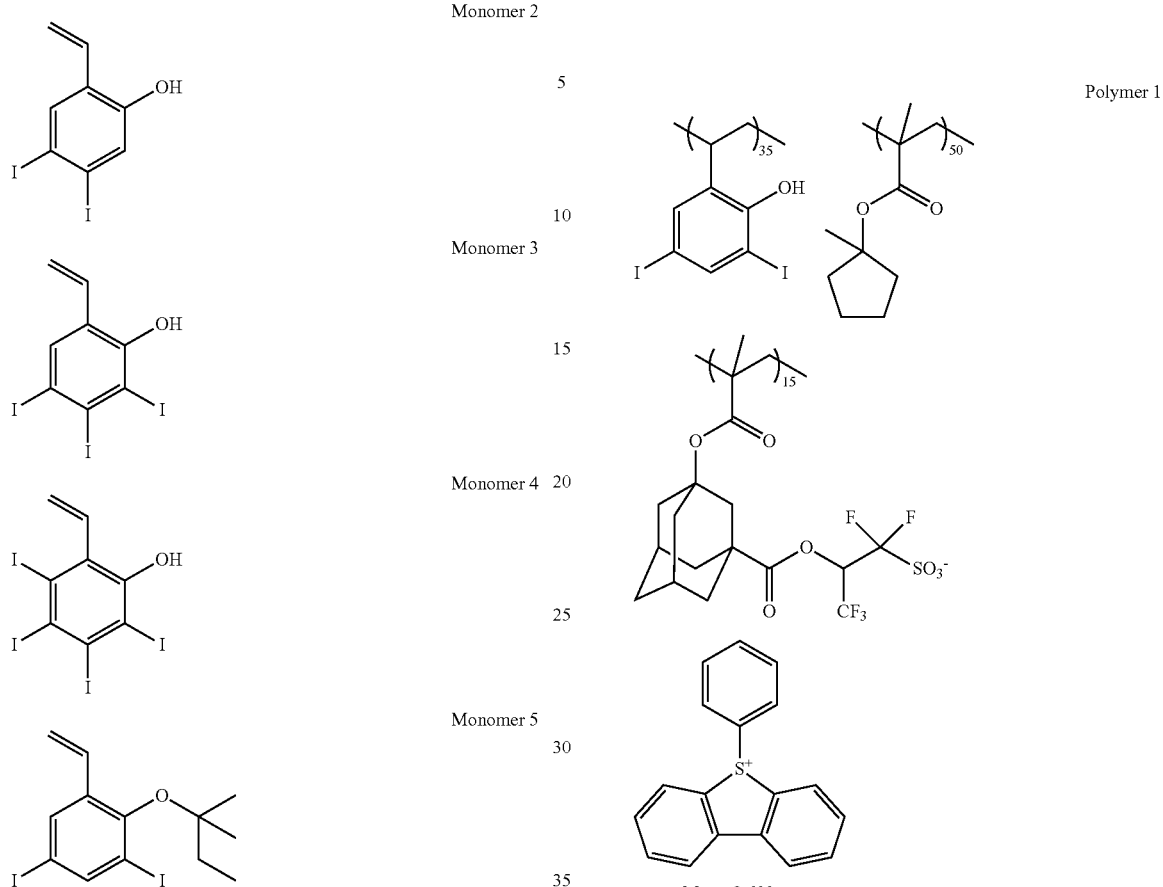

Example 2-1 Polymer 1

Polymer 1

Mw = 9,600
Mw/Mn = 1.87

Example 2-2 Polymer 2

Polymer 2

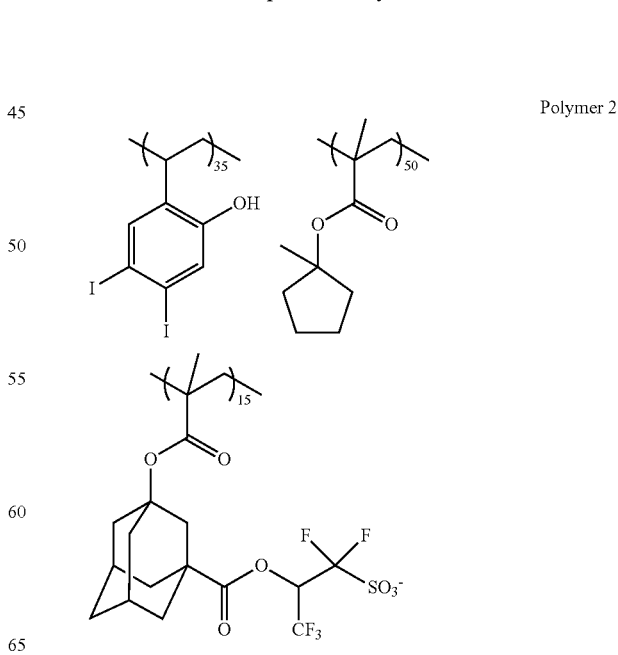

[2] Synthesis of Polymers

Each of polymers (Polymers 1 to 19 and Comparative Polymers 1 to 7) for use in resist compositions was prepared by combining monomers in cyclopentanone solvent, effecting copolymerization reaction, crystallizing from hexane, washing with hexane several times, isolation and drying. The polymer was analyzed for composition by 1H-NMR and $^{13}$C-NMR spectroscopy.

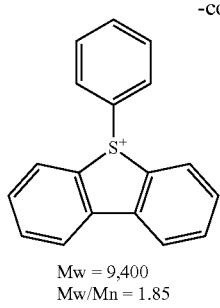
Mw = 9,400
Mw/Mn = 1.85
Example 2-3 Polymer 3
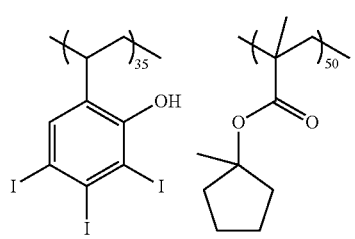
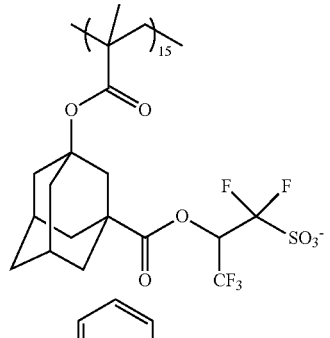
Mw = 9,300
Mw/Mn = 1.87
Example 2-4 Polymer 4
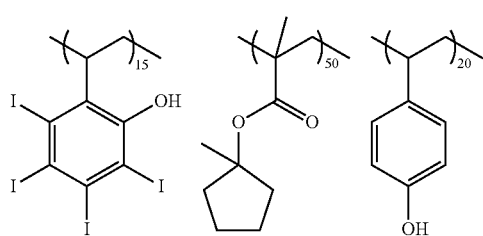
Polymer 3
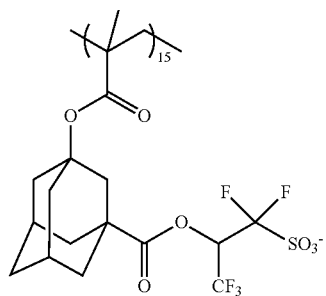
Mw = 9,300
Mw/Mn = 1.86
Example 2-5 Polymer 5
Polymer 5
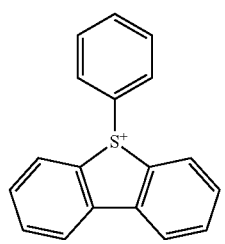
Polymer 4
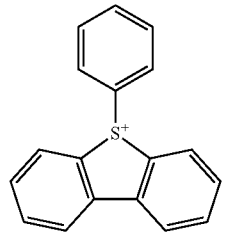
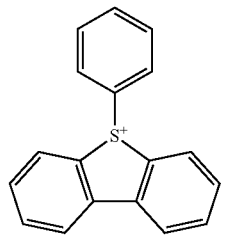
Mw = 9,500
Mw/Mn = 1.86

Example 2-6 Polymer 6
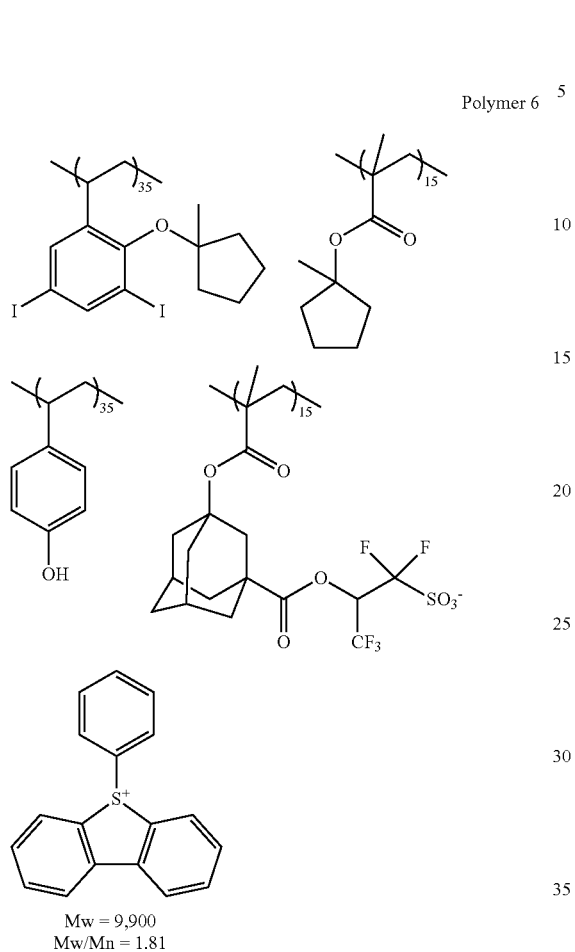
Mw = 9,900
Mw/Mn = 1.81
Example 2-7 Polymer 7
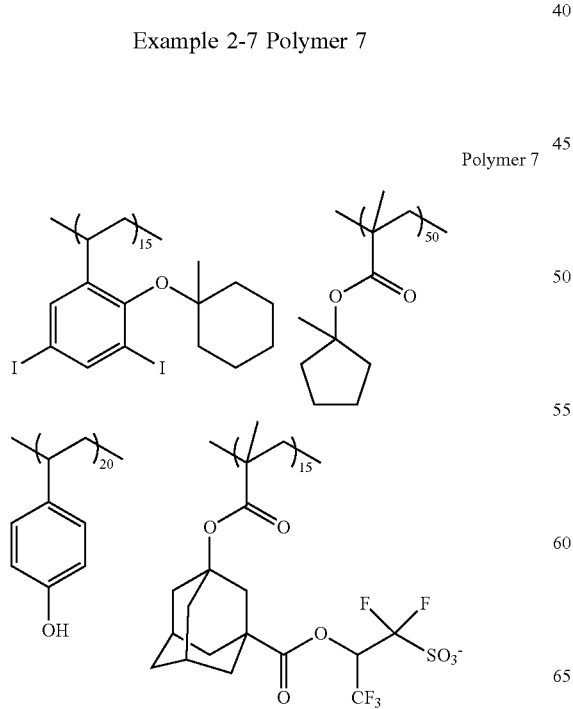
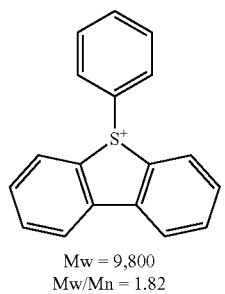
Mw = 9,800
Mw/Mn = 1.82
Example 2-8 Polymer 8
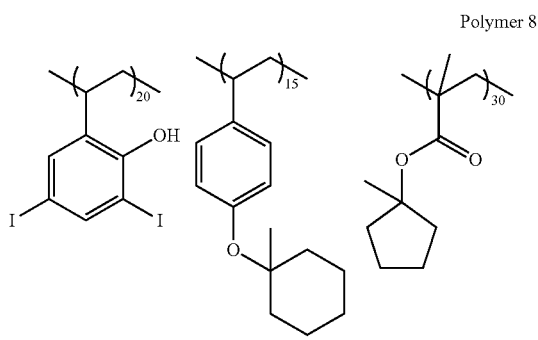
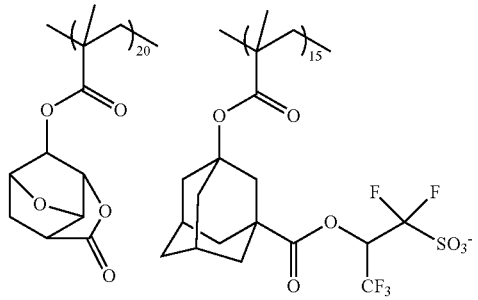
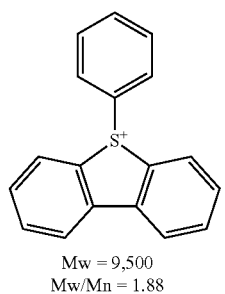
Mw = 9,500
Mw/Mn = 1.88

Example 2-9 Polymer 9
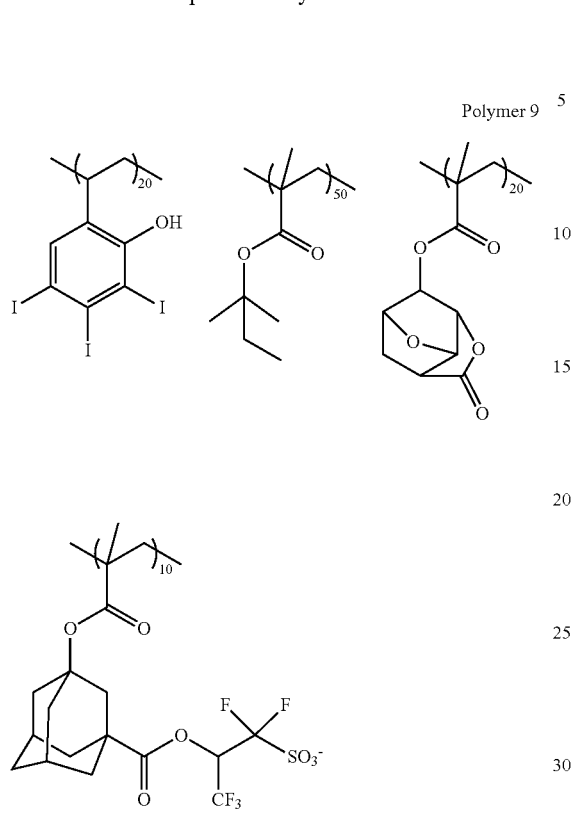
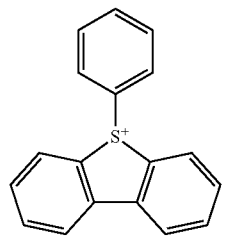
Mw = 9,700
Mw/Mn = 1.80
Example 2-10 Polymer 10
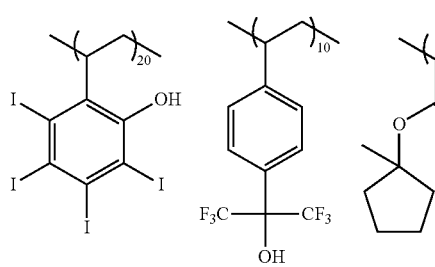
Polymer 10
-continued
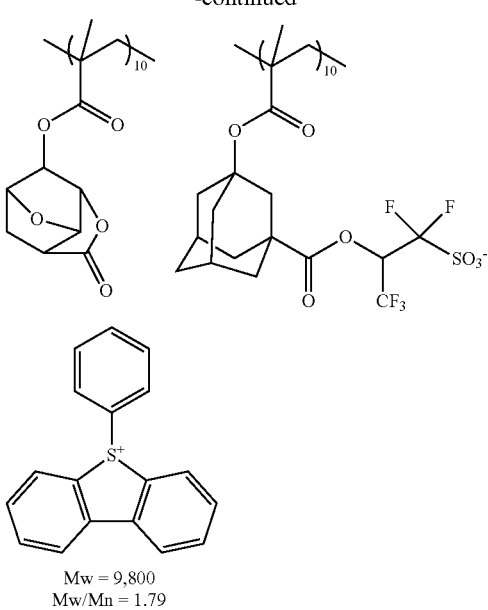
Mw = 9,800
Mw/Mn = 1.79
Example 2-11 Polymer 11
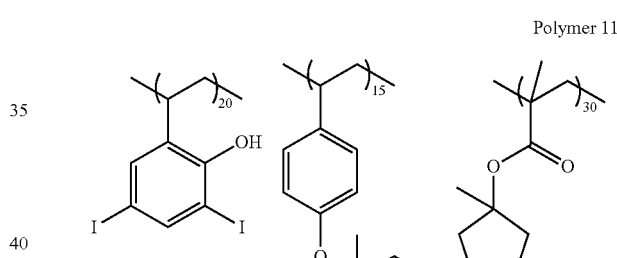
Polymer 11
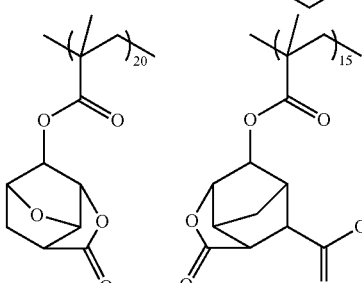
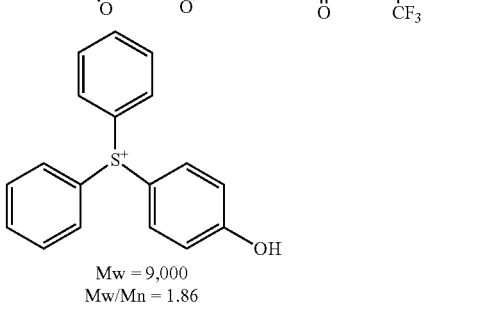
Mw = 9,000
Mw/Mn = 1.86

Example 2-12 Polymer 12
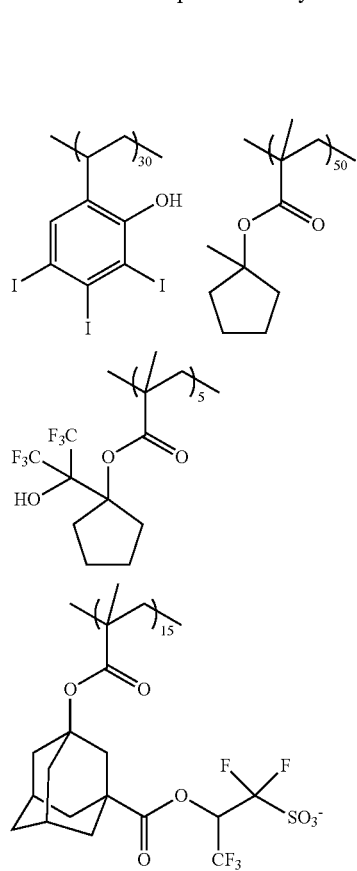
Polymer 12
Example 2-13 Polymer 13
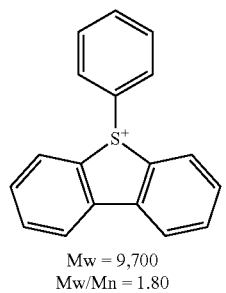
Polymer 13
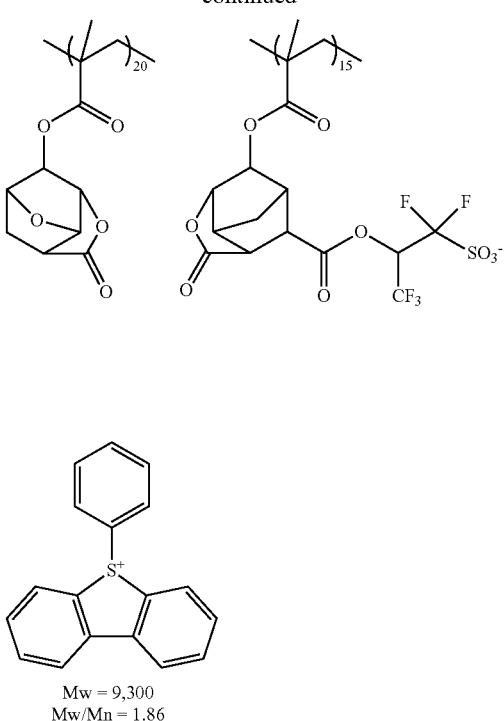
Example 2-14 Polymer 14
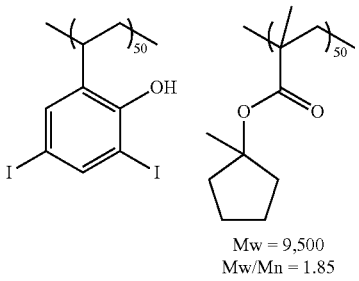
Polymer 14
Example 2-15 Polymer 15
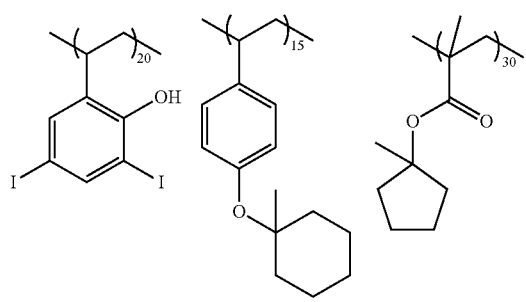
Polymer 15

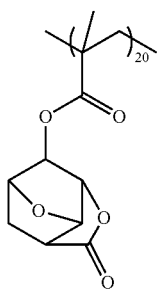
Mw = 9,800
Mw/Mn = 1.81
Example 2-16 Polymer 16
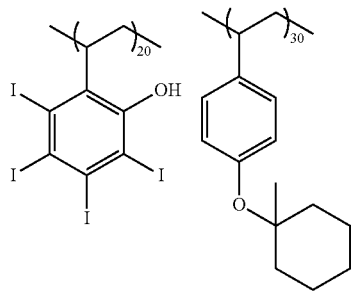
Polymer 16
Mw = 9,700
Mw/Mn = 1.89
Example 2-17 Polymer 17
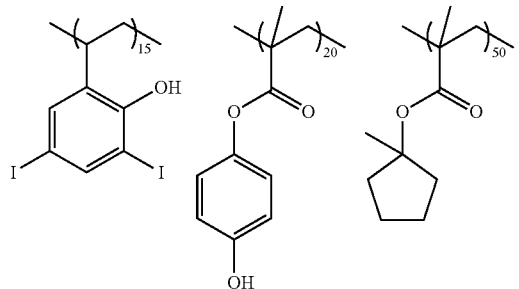
Polymer 17
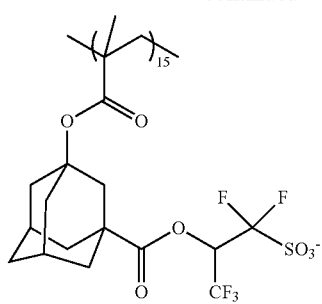
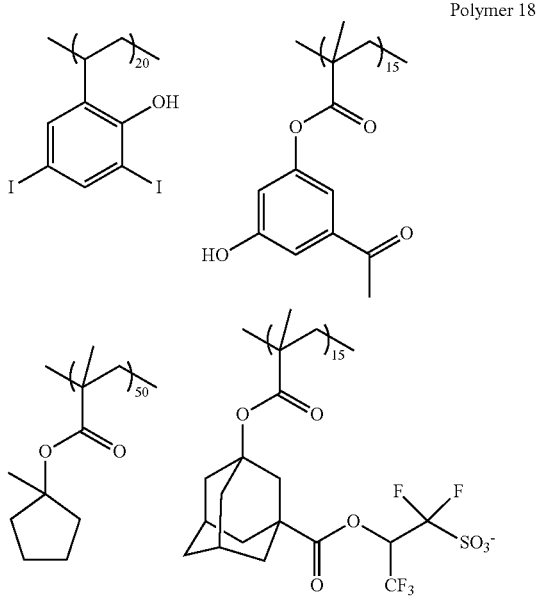
Mw = 9,100
Mw/Mn = 1.81
Example 2-18 Polymer 18
Polymer 18
Mw = 9,800
Mw/Mn = 1.79

189
Example 2-19 Polymer 19
190
Comparative Example 1-2 Comparative Polymer 2
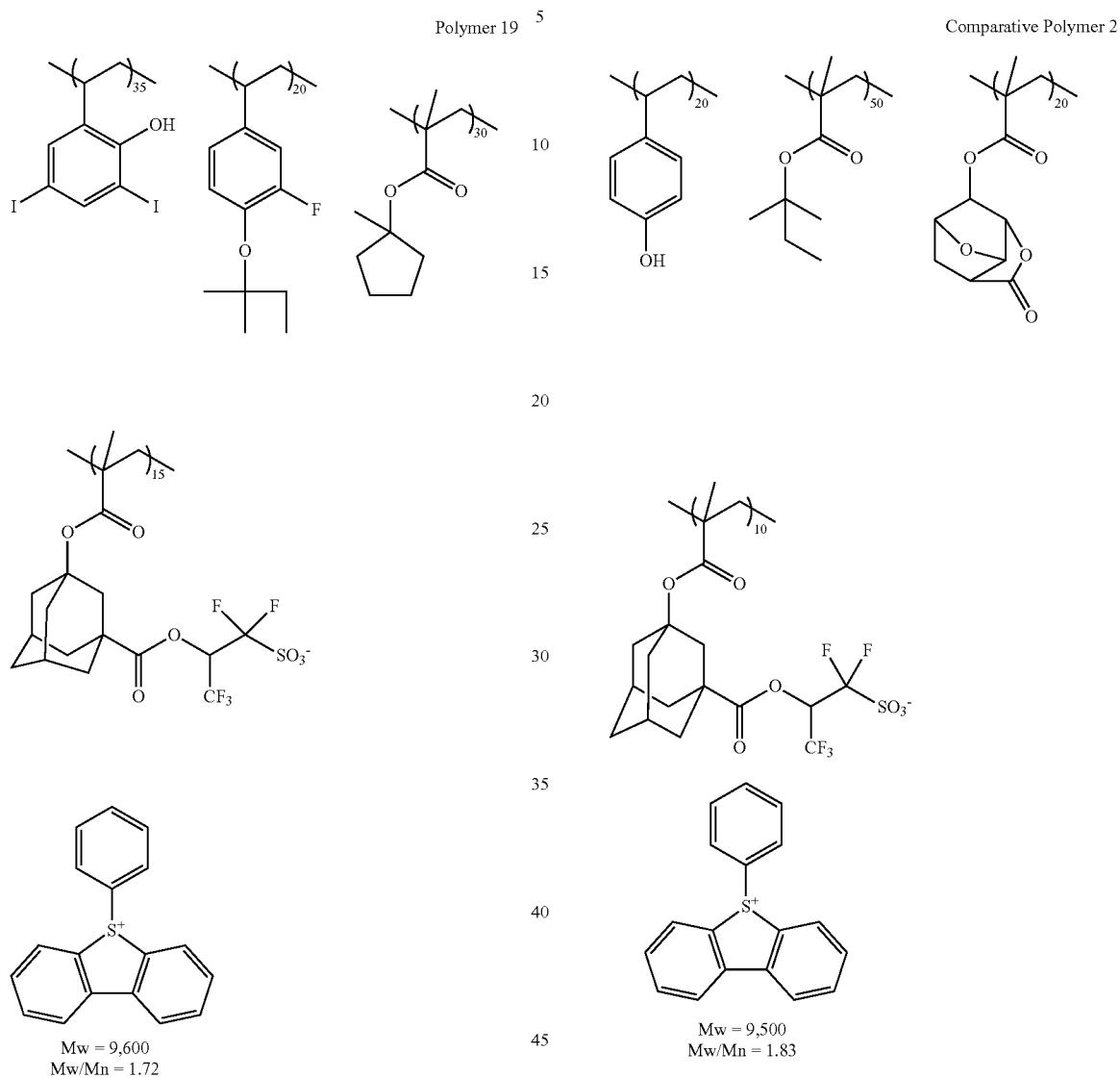
Comparative Example 1-1 Comparative Polymer 1
Comparative Example 1-3 Comparative Polymer 3
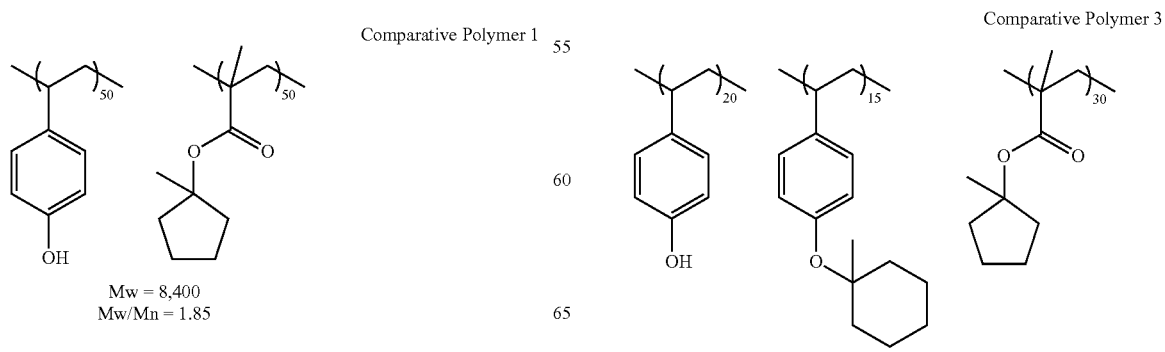

-continued
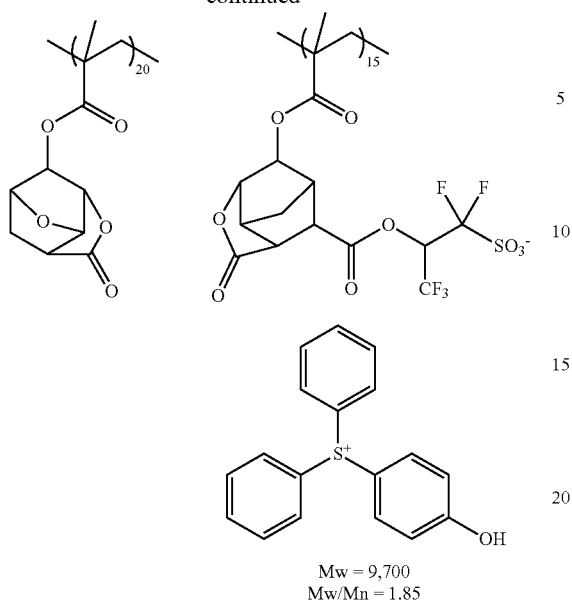
Mw = 9,700
Mw/Mn = 1.85
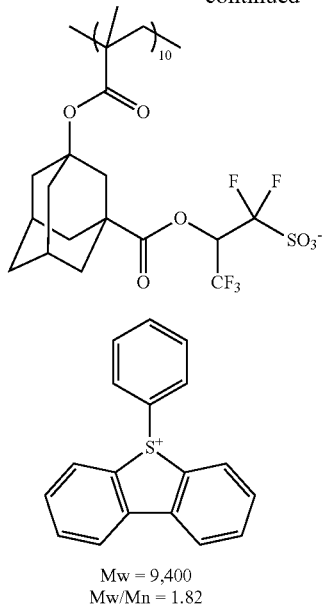
Mw = 9,400
Mw/Mn = 1.82
Comparative Example 1-6 Comparative Polymer 6
Comparative Example 1-4 Comparative Polymer 4
Comparative Polymer 4
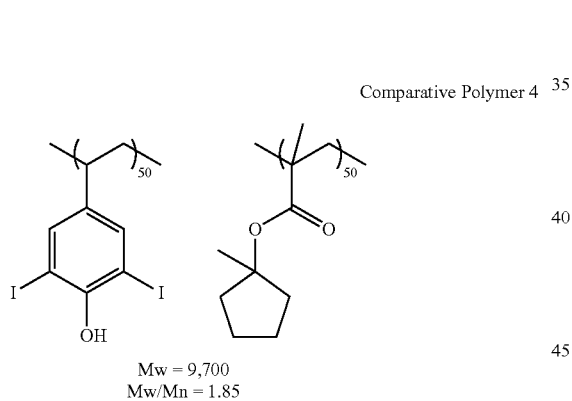
Mw = 9,700
Mw/Mn = 1.85
Comparative Example 1-5 Comparative Polymer 5
Comparative Polymer 5
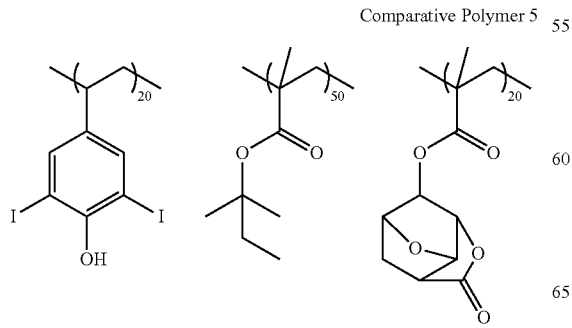
Comparative Polymer 6
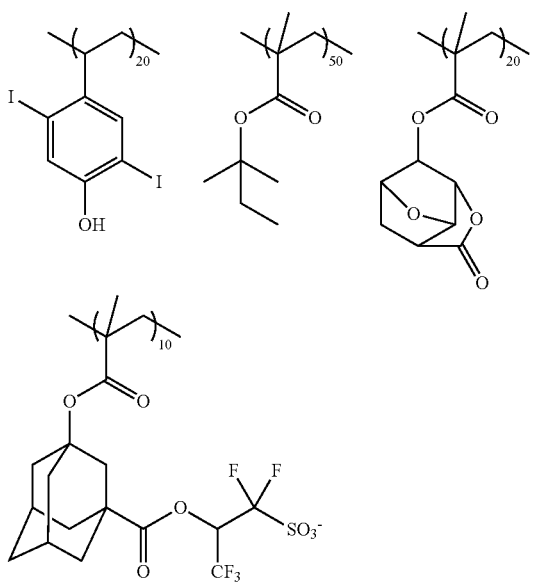
Mw = 9,300
Mw/Mn = 1.81

Comparative Example 1-7 Comparative Polymer 7

Acid Generator:
PAG-1 to PAG-3 of the following structural formulae

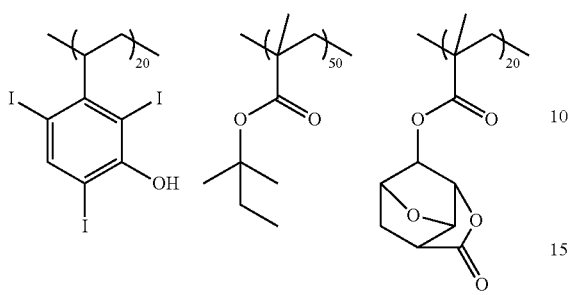

Comparative Polymer 7

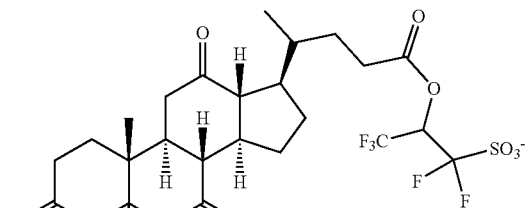

PAG-1

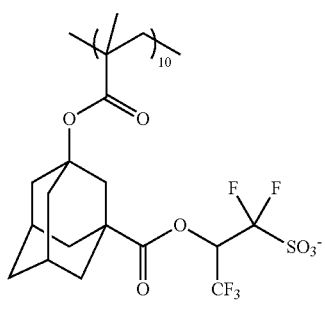

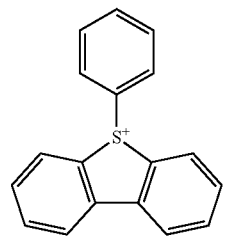

Mw = 9,100
Mw/Mn = 1.80

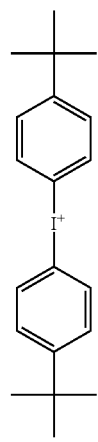

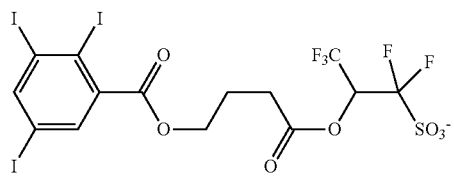

PAG-2

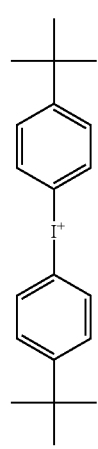

[3] Preparation of Resist Compositions

Resist compositions were prepared by dissolving the polymer and other components in a solvent containing 100 ppm of surfactant FC-4430 (3M) in accordance with the recipe shown in Tables 1 and 2, and filtering through a filter having a pore size of 0.2 μm.

The components in Tables 1 and 2 are as identified below.

Organic Solvent
  PGMEA: propylene glycol monomethyl ether acetate
  CyH: cyclohexanone
  PGME: propylene glycol monomethyl ether
  DAA: diacetone alcohol

PAG-3

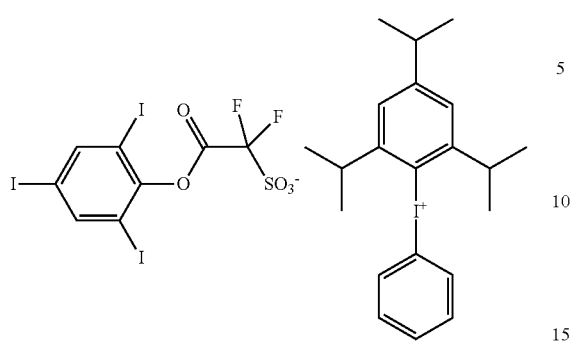

Quencher: Quencher 1 to 3 of the following structural formulae

Quencher 1

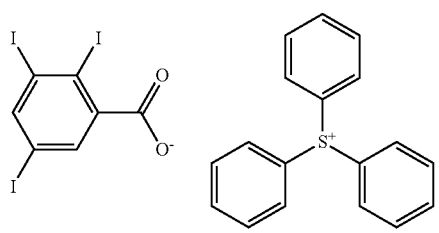

Quencher 2

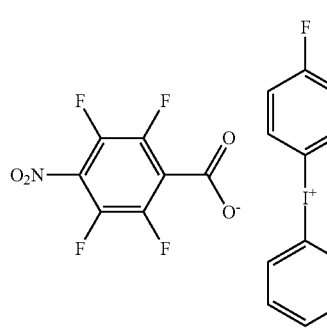

Quencher 3

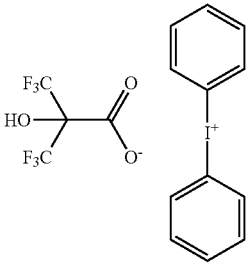

EUV Lithography Test

Examples 3-1 to 3-19 and Comparative Examples 2-1 to 2-7

Each of the resist compositions in Tables 1 and 2 was spin coated on a silicon substrate having a 20-nm coating of silicon-containing spin-on hard mask material SHB-A940 (silicon content 43 wt %, Shin-Etsu Chemical Co, Ltd.) and prebaked on a hot plate at 105° C. for 60 seconds to form a resist film of 60 nm thick. Using an EUV scanner NXE3300 (ASML, NA 0.33, a 0.9/0.6, quadrupole illumination), the resist film was exposed to EUV through a mask bearing a hole pattern having a pitch of 46 nm+20% bias (on-wafer size). The resist film was baked (PEB) at the temperature shown in Tables 1 and 2 for 60 seconds and developed in a 2.38 wt % TMAH aqueous solution for 30 seconds to form a hole pattern having a size of 23 nm.

The resist pattern was observed under CD-SEM (CG-5000, Hitachi High-Technologies Corp.). The exposure dose that provided a hole pattern having a size of 23 nm was reported as sensitivity. The size of 50 holes was measured, from which a size variation ($3\sigma$) was computed and reported as CDU.

The resist composition is shown in Tables 1 and 2 together with the sensitivity and CDU of EUV lithography.

TABLE 1

| | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|
| Example 3-1 | Polymer 1 (100) | — | Quencher 1 (4.0) | PGMEA (400) CyH (2,000) PGME (100) | 100 | 15 | 2.3 |
| 3-2 | Polymer 2 (100) | — | Quencher 1 (4.0) | PGMEA (400) CyH (2,000) PGME (100) | 95 | 14 | 2.6 |
| 3-3 | Polymer 3 (100) | — | Quencher 1 (4.0) | PGMEA (400) CyH (2,000) PGME (100) | 100 | 14 | 2.5 |
| 3-4 | Polymer 4 (100) | — | Quencher 1 (4.0) | PGMEA (400) CyH (2,000) PGME (100) | 100 | 13 | 2.5 |
| 3-5 | Polymer 5 (100) | — | Quencher 1 (4.0) | PGMEA (400) CyH (2,000) PGME (100) | 100 | 14 | 2.4 |
| 3-6 | Polymer 6 (100) | — | Quencher 1 (4.0) | PGMEA (400) CyH (2,000) PGME (100) | 95 | 14 | 2.7 |

TABLE 1-continued

| | | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| | 3-7 | Polymer 7 (100) | — | Quencher 2 (4.5) | PGMEA (400) CyH (2,000) PGME (100) | 100 | 13 | 2.5 |
| | 3-8 | Polymer 8 (100) | — | Quencher 2 (4.5) | PGMEA (400) CyH (2,000) PGME (100) | 95 | 15 | 2.8 |
| | 3-9 | Polymer 9 (100) | — | Quencher 3 (4.5) | PGMEA (400) CyH (2,000) PGME (100) | 100 | 14 | 2.5 |
| | 3-10 | Polymer 10 (100) | — | Quencher 3 (4.5) | PGMEA (400) CyH (2,000) PGME (100) | 100 | 13 | 2.5 |
| | 3-11 | Polymer 11 (100) | — | Quencher 2 (4.5) | PGMEA (400) CyH (2,000) PGME (100) | 100 | 15 | 2.8 |
| | 3-12 | Polymer 12 (100) | — | Quencher 2 (4.5) | PGMEA (400) CyH (2,000) PGME (100) | 100 | 14 | 2.4 |
| | 3-13 | Polymer 13 (100) | — | Quencher 3 (4.5) | PGMEA (400) CyH (2,000) PGME (100) | 100 | 15 | 2.4 |
| | 3-14 | Polymer 14 (100) | PAG-1 (10) | Quencher 1 (4.0) | PGMEA (400) CyH (2,000) PGME (100) | 100 | 19 | 3.0 |
| | 3-15 | Polymer 15 (100) | PAG-2 (15) | Quencher 1 (4.0) | PGMEA (400) CyH (2,000) PGME (100) | 100 | 17 | 3.2 |
| | 3-16 | Polymer 16 (100) | PAG-3 (15) | Quencher 1 (4.0) | PGMEA (400) CyH (2,000) PGME (100) | 100 | 16 | 2.9 |
| | 3-17 | Polymer 17 (100) | — | Quencher 2 (4.5) | PGMEA (1,900) DAA (600) | 100 | 16 | 2.4 |
| | 3-18 | Polymer 18 (100) | — | Quencher 2 (4.5) | PGMEA (1,900) DAA (600) | 100 | 17 | 2.4 |
| | 3-19 | Polymer 19 (100) | — | Quencher 2 (4.5) | PGMEA (1,900) DAA (600) | 100 | 22 | 2.0 |

TABLE 2

| | | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Comparative Example | 2-1 | Comparative Polymer 1 (100) | PAG-1 (10) | Quencher 1 (4.0) | PGMEA (400) CyH (2,000) PGME (100) | 95 | 35 | 3.8 |
| | 2-2 | Comparative Polymer 2 (100) | — | Quencher 2 (4.5) | PGMEA (400) CyH (2,000) PGME (100) | 100 | 29 | 4.3 |
| | 2-3 | Comparative Polymer 3 (100) | — | Quencher 3 (4.5) | PGMEA (400) CyH (2,000) PGME (100) | 100 | 25 | 4.2 |
| | 2-4 | Comparative Polymer 4 (100) | PAG-1 (10) | Quencher 1 (4.0) | PGMEA (400) CyH (2,000) PGME (100) | 95 | 20 | 3.5 |
| | 2-5 | Comparative Polymer 5 (100) | — | Quencher 2 (4.5) | PGMEA (400) CyH (2,000) PGME (100) | 100 | 17 | 3.4 |
| | 2-6 | Comparative Polymer 6 (100) | — | Quencher 3 (4.5) | PGMEA (400) CyH (2,000) PGME (100) | 100 | 17 | 3.3 |
| | 2-7 | Comparative Polymer 7 (100) | — | Quencher 2 (4.5) | PGMEA (400) CyH (2,000) PGME (100) | 100 | 17 | 3.2 |

It is demonstrated in Tables 1 and 2 that resist compositions comprising a polymer within the scope of the invention exhibit high sensitivity and improved CDU. The compositions are effective for lithography micro-processing.

Japanese Patent Application No. 2017-175900 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A monomer having the formula (A):

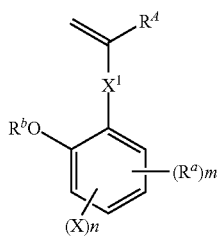

(A)

wherein $R^A$ is hydrogen, methyl or trifluoromethyl, $X^1$ is a single bond, $R^a$ is a $C_1$-$C_{20}$ monovalent hydrocarbon group in which any constituent methylene moiety may be replaced by an ether bond or carbonyl moiety, where at least two $R^a$ are included, two adjacent $R^a$ may bond together to form an alicyclic structure with the carbon atoms to which they are attached, $R^b$ is hydrogen or an acid labile group, X is iodine, n and m are integers in the range: $1 \leq n \leq 4$, $0 \leq m \leq 3$, and $1 \leq n+m \leq 4$.

2. The monomer of claim 1 wherein $R^b$ is an acid labile group.

3. A polymer comprising recurring units having a partial structure represented by the formula (B) on a side chain,

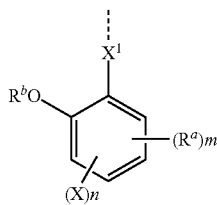

(B)

wherein $X^1$ is a single bond, $R^a$ is a $C_1$-$C_{20}$ monovalent hydrocarbon group in which any constituent methylene moiety may be replaced by an ether bond or carbonyl moiety, where at least two $R^a$ are included, two adjacent $R^a$ may bond together to form a ring with the carbon atoms to which they are attached, $R^b$ is hydrogen or an acid labile group, X is iodine, n and m are integers in the range: $1 \leq n \leq 4$, $0 \leq m \leq 3$, and $1 \leq n+m \leq 4$, the broken line denotes a valance bond to a polymer backbone.

4. The polymer of claim 3 wherein the recurring unit has the formula (a):

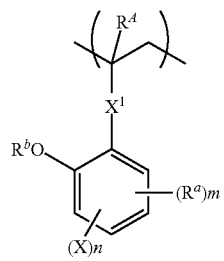

(a)

wherein $R^a$, $R^b$, $X^1$, X, n and m are as defined above, and $R^A$ is hydrogen, methyl or trifluoromethyl.

5. The polymer of claim 3, further comprising recurring units having a group capable of polarity switch under the action of acid.

6. The polymer of claim 5 wherein the recurring units having a group capable of polarity switch under the action of acid are represented by the formula (b1) or (b2):

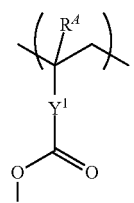

(b1)

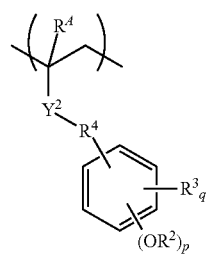

(b2)

wherein $R^A$ is each independently hydrogen, methyl or trifluoromethyl,
$Y^1$ is a single bond, phenylene group, naphthylene group, or a $C_1$-$C_{12}$ linking group containing an ether bond, ester bond or lactone ring,
$Y^2$ is a single bond, ester bond or amide bond,
$R^1$ and $R^2$ are each independently an acid labile group,
$R^3$ is fluorine, trifluoromethyl, cyano, $C_1$-$C_6$ alkyl, $C_1$-$C_6$ alkoxy, $C_2$-$C_7$ acyl, $C_2$-$C_7$ acyloxy, or $C_2$-$C_7$ alkoxycarbonyl group,
$R^4$ is a single bond or $C_1$-$C_6$ alkylene group in which at least one carbon atom may be replaced by an ether or ester bond,
p is 1 or 2, and q is an integer of 0 to 4.

7. The polymer of claim 3, further comprises recurring units having an adhesive group which is selected from the group consisting of hydroxyl, carboxyl, lactone ring, carbonate, thiocarbonate, carbonyl, cyclic acetal, ether bond, ester bond, sulfonic acid ester bond, cyano, amide, —O—C(=O)—S—, and —O—C(=O)—NH—.

8. The polymer of claim 3, further comprising recurring units of at least one type selected from recurring units having the formulae (d1), (d2) and (d3):

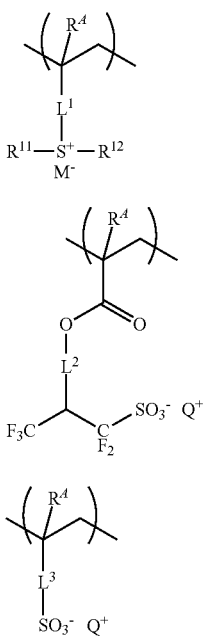

(d1)

(d2)

(d3)

wherein $R^A$ is each independently hydrogen, methyl or trifluoromethyl, $R^{11}$ and $R^{12}$ are each independently a $C_1$-$C_{20}$ monovalent hydrocarbon group which may contain a heteroatom, $R^{11}$ and $R^{12}$ may bond together to form a ring with the sulfur atom to which they are attached, $L^1$ is a single bond, phenylene group —C(=O)-$L^{11}$-$L^{12}$ or —O-$L^{12}$-, $L^{11}$ is —O— or —NH—, $L^{12}$ is a $C_1$-$C_6$ divalent aliphatic hydrocarbon group which may contain a carbonyl, ester bond, ether bond or hydroxyl moiety, or a phenylene group, $L^2$ is a single bond or -$L^{21}$-C(=O)—O—, $L^{21}$ is a $C_1$-$C_{20}$ divalent hydrocarbon group which may contain a heteroatom, $L^3$ is a single bond, methylene, ethylene, phenylene or fluorinated phenylene group, —C(=O)-$L^{31}$-$L^{32}$-, or —O-$L^{32}$-, $L^{31}$ is —O— or —NH—, $L^{32}$ is a $C_1$-$C_6$ divalent aliphatic hydrocarbon group which may contain a carbonyl, ester bond, ether bond or hydroxyl moiety, or a phenylene group, $M^-$ is a non-nucleophilic counter ion, $Q^+$ is a sulfonium cation having the formula (d4) or iodonium cation having the formula (d5):

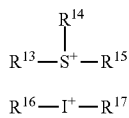

(d4)

(d5)

wherein $R^{13}$ to $R^{17}$ are each independently a $C_1$-$C_{20}$ monovalent hydrocarbon group which may contain a heteroatom, any two of $R^{13}$, $R^{14}$ and $R^{15}$ may bond together to form a ring with the sulfur atom to which they are bonded.

9. The polymer of claim 3 wherein $R^b$ is an acid labile group.

10. A resist composition comprising a base resin containing the polymer of claim 3, an organic solvent, and an acid generator.

11. The resist composition of claim 10, further comprising a quencher.

12. The resist composition of claim 10, further comprising a surfactant.

13. A resist composition comprising a base resin containing the polymer of claim 8, and an organic solvent.

14. A pattern forming process comprising the steps of coating the resist composition of claim 10 onto a substrate, baking to form a resist film, exposing the resist film to high-energy radiation, and developing the exposed resist film in a developer.

15. The process of claim 14 wherein the high-energy radiation is i-line, KrF excimer laser, ArF excimer laser, EB, or EUV of wavelength 3 to 15 nm.

* * * * *